United States Patent
Plachter et al.

(10) Patent No.: US 11,986,521 B2
(45) Date of Patent: May 21, 2024

(54) VIRAL PARTICLE-BASED VACCINE

(71) Applicant: VAKZINE PROJEKT MANAGEMENT GMBH, Hannover (DE)

(72) Inventors: Bodo Plachter, Ansbach (DE); Inessa Penner, Mainz-Kastel (DE)

(73) Assignee: VAKZINE PROJEKT MANAGEMENT GMBH, Hannover (DE)

( * ) Notice: Subject to any disclaimer, the term of this patent is extended or adjusted under 35 U.S.C. 154(b) by 0 days.

(21) Appl. No.: 15/734,634

(22) PCT Filed: Jun. 7, 2019

(86) PCT No.: PCT/EP2019/064941
§ 371 (c)(1),
(2) Date: Dec. 3, 2020

(87) PCT Pub. No.: WO2019/234219
PCT Pub. Date: Dec. 12, 2019

(65) Prior Publication Data
US 2021/0228711 A1    Jul. 29, 2021

(30) Foreign Application Priority Data
Jun. 8, 2018 (EP) .................................. 18176735

(51) Int. Cl.
*A61K 39/245* (2006.01)
*A61K 39/00* (2006.01)
*A61P 31/22* (2006.01)
*C07K 14/005* (2006.01)
*C12N 7/00* (2006.01)

(52) U.S. Cl.
CPC ............ *A61K 39/245* (2013.01); *A61P 31/22* (2018.01); *C07K 14/005* (2013.01); *C12N 7/00* (2013.01); *A61K 2039/5252* (2013.01); *A61K 2039/545* (2013.01); *C12N 2710/16121* (2013.01); *C12N 2710/16122* (2013.01); *C12N 2710/16134* (2013.01)

(58) Field of Classification Search
CPC .......... A61K 39/245; A61K 2039/5252; A61K 2039/545; A61K 39/12; A61P 31/22; C07K 14/005; C12N 7/00; C12N 2710/16121; C12N 2710/16122; C12N 2710/16134
See application file for complete search history.

(56) References Cited

U.S. PATENT DOCUMENTS

| | | | | |
|---|---|---|---|---|
| 2008/0019945 A1* | 1/2008 | Kemble | ............... | A61P 31/12 435/237 |
| 2011/0008387 A1* | 1/2011 | Grode | .................. | A61K 39/12 435/236 |
| 2015/0259387 A1* | 9/2015 | Schiedner | ............... | C12N 7/00 435/5 |
| 2015/0307850 A1* | 10/2015 | Fu | ......................... | A61P 37/04 435/235.1 |

FOREIGN PATENT DOCUMENTS

| WO | WO-00/53729 A2 | 9/2000 |
|---|---|---|
| WO | WO-2011/124371 A1 | 10/2011 |
| WO | WO-2012/051211 A2 | 4/2012 |

OTHER PUBLICATIONS

Stanton RJ, Baluchova K, Dargan DJ, Cunningham C, Sheehy O, Seirafian S, McSharry BP, Neale ML, Davies JA,, et al. Reconstruction of the complete human cytomegalovirus genome in a BAC reveals RL13 to be a potent inhibitor of replication. J Clin Invest. Sep. 2010;120(9):3191-208. Epub Aug. 2, 2010. (Year: 2010).*
Murphy E, et al. Human Herpesvirus 5 Towne-BAC isolate, complete sequence. GenBank: AC146851.1, Dec. 10, 2003. (Year: 2003).*
Dunn WS, et. al. Human herpesvirus 5 strain Towne, complete genome. GenBank: AY315197.2; Dep. Jan. 31, 2007. (Year: 2007).*
Patrone M, Secchi M, Fiorina L, Ierardi M, Milanesi G, Gallina A. Human cytomegalovirus UL130 protein promotes endothelial cell infection through a producer cell modification of the virion. J Virol. Jul. 2005;79(13):8361-73. (Year: 2005).*
Pepperl S, Münster J, Mach M, Harris JR, Plachter B. Dense bodies of human cytomegalovirus induce both humoral and cellular immune responses in the absence of viral gene expression. J Virol. Jul. 2000;74(13):6132-46 (Year: 2000).*
Cayatte C, Schneider-Ohrum K, Wang Z, Irrinki A, Nguyen N, Lu J, et. al. Cytomegalovirus vaccine strain towne-derived dense bodies induce broad cellular immune responses and neutralizing antibodies that prevent infection of fibroblasts and epithelial cells. J Virol. Oct. 2013;87(20):11107-20. (Year: 2013).*
Becke S, Aue S, Thomas D, Schader S, Podlech J, Bopp T, et. al. Optimized recombinant dense bodies of human cytomegalovirus efficiently prime virus specific lymphocytes and neutralizing antibodies without the addition of adjuvant. Vaccine. Aug. 31, 2010;28(38):6191-8. Epub Jul. 23, 2010. (Year: 2010).*
Plachter B, Buscher N, Sinzger C, Sauer C. Subviral dense bodies of the human cytomegalovirus containing the gH/gL/UL128-131A Complex as the Basis for Vaccine Development. ID023. European Congenital Cytomegalovirus Initiative, Apr. 24-26, 2016, Venice, Italy. (Year: 2016).*

(Continued)

*Primary Examiner* — Rachel B Gill
(74) *Attorney, Agent, or Firm* — Clark & Elbing LLP

(57) ABSTRACT

The present invention relates to nucleic acid molecules encoding a recombinant human cytomegalovirus (HCMV) strain, dense bodies produced by said HCMV strain and preparations of said dense bodies for use in medicine, particularly as a vaccine against HCMV.

18 Claims, 9 Drawing Sheets

Figure 1:
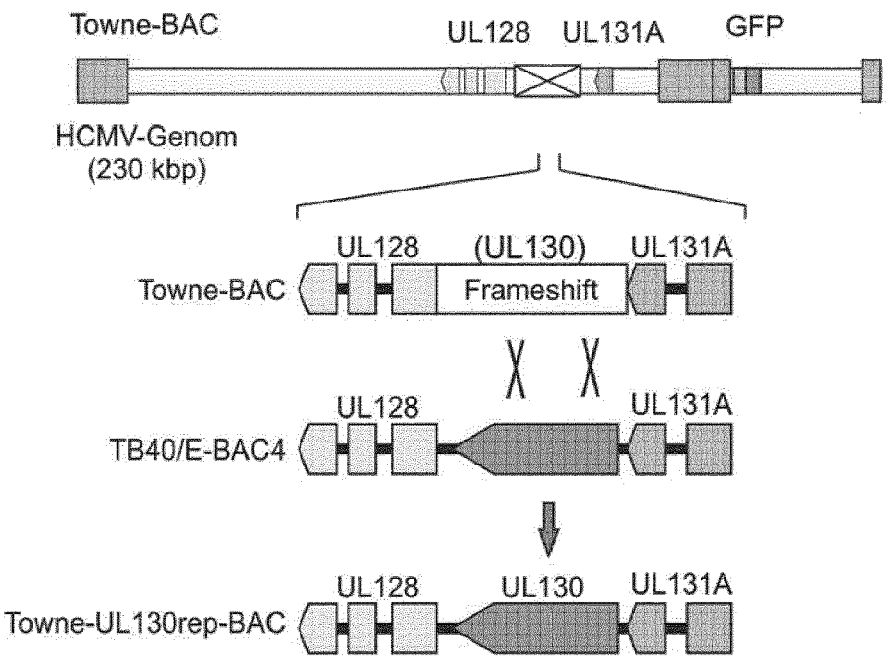
Figure 1:
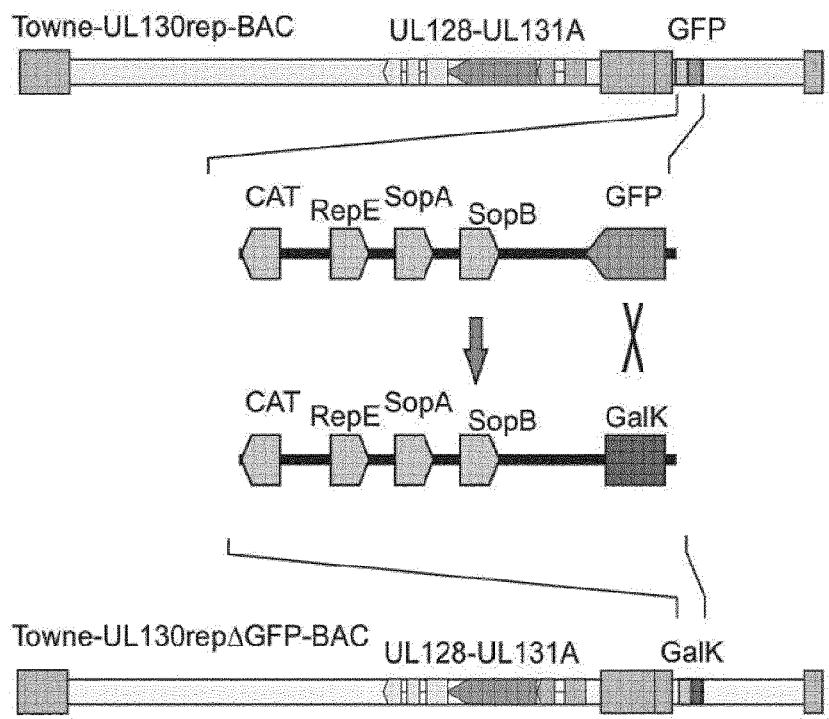
Figure 1:
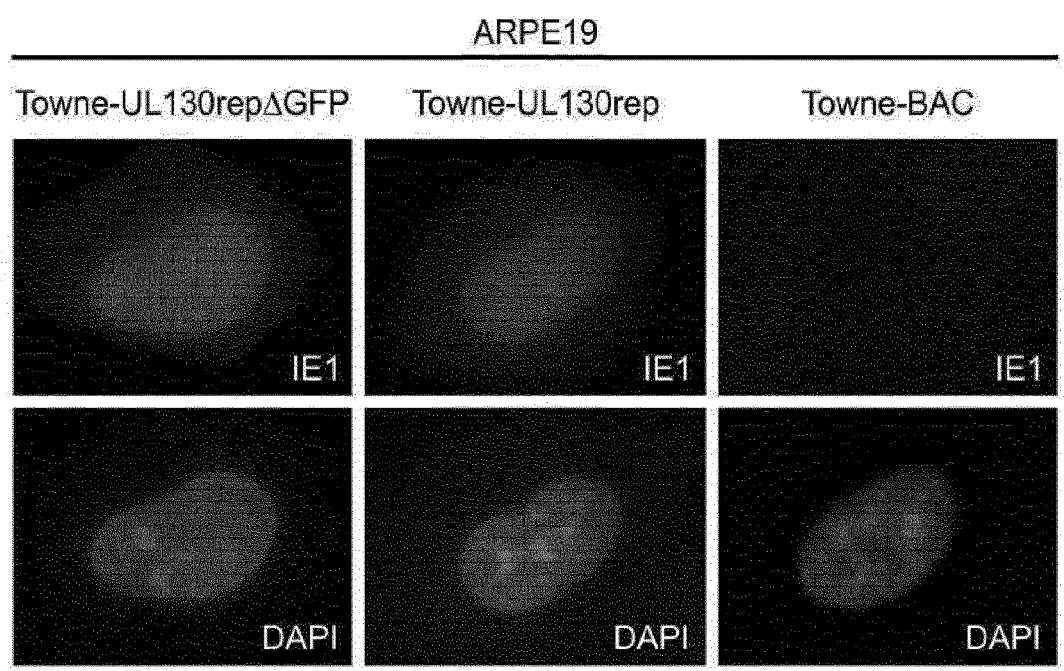
Figure 1:
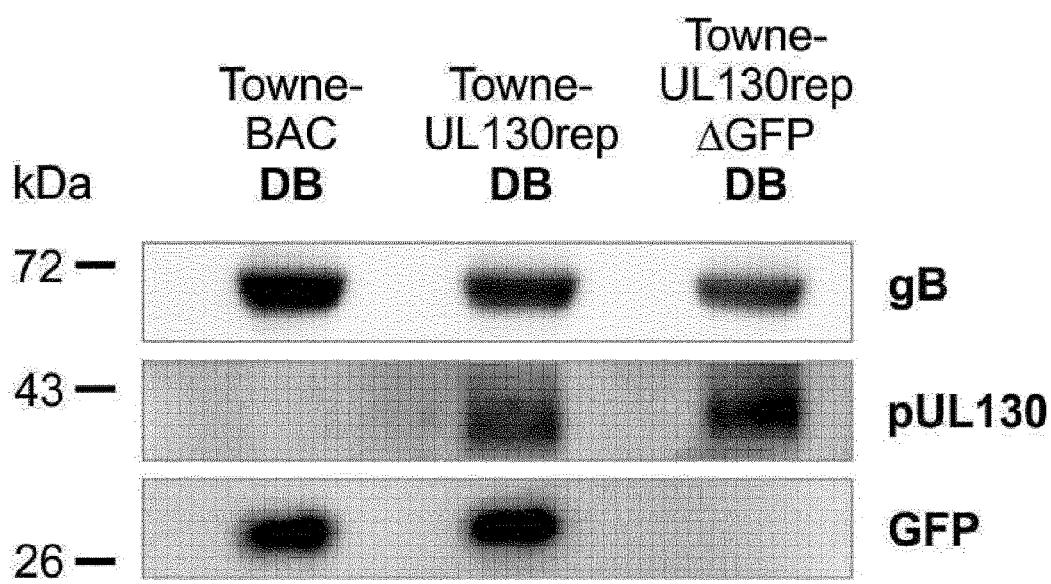

Specification includes a Sequence Listing.

(56) References Cited

OTHER PUBLICATIONS

Büscher N, Paulus C, Nevels M, Tenzer S, Plachter B. The proteome of human cytomegalovirus virions and dense bodies is conserved across different strains. Med Microbiol Immunol. Jun. 2015;204(3):285-93. Epub Mar. 3, 2015. (Year: 2015).*

Freed DC, Tang Q, Tang A, Li F, He X, Huang Z, Meng W, Xia L, Finnefrock AC, Durr E, et al. Pentameric complex of viral glycoprotein H is the primary target for potent neutralization by a human cytomegalovirus vaccine. Proc Natl Acad Sci U S A. Dec. 17, 2013;110(51):E4997-5005. Epub Dec. 2, 2013. (Year: 2013).*

Lehmann C (nee Sauer). 2013. Impact of Subviral Particles of the human cytomegalovirus on the induction of the antiviral immune response. PhD Thesis. Johannes Gutenberg University Mainz, Mainz, Germany. English translation. (Year: 2013).*

Smith GA, Enquist Lw. A self-recombining bacterial artificial chromosome and its application for analysis of herpesvirus pathogenesis. Proc Natl Acad Sci U S A. Apr. 25, 2000;97(9):4873-8. (Year: 2000).*

Brechtel T, Tyner M, Tandon R. Complete Genome Sequence of a Cytomegalovirus Towne-BAC (Bacterial Artificial Chromosome) Isolate Maintained in *Escherichia coli* for 10 Years and Then Serially Passaged in Human Fibroblasts. Genome Announc. Sep. 26, 2013;1(5):e00693-13. (Year: 2013).*

"Green fluorescent protein." Wikipedia.org. https://en.wikipedia.org/wiki/Green_fluorescent_protein. Accessed Aug. 22, 2023. (Year: 2023).*

Yue JX, Holland ND, Holland LZ, Deheyn DD. The evolution of genes encoding for green fluorescent proteins: insights from cephalochordates (amphioxus). Sci Rep. Jun. 17, 2016;6:28350. (Year: 2016).*

Marchini A, Liu H, Zhu H. Human cytomegalovirus with IE-2 (UL122) deleted fails to express early lytic genes. J Virol. Feb. 2001;75(4):1870-8. (Year: 2001).*

Green E. "Gene: Definition". National Human Genome Research Institute. https://www.genome.gov/genetics-glossary/Gene. Updated Aug. 21, 2023. (Year: 202).*

Dunn W, Chou C, Li H, Hai R, Patterson D, Stolc V, Zhu H, Liu F. Functional profiling of a human cytomegalovirus genome. Proc Natl Acad Sci U S A. Nov. 25, 2003;100(24):14223-8. doi: 10.1073/pnas.2334032100. Epub Nov. 17, 2003. (Year: 2003).*

Dunn W, Trang P, Khan U, Zhu J, Liu F. RNase P-mediated inhibition of cytomegalovirus protease expression and viral DNA encapsidation by oligonucleotide external guide sequences. Proc Natl Acad Sci U S A. Dec. 18, 2001;98(26):14831-6. Epub Dec. 11, 2001. (Year: 2001).*

Andreoni et al., "A rapid microneutralization assay for the measurement of neutralizing antibody reactive with human cytomegalovirus," J Virol Methods. 23(2):157-67 (1989).

Baldick et al., "Human cytomegalovirus tegument protein pp71 (ppUL82) enhances the infectivity of viral DNA and accelerates the infectious cycle," J Virol. 71(6):4400-8 (1997).

Becke et al., "Optimized recombinant dense bodies of human cytomegalovirus efficiently prime virus specific lymphocytes and neutralizing antibodies without the addition of adjuvant" Vaccine. 28(38):6191-6198 (2010).

Belzile et al., "Trehalose, an mTOR-Independent Inducer of Autophagy, Inhibits Human Cytomegalovirus Infection in Multiple Cell Types," J Virol. 90(3):1259-77 (2015).

Bianco et al., "Restriction of Human Cytomegalovirus Replication by ISG15, a Host Effector Regulated by cGAS-STING Double-Stranded-DNA Sensing," J Virol. 91(9):e02483-16 (2017).

Borst et al., "Cloning of the human cytomegalovirus genome as an infectious bacterial artificial chromosome in *Escherichia coli*: a new approach for construction of HCMV mutants," J Virol. 73(10):8320-8329 (1999).

Chee et al., "Analysis of the protein-coding content of the sequence of human cytomegalovirus strain AD169," Curr Top Microbiol Immunol. 154:125-69 (1990).

Dunn et al., "Functional profiling of a human cytomegalovirus genome", Proc Natl Acad Sci USA. 100(24):14223-8 (2003).

Extended European Search Report for European Patent Application No. 18176735.1 dated Oct. 18, 2018 (12 pages).

Fleckenstein et al., "Cloning of the complete human cytomegalovirus genome in cosmids," Gene. 18(1):39-46 (1982).

GenBank database accession No. AY315197, dated Jan. 31, 2007 (43 pages).

GenBank database accession No. EF999921.1, dated Jul. 26, 2016 (103 pages).

GenBank database accession No. GQ121041.1, dated Dec. 1, 2016 (122 pages).

International Search Report for International Patent Application No. PCT/EP2019/064941, dated Jul. 25, 2019 (6 pages).

Jones et al., "A cluster of dispensable genes within the human cytomegalovirus genome short component: IRS1, US1 through US5, and the US6 family," J Virol. 66(4):2541-6 (1992).

Kim et al., "Consecutive Inhibition of ISG15 Expression and ISGylation by Cytomegalovirus Regulators," PLoS Pathog. 12(8):e1005850 (2016) (28 pages).

Marchini et al., "Human cytomegalovirus with IE-2 (UL122) deleted fails to express early lytic genes," J Virol. 75(4):1870-8 (2001).

McVoy, "Cytomegalovirus vaccines," Clin Infect Dis. 57(Suppl 4): S196-9 (2013).

O'Connor et al., Construction of large DNA segments in *Escherichia coli*, Science. 24(4910):1307-12 (1989).

Plotkin et al., "Candidate cytomegalovirus strain for human vaccination," Infect Immun. 12(3):521-527 (1975).

Sampaio et al., "A TB40/E-derived human cytomegalo-virus genome with an intact US-gene region and a self-excisable BAC cassette for immunological research," Biotechniques. 63(5):205-214 (2017).

Sauer et al., "Subviral dense bodies of human cytomegalovirus stimulate maturation and activation of monocyte-derived immature dendritic cells," J Virol. 87(20):11287-91 (2013).

Scherer et al., "Emerging Role of PML Nuclear Bodies in Innate Immune Signaling," J Virol. 90(13):5850-5854 (2016).

Schneider-Ohrum et al., "Production of Cytomegalovirus Dense Bodies by Scalable Bioprocess Methods Maintains Immunogenicity and Improves Neutralizing Antibody Titers," J Virol. 90(22):10133-10144 (2016).

Schuessler et al., "Mutational Mapping of UL130 of Human Cytomegalovirus Defines Peptide Motifs within the C-Terminal Third as Essential for Endothelial Cell Infection," J Virol. 84(18):9019-26 (2010).

Sinzger et al., "Cloning and sequencing of a highly productive, endotheliotropic virus strain derived from human cytomegalovirus TB40/E, " J Gen Virol. 89(Pt 2):359-368 (2008).

Sinzger et al., "Modification of human cytomegalovirus tropism through propagation in vitro is associated with changes in the viral genome," J Gen Virol. 80(Pt 11): 2867-2877 (1999).

Tavalai et al.,"Intrinsic cellular defense mechanisms targeting human cytomegalovirus," Virus Res. 157(2):128-33 (2011).

Tullis et al., "Efficient replication of adeno-associated virus type 2 vectors: a cis-acting element outside of the terminal repeats and a minimal size," J Virol. 74(24):11511-21 (2000).

Vashee et al., "Cloning, Assembly, and Modification of the Primary Human Cytomegalovirus Isolate Toledo by Yeast-Based Transformation-Associated Recombination," mSphere. 2(5):e00331-17 (2017).

Villarroya-Beltri et al., "ISGylation—a key to lock the cell gates for preventing the spread of threats," J Cell Sci. 130(18):2961-2969 (2017).

Warming et al., "Simple and highly efficient BAC recombineering using galk selection," Nucleic Acids Res. 33(4):e36 (2005) (12 pages).

Written Opinion for International Patent Application No. PCT/EP2019/064941, dated Jul. 25, 2019 (8 pages).

Baldanti et al., "Human cytomegalovirus UL131A, UL130 and UL128 genes are highly conserved among field isolates," Arch Virol. 151(6):1225-33 (2006).

(56) References Cited

OTHER PUBLICATIONS

Mersseman et al., "Refinement of strategies for the development of a human cytomegalovirus dense body vaccine," Med Microbiol Immunol. 197(2):97-107 (Jun. 2008).

* cited by examiner

A

B

C

D

VIRAL PARTICLE-BASED VACCINE

SEQUENCE LISTING

The instant application contains a Sequence Listing which has been submitted electronically in ASCII format and is hereby incorporated by reference in its entirety. Said ASCII copy, created Sep. 14, 2020, is named 51537-002001 Sequence Listing 9.14.20 ST25 and is 13,744 bytes in size.

The present invention relates to nucleic acid molecules encoding a recombinant human cytomegalovirus (HCMV) strain, dense bodies produced by said HCMV strain and preparations of said dense bodies for use in medicine, particularly as a vaccine against HCMV.

Infection with the human cytomegalovirus (HCMV) is a major cause of disease in patients with a compromised immune status, e.g. following solid organ or hematopoietic stem cell transplantation. Furthermore, transmission of the virus during pregnancy may result in congenital infection. Such infection may occur at a frequency of up to two percent of all life births in Western countries. Thus congenital HCMV infection is a major public health concern. The development of an HCMV vaccine consequently is a top-priority health-care goal.

Several vaccine candidates have been established. These include recombinant protein vaccines based on the immunodominant envelope glycoprotein B (gB), vaccines expressing immunogenic viral gene products including gB plus the T cell targets ppUL83 [pp65] and/or the major immediate early protein 1 (IE1) using DNA plasmid or peptide-based technologies; vector-based vaccine approaches including the expression of gB and other HCMV antigens using life virus or virus-like particle (VLP) systems; and replication-impaired or replication-effective HCMV (attenuated vaccines or disabled single-cycle vaccines).

Dense bodies (DBs), i.e. viral particles released after infection of mammalian cells by HCMV which are surrounded by a lipid membrane in which viral glycoproteins are embedded but which do not contain viral DNA nor capsids, were found to be highly immunogenic as described in WO 2000/053729 the content of which is herein incorporated by reference. DBs containing fusion proteins are described in WO 2011/124371 the content of which is herein incorporated by reference.

A recent publication demonstrates that DBs stimulate the maturation and activation of monocyte-derived immature dendritic cells (1). In the course of these studies it was found that DBs, expressing a pentameric complex of the viral proteins gH, gL, UL128, UL130 and UL131A generate a strong neutralizing antibody response against HCMV infection.

According to the present invention it was found that a pentamer-positive variant of the HCMV laboratory strain Towne, generated by two steps of BAC mutagenesis, is capable of producing pentamer-containing DBs.

Starting from the genome of the HCMV strain Towne as described in (2), which was cloned in the Bacterial Artificial Chromosome (BAC) vector Towne BAC (3) and sequenced (4) (c.f. GenBank database accession no. AY 315197), a novel HCMV strain Towne-UL130repΔGFP was generated which will serve as the parental genome for the development of a new-generation DB-based vaccine against HCMV.

The HCMV strain Towne-UL130repΔGFP is characterized by its capability of expressing a functional pentameric complex of the viral proteins gH, gL, UL128, UL130 and UL131A and the absence of a functional gene encoding the Green Fluorescence Protein (GFP) which is present in the parental strain Towne-UL130rep.

The deletion of the GFP gene was carried out by insertion of a bacterial galactokinase (GalK) gene in the genome of Towne-UL130rep. The expression of GalK in a GalK-negative bacterial host cell allows a positive selection of recombinant constructs on minimal agar plates when adding galactose (5). The GalK gene is in operative linkage with a bacterial promoter. The resulting BAC vector also comprises a chloramphenicol resistance gene in an operative linkage with a bacterial promoter as an additional selection marker in bacterial host cells.

Further, the present inventors have performed a study to investigate the impact of DBs produced by Towne-UL130repΔGFP on the host immune system. Surprisingly, it was found that DBs comprising an immunogenic pentameric complex are capable of maintaining the intrinsic host immunity, are effective in stimulating an interferon reaction and promote autophagy of viral proteins resulting in intracellular degradation and presentation by MHC class I and/or II molecules. Thus, the DBs of the present invention have a high potential as a vaccine being effective in preventing and/or ameliorating an occurrence of an HCMV associated disorder in a vaccinated human subject, particularly a human subject, and/or inhibiting transmission of an HCMV infection to another human subject.

A first aspect of the present invention refers to a nucleic acid molecule encoding the genome of a recombinant HCMV strain,
   wherein the recombinant HCMV strain is a genetically modified variant of the HCMV strain Towne,
   wherein the recombinant HCMV strain encodes a functional UL130 protein and does not encode a functional Green Fluorescent Protein (GFP).

The recombinant HCMV strain is a genetically modified variant of the HCMV strain Towne as present in the Towne-BAC clone (3, 4) according to GenBank Accession No. AY 315197. The genetic modification includes the presence of a functional gene encoding the viral UL130 protein and the absence of a functional gene encoding the Green Fluorescent Protein (GFP) in contrast to the previous available Towne genome present in Towne-BAC. The recombinant HCMV strain of the invention is preferably characterized by a sequence identity of at least 90%, at least 95%, at least 98%, at least 99%, at least 99.5%, or at least 99.8% over its entire length—except for the sequences encoding the UL130 gene and the GFP gene—to the nucleotide sequence of the HCMV strain Towne as present in the Towne-BAC clone (3,4) according to GenBank accession no. AY 315197.

The nucleic acid molecule of the invention encodes functional viral proteins capable of forming a pentameric complex, namely a complex comprising the viral proteins gH (UL75), gL (UL115), UL128, UL130 and UL131A, in particular the gH, gL, UL128 and UL131A proteins from the HCMV strain Towne as present in the clone Towne-BAC (AY315197) and a functional UL130 protein from the HCMV strain TB40. This strain has been isolated and cloned into a BAC vector (6,7). The complete nucleic acid sequence of the clone TB40-BAC4 is described under GenBank accession no. EF999921.1.

In particular embodiments, the recombinant strain of the invention encodes the protein gH (UL75) Towne (from GenBank accession no. GQ121041.1) having an amino acid sequence as shown in SEQ ID NO. 1, or an amino acid sequence having an identity of at least 90%, at least 95%, at least 98% or at least 99% over its entire length to SEQ ID NO. 1, the protein gL (UL115) Towne (from GenBank accession no. GQ121041.1) having an amino acid sequence as shown in SEQ ID NO. 2 or an amino acid sequence having an identity of at least 90%, at least 95%, at least 98% or at least 99% over its entire length to SEQ ID NO. 2, the protein UL128 Towne (from GenBank accession no. GQ121041.1) having an amino acid sequence as shown in SEQ ID NO. 3 or an amino acid sequence having an identity of at least 90%, at least 95%, at least 98% or at least 99% over its entire length to SEQ ID NO. 3, the protein UL130 TB40-BAC4 (from GenBank accession no. EF999921.1) having an amino acid sequence as shown in SEQ ID NO. 4 or an amino acid sequence having an identity of at least 90%, at least 95%, at least 98% or at least 99% over its entire length to SEQ ID NO. 4 and the protein UL131A Towne (from GenBank accession no. GQ121041.1) having an amino acid sequence as shown in SEQ ID NO. 5 or an amino acid sequence having an identity of at least 90%, at least 95%, at least 98% or at least 99% over its entire length to SEQ ID NO. 5.

In certain embodiments, the nucleic acid molecule may additionally encode a fusion protein, e.g. a fusion protein as disclosed in WO 2011/124371. In certain embodiments, the nucleic acid molecule does not encode any functional heterologous, i.e. non-HCMV protein.

In certain embodiments, the GFP gene present in the original HCMV strain Towne is deleted and a heterologous gene, particularly a bacterial galactokinase gene is inserted at its previous position in the HCMV strain Towne genome.

In a specific embodiment, the nucleic acid molecule encodes the genome of the recombinant HCMV strain Towne-UL130repΔGFP, the preparation of which is described in the present Examples.

In certain embodiments, the genome of the recombinant HCMV strain is characterized by the absence of a nucleic acid sequence encoding a selectable marker in a form which can be expressed in a mammalian cell, e.g. a human cell. For example, the genome of the recombinant HCMV strain may include selection marker genes such as galK or a chloramphenicol resistance gene in operative linkage with prokaryotic expression control sequences which cannot be expressed in a mammalian cell.

The nucleic acid molecule of the present invention may be any single-stranded or double-stranded nucleic acid molecule, e.g. an RNA or a DNA. In certain embodiments, the nucleic acid molecule is a double-stranded DNA.

The nucleic acid molecule may be present as such or being located on a vector, e.g. a BAC vector or a yeast vector. Suitable yeast vectors are described in (8).

Transfection of mammalian target cells with the nucleic acid molecule of the invention results in the production of viral particles and dense bodies, i.e. viral particles without capsid or viral DNA. In certain embodiments, the target cell is a human cell, e.g. a human fibroblast cell, such as a human foreskin fibroblast cell (HFF) or a human lung fibroblast cell, such as MRC-5 (ATCC CCL-171).

A further aspect of the present invention is a dense body (DB) produced by transfection of a mammalian target cell, particularly a human target cell, e.g. a human fibroblast cell, with a HCMV strain, particularly by transfection with a HCMV strain as described above, wherein the DB comprises the pentameric complex consisting of viral proteins gH, gL, UL128, UL130 and UL131A and is free from GFP.

A DB according to the present invention may be a viral particle released after transfection of a mammalian target cell, e.g. a human fibroblast cell, by HCMV, in particular after transfection by a recombinant HCMV strain as described above, wherein:

the particle is surrounded by lipid membrane in which viral glycoproteins are embedded,
the particle does not contain substantial amounts of viral DNA or capsids,
the particle comprises a pentameric complex consisting of viral proteins gH, gL, UL128, UL130 and UL131, in particular as described above, and
the particle is free from GFP.

A further aspect of the present invention is a dense body (DB) produced by infection of a mammalian target cell, particularly a human target cell, e.g. a human fibroblast cell, with a HCMV strain, particularly by infection with a HCMV strain as described above, wherein the DB comprises the pentameric complex consisting of viral proteins gH, gL, UL128, UL130 and UL131A and is free from GFP.

A DB according to the present invention may be a viral particle released after infection of a mammalian target cell, e.g. a human fibroblast cell, by HCMV, in particular after infection by a recombinant HCMV strain as described above, wherein:

the particle is surrounded by lipid membrane in which viral glycoproteins are embedded,
the particle does not contain substantial amounts of viral DNA or capsids,
the particle comprises a pentameric complex consisting of viral proteins gH, gL, UL128, UL130 and UL131, in particular as described above, and
the particle is free from GFP.

The dense body may be isolated from cell culture supernatant of virus-infected cells as described above by conventional methods, e.g. gradient centrifugation as described in the Examples. By this means, a preparation of DBs is obtained.

A further aspect of the present invention relates to a preparation of DBs as described above in a pharmaceutically acceptable carrier, e.g. a liquid carrier including an aqueous carrier, a non-aqueous carrier or any combination thereof.

In certain embodiments, the preparation comprises DBs which have been subjected to an inactivation treatment, e.g. UV irradiation. Inactivation may be determined by the absence of detectable virus contamination. This may be achieved, e.g. by the absence of de novo HCMV IE1 protein expression in indicator cell cultures (9), by the quantification of the DNA content of DB-preparations, by the quantification of viral genomic DNA in cell culture supernatants of indicator cell cultures, exposed to the DB-preparations or by electron microscopic analysis of DB-preparations.

In certain embodiments, preparation comprises DBs which have not been subjected to an inactivation treatment.

The preparation of DBs according to the present invention has been characterized by the lack of a negative effect on the intrinsic host immunity and to efficiently stimulate the interferon response, thus being capable of eliciting an immediate antiviral immune response in a vaccinated host.

Furthermore, it was found that DBs are capable of inducing autophagy in human target cell, e.g. in a human fibroblast cell or in a human endothelial cell. Autophagy may result in intracellular degradation of viral proteins and presentation of derived viral peptides by MHC molecules, particularly by MHC class I and/or class II molecules. Moreover, it is expected that the DBs may also induce autophagy in immune cells, such as dendritic cells and other antigen presenting cells, thus supporting presentation of viral peptides by these cells.

A further aspect of the present invention refers to a preparation of DBs as described above for use in medicine, particularly in human medicine, more particularly for use as a vaccine against HCMV. The preparation of the present invention is suitable for use in preventing and/or ameliorating the occurrence of an HCMV associated disorder in a vaccinated subject, e.g. a human subject, and/or for inhibiting transmission of an HCMV infection from a vaccinated subject e.g. a human subject, to a further subject.

For example, the preparation may be used for the treatment and/or prevention of HCMV-related complications of transplantation, e.g. the transplantation of solid organs such as hearts, kidneys, livers, or lungs or of hematopoietic stem cells. Further the composition is suitable for preventing the pre- or perinatal transmission of HCMV.

The composition of the present invention is suitable for administration by the parenteral route, e.g. by subcutaneous or intramuscular administration. In certain embodiments, the preparation is administered together with an adjuvant. In other embodiments, the preparation is administered without additional adjuvant.

The vaccine of the invention may be used to prevent prenatal infection or HCMV related disorders second to prenatal infection. A desired target population for the vaccine would consequently be children or adolescent female subjects. A second desired target population would be patients receiving allogeneic or autologous transplants, e.g. solid organs or hematopoietic stem cells. On a further perspective, a vaccination of the general population would be conceivable.

In a particular embodiment, the preparation is suitable for use in maintaining the intrinsic immunity of a vaccinated human subject thereby avoiding the occurrence of undesired proviral side-effects after administration.

In a further particular embodiment, the preparation of the invention is for use in stimulating an interferon reaction in a vaccinated human subject.

In a still further embodiment, the preparation of the invention is for use in promoting autophagy of viral proteins in a vaccinated human subject, wherein the autophagocytized proteins are degraded and presented by MHC molecules, particularly by MHC class I and MHC class II molecules.

Furthermore, the present invention relates to a method of preparing a dense body preparation as described above by infection of target cells, e.g. human fibroblast cells as described above, and isolating DBs from the supernatant of the cell culture medium.

Furthermore, the present invention relates to a method of preparing a dense body preparation as described above by transfection of target cells, e.g. human fibroblast cells as described above, and isolating DBs from the supernatant of the cell culture medium.

Finally, the invention relates to a method for vaccinating a subject, particularly a human subject, against HCMV, comprising administering an immunogenically effective dose of a DB preparation as described above to a human subject in need thereof.

Further, the present invention shall be explained in more detail by the following Figures and Examples.

FIGURE LEGENDS

FIG. 1. Characterization of Towne-UL130repΔGFP. Schematic representation of the BAC-cloning strategies to establish A) Towne-UL130rep-BAC and B) Towne-UL130repΔGFP-BAC. The gene for the Green Fluorescent Protein (GFP) is depicted in A and B. The prokaryotic genes for the chloramphenicol acetyltransferase (CAT), the chromosome partitioning proteins SopA and SopB, the replication initiation protein RepE, and for the galactokinase galK are depicted in B). C) Indirect immunofluorescence analysis of the infection of ARPE-19 cells with Towne-BAC, Towne-UL130rep and Towne-UL130repΔGFP. D) Immunoblot analysis of the packaging of pUL130 and GFP into Towne-BAC-, Towne-UL130rep-, and Towne-UL130repΔGFP-DBs.

Figure 2:
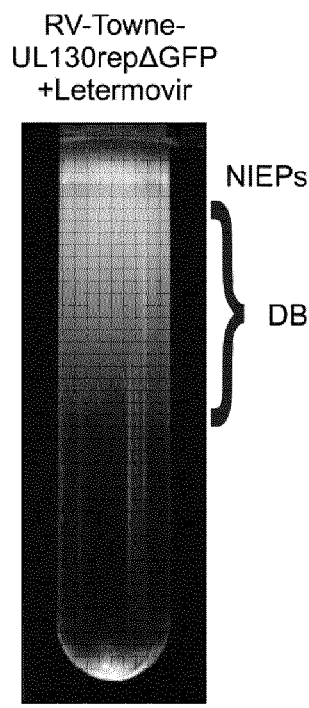

FIG. 2. Separation of extracellular HCMV particles by ultracentrifugation. Clarified medium from Towne-UL130repΔGFP infected HFF cells, grown in culture medium with 50 nM Letermovir was layered on top of a glycerol tartrate gradient and centrifuged (60 min, 23,000 rpm and 10° C.) in a Beckman SW41 rotor. Illumination from the top of the gradient revealed two light-scattering bands designated as noninfectious enveloped particles (NIEPs) and a broad area containing dense bodies (DB).

Figure 3:
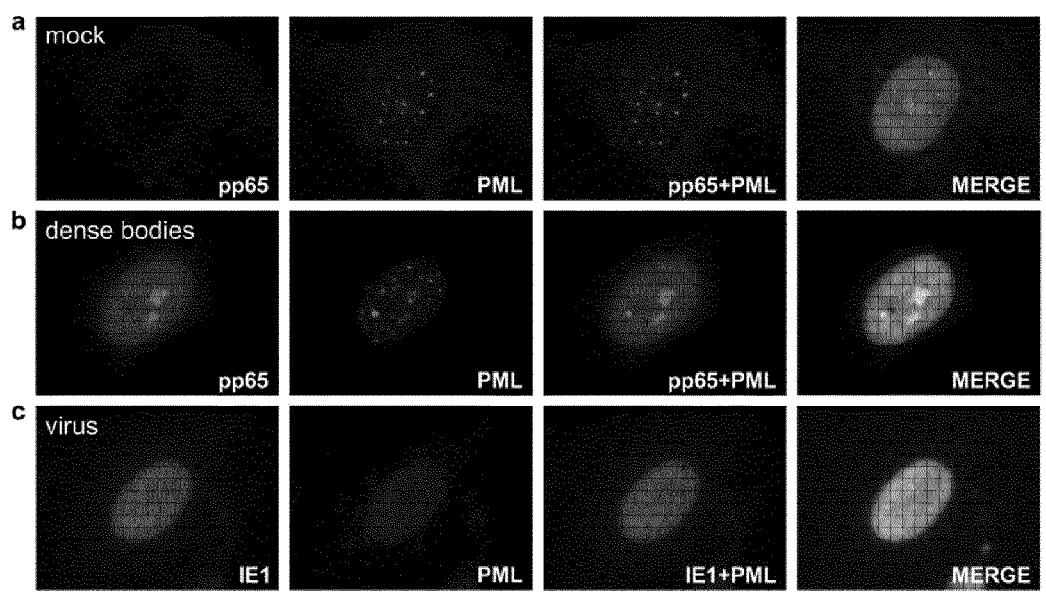

FIG. 3. Effect of DB-administration on the distribution of PML in HFF cells. (a) Uninfected cells (mock) show the typical dot-like nuclear distribution of PML. HFFs show an average of 20 PML bodies of unequal size (b) At 24 hours post application (h.p.a.), cells exposed to UV-inactivated DBs showed the speckled profile of uninfected cells. (c) HCMV infected cells showed a disruption of PML in presence of HCMV IE1 expression at 24 h.p.a.

Figure 4:
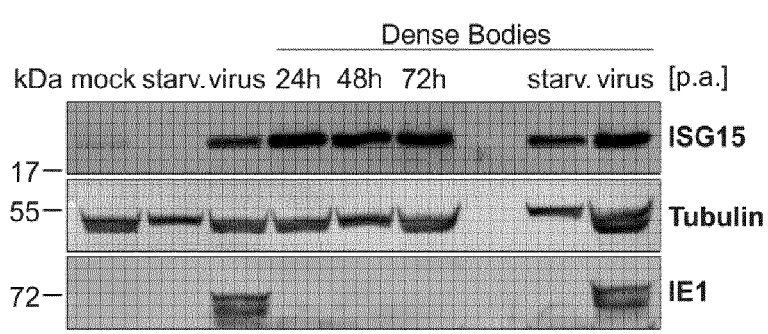
Figure 4:
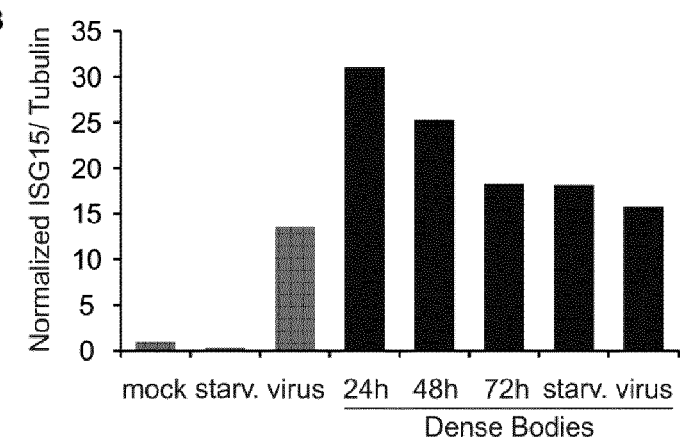

FIG. 4. DB induced ISG15 expression in HFF cells. (A) Total protein from HFF mock infected (mock), serum starved (starv.), HCMV infected (strain TowneUL130repΔGFP; virus), and HFFs exposed to 10 µg/µl UV-inactivated DBs was collected at the indicated times. The mock, starv., and virus samples were collected at 48 h.p.a. The protein samples were separated by SDS-PAGE and analyzed by immunoblotting, using antibodies specific for ISG15, IE1 and tubulin (loading control). (B) Quantification of the protein level of ISG15 by densitometry normalized to tubulin.

Figure 5:
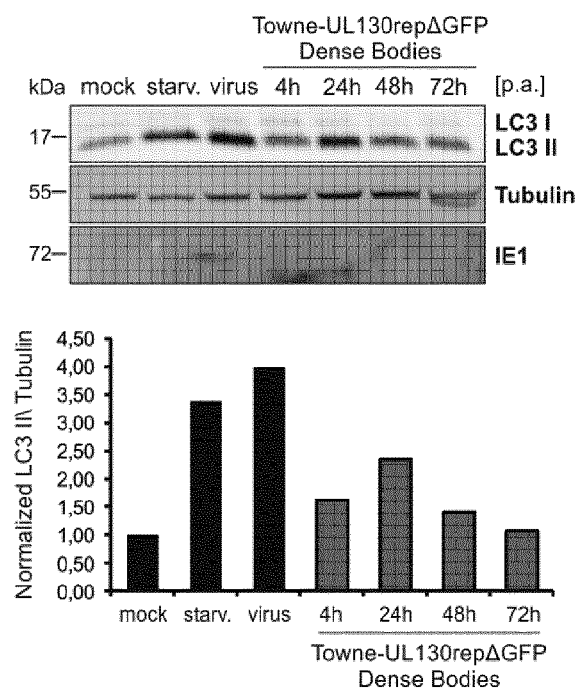

FIG. 5. DB induced autophagy in HFF cells. (A) Immunoblot analysis of LC3II levels in HFFs that were mock infected (mock), starved (starv.), HCMV infected (strain TowneUL130repΔGFP; virus; MOI 1), or exposed to 10 µg/µl UV-inactivated DBs for the indicated times. The mock, starv., and virus samples were collected at 48 h.p.a. Antibodies specific for LC3 and IE1 were used. Tubulin was used as a loading control. (B) Quantification of the protein level of LC3II by densitometry, normalized to tubulin.

Figure 6:
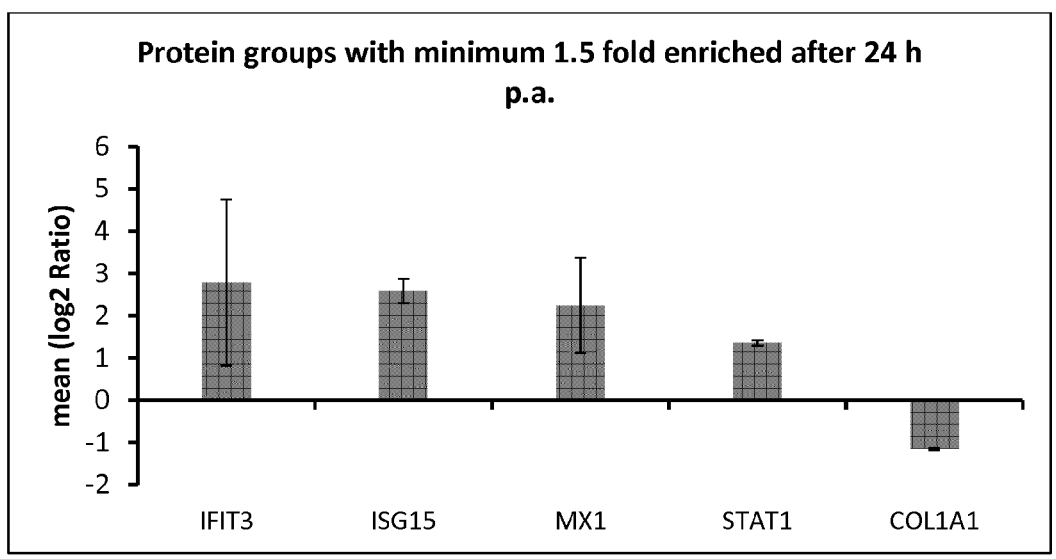

FIG. 6. Cellular proteins enriched after exposure to non-UV-inactivated DBs for 24 hours. IFIT3, Interferon Induced Protein With Tetratricopeptide Repeats 3; ISG15, Interferon-stimulated gene 15; MX1, MX Dynamin Like GTPase 1; STAT1, Signal transducer and activator of transcription 1; COL1A1, Collagen Type I Alpha 1 Chain.

Figure 7:
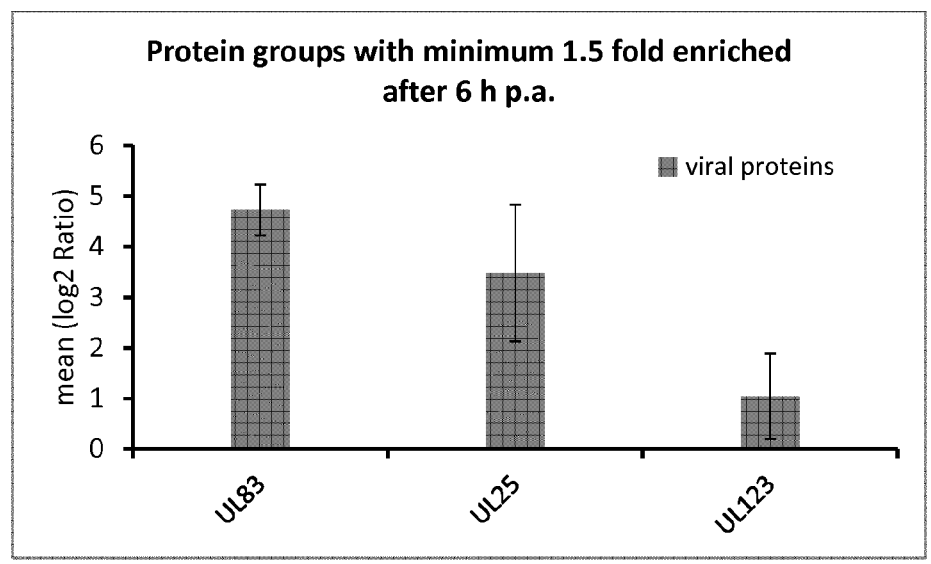

FIG. 7. Viral and cellular proteins enriched after exposure to UV-inactivated DBs for 6 hours. UL83, 65 kDa phosphoprotein pp65; UL25, tegument protein UL25; UL123, IE1.

Figure 8:
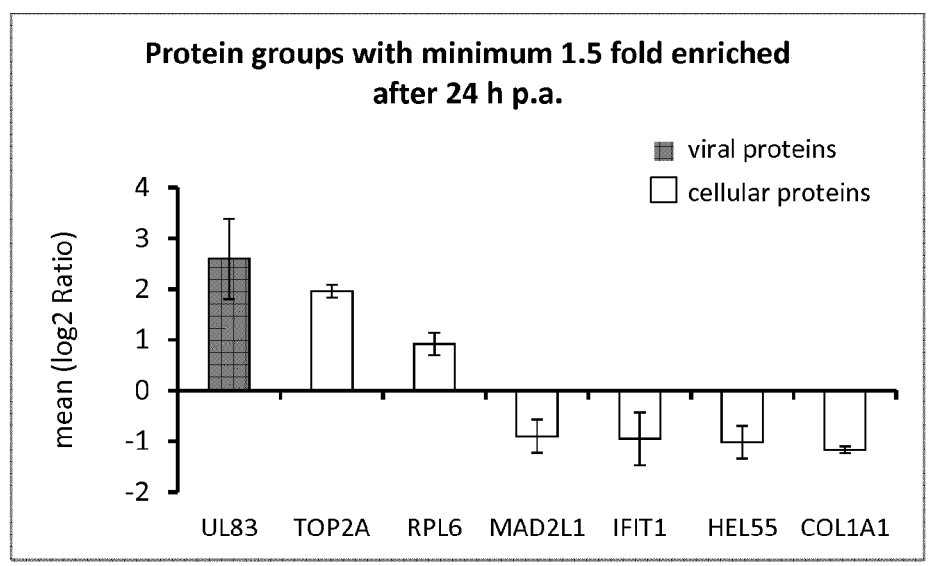

FIG. 8. Viral and cellular proteins enriched or reduced after UV-inactivated DB-exposure for 24 hours. UL83, 65 kDa phosphoprotein pp65; TOP2A, DNA topoisomerase 2-alpha; RPL6, 60S ribosomal protein L6; MAD2L1, Mitotic spindle assembly checkpoint protein MAD2A; IFIT1, Interferon-induced protein with tetratricopeptide repeats 1; HEL5, 5 Epididymis luminal protein 55; COL1A1, Collagen alpha-1(I) chain.

Figure 9:
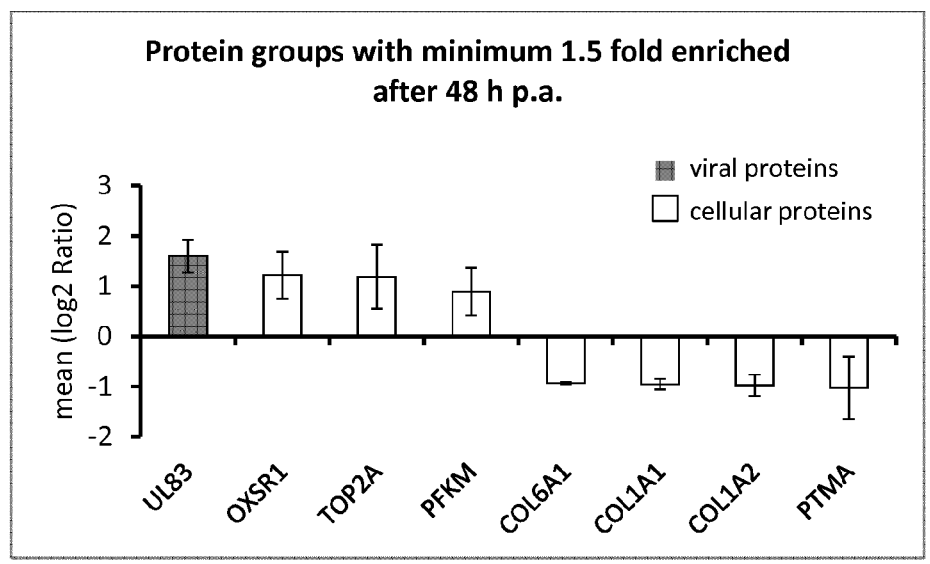

FIG. 9. Viral and cellular proteins enriched or reduced after exposure to UV-inactivated DBs for 48 hours. UL83, 65 kDa phosphoprotein pp65; OXSR1, Serine/threonine-protein kinase OSR1; TOP2A, DNA topoisomerase 2-alpha; PFKM, ATP-dependent 6-phosphofructokinase; COL6A1, Collagen alpha-1(VI) chain; COL1A1, Collagen alpha-1(I) chain; COL1A2, Collagen alpha-2(I) chain; PTMA, Prothymosin alpha.

EXAMPLES

Example 1

Generation of a Pentamer-Positive, DB-Producer Strain.

DBs were produced in human fibroblast cells upon infection with a recombinant HCMV seed virus. This seed virus was obtained upon transfection of cells with a BAC-plasmid encoding a genetically modified version of the genome of the HCMV Towne strain as described in the following.

The HCMV Towne-BAC constituted the basis to generate the Towne-UL130repΔGFP-BAC that will serve as the parental genome for the generation of a new-generation DB vaccine. The HCMV Towne-BAC was constructed by homologous recombination of a modified version of the vector pMBO1374, named pUSF-3, and the wild-type Towne viral DNA (3). pMBO1374 is a derivative of the F-plasmid vector pMBO131, in which a 645 bp HaeII fragment containing the multiple cloning site-embedded lacZ gene of pBluescript II KS (+) was subcloned into the unique SalI site of pMBO131, resulting in the insertion of several unique cloning sites (10). pUSF-3 additionally contains prokaryotic genetic elements for maintenance as BAC in E. coli, HCMV DNA sequences for direct homologous recombination to the unique short region of the viral genome, and a GFP marker for identification and purification of recombinant HCMV in eukaryotic cells (3).

In order to construct pUSF-3, the unique BamHI site and one of the two ClaI sites in pMBO1374 were removed. The two HCMV DNA fragments in pUSF-3 that were used as flanking HCMV DNA for homologous recombination were derived from the cosmid clone pCM1052 that contains a fragment of the genome of HCMV strain AD169 (11) by PCR. The primers used for amplification of the DNA fragments were derived from the published sequence of AD169 HCMV (12), and extended with BamHI and HindIII overhangs. The HCMV DNA fragments were digested with BamHI and ligated to yield a 5.2 kb fragment, which in turn was digested by HindIII and cloned into the HindIII site. Finally, a PCR amplicon with the SV40 early promoter, GFP gene and polyA derived from pGET-07 (13) was cloned into the remaining ClaI site. For homologous recombination, human foreskin fibroblast (HFF) cells were electroporated with wild-type Towne viral DNA purified from total virus particles isolated from HFF cells infected with the Towne strain of HCMV, with linearized (BamHI digested) pUSF-3, and with an expression plasmid for HCMV tegument protein pp71 (14). Upon homologous recombination, the flanking DNA deletes 8.9 kb of DNA within the US region of HCMV (IRS1 after aa719, reading frames US1 to US11 plus the C-terminal third of US12) that are dispensable for HCMV replication in cell culture (15). Sequences of the Towne-BAC isolate have been deposited in the GenBank database (accession no. AY315197) (4) which is herein incorporated by reference.

HCMV Towne DBs do not harbor the pentameric complex due to a frameshift mutation in the open reading frame (ORF) of the UL130 gene, and contain fortuitously packaged GFP.

In order to avoid the potential risk of adverse effects of GFP following DB-application to humans, and to reconstitute the formation of the pentameric complex, which is crucial for eliciting a broad immune responses, the inventors genetically modified the original HCMV Towne-BAC to generate the Towne-UL130repΔGFP-BAC by using a galactokinase (galK) negative-positive selection procedure: First, the mutated UL130 ORF was replaced with its functional homolog from the TB40/E strain (FIG. 1A). Second, the GFP gene was deleted from the resulting Towne-UL130rep-BAC (FIG. 1B). Reconstitution of the pentameric complex enabled Towne-UL130repΔGFP virus particles to infect epithelial cells (FIG. 1C). Moreover, as measured by the presence of pUL130, formation of the pentameric complex was restored and packaging of GFP was prevented in the DBs obtained upon infection with reconstituted Towne-UL130repΔGFP virus (FIG. 1D).

For particle purification $1.8 \times 10^6$ primary human foreskin fibroblasts (HFF) were grown in 20 175-cm$^2$ tissue culture flasks in minimal essential medium (MEM; Gibco-BRL, Glasgow, Scotland) supplemented with 5% fetal calf serum (FCS), L-glutamine (100 mg/liter), and gentamicin (50 mg/liter) for 1 day. The cells were infected with 0.5 ml of a frozen stock of the strain Towne-UL130repΔGFP of human cytomegalovirus. The virus inoculum was allowed to adsorb for 1.5 h at 37° C. With the addition of 50 nM Letermovir (MedChem Express (MCE), HY-15233, 10 mM in 1 ml DMSO) in culture MEM the cells were incubated for at least 7 days. Letermovir was refreshed every 3 days.

When the cells showed a CPE (cytopathic effect) of late HCMV infection (usually at day 7 post-infection [p.i.]), the supernatant was harvested and centrifuged for 10 min at 2,800 rpm to remove cellular debris. After that, the supernatant was collected and centrifuged at 30,000 rpm (70 min; 10° C.) in a SW32Ti rotor in a Beckman Optima L-90K ultracentrifuge. The pellets were resuspended in 2 ml of 1× phosphate-buffered saline (PBS). Glycerol tartrate gradients were prepared immediately before use. For this, 4 ml of a 35% Na-tartrate solution in 0.04 M Na-phosphate buffer, pH 7.4, was applied to one column, and 5 ml of a 15% Na-tartrate-30% glycerol solution in 0.04 M Na-phosphate buffer, pH 7.4, was applied to the second column of a gradient mixer. The gradients were prepared by slowly dropping the solutions into Beckman Ultra-clear centrifuge tubes (14 by 89 mm), positioned at an angle of 45°. One 1 ml of the viral particles was then carefully layered on top of the gradients. Ultracentrifugation was performed without braking in a Beckman SW41 swing-out rotor for 60 min at 23,000 rpm and 10° C. The particles were illuminated by light scattering (FIG. 2) and were collected from the gradient by penetrating the centrifuge tube with a hollow needle below the band. Samples were carefully drawn from the tube with a syringe.

The particles for the initial analysis of Towne-UL130repΔGFP DBs, were washed with 1× PBS and pelleted in an SW41 swing-out rotor for 90 min at 24,000 rpm and 10° C. After the last centrifugation step, the DBs were resuspended in 250 μl to 350 μl 1×PBS and stored at −80° C. The protein concentration of the purified DBs was determined with the Pierce BCA Protein Assay Kit (Thermo Scientific, Bonn, Germany).

Example 2

UV-Inactivation of Dense Bodies

Before UV-inactivation, the amount of DBs needed to be adjusted because the liquid sticks to the spot plate. The needed amount of DBs was added to 200 μl PBS and dripped on a spot plate so that after inactivation 10 μg DBs were resuspended in 150 μl PBS. Afterwards the spot plate was placed under the UV-lamp and the switch with the wavelength of 254 nm was actuated for 2 minutes. For UV-inactivation of DBs, the UV-Hand lamp (Herolab GmbH Laborgeräte, Wiesloch; Type NU-4) was used. 150 µl of the PBS/DBs suspension (10 µg DB in 150 µl PBS) was transferred into a new tube. For DB-application to $5\times10^5$ HFFs in 10 cm dishes, 1350 µl culture MEM and 150 µl DB/PBS were mixed and the DB-inoculum was allowed to adsorb 1.5 h at 37° C. Then culture MEM was added and the cells incubated for indicated times.

Example 3

Impact of DBs on the Nuclear Body (NB) Mediated Intrinsic Immunity

The protein PML has previously been shown to be essential for the formation of ND10 domains, also known as nuclear bodies (NBs, for review see (16, 17)). These nuclear substructures represent accumulations of multiple cellular proteins that counteract herpes-viral infection. Based on previous data, that showed an interferon-inducible up-regulation of ND10 domains, it was suggested that PML contributes to an intrinsic antiviral defense mechanism of the cell. HCMV has evolved strategies to counteract this antiviral activity. During HCMV infection the immediate early protein 1 (IE1) accumulates at PML bodies and subsequently induces the dispersal of PML, thereby antagonizing NB-mediated intrinsic immunity. The impact of DBs on PML dispersal was analyzed.

For indirect immunofluorescence analysis, HFF cells ($2\times10^5$) were grown on coverslips in 6-well plates. On the next day, cells were either mock-infected, infected with HCMV (strain Towne-UL130repΔGFP), or exposed to 10 µg UV-inactivated DBs (HCMV strain Towne-UL130repΔGFP). DBs were inactivated by applying the minimal exposure time (2 min) to UV light required to abolish detectable virion contamination and de novo CMV gene expression, as determined by staining for the expression of the immediate-early 1 protein (IE1). After 24 hours, cells were washed once with 1× PBS and fixed in methanol for 10 min at −20° C. After washing 3 times with 1× PBS for 10 minutes, cells were blocked for 30 minutes with 1% BSA/1× PBS at room temperature. For detection of endogenous PML protein, primary monoclonal antibody PG-M3 (Santa Cruz Biotechnology, SantaCruz, Calife) was added for 1 h in a humidified chamber at 37° C. The second primary antibody against IE1 (p63-27) or against pp65 (65-33, provided by W. Britt, UAB, Birmingham, AL), was added after a washing step for another hour at 37° C. Following a preceding washing step, the cells were blocked for another 10 minutes with 1% BSA/1× PBS before the incubation with secondary antibodies. Detection was performed by adding an anti-mouse Alexa 546 or anti-rabbit Alexa 488 conjugated (Molecular Probes) secondary antibody for another hour in a humidified chamber at 37° C. and nuclear stain (DAPI) for 10 minutes at room temperature. The cells were washed 3 times with 1× PBS for 20 minutes and then once with ddH 2 O. Cover slips were embedded with mounting medium on microscope slides, dried over night at 37° C. and stored at +4° C. till analysis.

Here we investigated the effect of DBs on the subcellular localization of PML in human foreskin fibroblasts (HFF cells), 24 hours post-application (h.p.a.). In uninfected cells, PML was associated with the characteristic dot-like pattern of distribution in the nucleus. HFFs showed an average of 20 PML bodies of unequal size (FIG. 3a). A disruption of PML bodies was observed in HCMV infected cells, where the effect was attributed to the IE1 expression (FIG. 3c). This intervention of IE1 is required for efficient viral replication. Cells exposed to UV-inactivated DBs showed the speckled profile of uninfected cells (FIG. 3a, b) assuming that DBs have not affected the distribution of PML bodies.

These experiments showed that DBs alone were unable to disperse PML bodies. Consequently, the proviral dispersal of PML bodies, seen after HCMV infection is not mimicked by DBs, excluding a proviral effect of these particles at this level. This further underlines the notion of DBs as being a suitable vaccine for HCMV.

Example 4

Impact of DBs on the Induction of Interferon-Stimulated Gene 15 (ISG15) Expression Interferons are essential for the innate immune response to virus infections. All interferons trigger the transcription of hundreds of interferon-stimulated genes (ISGs), whose protein products exhibit antiviral activity. The interferon-stimulated gene 15 encodes an ubiquitin-like protein (ISG15) which is induced by type I IFN. Protein modification by ISG15 (ISGylation) is known to inhibit the replication of many viruses (18). HCMV induced ISG15 accumulation is triggered by the hosts' detection of cytoplasmic double-stranded DNA (dsDNA). However, this accumulation is later suppressed by HCMV IE1 expression (19, 20).

The question addressed in this section was, if DB-application to HFF cells would induce ISG15 expression.

For immunoblot analysis, HFF cells ($5\times10^5$) were grown in 10 cm cell culture dishes. The next day, cells were either mock-infected, starved in serum free MEM medium, infected with HCMV (strain Towne-UL130repΔGFP, MOI 1), or exposed to 10 µg UV-inactivated DBs (HCMV strain Towne-UL130repΔGFP). DBs were inactivated, given the minimal exposure (2 min) to UV light required to abolish virion contamination and de novo CMV gene expression determined by staining for the expression of the immediate-early 1 protein (IE1).

At indicated hours post application (p.a.), HFF cells were washed with PBS, scraped off and collected. After centrifugation of 15,000 rpm×5 min and washing with PBS, cells were counted and adjusted to $1\times10^5$ cells/10 µl in Laemmli cell lysis buffer. Then, the mixture was boiled at 95° C. for 10 minutes. Afterwards, 20 µl of each sample was loaded on bis/acrylamide gels (Invitrogen, Thermo Fisher Scientific). After resolution of the protein samples in sodium dodecyl sulphate polyacrylamide denaturing gel electrophoresis (SDS-PAGE), the separated proteins were transferred to a PVDF membrane. Then the PVDF membrane (Millipore, Burlington, MA) was blocked for 1 h at 5% nonfat dry milk powder in TBST and incubated with primary antibodies at 4° C. overnight. The primary antibodies used in this study were mouse anti-IE (p63-27), mouse anti-ISG15 (Santa Cruz, 1:500 dilution), and mouse anti-tubulin (Sigma, 1:500 dilution). After washing 3 times with TBST for 10 minutes, anti-mouse IRDye 800 secondary antibody was used for incubation 2 hours at a 1:10,0000 dilution. Protein concentrations in each band were quantitatively estimated by normalization to the tubulin level using the Image Studio Lite software provided by LI-COR.

The experiments show that UV-inactivated DBs are able to induce ISG15 expression. Since DBs do not contain viral DNA, this effect appears to be independent of dsDNA (one known inducer of ISG15 expression). Since it is known that ISG15 is induced after infection with HCMV, virus infection was used as positive control. ISG15 induction reached high levels at 24 hours after DB-exposure and decreased afterwards. There was a trend towards higher levels of ISG15 expression in samples from cells that were concomitantly exposed to DBs and virus, compared to virus infection alone.

The experiments provide evidence that DBs do induce ISG15 expression, which as such is thought to confer antiviral activity. Thus DBs appear to provide an antiviral effect on this level.

Example 5

DB Application Induces Autophagy

We and others have shown that application of DBs leads to a distinct Major Histocompatibility Complex (MHC)-class I mediated presentation of viral peptides. We follow the hypothesis that DB-derived antigens are introduced into the MHC-class I pathway through induction of autophagy. Here we show, that application of UV-inactivated DBs of HCMV to human foreskin fibroblasts indeed results in an induction of autophagy.

DBs were again applied to HFF cells. At 4, 24, 48 and 72 hours p.a., HFF cells were washed with PBS, scraped off and collected. After centrifugation of 15,000 rpm×5 min and washing with PBS, cells were counted and adjusted to $1 \times 10^5$ cells/10 µl in Laemmli cell lysis buffer. Then, the mixture was boiled at 95° C. for 10 minutes. Afterwards, 20 µl of each sample was loaded on bis/acrylamide gels (Invitrogen, Thermo Fisher Scientific). After resolution of the protein samples in sodium dodecyl sulphate polyacrylamide denaturing gel electrophoresis (SDS-PAGE), the separated proteins were transferred to a PVDF membrane. The PVDF membranes (Millipore, Burlington, MA) were blocked for 1 h at 5% nonfat dry milk powder in TBST and incubated with primary antibodies at 4° C. overnight. The primary antibodies used in this study were mouse anti-IE (p63-27), rabbit anti-LC3II (Cell Signaling Technologies, 1:1,000 dilution), mouse anti-tubulin (Sigma, 1:500 dilution).

After washing 3 times with TBST for 10 minutes, anti-rabbit Alexa Fluor 680 and anti-mouse IRDye 800 secondary antibodies were used for incubation 2 hours at a 1:10,000 dilution. Protein concentrations in each band were quantitatively estimated by normalization to the tubulin level, using the Image Studio Lite software provided by LI-COR.

The infection of HFF cells with human cytomegalovirus (virus) and starvation both resulted in the induction of autophagy and served as positive controls (FIG. 5). This is demonstrated by the increased lipidation of microtubule-associated protein 1 light chain 3 (LC3II), a hallmark of autophagy. HFFs exposed to 10 µg/µl UV-inactivated DBs showed an increase in LC3II expression (FIG. 5). Increase was seen as early as 4 h.p.a. and reached peak levels at 24 h. The level of LC3II decreased gradually from 48 to 72 h.p.a.

The experiments demonstrate that autophagy is induced by DBs. This may lead to an increased presentation of viral antigens by MHC-class I and MHC-class II molecules. In addition, as induction of autophagy has been shown to reduce HCMV replication (21), the induction by DBs may be considered to have an antiviral effect.

Example 6

Mass Spectrometry of the Cellular Proteome Following DB-Exposure

To obtain a more comprehensive picture of the impact of DBs on cells, label-free mass spectrometry was performed on DB-treated HFF cells.

In a first preliminary experiment, HFF cells ($5 \times 10^6$) were grown in 10 cm cell culture dishes. The next day, the cells were either mock-treated or exposed to 2 µg DBs (HCMV strain Towne-UL130repΔGFP; preparation of DBs from cultures, kept under Letermovir inhibition [see above]). DBs were not inactivated by UV.

At 24 h.p.a., HFF cells were washed with PBS twice, scraped and collected. After centrifugation of 15,000 rpm×5 min and washing with PBS, cells were lysed in 50 µl Laemmli buffer and boiled at 95° C. for 10 minutes. Then the samples were prepared for the Proteomics Core Facility (AG Butter, Institute for Molecular Biology, Mainz), see below.

We identified some upregulated proteins that were known to be interferon responsive (IFIT3, ISG15, MX1 and STAT1) and were reported to have antiviral effects (FIG. 6). Furthermore we observed a downregulation of collagen (COL1A1).

In a second quantitative mass spectrometry-based (MS) proteomics experiment, HFF cells ($5 \times 10^5$) were grown in 10 cm cell culture dishes. The next day, cells were either mock-infected, infected with HCMV (strain Towne-UL130repΔGFP, MOI 1), or exposed to 10 µg UV-inactivated DBs (HCMV strain Towne-UL130repΔGFP; preparation of DBs from cultures, kept under Letermovir inhibition [see above]). DBs were inactivated by applying the minimal exposure (2 min) to UV light required to abolish virion contamination.

At 6, 24, and 48 h.p.a., HFF cells were washed with PBS twice, scraped and collected. After centrifugation of 15,000 rpm×5 min and washing with PBS, cells were lysed in 50 µl Laemmli buffer and boiled at 95° C. for 10 minutes. Then the samples were prepared for the Proteomics Core Facility (AG Butter, Institute for Molecular Biology, Mainz).

Sample preparation:
Reagent Reduced Sample 19.5 µL (min. 20 µg)
NuPAGE®LDS Sample Buffer (4×) 7.5 µL
1 M dithiothreitol (DTT) 3 µL
Total Volume 30 µL
Then the samples were heated at 70° C. for 10 min.

After the samples were measured, mass spec data were filtered using MaxQuant (Version: 1.5.2.8; Download: www.maxquant.org (http://maxquant.org)). The output table was filtered, including removal of potential common contaminants and reverse database entries. The search was performed against the following Fasta databases:
Homo_sapiens_(HUMAN)_Uniprot_20180108.fasta
Human_cytomegalovirus_(HCMV)_
  Uniprot_20180108.fasta
Human_cytomegalovirus_(HCMVA)Uniprot
  (strain_AD169)_20180108.fasta
Human_cytomegalovirus_(HCMVT)Uniprot(strain_
  Towne)_20180108.fasta As quality control the distribution and normalization of the labeled protein groups was used. Normalization can only be used if the majority of the proteins remain unregulated. Only identified proteins with at least 2 peptides (1 needs to be unique) were allowed. These initial analyses were a service of the Proteomics Core Facility. The identified proteins were provided as an excel file.

The received data was filtered over the log 2 converted ratio. Protein groups with minimum 1.5-fold enriched were indicated.

In our results (FIGS. 7, 8 and 9), we detected pUL83 (pp65) and pUL25, previously reported to be HCMV Dense body proteins. pUL83 (pp65) is the predominant tegument protein present in DBs. pUL25 has been found to be abundant in DBs, too. Only UL83 could be detected at all three time points, decreasing over time. Furthermore we observed consistent downregulation of collagens (COL1A1, COL6A1, and COL1A2).

LIST OF REFERENCES

1. Sauer C, Klobuch S, Herr W, Thomas S, Plachter B. 2013. Subviral dense bodies of human cytomegalovirus stimulate maturation and activation of monocyte-derived immature dendritic cells. J Virol 87:11287-11291.
2. Plotkin S A, Furukawa T, Zygraich N, Huygelen C. 1975. Candidate cytomegalovirus strain for human vaccination. Inject Immun 12:521-527.
3. Marchini A, Liu H, Zhu H. 2001. Human cytomegalovirus with IE-2 (UL122) deleted fails to express early lytic genes. J Virol 75:1870-1878.
4. Dunn W, Chou C, Li H, Hai R, Patterson D, Stoic V, Zhu H, Liu F. 2003. Functional profiling of a human cytomegalovirus genome. Proc Natl Acad Sci USA 100: 14223-14228.
5. Warming S, Costantino N, DL C, Jenkins N A, Copeland NG. 2005. Simple and highly efficient BAC recombineering using galK selection. Nucleic Acids Res 33: e36.
6. Sinzger C, Schmidt K, Knapp J, Kahl M, Beck R, Waldman J, Hebart H, Einsele H, Jahn G. 1999. Modification of human cytomegalovirus tropism through propagation in vitro is associated with changes in the viral genome. J Gen Virol 80 (Pt 11):2867-2877.
7. Sinzger C, Hahn G, Digel M, Katona R, Sampaio K L, Messerle M, Hengel H, Koszinowski U, Brune W, Adler B. 2008. Cloning and sequencing of a highly productive, endotheliotropic virus strain derived from human cytomegalovirus TB40/E. J Gen Virol 89:359-368.
8. Vashee S, Stockwell T B, Alperovich N, Denisova E A, Gibson D G, Cady K C, Miller K, Kannan K, Malouli D, Crawford L B, Voorhies A A, Bruening E, Caposio P, Fruh K. 2017. Cloning, Assembly, and Modification of the Primary Human Cytomegalovirus Isolate Toledo by Yeast-Based Transformation-Associated Recombination. mSphere 2.
9. Andreoni M, Faircloth M, Vugler L, Britt W J. 1989. A rapid microneutralization assay for the measurement of neutralizing antibody reactive with human cytomegalovirus. J Virol Methods 23:157-167.
10. O'Connor M, Peifer M, Bender W. 1989. Construction of large DNA segments in *Escherichia coli*. Science 244:1307-1312.
11. Fleckenstein B, Müller I, Collins J. 1982. Cloning of the complete human cytomegalovirus genome in cosmids. Gene 18:39-46.
12. Chee M S, Bankier A T, Beck S, Bohni R, Brown C M, Cerny R, Horsnell T, Hutchison C A, Kouzarides T, Martignetti J A, Preddie E, Satchwell S C, Tomlinson P, Weston K M, Barrell B G. 1990. Analysis of the protein-coding content of the sequence of human cytomegalovirus strain AD169. Curr Top Microbiol Immunol 154:125-169.
13. Tullis G E, Shenk T. 2000. Efficient replication of adeno-associated virus type 2 vectors: a cis-acting element outside of the terminal repeats and a minimal size. J Virol 74:11511-11521.
14. Baldick C J, Jr., Marchini A, Patterson C E, Shenk T. 1997. Human cytomegalovirus tegument protein pp71 (ppUL82) enhances the infectivity of viral DNA and accelerates the infectious cycle. J Virol 71:4400-4408.
15. Jones T R, Muzithras V P. 1992. A cluster of dispensable genes within the human cytomegalovirus genome short component: IRS1, US1 through US5, and the US6 family. J Virol 66:2541-2546.
16. Scherer M, Stamminger T. 2016. Emerging Role of PML Nuclear Bodies in Innate Immune Signaling. J Virol 90:5850-5854.
17. Tavalai N, Stamminger T. 2011. Intrinsic cellular defense mechanisms targeting human cytomegalovirus. Virus Res 157:128-133.
18. Villarroya-Beltri C, Guerra S, Sanchez-Madrid F. 2017. ISGylation—a key to lock the cell gates for preventing the spread of threats. J Cell Sci 130:2961-2969.
19. Bianco C, Mohr I. 2017. Restriction of Human Cytomegalovirus Replication by ISG15, a Host Effector Regulated by cGAS-STING Double-Stranded-DNA Sensing. J Virol 91.
20. Kim Y J, Kim E T, Kim Y E, Lee M K, Kwon K M, Kim K I, Stamminger T, Ahn J H. 2016. Consecutive Inhibition of ISG15 Expression and ISGylation by Cytomegalovirus Regulators. PLoS Pathog 12: e1005850.
21. Belzile J P, Sabalza M, Craig M, Clark E, Morello C S, Spector D H. 2015. Trehalose, an mTOR-Independent Inducer of Autophagy, Inhibits Human Cytomegalovirus Infection in Multiple Cell Types. J Virol 90:1259-1277.

The invention claimed is:

1. A nucleic acid molecule encoding the genome of a recombinant human cytomegalovirus (HCMV) Towne strain, wherein the Towne strain sequence of SEQ ID NO: 6 is modified to comprise the elements necessary to express the genome as a Bacterial Artificial Chromosome (BAC), wherein the recombinant HCMV comprises an open reading frame (ORF) encoding Green Fluorescent Protein (GFP) which is disrupted by the insertion of a gene heterologous to HCMV Towne strain, wherein the recombinant HCMV encodes a functional heterologous UL130 protein, and wherein the nucleic acid molecule has an identity of at least 90% when compared to the genome of the HCMV strain Towne as deposited under GenBank accession no: AY315197 (SEQ ID NO: 6).

2. The nucleic acid molecule of claim 1, which has an identity of at least 95% to the sequence of SEQ ID NO: 6.

3. A vector comprising a nucleic acid molecule encoding the genome of a recombinant human cytomegalovirus (HCMV) Towne strain, wherein the Towne strain sequence of SEQ ID NO: 6 is modified to comprise the elements necessary to express the genome as a Bacterial Artificial Chromosome (BAC), wherein the recombinant HCMV comprises an open reading frame (ORF) encoding Green Fluorescent Protein (GFP) which is disrupted by the insertion of a gene heterologous to HCMV Towne strain, wherein the recombinant HCMV encodes a functional heterologous UL130 protein, and wherein the nucleic acid molecule has an identity of at least 90% when compared to the genome of the HCMV strain Towne as deposited under GenBank accession no: AY315197 (SEQ ID NO: 6).

4. A dense body produced by infection of a mammalian target cell with a HCMV strain having a genome according to claim 1, wherein the dense body comprises a pentameric complex consisting of viral proteins gH, gL, UL128, UL130 and UL131A and is free from GFP.

5. The dense body of claim 4, wherein the viral proteins gH, gL, UL128 and UL131A are from HCMV strain Towne and wherein the viral protein UL130 is from HCMV strain TB40/E.

6. A preparation of dense bodies (DBs) according to claim 4 in a pharmaceutically acceptable carrier.

7. The preparation of claim 6, wherein the DBs are subjected to an inactivation treatment and wherein the inactivated DBs induce an interferon-stimulated gene 15 (ISG15) expression and to increase expression of lipidation of microtubule-associated protein 1 light chain 3 (LC3II) and wherein the inactivated DBs do not induce detectable HCMV replication.

8. The preparation of claim 6, which has not been inactivated.

9. A method for vaccinating a human subject against HCMV, comprising administering an immunogenically effective dose of a dense body preparation of claim 6 to a human subject in need thereof.

10. The method of claim 9, wherein the method prevents and/or ameliorates an occurrence of an HCMV associated disorder in the human subject and/or inhibits transmission of an HCMV infection to a further human subject.

11. The method of claim 9, wherein the method maintains the intrinsic immunity of the vaccinated human subject.

12. The method of claim 9, wherein the method stimulates an interferon reaction in the vaccinated human subject.

13. The method of claim 9, wherein the method promotes autophagy of viral proteins in the vaccinated human subject, wherein the autophagocytosed proteins are degraded and presented by Major Histocompatibility Complex (MHC) molecules.

14. The method of claim 13, wherein the MHC molecules are MHC class I or MHC class II molecules.

15. The nucleic acid molecule of claim 1, wherein the gene heterologous to HCMV Towne strain is a bacterial galactokinase gene, which disrupts the ORF encoding GFP.

16. The vector of claim 3, wherein the vector is a BAC vector.

17. The preparation of claim 7, wherein the inactivation is by ultraviolet (UV) irradiation.

18. The nucleic acid molecule of claim 1, which has an identity of at least 98% when compared to the genome of the HCMV strain Towne as deposited under GenBank accession no: AY315197 (SEQ ID NO: 6).

* * * * *

SEQUENCE LISTING

```
<160> NUMBER OF SEQ ID NOS: 6

<210> SEQ ID NO 1
<211> LENGTH: 742
<212> TYPE: PRT
<213> ORGANISM: Human cytomegalovirus

<400> SEQUENCE: 1

Met Arg Pro Gly Leu Pro Ser Tyr Leu Ile Val Leu Ala Val Cys Leu
1               5                   10                  15

Leu Ser His Leu Leu Ser Ser Arg Tyr Gly Ala Glu Ala Ile Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60
```

```
Leu Arg Asn Ser Thr Val Val Arg Glu Asn Ala Ile Ser Phe Asn Phe
 65                  70                  75                  80

Phe Gln Ser Tyr Asn Gln Tyr Tyr Val Phe His Met Pro Arg Cys Leu
             85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
            115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
                180                 185                 190

Gln Thr Cys Ile Leu Phe Asp Gly His Asp Leu Leu Phe Ser Thr Val
            195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
    275                 280                 285

His Ser Tyr Leu Lys Asp Pro Asp Phe Leu Asp Ala Ala Leu Asp Phe
290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
    355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
            435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
```

```
                    485                 490                 495

Leu Ala Glu Leu Ser His Phe Thr Gln Leu Ala His Pro His His
            500                 505                 510

Glu Tyr Leu Ser Asp Leu Tyr Thr Pro Cys Ser Ser Gly Arg Arg
            515                 520                 525

Asp His Ser Leu Glu Arg Leu Thr Arg Leu Phe Pro Asp Ala Thr Val
        530                 535                 540

Pro Thr Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Val Val Thr
            580                 585                 590

Asn Gln Tyr Leu Ile Lys Gly Ile Ser Tyr Pro Val Ser Thr Thr Val
            595                 600                 605

Val Gly Gln Ser Leu Ile Ile Thr Gln Thr Asp Ser Gln Thr Lys Cys
        610                 615                 620

Glu Leu Thr Arg Asn Met His Thr Thr His Ser Ile Thr Ala Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
            675                 680                 685

Ser Pro Arg Thr His Tyr Leu Met Leu Leu Lys Asn Gly Thr Val Leu
        690                 695                 700

Glu Val Thr Asp Val Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
            740

<210> SEQ ID NO 2
<211> LENGTH: 278
<212> TYPE: PRT
<213> ORGANISM: Human cytomegalovirus

<400> SEQUENCE: 2

Met Cys Arg Arg Pro Asp Cys Gly Phe Ser Phe Ser Pro Gly Pro Val
1               5                   10                  15

Ala Leu Leu Trp Cys Cys Leu Leu Pro Ile Val Ser Ser Ala Thr
            20                  25                  30

Val Ser Val Ala Pro Thr Val Ala Glu Lys Val Pro Ala Glu Cys Pro
        35                  40                  45

Glu Leu Thr Arg Arg Cys Leu Leu Gly Glu Val Phe Gln Gly Asp Lys
    50                  55                  60

Tyr Glu Ser Trp Leu Arg Pro Leu Val Asn Val Thr Arg Arg Asp Gly
65              70                  75                  80

Pro Leu Ser Gln Leu Ile Arg Tyr Arg Pro Val Thr Pro Glu Ala Ala
            85                  90                  95

Asn Ser Val Leu Leu Asp Asp Ala Phe Leu Asp Thr Leu Ala Leu Leu
            100                 105                 110
```

```
Tyr Asn Asn Pro Asp Gln Leu Arg Ala Leu Thr Leu Leu Ser Ser
            115                 120                 125

Asp Thr Ala Pro Arg Trp Met Thr Val Met Arg Gly Tyr Ser Glu Cys
130                 135                 140

Gly Asp Gly Ser Pro Ala Val Tyr Thr Cys Val Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
            195                 200                 205

Pro Val Ser Thr Ala Ala Ala Pro Glu Gly Ile Thr Leu Phe Tyr Gly
            210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
            275

<210> SEQ ID NO 3
<211> LENGTH: 171
<212> TYPE: PRT
<213> ORGANISM: Human cytomegalovirus

<400> SEQUENCE: 3

Met Ser Pro Lys Asn Leu Thr Pro Phe Leu Thr Ala Leu Trp Leu Leu
1               5                   10                  15

Leu Gly His Ser Arg Val Pro Arg Val Arg Ala Glu Glu Cys Cys Glu
                20                  25                  30

Phe Ile Asn Val Asn His Pro Pro Glu Arg Cys Tyr Asp Phe Lys Met
            35                  40                  45

Cys Asn Arg Phe Thr Val Ala Leu Arg Cys Pro Asp Gly Glu Val Cys
        50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
            115                 120                 125

Pro Tyr Arg Trp Ile Asn Leu Glu Tyr Asp Lys Ile Thr Arg Ile Val
            130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170

<210> SEQ ID NO 4
<211> LENGTH: 214
<212> TYPE: PRT
<213> ORGANISM: Human cytomegalovirus
```

<400> SEQUENCE: 4

```
Met Leu Arg Leu Leu Leu Arg His His Phe His Cys Leu Leu Cys
1               5                   10                  15

Ala Val Trp Ala Thr Pro Cys Leu Ala Ser Pro Trp Ser Thr Leu Thr
                20                  25                  30

Ala Asn Gln Asn Pro Ser Pro Leu Trp Ser Lys Leu Thr Tyr Ser Lys
            35                  40                  45

Pro His Asp Ala Ala Thr Phe Tyr Cys Pro Phe Ile Tyr Pro Ser Pro
        50                  55                  60

Pro Arg Ser Pro Leu Gln Phe Ser Gly Phe Gln Arg Val Leu Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
145                 150                 155                 160

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Val
        210
```

<210> SEQ ID NO 5
<211> LENGTH: 129
<212> TYPE: PRT
<213> ORGANISM: Human cytomegalovirus

<400> SEQUENCE: 5

```
Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
                20                  25                  30

Val Pro His Tyr Trp Asp Ala Cys Ser Arg Ala Leu Pro Asp Gln Thr
            35                  40                  45

Arg Tyr Lys Tyr Val Glu Gln Leu Val Asp Leu Thr Leu Asn Tyr His
        50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn
```

<210> SEQ ID NO 6
<211> LENGTH: 222031
<212> TYPE: DNA
<213> ORGANISM: Human herpesvirus 5 strain Towne
<220> FEATURE:
<221> NAME/KEY: misc_feature
<222> LOCATION: (29519)..(29519)
<223> OTHER INFORMATION: n is a, c, g, or t
<220> FEATURE:
<221> NAME/KEY: misc_feature
<222> LOCATION: (29535)..(29535)
<223> OTHER INFORMATION: n is a, c, g, or t

<400> SEQUENCE: 6

```
cctcgcctat ttaacctcca cccacttcaa cacacacctg ccgcacaatc atgccagcca      60
cagccacaaa cagcacccac accacgccgc ttcacccaca gtaccaacac acgctaccct     120
tacaccacag caacacacaa ccgcctatcc aaacctcgga caaacacgcc aacgaagaac     180
accgcacgca gatggagctc gacgccgcgg attacgccgc ttgcgcgcag gcccgccaac     240
acctctacgc tccaacacaa ccccaactac acgcataccc cgacgccaac cctcaggaaa     300
gcgctcattt ttccacagaa catcaccatc aactgacgca tctacttcac aacattggcg     360
aaggcgcagc gctcggctac cccgtccccc gcgcggaaat ccgccgcggc ggtggcgacc     420
gggccgacag cgcaagcgac ttcgacgccg actgctggtg catgtgggga cgcttcggaa     480
ccatgggccg ccaacctatc gtgaccttac tgttggcgcg ccaacgcgac ggcctcgctg     540
actggaacgt cgtacgctgc cgcggcacag gctttcgcgc acacgattcc gaggacggcg     600
tctgtgtctg gcgtcagcac ctggtttttt tactcggagg ccacgccgc cgtgtacagt     660
tagaacgtcc atccgcggga gaagcccaag ctcgaggcct attgccacgc atccggatca     720
cccccatctc cacatctcca cgcccaaaac caccccagcc caccatatcc accgcatcgc     780
acccacatgc tacgactcgc ccacatgaca cgctctttcc tatcccttct cacccctcag     840
ccacggttca caatccccga aaccacgccg tccaacttca cgccgaaacg acccgcacat     900
ggcgctgggc acgacgcggt gaacgtggcg cgtggatgcc ggccgaaaca tttacatgtc     960
ccaaggataa acgtccccgg tagacggggt aggggatct accagcccag ggatcgcgta    1020
tttcgccgcc acgctgcttc accgatatcc aataaaccca tccctcgcc acgacgtctc    1080
cgcgtatctt tgtagcctca ggaatccgtc cccacgtcca tccatcccga gcactccaca    1140
cgctataaca gaccacggac acggcaaatg catgcaaact tctcatttat tgtgtctact    1200
actctgtgtt gctacaggga gtgaaggggg tgaaggcaaa caaaaaaaaa aggaacaaaa    1260
taatagatta gcagaaggaa taatccgtgc gaccgagctt gtgcttcttt tgttataagg    1320
aggcaaatat actagggaaa acttaagaat aggaagaaac cgaggtttgg gagaaaagct    1380
gagataaaat agcgcatttt ccatacagag gttgttgttt ttgtggatcc taagaggttt    1440
caagtgcgaa tctcaaagtt ctcacgagaa tattgtcttc aagaatcgac aactgtggtc    1500
caagattttt ttttggtctt tttaggttct gcgagggaca tcacgatgga tcgttgcgat    1560
gaagtcacgc gtacgcctct ggtgtggcgc ggtgtcgtga caggagagtg tgttttcagt    1620
gcagagctgt cttgattcct atatccgagt atctgttttc tcgtaaggac ggtaatcttc    1680
tttggtgtaa gtacatctaa aagctgcaaa ctatatttta agggctgtct ctaggtgtac    1740
tttgatgctg gagttttttcg ctgtgttgat gtgaataaat ctactactac tattatatgc    1800
agaaagagtg attatgccga gacaagattg cattggctga actgtttcaa aaacgcctac    1860
actctactta tccgtaaacc taaggtaata ctatgtgtaa gttgttttttt ttcttttttg    1920
```

```
tagtaaaatg gtgatacgtg caattaaaac tgtattccat gtttccatcc tttcatttca    1980
actttaaagg cggctttgag agcgaagaag tgcgaggata aaaatggatg actccttcgt    2040
gtccagggag tcgactactg caacgctgat tgattaaaag atggtctccg atgatgatgt    2100
tgttattgat cgaatcatgg tgcagaacgg cgacggagag gagcgtgtcc gccgccggga    2160
aggtggtctc tttctctttt cttttttcaa gaaatcttcc atgtgtttat cgtagtgatc    2220
gaaatcgact gatctcgggt tcttttttgtt ggtttctttt cggttaatca tgtattgttt    2280
tcttttttta cagaaagata cttttttcat gagcaattcc tcgcccggcg ccggcatgcc    2340
gaggtggggc cactgcgatc agcggcatgc cgacgccgac ccggggatct tggattcacc    2400
gttttctctc ttctctctct acatacagac cgggtggcag gagcggtaag gaatcatcgt    2460 cgtcttttcat tcttcgatga ttatggtaat actaaatctt atctaggagc atatacatct    2520
aagattggag tactagtagt cgtttgtggt ttctattttt ttttatattt atctatgaca    2580 gttttttctgt ttttcgtttt gataataata taataaaaac tcatgacgt gaaatctggc    2640 ttggttgtgg tgatttcatt ctcattattg ttgttttctt tccgtcttgc ggatgaagat    2700
gttgcgatgc ggttgttgtt ggtgttgcta tacaccgaga gagatgatct tttgttctt    2760 ctggttcatt tcctatgatt gtttggctgc tgaccgacgc gtcaggatgt gcagggcatg    2820
cggggaatca ggaccggaca cgggataatt tcatctacct atacggagat cgcggtcctc    2880
gccatgagga tcgcgacagg cgcgtcgagg gggcaggaac acccttgcgg attgacattc    2940
ttggtggtgt ttcgttgttg tcggtagttg tgttgacga tgaggataaa taaaaatgac    3000
cttgtttttg ttctgtttc tctcgttggg aatcgtcgac tttgaattct tcgagttatc    3060
ggaaagctga ggtacccaaa tgtctgtagc tttttttcttt ttaccctctt gttatcatc    3120 tgcgattcgt ggtaggtagg agagggaaat gataatccga gattaaggaa aggagaagat    3180
aaaaaataaa aaaaaataat aaaacagaag ccgaccggcc gccgacccgt tccccaggac    3240
cagcctacga ggaacggata acgcggtggc gacggcagcg gtggtggcgc tgggggtggc    3300
ggtagtggtg ctgctgatgg tagtcgggac ggaggagaga cgatgcatac atacacgcgt    3360
gcatgctgca tgggtggatg gtacggccgg gagacgcgga agagaaactc acataaaaag    3420
gtgataaaaa gagcggttga aaaagaaaa cgagattcga ccagacagaa gagaaggacc    3480
ggggcttggc gacccttcca cgactgccgt tgtcatctcg gctcctccat cttctcccgg    3540
ccacgggcgg ctaagtcacc gccgttctcc ccatccgtcc gagcgccgac cgaccagccg    3600
gccgattcgc ccgccgggc ttctggagaa cgccggggca gcagcgatct ggggaagccg    3660 ctaaaccct gcgttttat atggtagctc tgccgagcgc gggctgacgc gttgagtaag    3720
cggaaagacg tgtgtgacga aaggggtcc catggtattt cacgtgacga tgaggagatg    3780
cggtttggag cacatacggt ttagaaaaag ggagttgtcg tgacaagggc tgagggacct    3840
ctgtctccat gtgtgtataa aaagcaaggc acgttcataa tgtaaaaaag aacacgttgt    3900
aaacaagcta ttgctgtatc attcggctga ctatgcttca ttcggactga ttttcttttc    3960 ctaacgcgt aacttaaagt gattaacgta tgatatttgt tccccagagt tatactatag    4020
tcatcatcct aaaattcaga tataaatgaa cacatgtcgt atgggattat taagaaaccg    4080
aaactctcca cagttcacca tcttcttcgt cattcaaccg atgacccact ccgtacaacg    4140
aatcagtctg ctgcgtcata ttgcaaagca caagcgacgt atgcgaacaa cttgaaacac    4200
aggctgttgt attgatgacc gttgtaccat tattagtcac atcgtataga gactctccac    4260
```

-continued

```
cgtcatccca tgtttcccac ccgatggaaa accgtcttct atcatcaact gtggtaagat    4320
ttcgaccctg cgaggtattc agtttcctca tatccataac ctggatttta tcattaaacc    4380
ccaatattaa acacttttt agtacccccc acccaccaaa aaatgtgact ggaccggttc     4440
ctagcagctc tgggagccat gttcaggttg aaccacagct acagcgaaac cgagtccagt    4500
gaccggtaac cacgtccagc ccctgcgtat gtaccagtcc aagcacgtcc ggtcattgtt    4560
ctacacagga atctaactag gtcaacgta acctaacact ctctaaacct aatttttagt    4620
agtcaaatac cataattcac cgctgtactc gtctttattc tctccgaacc aacgaccaag    4680
gtcgacaacg ccatcgttac ccttcgtgat attgcacaga tctaaagatg tatgagtaca    4740
attcgttaca caaacgcttg atccattatt cactagaggt gcatgtctcc ctgttacatt    4800
acataaccat ccttgattca gatggctcca tttcgtagtc atcgggtcgt ttttgtgttc    4860
aatggttaca ttgtcaccac ttttaacctc tactttattg aaacccgcac cttcatgtat    4920
aaacaccgtc atgaaacacg ctataagtac ccccccccc acaatggaat gctgccaaac    4980
cggttatttc ccgttatagc catggcgttc ctaagcaaga gctaacgccg aacctaatgc    5040
agtaaaaagc gcttgcagcc agaaccagct tatgtaccag ccacgataac atccggtgat    5100
tgtttccaca ggaaatccta ccaggcaaag ccccgcttgt tgtgttcctg accaccttgt    5160
ttagcaattc gtaaactgtc agcctagcga cgtccgttta gatcaaaagt cacgtatata    5220
gcgacgctgt ttccacccgt ttccccgtcc cgccgtttcc gaacaaccca cccgggttca    5280
gacaaccgac caccaacaga atatacaca cagaccaccg ggagttcagt taaagatttc    5340
atcaggttta ttttggctgc tgctagtctt ttgcttctta gaaaaaaat acccatatag    5400 agaaataatg atagtttgac aacacatatg gcagggattt cttcttcatc aataagatat    5460
gcaattcccc cagggagaga ctttcaacaa ttgaatttac aaaaacaaaa ttacatcagg    5520
agaaagagag gatacattaa taaatatatt atatctggtg tatatactga atgctgctgg    5580
ttcataaggt aacgatgcta ctttttttaa ttccaagatg gttttctttt gttagtcttt    5640
tgttgacttg ctggttccta aaagttcgca aaaacgattg tgtgaagatt ttatgacgtt    5700
ggttgactag ttcatgagat tctgctgtac gtgtgatggt tattcgctgg ttcgttctaa    5760
gatgagtatc gtactgtgtc tgcgatggtc gtctcttact ggcattctct cggctgcctc    5820
ttgctttcat gattgaaaag gaaaaaagga ctccgagggc gcggtcatct tttacttttc    5880
ggttttctca ttggcgggtc agaggtagtc agatcatgag actgtcgtgg tcgatgaaac    5940
tgtgtctgct caagtgacgt ccatttcttg tacgagaaa aaagtcatcg ggataaataa     6000
ggctatacaa ggcgttgtca agcgtgcggc tctaaacaaa ttaagcgata caaaattaca    6060
gtaatacgaa tataaaatta ccccctccc cctgtggtcc cccgagacga gagccaccca    6120
tcgtgtactc tcgcaccacc cacgaccaca gagggaggcg ggacgaagag acgacgcaga    6180
gcgccatctc ctcctgaagg ccggcgacgt taactgctac agctgcgcg gcgacgacga    6240 cagctgcgat ttgtcggccg acatgccgat ggtatgggcg gcggcggcag tggccgcggc    6300
agcggggagg agaggagaga gaagaggagc ggggcgtccg aaggcgagga tggcatggtc    6360
tcgccggagc gcccggcttt tatgggcaca tcgcgtccgg ttgggcattg cccacaggaa    6420
gatgagtcac aacttccaaa ccatcttgag acccgagtaa cggtttacag gtcgcacgcc    6480
agtctcagct aaaacagcg acagtcccca cgctgtttct gttgtggctc tctccagttt    6540
cctcatcgcc atcccggtct ccgtcgtcat cggaagaata ccatccgctc tcatgcggca    6600
gtcgatcgac ctcgacgaac gagacgcggc gacgcctctc tacggccgac tggttgtggt    6660
```

```
ggtgaaagaa gagcaccagc aatcccagga ggagcaacaa gccctcacat gtccaggagg   6720
tcggggagag ggcctgtcgg agatggccgt gaggcatcac gtacggcagc tgaggagaaa   6780
cggagaagaa aggaaaatta ccgtcagggg ccggggttct tattagaaaa acagcacgta   6840
ggtcaggatc cagatgctaa tggcgatcat gatgacgatg atcatgcagg ccaagacgcg   6900
gcgcaccaat gccgaatcca agagccgccg tgccgccggt tggtggctgg cggcatctag   6960
agacatggtt tgggggggac cggcggcgcg aaaagacagg gagatggaca gtgacacggt   7020
gttttgttat gattaggaca tggggaccgg aagccgagac agagtactac agagtgttga   7080
agggtaacgt gagggagatc atgtcatggg cgggctgaag accgtgcggg gaggatcgac   7140
gtgtgcggtg cttgtggaac acggtgtttt aatatgtatc cgcgtgtaat gcacgcggtg   7200 tgcttttttag cactcggttt gataagctac gtggccgttt cgccgaaaa cacgttacc    7260 accaattgtc tcgtgaaaac agaaaatacc cacctaacat gtaagtgcaa tccgaatagc   7320
acatctacca atggcagcag gtgccacgcg atgtgcaaat gccgggtcac agaacccatt   7380
acaatgctag gcgcatactc ggcctggggc gcgggctcgt tcgtggccac gctgatagtc   7440
ctgctggtgg tcttcttcgt aatttacgcg cgcgaggagg agaaaaacaa cacgggcacc   7500
gaggtagatc aatgtctggc ctatcggagc ctgacacgca aaaagctgga acaacacgcg   7560
gctaaaaagc agaacatcta cgaacggatt ccataccgac cctccagaca gaaagataac   7620
tccccgttga tcgaaccgac gggcacagac gacgaagagg acgaggacga cgacgtctga   7680
caaggaaggc gagaacgtgt tttgcaccat gcagacctac agcaccccccc tcacgcttgt   7740 catagtcacg tcgctgtttt tgttcacaac tcagggaagt tcatcgaacg ccgtcgaacc   7800
aaccaaaaaa cccctaaagc tcgccaatta ccgcgccacc tgcgaggacc gtacacgtac   7860
tctggttacc aggcttaaca ctagccatca cagcgtagtc tggcaacgtt atgatatcta   7920
cagcagatac atgcgtcgta tgccgccact ttgcatcatt acagacgcct ataaagaaac   7980
cacgcatcag ggtggcgcaa cttttcacgtg cacgcgccaa aatctcacgc tgtacaatct   8040
tacggttaaa gatacgggag tctacctcct gcaggatcag tataccggtg atgtcgaggc   8100
tttttacctc atcatccacc cacgtagctt ctgccgagct ttggaaacgc gtcgatgctt   8160
ttatccggga ccaggagag ttgtggttac ggattcccaa gaggcagacc gagcaattat    8220
ctcggattta aaacgccagt ggtccggcct ctcactccat tgcgcctggg tttcgggact   8280
gatgatcttt gttggcgcac tggtcatctg cttctgcgg tcgcaacgaa tcggggaaca    8340
ggacgctgaa cggttgcgga cggacctaga tacggaacct ctgttgttga cggtggacgg   8400
ggatttggag taaaagatgc gcacacaaca tcgacggtgg aacaagtcat catatacgca   8460
aataatatgc atgtttatta tttttggat tctgcagaaa agcaagtgta acaacaccac    8520
tatcgccaat acttccacgt cgattacacc cacaagctta atatctacta cacaactgac   8580
atctacgtta caaccaccg aaatgtctac cactatgttc acatcctcca atggcaacgt    8640
caacacatcc acaggattca ctgcaagctc tgtaaaaggc acagacgtga cctcaactat   8700
ttccaccata tctacccaaa catctacaac taacgtaact gtaataacaa cttcaccaaa   8760
cggcgacacg aattcatcga cacagcatgt aaccgatagt actgtgactt tgcaaactat   8820
atcattatca accaacacta ctactatgat aaatgcaaat gaaaacgtca ctacaccgct   8880
tccaacttgc tcatcgccta acagtacaaa taatacgata tcaaaagaat ctgaaacatt   8940
attggaggcg gcacaaggag acaatattac tataacacac aacctaacca tcacatcgtg   9000
```

```
ctacaaaaca gcctggctta gacattttaa tatatccaca cacggaaaat acacccatcc    9060
caacataaga aatggaaaat atcataacca ttcattgaaa atcctccatt cgcgtatact    9120
atgtgagtgg cacacaaatt atctaaaaca tcactatgat ttatgtttta catgcgatcg    9180
taatttatct ttatctctgt acggtcttaa ttttactcat tctggtaaat atagctttcg    9240
atgttataaa actgggcatc cctccgaaca aaatcaaaac tttaatctgc aaatacatcc    9300
tagaaacaac acaaacggga cacacgtgaa tccctgggta tgtgaagaac caaagcacga    9360
atgggacact tctcataaac cgaccaatta tgaagacaat acagccacat catctataga    9420
tcatttatac cgctataaca atcattctaa cacatcacac ggcagacgca ctacgtggac    9480
gttagcatta atttgtgtag cctgcattct cctattttc gtccgacgag ctctaaataa    9540
aaaatatcat ccattaagtg acgatataag tgaatcagaa ttcatagttc gatacaatcc    9600
tgagcacgag gactaagcaa cgtttccgga taaatgtctt atgagaccat atcagaaaat    9660
aaacgggcaa gaaagatcaa caacgtccga agaaacatca atgcccgtta accgaaattt    9720
aataacgtta tggactggag atttacggtt aagtggacgt tactgatgat tacgatatct    9780
gaaggttgca atgacacgtg ctcctgtccg tgcaattgcc tttacctcca ccgcctccac    9840
tatcacaaat tcttctaact ctgtcaccga tgctaacagc acttcagcta tcgcaaatgg    9900
aaccacgcac aaaccctcta ccgcttcttc agtcgcatca gcaaccactt caacgctttc    9960
aaaatcatcg tcaagcgcta cgccaacatt aacgttttct accattcata gtactactcc   10020
ctggttgaat accagcaaca taacttgcaa tggcagtttg tacaccgttt ataaacactc   10080
taatttaaat tacgaagtaa ttaatgtaac aggatatgtc ggtggatacg tcactttgaa   10140
aaactgcagt agaacggatg tatggcacga tatagaatgg ataaaatatg gacctcgcgc   10200
acaccaactg tgcagcattg gacattatta ttcaacttcc ccactgaacg gcatgtgttt   10260
agactgcaat aagacctctc tcactatata caacgtaact accgaacacg ctggaaaata   10320
cgttttgcaa cgttacagtg acggtaaaaa ggaaaactac tatttaaccg tgttatcagg   10380
aactgcaaca tcgtctccta tacctgataa atgtaaaaca aaagaggaat cagaccagca   10440
taatagcaga acgtgggaca atgtaataaa aactgtaaaa aacactaaca ttcccctggg   10500
aattcatgct gtatgggcgg gtatagtggt atctgtggca cttatagcct tatacatggg   10560
tagccgtcgc gtccccagaa gaccgcgtta tacaaaactt cccaaatacg acccagatga   10620
attttagact aaaacctaac atgcacatca ataaactttt gtttttattt ttagccaata   10680
atgtctccgt gtggttttg tgggttaagc acttatggtg tgaagcagaa tattcatagt   10740
tattaaaaac atgggtatac aatgtaacac taaactactg ttactagccg cgctaatagc   10800
aactgcaacc attctaacta gcattttagt tccggtactt ttacatgaac aagaaaaaac   10860
attttaccgg cgatttttta cgcaaagtca acatgtagaa agacccatca cggtaactca   10920
gggagataca gttacctga acggtagtaa taatccctgc aactattcca gtttctggaa   10980
ctacggcagt tgcgaacttt gtggatggaa cggatacata cataaacagt accacgaaaa   11040
caaatcatgc tctccgcgat ttacatgttt taacgacaca aaaggtctca gacttaataa   11100
cgttacatct agcgattcag gaacatacac ggaatacgtg tatgaatgcg atttgccatg   11160
taatacaagt gactatgatg aatatgacat actaaactat cttgacaatt gtactactac   11220
cataaacagc accaattata ttattaccgt attgtctcca cgtcattcta aacacaccaa   11280
ttcccacata tccacgctgg ttggacagct gccgtggtga cggtaattat aatctgcgtt   11340
ttgacttact ttaacgttcc ggcaaccctg aaacgcaaac tacgaactag aaacaacgct   11400
```

```
acccacatac cgtgattaca aagtacccac actagttcat tcaggataaa tttgtgcttt    11460
gtgtagctct cagaaattgt acaacccgc ttttccactc cgtcatgaaa gatcgtaata    11520
aactacttat atgtattatc tttattttca ccatgtgcct catctgtctt tactttaaac    11580
gccgttgtat tcctacccca tctccagaca aggcagatct gcgagtggaa tttccttcgt    11640
tatctccgtg tgtcggcata cagtgcgctc catgaaaaga cgcgtgatac atagcgtact    11700
ccaggacggt acagtttatg agaacataat tcaaggaaag tgcaggttcc tgttgctatg    11760
ttaccacagg agatcacgga acataaatgt tttctgcgta tgttttttata aaagagcgtc    11820 tcgaagcagt ttgagccaca ctacggtcca gatgacgagc gtaatcaaaa atatgccgcg    11880
tagtagtcga aagccgtact gagcgtgcga agcgggtagg gtgccgaacg acgggtatgc    11940
gtcgtcgtca tctttgacta taaggatcgc gaccgagttt tctggcatgg taaaagctgc    12000
ccactgtggc aggtatgtag cgtatccggt ttggaatcgt tcggctctgg tccgggggat    12060
agtgaggaat tctcagggga tgatatggga cccaatcact ggataagaca agggttttttc    12120 cccgtaagat gatcctcgta tcacatgagg tctggatatg tataaatgag gagtgaaata    12180
ggcacaggga atcagatgcc ggccttgtga tgcagccgct ggttctctcg gcgaaaaaac    12240
tgtcgtcttt gctgacttgc aaatacatcc cgccttaagt gatgagtcta taaagcaccg    12300
ttgtctgggt acggtaaaag tgactcggat tgtagcacgt cattttttttt tgttttttgca    12360 tcgtttatcg tcaccactag tgcaatattt tgatcgtaag gctgaaagag tatcgttatg    12420
atgcttagag cgtggagatt gatggtacta cttgccgcgt actgttatta tgttttttgcg    12480 aattgttcaa tcagcacgac gactgctcct gtggaatgga agtctcccaa ccgtcagatt    12540
cccaagaata ttacttgcgc taattactca gggaccgtcg gcggtaacgt tacttttcag    12600
ggtctcaaga ataaaacgga agatttttta tcttggctac tcgggtctgg ttataagtcc    12660
atttgctcgt tcttcccgca actccctggt gattctaatg agcagcatta cagatatgaa    12720
gtaaccaacc tcacgtacaa ttgcacctat gaccgcctga cgttactgaa tctgacaacg    12780
gaaaacagca ggaattacta tttcagaaga gaagatgcga attccacctt ctattactct    12840
tgttacaatc tgaccgtgtc ctaaagatcg cacgtgaagt tccacagaac cgcgcagctg    12900
tagctattgt gtttacgttg cttttgaaat gttaagcgtc cctacggcgc taacatgttt    12960
ctaggctact ctgactgtgt agatcccggc cttgctgcgt atcgtgtatc tagatcacgc    13020
ttaaagctcg tgttgtcttt tgtgtggttg atcggtttgc gtctccatga ttgtgccacg    13080
ttcgagtcct gctgttacga catcaccgag gcggagagta acaaggctat atcaagggac    13140
gaagcagcat tcacctccag cgtgagcact cgtacaccat ccctggcgat cgcgcctcct    13200
cctgaccgat cgatgctgtt gtcgcgggag gaagaactcg ttccgtggag tcgtctcatc    13260
atcactaagc agttctacgg aggcctgatt ttccacacca cctgggtcac cggcttcgtc    13320
ttgctaggac ttttgacgct tttcgccagc ctgtttcgcg taccacaatc catctgtcgt    13380
ttctgcatag accgtctccg ggacatcgcc cgtcctctga aataccgcta tcaacgtctc    13440
gtcgctaccg tgtagctagt tagccagctg tgtatagttt gttgtgtttt gcttttgcat    13500
atttgttttc agtcagagag tctgaaacgg ggtgggaggg acttttgcgg gtagtgcacg    13560
ctaagatgaa cgggtgggct ggggtgtgct tgataactca ctgtttgaat acgcgctcac    13620
gcacatatgt agcactcaac atgttagctt ttgcccgcac gccccggggc atgccgagct    13680 gccttttttaa taaagtctgg gtttccagat acgcgctggt tctgattttg atggtttgtg    13740
```

```
cctctgaagg ctcaacgaat tgggtcgtgg tttctcatag gctgcctaac tgtagcgcgg    13800
tatctacaac agtgggacaa aacgttgagt tatgcggctc ggcgtcatca ggttgtaaca    13860
taacccaatg gggacgttac cagaatggaa gtacgctggg gccatggtgt accctgtggg    13920
gaccatatac ccaagtctca ttaggacatc gtgtagcgtt cggctgttct tggacaacgt    13980
tttttatgta caacctttct caaaatcata gtggcactta ttatcgaaaa ggtgacaact    14040
gtaccgacaa acatataaca ctatcttgtt tcaacttgac ggtgcatccc aaggcggctc    14100
agagcacaac caccgtagtg acacccacgg tagttacaaa cgccacggcg aatgtgtcac    14160
ccattacgtc gactctagcg gtaaattcca gcgcgtttaa acacgttagt tatcaacggc    14220
aacagcgtgt cgaaaacagg acgtcatcca agaacataac taacttggca ttcacctatg    14280
gcagctgggg cgttgcgatg ctgctgttcg ccgccgtgat ggtgctcatt gatttgggtt    14340
tgcctcaatc ggcttggcgg cgctggcgaa tccacgtgga cgatgaagaa cgtggtctgt    14400
taacgtagga aataaaaagt actgtttgag cgtgactgtt tccaaatcgt accgtggtaa    14460
ataaatcatg gtttccggcg tgggttctca tcttatgacg gttccacgat tccgttggac    14520
agtgcatcat gtgtacaata aactattgat tttggcgttg tttgcccccg tgattttgga    14580
atccgtcatc tacgtgtatg cgccagaggg agggaacgtt accctggtat ctaacttcac    14640
ttcaaacatc agcgtacggt ggtttcgctg ggacggcaac cacagtgatc tcatctgttt    14700
ctacaagacc aaagaaggat tttcaacgcc ttatgtgggt ttaagtctaa gttgtgcggc    14760
tagccagatc accatcttca acctgacgtt gaacaactcg ggtcgttacg gagcagaagg    14820
tttcatgaaa agcggcgaaa atgaaacgtt cctgtggtac aacttaaccg tgacactgaa    14880
atctctgaaa actacctcag ctaataacgt aacaaccatc gttacaacga cgccgacggt    14940
gactggcgcg gagagtaacg ggactagaaa tgccatttta acaccacaac tacgtgctgt    15000
tgctggattc tccaatcaaa cgccctcgga aaacaacaca cacctggcct tggtaggtgt    15060
tgtcgtgttt tgattctga tagttgtttg tattatgggg tggtggaaat tgttgtgtag    15120
taaatcagaa ttatagtaat gtgctttta tcagggagaa ggttttgtgc ccacaatgac    15180
tagcccggga ctatctacgt cggaaaatta caacggaaat tatggactca cgaagaccgc    15240
caatacaacg cgtacaaata acagtgaccg gacaacgtta ggagccagtg cgtcgttgtt    15300
gggaagcacg gagactgcgg taaactttga caacgcgact acgattatcc cacaacgtgt    15360
ggaacacccg gttgggggaaa tacaatatca gagaacgaca acacattatt cttggatgct    15420
aattattgtc atcattctca ttatttttat tatcatctgt ctgcgagcac ctcgaaaagt    15480
ttacgatcgc tggaaagaca gtaaacagta tggacaagtg ttcatgacgg acacagaact    15540
atgatgttcc ggtacgcgtt attacttcga tggataacaa tcattctttg tacacgaaaa    15600
tccaattatt ggaactacat atcaacgcca tgtacttcta tagttggcta cagtggccag    15660
aatatcagct tatctcccgt taacaaattg tcagtcaaag acgatgcttt tcaatggtat    15720
atagacaaac cgagagttac taacgcacta tgtatttatc aaaataacga gtgcagtgta    15780
caacccaatg agaacgctcc gaacattaag tggcaatgtg tacagaatca tacacttatt    15840
cttattaatt taacaactac atatagtaga aattactatt ttaattcttt tgaaacccctt    15900
ggagtaacaa tagcaaaata caataccctg tgttacaatg tcagtgtaca ttctgcctac    15960
caaacacact gttgtacaac cacgttatcc atgtattcac ccacacccgt acacaggtca    16020
tacacattaa cttcaaccaa cttcacacat gtcgcggtcc attataccgc cggtaacgtt    16080
gaagcacaac acgatactgc cacccacat acaatgtgga tcatacccct agttatcgtt    16140
```

```
ataacaatta tcgttttaat ttgtttcaaa tttccccaga aagcttggaa taaattcaca    16200
caataccgat acaacagtat gctcgccgcc acttaaagaa tcaccgtcga ggaaactaaa    16260
agctatgtac gtttattttt cagctcactg tttgaatacc gtaaacataa tgacgtacat    16320
atacgtggtt atacaacagg tgtttgtgct atgcggagac tgattaacca tatcgtgaac    16380
catgatcttt tccgatggtc tgtcgtgacc gcaatgatat tttacaggta ttccgaaacc    16440
tgtatggagg tcactgtcag agtaggtgat ccagttaccc tcggtagtgg acatggttat    16500
catccaggac aaaaagtaca ctggtataac cagtcatgcg tcggcatcag caacggcgaa    16560
aatacgcatc ctatctgcac ctacgaccct cctaaacctg gtagacaaaa gacaatgaaa    16620
accactccgt tgccatcacc actgttgtat gaatgtcaca attccacatt aagcattctt    16680
catgtaaacg tctcagatcc cagaaactat tgcaggcgaa aatgtccacc aaagggtaac    16740
tgtgagtttc ccacatgttt tacattatcg ctgatttcta gaacgacaac caccagaaga    16800
cccggacaaa aaactacgtt gtcgcgatta aaaccacgc caaataaaca tacgcagcac    16860
aaaagatcca cgcgaggaac gtcacctaaa gattacaatg taacgggtct gccgaaaggc    16920
tttgcggact cgtttaccgg taacgtagag gcacatagag ccaaagatgc cgcacacagc    16980
gcatggattc tcattgtcat catcattatc atagtcgtca ttctgttttt cttcaagatt    17040
cctcaaagac tccgagagaa atgggacacc aagggatacc tttacaaagg gaccgatggc    17100
ctgcccacta cggactaatt atcgtgagcg gacggatatg tccggtttca aactcactgt    17160
ttgaatatag ggacagtccc tacgaaacct gagaacatgt ggaaatcacc tgtggtagaa    17220
tgctgctcag gtacattacc tttcatcgcg aaaaggtact ttacctaacg gctgcatgca    17280
tctttggtgt ctacatcagc ctccatgatg cctgcatacc ggtggttggc aagataggta    17340
ccaacgttac gttgaacgcg gtagatgttc tcccccctcg cgatcaagtt cgttggtcat    17400
acggtccagg cgggcaaggc tacatgttat gcattttcac tggcacatca acaacaacgt    17460
ttaacagcac gcgctttaat ttttcatgtc tgagtaatta cagcctcctc ctcattaacg    17520
ttaccgcgca gtatagtact acctatcgta ctatgacatc gctagacgat tggcgtcacc    17580
aacaacataa ccatggtttt cgatggactt tagacacatg ttacaatctg acagtgaacg    17640
aaaacggtac attccccact accaccacca aaaagcccac tacgactacg agaacgacaa    17700
ctaccacaac acaaaaaaca accaccacga gaacaaccac caccgccaag aagacgacga    17760
taagcactac ccatcataaa cactccagtc ccaaaaaatc caccacccct aacagtcacg    17820
tagaacatca cgttggtttt gaagccacag cagcggaaac accgttacaa ccaagcccac    17880
agcaccaaca cgtggctaca cacgccctct gggttttagc ggtcgtaatc gttattatca    17940
tcattatcat tttctacttt cgaataccgc aaaagctgtg gctgctctgg cagcatgaca    18000
agcacggcat cgtgctcatc ccccaaaccg atctgtaagc aagtcgcgta ggaaatgatt    18060
gcatgaaatc actgtgaaac gccaactccg tgccagctgg cgcggcggac aggcctttga    18120
cgtatttgaa gccaggcgcg ctctcgatac cgaaaggatc caaggggggct ttccaaagcc    18180 gacgtccctg attcccttca taaagctgtt gaccggccct agaaagacca agagcatgct    18240
gtgggccgac tgcggtcgct tcttgcgtta tcatctgctc ccgctgctac tgtgtagact    18300
gccattctta ctcttttttc agcggccgca gtgggcccac ggcttggaca ttgtcgagga    18360
ggacgagtgg ctacgggaaa tacaaggagc gacgtaccag ctgtccatag tgcgccaagc    18420
tatgcagcac gccggattcc aagtcagagc ggcgtcggtc atgatacggc gaaacgccgt    18480
```

```
tgacctggac cgaccgccgc tttggtcggg atcgctcccg catttgcccg tctacgatgt    18540 gcgttcccg cggccgttga gaccgccgtc atcacagcat cacgccgtat cacccgaact    18600
gccgtcgcga aacgggatac gttggcagta ccaagagctg cagtatctgg tggaagaaca    18660
acggcggcga aatcagtcgc gtaatgcgat tccgagaccc tcgttccccc ctccggatcc    18720
accatcgcag ccggcagagg atgcacgaga cgcggacgca gaacgtgccg aatcaccaca    18780
cagtgcagaa agcaccgtca gccacggcgc gagtgacaac gcagtgcggc gacggcacga    18840
aagacggcgc tataacgctc tgacggtccg cagcagggac tcgctgctcc tgacgcgaat    18900
acgcttctcc aaccaacggt gtttcggacg cgggcgtctg agacatcccg cgggaagcgg    18960
tcccaacacc ggcggaccgc gacccggcgg tgcgggactc cgtcaactac gccaacaact    19020
gacggtccgc tggcagctgt tccgcctacg gtgccacggt tggacacagc aagtctctag    19080
ccagatcaga acccgctggg aggaaagcaa cgtcgtgagc cagacggcca cgcgagtacg    19140
tacgtggttt gtgcaaagaa ccacgttgtg gcgtcgcacg tgggttccgg gacagaaccc    19200
ggcggccgaa gcgcaagaac tggccgtcat accgccggca cccacggtgc tccggcagaa    19260
cgaggaacca cgtcaacagc ttacgggaga ggagacaaga aattcaacgc acactcaacg    19320
tgaagaagtg gaggacgttt cgagagaggg cgcgagagaa gggaatgatg ggagccgagc    19380
aagtggaaac gacgagagaa ggaataatgc gggaagatat gatgatgatc atgaggttca    19440
agagccgcag gtcacttatc cagcgggaca aggagaactg aataggaggt cacaggagga    19500
gaacgaggaa ggtggaccgt gtgaatcgcc gccaatgacg acaaatacgc tgaccgtggc    19560
ctgtccgccc cgagaacccc cgcatcgtgc cctgtttcgt ctatgcttag gactgtgggt    19620
ctcgagctac ctggttcgac ggcccatgac gatttagaat acaccgagcc attcctttat    19680 ttcccccat ccccggtcgc ttatgcgtgt caaacactac caataaagat aatctgccaa    19740 tcgcaccta tatataatat gtggtcgcgt gtggtctttt taaggagctc tgaaacacag    19800
acaggtatgg gcgtggccg gctgccgccg ctgtggctgc cgctgctgat cgcctggagc    19860
gagtggggca actgctgcct cgatgcgcct ccggtggtgc gttcgccctg tctgcagccg    19920
gtgcgcgacc gcaaccgcga gcggaacccg ggctcaccgc agttgctgcc ttacggcgac    19980
cgtctggagg tggcctgcat cttccccgcg cacgactggc cagaggtctc tatccgagtc    20040
cacctctgct actgggccga gatcgtcgt tcgctggtgg tggacgcacg cagcggtcag    20100
gtgttacaca acgacgccag ctgttacatc gccggcgggc gctggcgctt cgaggacggc    20160
ggcgcggcgc agcggctgag cctctcgttt cggcttatca ccgagaccgc gggcacctac    20220
acctgcgtgc tgggcaacga gacccacagc ctggcgaccg agaccacggc gctggtggcc    20280
gacgtgcacg acctgcgcca ctcggaccgc tcctgcgacc tagctttcgg atctcgctca    20340
cagacgcggt acctgtggac gcccgatccc tccaggttgc gcagtataaa ctgtggttgg    20400
gagggtgaac ggcaccgcgt ggtccactac atccccggca cctcgggtct gctgccctcg    20460
tgcgaggagg acgagcgcga actgtgcgtg cccttcatca gccagagcat cgcggacaac    20520
aactgcagcc accggcatcg ggtagacggc gctaggcggc gctatcatct gcggagggat    20580
tactggctga cggatccgaa gatcgggctg ctggccgcgg gatcggtggc cctgacctcc    20640
ctctgccacc tgctgtgcta ctggtgttcc gaatcgtacc ggcgtctgaa caccgaagag    20700
gaaaacgagg cggcagagga aactgccgcg ggagaagcct ctgcggtagc ggcggcggcc    20760
gtctctgagg aagagcagca gcgggagtaa acgaggagag ccatgaagcg gatgattcgc    20820
agtcacggca ggaaaacgga atgtcagatg acgggcgccg gcgagcgacg cggctctgcc    20880
```

```
gtcggtgcgc tcatctgcgg cagcggtacc cgacgcggca gcggcgccaa cgaacgccgc   20940
gactccgacg tcggtcccat cgcccacagt agcggtacca gacgcggttc ggcgaatgaa   21000
acgtccgcct gtacgcggac cgatcaccag aaggcggaca ttgggctgtg gttcatgttt   21060
ctggtttttg gactgtgttc gtggttggcg atgcggtatc gcgcacaata aattttgaat   21120
cgatgtcaag gaacgcgtgt tttgtatttt attgggaata ttggcgggga taaaccggtt   21180
tcggatgttt acccttaatc ttaccgggga cctcgttgtc ctctcctcct tcttcctcgg   21240
acacggggct ccatgctgac gtaggtaccg actggggtca aaagcctggg tacttatggg   21300
gagcgcgcac aaaggaccgt caggcgccgg catggagcgt cgccgaggta cggtaccgct   21360
gggatgggtg ttttttgttc tttgcttatc tgcctcttcc ccgtgtgctg ttgacctggg   21420
tagcaagtcc tccaactcga cctgccgctt gaatgtgact gagttggcct cgatccatcc   21480
tggggaaacg tggacgttac acgggatgtg tatttctatc tgctactacg agaatgtgac   21540
cgaagacgag atcatcggcg tggcttttac ttggcagcat aacgagtctg tggttgacct   21600
gtggttgtac cagaacgaca cggtgatccg caatttcagc gacatcacca ctaacatctt   21660
gcaagacgga ctgaaaatgc gaaccgtccc tgtgactaaa ctgtacacca gccgcatggt   21720
cactaatctt accgtgggcc gctatgactg tttacgctgc gagaacggta cgatgaaaat   21780
aatcgagcgc ctctacgtcc gattgggctc actatatccg agaccgcccg gatccgggct   21840
cgccaaacac ccctccgtaa gcgccgacga ggaactgtcc gcgaccttgg cgagagacat   21900
cgtgttggtc tcggccatca ctctgttctt cttcttgttg gccctacgga tcccccagcg   21960
attgtgtcag cggctgcgca ttcgcctgcc gcatcgatac cagcggttac gcaccgagga   22020
ctgaacggat aaccgcaaag gccacgtgca acgttcacgc tgctataaga aggccatgtc   22080
ccccgtggac gggtctcttt gacacgagcg cggcacgccg ttgccacgag catggatcac   22140
gcgctcttca cacacttcgt cggccggccc cgtcactgtc ggttggaaat gttgattctg   22200
gacgaacagg tgtctaagag atcctgggac accacggttt accacaggcg ccgcagacat   22260
ctacctcgac gccgcgctcc gtgcggcccc cagaggcccg ccgagattcc caaaagaaga   22320
aaaaaggcgg ccgtccttct attttggcac gatttgtgct ggctgtttcg acgactttc   22380 tttcctcggg aggactcgga gccactgatg tcggatccgg cacggtctcc cgaagaggag   22440
gagtaaacaa cacacggcta agaggataca tcatcaaaga agataggagg ggtcaaaacg   22500
cggactgaaa gtatataacg ccgatcatgt ccgaggaact gttaataaaa cgccatgatg   22560
acaacgtggt gtctgacgtt gtttgtgctg tggatgttga gagtggtggg aatgcacgtg   22620
ttgcgttacg ggtacacggg gattttcgat gatacatcgc atatgacgtt gaccgtcgtg   22680 gggattttg acgggcaaca cttttttacc tatcacgtta attccagcga tagaacgtca   22740
agtcgggcca acggtaccat ttcttggatg gccaacgtct cggcggccta ccccacctac   22800
ctagacgggg aaagagccaa aggtgacctt attttaacc aaaccgagca aaacctgtta   22860
gagctggaaa ttgcgttggg ttaccggtca cagagcgtgc tgacgtggac gcacgagtgt   22920
aataccacgg aaaacggtag ttttgtagcc ggttacgagg gatttgggtg ggacggggaa   22980
actttaatgg agctcaagga taacctgaca ctatggacgg gccccaatta cgaaattagt   23040
tggttgaagc aaaacaaaac gtacatcgac ggtaaaatta aaacatcag cgaggggat   23100 actacaatac aaaggaacta tctcaagggt aattgcactc aatggtccgt catttatagc   23160
gggtttcaaa cccccgtcac ccacccagtg gtaaagggcg gtgtccgaaa ccagaatgac   23220
```

```
aacagagctg aagcattctg tacatcttac gggttctttc caggggaaat taatattact    23280
tttattcatt acggtgataa ggtgcccgag gatagcgagc ctcaatgcaa tccgctactt    23340
cccaccttgg atgggacttt ccatcaggga tgttacgtag ccatcttttg caatcaaaac    23400
tacacctgcc gcgttacaca cggtaattgg acggtggaaa tccccatcag cgttacctca    23460
cctgacgaca gttcctcggg ggaggtcccc gatcacccga cagctaacaa acgctataac    23520
accatgacca tcagcagtgt cctcctagcc ctgcttttat gcgctttgct attcgcgttc    23580
ctgcactact ttaccacctt gaaacaatac ctacgtaacc tggcctttgc gtggcgctat    23640
cgcaaggtcc ggtcgtcatg accatcaacg ccctgtatga gctgtttcga cgtcggttac    23700
cgcgtgcccc cgtcaacacg gtcatgtttc tcacgcgacg cactcgtgat gggttctgcg    23760
gtcggttgac gtccatcgcc acgaattccc actacactat gttcgtgttg gatcacgggt    23820
ccgtgcgcat cgagcgaccg agtcagtcag aagtggattg cgccagttta atggaaacgc    23880
tgaagcggat tcggttacga aattcgtggg tagcgtcaga agacgagcta gatgtgagtc    23940
gcagggacgc gtgacacgaa acgcgttcag gattaacgta ggttttcaaa ataacctacg    24000
tccgtgagtg acgcggtttc gtgttgaaac ccgcgcccgg ttcccacggt ggtttatgat    24060
gaaaccggcg ttggggatct acgcgggttc ctcattcaac ctgcgaaaag aggaagttgc    24120
ggtaaaacca cgtcaataaa gacgtcaatg cacctcaat gttgcgttgg aacggtcttt    24180
atatatacaa acgccgttat gctcagtgtc cggcaagatg ctcgggatac gggctatgct    24240
ggtgatgctg gattactact ggatacagtt gacaacgctc aatggcaccc gaaccaacaa    24300
taccgatacc atctttgtgt ctctccttac cggtcccaac ggagttaccc gcacggccat    24360 cggggggtttg tattcaaact acactaattt aactggacca tttggcttca cttcaacaaa    24420
cgcatcaata accaactctt ccactgaggg taattggagc gtggctaatc tgacagagag    24480
ctgcatcaac cgcggtgagt cctatctgac taccctctgg cttctgaact gcactcaaaa    24540
caatacttat tggtattctg gaaatgctta caaccatacc aatagcacct gtgaaaatca    24600
agtttcgaaa tatctctttt ccggcatgtg ccagctatgg aaaaattgga tcaatattac    24660
ttttaataac actatcaaag tcgagttgct gggaaatgaa acacgctgca tgctgcttcc    24720
taaacagtat actctgaacg ctacggtaga atggtacaac aaatctgaag gtaacgtacc    24780
aaaagaattt atggactatg ttatcctgac ccccttggca gtgcttacat gtggacttca    24840
ggaagcttat atagtcgaca agggtcgtag atacatgtat ctgttctccg tgtcctgcgc    24900
gggaatcaca ggtaccgtat ctattatact cgtctcccta tcgctgctca tcctcatctg    24960
ttactatcgc tgtggccggc ttctgatatg cccacgcggc tttgaactct tgccagaatt    25020
cactgaggaa gaggaggaaa aagaaaaatt gttaacgcac aaggacattg aagtccaggt    25080
gcctatccgc acgcggcgac tgctcgtccc ttggatccgg gagagcaaaa tgtgggtact    25140 accaccccg ctgcctccac gacctcccca cttaatagaa ttcccgccgt ctcctccgcc    25200
atcgcctgga cccatgcaca tggtggtctg catgccagca tgacgactt tggactctga    25260 gccccaagcg gtacggacta catattttcc ataaatctac actgaacttg agcacaaaaa    25320
tactgacaat ggactggata tacagactt tatatgatcc ctgtacagat gtaaataaaa    25380 tgctttatt taaaactggt cccaatgttc ttcgggaatc atgggatggg gacgaggtac    25440
gcggtaggga gcaaaaccgg gcacatgggg gggaacatcg tccagcagta gcaccagcgg    25500
attgggcagg ggctgttgcg gaggtcggtc gatgacgatg tcgatctcca tcggcagatc    25560
cggtaacatc tcttcgtctc cctcaccgac cagcactcgg cgctgttctg gatgtatatg    25620
```

```
attctggaaa agcctccgac gagctcgcgg cgcgtagaaa gccaagcggc gcaagggccg    25680
gcgagcccga aagtccatgc gcacagatgg catgagtcct tgagtgacgg tggtgagctg    25740
gggaacaggg ctacctccca tcgcgacggt gacagtggat ccatgagaga ggcgccgcac    25800
gctgcatggc taaataccgt gaatccctg acgtcgtctt tcgtcccgaa cgcgtcatgt     25860
tgggggcgag gcgtaaaccg tcgaggttga aaaccgcgt atctgcggtt cgtccggact     25920
acgttgtttt tcagaagcgg ccacatgacc tcgagatgtc gtcacccaag gtatttaacg    25980
gcacacagcc agacgcgttc gtcagcagcg acgccgacaa gacctcagca tggctcggag    26040
gctatggata ctgagcttag ccgtgacctt gacggtggct tggcggcac cttctcagaa     26100 atcgaagcgc aggtaaacag gtaagaaata caaaaaataa cgtgattgtg aacgcggtta    26160
tcgtgttttt gcagcgtgac ggtggaacaa cccagtacca gcactaactc cgatggtaat    26220
accaccccca gcaagaacgt aactctcagt caggggggat ccaccaccga cggaaacgaa    26280
gattactccg gggaagagta tgacgttttg attacagacg gagatggcag cgaacatcag    26340
caaccacaag agaagaccga cgaacacaag ggagaacaca ccaaagaaaa tgaaaagacc    26400
cagtagcagc agatcccaag ggttaaagac catgttgact atcttgtttt ttattaaaaa    26460
gctgtaaggt tctgctctaa aaacaccccg cctccggtct tttttctttt gtattcggca    26520
cgcgaaacat ggtttcttcc catagcctgt ctaactagcc ttcccgtgag agtttatgaa    26580
catgtatctc accagaatgc tagtttgtag aggctatgcg ggatgctgcg gcggcgcgac    26640
cttccctctc cacccagccc cgtcaaaaca cacgcgactc gagcggttcg tatgaaaaat    26700
aaaaaacagc ttttttattta caggaacggg gaaaaaaag gcacacggtc cgtgggagac    26760
gcgggttcac gcgtcgtcaa aaagttggtg gtccactccg taaggacagg taggcttatt    26820
tagcttccgc atgctcctgg ttccgtaata aatgccgttt tcgtggcagc gtgtcatgcc    26880
gcgagtcaca aactccatca aactgtcggc cacgatgcaa acgtgctgat tgttggcagc    26940
aaagacgcgc atacagtcgt ccacgaagag gttgatcacg tcgtagggc ttaccaacca     27000 gcctaaaggt tccacgtggt tactgccgac catgaccctc cagtcgttaa tctcgctcca    27060
gtcgtacagc cgaatcgtgg agacgcgaat gacgctgtaa tcacccatga ccatgagtcg    27120
gccgcgatac gtagcacgcc actgcgcgaa cgcgtggatg tgcatgcagc cggccagcgc    27180
tctaagcgag gcggtgtgcg gcagctcctc tgggacggtt atgaagttgc agcgtcgcaa    27240
accgatgttg agaaattcag tgatgctctc ggccacaaag gtcaacgagt cagagtagat    27300
gtggtcggtc cacaggtaca tggcgcccga ggcgcccagg tacagttcag acggcacgtt    27360
gtgatcgccc ttgtgtttaa gaaagttgta ggtgcagatg ctgccgacga aacgcagcgg    27420
ctcggggcag cagaggtagc tggccagacg ctgtgcatcc cgtccttcgt cgcgcaccaa    27480
gcgccagcga cgccggataa cgaggcagcg gtctttgggc cagaccaggg ccacgcgttg    27540
cccgggtttc cacggtcgcg acgtcttagg aggcctccag cggtcgagca gattgagaaa    27600
acagtccttg attaccgaca tcgcggtcgc gcgtcggtgg acaaaaagaa atcgggccga    27660
tccggaaaaa aaaaaaacg acggcaaaac accgccgtgc tcgagcgaag ggtggcggag    27720
ggccagaaga tgcggccttg acggcgttgg cagcgaaaaa attggcacgc gagtcaaacg    27780
ggaagtagcg tcggtgtttt atgcccaag cagcgtcgtc gtcactcgtg gcgtcacagt     27840
caacggtgct gacgtccttt ggggcagtcg ggcacgcgat cgtagatgcc gttgtggccg    27900
ctgaaacgtc ggttttcaaa cagcaggtta agtcccagac acatgaacgt gttgagatta    27960
```

```
tctcccaccc ggatgtagcg gtcgtcgcgc acgtcgcagg cgtagacggc cccggtatag    28020
gcgacgacga tggggataag gtcgacgggc cagcgcaagt gaggaaaggg cgcgttctcg    28080
cccttgaggc tgacggttcc caggccgaga acgcgcattc cgaaagcggt tttgatgttg    28140
cgcagcaagt gaccgccttc cacgctgttt tcgaaacacc tgaggttgca tagacgcagt    28200
tccgttcccg gcgggtacgt caacggcatg aactgcccgt ggtggcggat gatgaatcgc    28260
gccatggtat ccaaaccgag gctccaggcg cgcaacagcg ggcgaaagta gcgcttaacc    28320
aacgacgagg tcaggtagcg catgcagtgc agggtctcga cggcgcgcag cccgacgcgc    28380
gcaaactcca tgaggttgcg ggccaggtag tagacggcgg tgtcctcgcg tacatagcaa    28440
aaaacatagc cctcgtccga gatgaggcac acagcggtct tcttctgctg atccggcgac    28500
aacacgccct cgttcacgaa gcgacccacg aaggccaggc gcgtctggca acacaggtag    28560
tgactccaag ccttcacgtc ctccggtttg aagtcctcgt ccgtctcgat ctcctgcagc    28620
actaggttcc agcccggcgg ccagaccacg ggcaacacct ggcctgcgtt gatgcgcacg    28680
taagcttcca gacagcccag gccgaactcg gccgtgagcg ccaggctagc cagatcgctc    28740
atgtgacgcg ccgagtcagt gggcgagccc gggggcccgt cgcacaccac gctccgtctt    28800
cttgtcctca ccgcggccag cgtggcgagg acactttccg cgcccgaggc tgtatcttcg    28860
gtttgcccgc cggagccggc cctcactata taacgtcccg cccgggtctc ctccatgtat    28920
gcaggtaagc aactgagccg aacgcacctc agcagacgag aggatgtcgt cgcggcgtcg    28980
cagctcgtca cgtcgctctg gcgaaccctc gacggtgatt tatatcccct cgagcaacga    29040
ggacacgccg gcggatgagg aggcggagga cagcgttttc acgagcacgc gggcgcgcag    29100
cgccacggaa gatctggatc gcatggaggc cggtttgtcg ccctacagcg tctcctcgga    29160
cgctccgtcg tccttcgagc tcgtgcgcga accggcggc accggcgccg ccaagaaacc    29220
gagcgaaaag aaacgatcgt cgtcgcgtcg gcaaccgcag atcgcagcgg gcgcgcctcg    29280
gggctcgccg gcgacaccca aggccggcaa gtcgcctaaa gtctcgcgac cgcctagtgt    29340
gccctcgctg cccgagaacg cgccggcgg cggtggcgac gaatacagca gcagcggcgg    29400
tagcagcagt cgcaccacca gtaacagtag cagaagtacc agtcccgtgg cgccaggtga    29460
gccgtccgct gccgagggcg atgagttttc cttctgcgac agcgacatcg aagacttgna    29520
gcgcgaatgt taccgggtca gcgtggccga caatctgggc ttcgagccca gcgtggtcgc    29580
gccgcagcac gtcgagtatc tcaaattcgt gctgcaagac tttgacgtgc agcacctccg    29640
ccgcctcaac gaatgcatac ccatgccggc cttcgcgctc accagcctcg tcgaccccgt    29700
cttaaacaac gtagcgcctg gcgagcgcga tctcacgcgt cggataatca cgcacgcggt    29760
gatcatcaac tattactacg tggcgcaaaa gaaagcgcgc cacatggtgg aggccatacg    29820
gaccaccgtg cggggcgaca cggtacgcca ggtagccgcg caggtcaaca accagagccg    29880
ttcggggcgt gcgccgcgc tagcgcttca ctttctcacg tcacgaaaag gagtgacgga    29940
cggccagtac gccacgtctc tgcggcggct ggacgaagag ctgcggcatc gcggcacgcc    30000
cgaatcgccg cggctcaccg aggtctacca gacgctacgc gattacaacg tgctcttcta    30060
taccgcccac tacacctcgc gcggcgcgct ctacctctat cgacaaaacc tgcagcggct    30120
caacgagaac caccggggca tgctccggct gctttcggtc gaagagatat gcgaagagca    30180
cacgctcaac gatctggcgt tcctagtagg cgtcgagctt atgatcacgc actttcaacg    30240
caccattcgc gtgctgcgct gctatctcca gcaccagctg cagagcatct cggagctgtg    30300
ttacctcatc tatgtacaac tgccgtcgct gcgcgaagac tacgcgcagc tcagtgacgt    30360
```

```
gctctactgg gccgtcagtc aaaactacga ctacgcgctc tacgcgagca cgccggcgtt   30420
gtttgacttt ttacgcgtcg tgcgtcagca ggacgccttc atttgcaccg actacgtgta   30480
ttgcgccctg cgcctgctgg cctgtcccga ccgacctatt atcggtgaca ccggcggcag   30540
cagtagctcc caacgcctcg taggtgagtt tatggtgcgc gatccgctgt tgcgcgaccc   30600
gcgcgccacc cacctgcgcc agaaactcat cacccgagac atatgcgtgg cgcggttgca   30660
agcgcagccc tcgagtcgac acattccggt cgaacacacg ggtgtctcct ccgtcaccct   30720
gctcaaaatc tttagccagg tccccccccga cgaacgcgaa gaagacacgt tacgcgagat   30780
ggctcttaaa gcgtttatgg aagcgaacgg taatcacccc gaacaaatct gccgatcccc   30840
accacccccg ctgccgccgc gcgactatcc tcaacgcgac gagcgggacc gtcaccgtcg   30900
cgaccgccgc gacagcgggg aatactgttg ctgatggtgg aacgaagcag cagggcggaa   30960
cggtttatga taaaaagtca caggaaagta tgtgttgttt tttaatgtac caagaataaa   31020
aaatgcgtct acgaccaaag cggtgtgtgg acgctcgtcc tctctgtctt ctccgggttt   31080
tttttttcat gttttttttt cttcctattt tgttacggca acagcgctga tggcacgttg   31140
ccggcttcga acatcgcgtc ggtgatttct tgcttgcccg cgtcacacg gtgacgtagc   31200 agcgcgcggc tcacgtagca ggctgactcg cggatgacct ggccgtcggc gtcgcgtcgc   31260
aggcccgagc gtttgccgtg acgcagtctg ccctgcgcag cgcgctccac gtcttcaaag   31320
tagctgtgta gcaggccgcg ctccagcagc tgcggcagcg agtcggcggc gcgcaccaca   31380
aagttctcac ggctgatctc gtagcacagc acgctgccgt cggccgccac gccggccacg   31440
ctgcggtccc aactgaaaag gttggcgagt ccgatggtgc cgatgacgcg caactgaccc   31500
tgggtcacca ccagcagctt ccagtattct acgtcgcgcg gggtgaggat ggtctcctcc   31560
acgtcgcaga caaacagcgt gtagccgcgc ggatagggca gatccaggtg gcgaccgcgc   31620
tggcggcgca taaatcgtc taaattcaaa ccgccgtcgg gtgcgcgcct gctcgtcatc   31680
gccgcgcctc gtcggtcgat gaccccacgg tgcttataac gcgccgccac ggcttcatgt   31740
ggcgtgacct ccgacctcgt gaggccgaaa acggcgtaca tgaagacgct caaacttttg   31800
aatgtgggcc cggtagcgca ccgagggccc cggggcggcg acgacggcgg gtccgagttc   31860
cagcggggcc ttgcggcggc agcggttagc ctggttgctc agctcggcgt ccgagagcgc   31920
cgagctgaac tgcggcagcc gcgtgcgatc ctgcggcgcg tccccgtgtc gcagcgagtg   31980
ccagagcagg cgctggacgc gcgccgtctc gggcgtcggc ggcgcgcgac agccccggcg   32040
cagcgtgaaa acgtgcaggc acaacagctc gcgcttgatg cgcagcgaca cgctgcgta   32100 gtcgggaatc cgctgcacca gctcgagaaa gtcgcagaag gtctccacga acgtgtcctc   32160
ggtgaagcga atgcgcttca gatcgtggac gtgtttgcga aaccgcgaca gttctcgacg   32220
ttgcacgggg ttctgagcga gtcccttgcg cagcagcgca gcctcgcctt taaacagcct   32280
gatgagccgc tgcacgtccc cgctcaacat acgtatacac gccgtgtact cgtgacgtat   32340
actggcgcgc agcagccgaa tgatacgcag ggccagcacg gcgttggagg ccaggtacat   32400
ggcgtagccg cgacgcgggt tggcacaggc ccagcccgcg gggagcagaa agtagtcgtc   32460
gaccagcgtc tgcgaccagt cggcgaagcc caggtcacgt gatacgctgt cctgacgcg   32520 ggccacgtcg ccggccgtga ggtggcggat cgccggcagg tgaaacgcgc ccaggtgtcg   32580
gttgcgctcc agtctcagct cggcgtgctc caaacgggaa tggtgggacg ccaccgcgga   32640
gggcgacaaa gaggagtggt cattgccgcc gtggttaccg ttgtggttac cgccgttgtc   32700
```

```
gcgcccgtcg ccgcactcgc aaaaggccgc gtagaggtcc ttcaacgccg cttcggctcg   32760
cgccataaac gtggcgtgga aaaaacggc ggcgcggtgc gtccggtact tgacgggcaa    32820
cccgcggcac agggccgccg gcaggcagcg gccgatgagt tcgcgctcct cgggctccag   32880
aaacaggcac agggtgccgt ccaggcgcag gtacagctcc tcggtcatcg agcatagctg   32940
ccgcaaataa tgggtgcgcg tcccaaaggt cttgtaatcg agcaacgtgc acaccacgta   33000
ttgccccgtg gccacggcca gagcgatgcg tttggcggcg cgactgatct ctggcaagta   33060
ctgcgcctcg tgcaccagac ggcggaaagc gccggcgttg agccagcgaa aatgctgcgg   33120
atcgggcggc aagggcacgc ctcgaagcgc ggcccagacg gcgaggtccg actgagcgt    33180 cagaccgcgg atgtcgtact tgccgtgcgc cgtagcgcag gccgaatgga ccagacagct   33240
gcggcgaatg tacaccatgg cgtgcttggg atgtttgggc gccggcgttt tcttttctg    33300 accgccggcg gccgccagat cctcgggcgt gcgacacaac aggccggcgc gcacagcctc   33360
ctgtcgatta cgaatcggcg tcaggtaggc gcgcaggaac tggtgacaaa actcctcatc   33420
atcacgacag tcgtcgagat actcgtacgt ggtgagcgga tcacgaaata ggcgctcgtc   33480
accgtcgtca tggtcttctt tagcctgctc ctccggctgc tgggttggca gtggaggcgg   33540
cggctgatcc acggggttca tgactgagag gaagaagaag gtggcggcga agcgacgcgg   33600
agcgacggcg gtaaagccaa acaccggcta tatagctagt catcacagtc cctccttca   33660 cgacgccccc gtgccgctca cgctatccag cacgctacgg cccgaaaaca cgtactcgct   33720
gacgtcgtac gcgggcgatg tatggctgct caccggtttc gcggcgacgg ttgcgctcga   33780
gtccaacggc gagaagcaaa aacgccgtgg gcaacgaaac cagaaggagc cctgacggat   33840 aaaccgcgc agcgtctcgg ccaacttaac cagcatcgta ccgtacagca gtacgtgaat    33900
gccgccgtgc gcgtccataa atacggcttt gttcacgggc tccatccatc cgatgactac   33960
aaagtgggcc tgttctagca cgccgatcac aaaattgttg gcctcgtcgg cctcggccac   34020
gttccacgag ccgaaagtga agtacaagc gggcgagccg cccaggcgga tcttgctacc    34080
ggcgtggagc tgacatacgc gcagcagatt ggtgcggtcg tgcagtatct gggagagttc   34140
gtacatgccc gcaaaggtgt gcttaaacca cgcgccctct acgatttcat ccacgtagtc   34200
gcgctcaaag aagctgtaca cggcaaagag gccgttctca aaaaactcgc cgaacgagag   34260
ccccagtacg tacaccttgt cctcgccggg caggtacgca aaggcgtgcc cgtgcccgga   34320
gacccagatc tcgggcgccg tgtttgcgtc cggcacgcat tcgtacacac tgacgaggcc   34380
gataaagtac aagcggccag cctggcgcag gcacgagaag cgccggtagg tcttgtgatc   34440
gcgcaccacc ccaaagtact gagtgtcgcc cagcatgatg ccgtgcagcg gcggccagca   34500
cagcgggagc caacgacccg ccgtggcgcg cacgtagcgc tgcaggtgaa ccccgctcgc   34560
acgctcgcgc ggcttcgggc gcttgtgggt ccaggcatca cgcagaccgc gccagatgct   34620
gctgaacttg ggctgcccgc gcagatagag cgacgagagc gagtcaaagt agcccacgac   34680
gagcctgtcg ggagacacaa gagcgcgaaa atcaaaccta gagcgacgac ggtgaaaaaa   34740
ccgaccagaa gcgcgtgtct caaacacgct actttcggtt ataaaaacac cgtcgcccta   34800
tttctgggcg tgtgtacact gatgactcac ctacgctttt tgaacggcag tctcagctcg   34860
ggattggcct cgtacagcga gctgcggtcc acggggccga tactctcgta gcgaaagtcg   34920
tcgatgagca gcgccagccc cacgcgcacg aagcccctga ggtcgcgcgc cagccgcacc   34980
aacttatcct gccccaccag cgccgcgtac acggtgcccg tgtcgccgca gagaatccgc   35040
acgcggtgaa agaaggtctt gtcctcggcg ccctcaattt cgcccagcgg catgacgggc   35100
```

```
tcgcgcgtgt acaacgaacg ttgaaagcgg cgcagcatcg aggccgagag ccccagatcg   35160
cgcgccgtgc gcagcactag ggaatgcttc tcgggccaga tgagggtcag ttgcgcctcg   35220
cggtgcgcct ctacgtaggc gcagcgagcg gcggtgtcct cgcaggccag caactcgcgg   35280
aaagccagca acgaacgtag gtagcgaccg cgagcggagg cgcgcgagcg gcggcacagc   35340
tcggcccgat ggtcgggatg caccaagggc acgttgggtt gcagacgcgc gcagatggat   35400
tcgtgcaccg ggtcgcagcg gatcatgccc ttggcaaaaa atccggccag atccgaggcc   35460
aactcgtaca ggcagtcctc ttgcgcgtcg taggcgaaca cggcgccgta cgcgtccacg   35520
aacacctggt accggcaggt ggcgtgcgag accgtgccaa tgagatgcag agctcggaat   35580
tcgccgaaaa agtcgttctg gcagtgctcc agatcgatct cggtcagcga gtgcggcgaa   35640
tgctcgcccc cgaccacgta gatgcactgc gagggccagc ccagcgatac gcacgagccc   35700
tcgaagcgcc gcaaataacg ccgcaggccc tcatagtcgc gtcgcacgca cagatcggcc   35760
aagtcgcgcg tgcaaaagac ctcgggtacc aagcagcgtt tgcgacgcgg ccgacgcgcg   35820
tgcccgggca gaggaggaag gcgcgacggc ggcgacgacg aggaggaaga cgccgtggcc   35880
gccgagcagc ccttgcgacg gccggacatg ccggcagtcc gcgacgatcc acaggagaca   35940
aaaaagcaga agcagcagta gtctcggcga cccgctccac cccgtcctcc acacgctcag   36000
ccgcgactga gcgccgggc gcgccgctac ttgggttttt atagccatct gccccccgtc   36060
tcgggcaccc gggagcgatc tacggagacc tgacagcagt tgggcaacac aagacaggga   36120
aatacaaaga cacttttaat aaaaaacgag actactttgt gtgtgtgctc cgtaaactgt   36180
ttattctccc cctccgtctc gctctggatg ggctccgggt ccgtcaacac gcgacccgcg   36240
cggcaaaagg cacgctgttg acggcgcgag agcccgtcgt gatagtccat catgccccgg   36300
agatcgtgca caaagcagct gtcgccgcgc agaaaccgac gcagcgtctc cacgtgctgc   36360
agctgtcggc gcgtatcagg agccgtcatc gccgatgtcg tcatctccct gacaggcgcg   36420
tagatggctc cgcgagatca tgcgcgtttt caaccgccgt gacacatcag gtccatcttg   36480
agctggcgcc gggcctcgcg caggtctcgc acgcgttgtg agcgggaggc gagttcggct   36540
tcttgctcga actcctgctg ctcactgtcc gagagggtgc gataaaaggc ggcaaagtcc   36600
tccaagtcgg ctacatgcgc cctgggtctg acgctccaaa gcgtacgcag tctgatgaag   36660
cggacccatc gagcgtcacg gcacgccgtc ttgaacgcgg ggcccgggaa gaggttcttc   36720
tccccggcgc gctcgggccg gcgaggccga cgcggtttat atacaccgtc tcggacggcg   36780
ggacgccgag cccgcgccgc ggccgctcat ccggagacgg cggaaaccgc ggcgccgag   36840 gaaacgggga ccggcaacga cggcggcggc gaccagatta tgggggacaa gcccacgctt   36900
gtgaccctgt tgaccgtcgc cgtgtcgtcg ccgccaccgt cgtcgccgct gccgctcgtc   36960
agcttcacgg agctgctgtt accgccgccg tccgtcgccg ccgctgcggt ggcggcaaca   37020
gcgacgagcg aggtgggcga gaaaaccgcg gagcaagagg tagcggctgc gggtccggag   37080
accgggaatg agagaagaga aaacagggag gacgaaggag gggagacgag gacgacgggc   37140
accaccgcgg tcaaaaggtc gcacgacggt atccctcgcc aactggcaga gcgcctgcgg   37200
ctgtgccgcc acatggaccc cgagcaggac tatcgtctgc cggcgcagga cgtggtgacc   37260
tcgtggatcg aagcgctacg cgacgcggac cgcgacaact acggtcgctg cgtgcgccac   37320
gccaagattc accgttcggc ctcgcacctg acggcctacg agtcgtactt ggtgtccatc   37380
accgagcagt acaacacggc ctcgaacgtg acggagaaag cttcgtacgt gcagggctgc   37440
```

-continued

| | |
|---|---|
| atctttctct cgtttcccgt catttacaac aacacgcagg gctgcggcta caagtacgac | 37500 |
| tggtccaacg tggtgacgcc caaggcggcg tacgccgagc tcttctttct gctctgctcc | 37560 |
| accagcgaga gttccgtggt gctgcaaccg ctcatcacca agggcgggct ctgctcgtcc | 37620 |
| atggcggttt acgacgagga aaccatgcgg cagtcgcagg cggtgcagat cggttttctg | 37680 |
| cacacacaac tggtcatggt gcccttcgtg ccgcacgcct gcccgcatta cgccgtgcct | 37740 |
| ttcacgacgc cgggaaagcc gggctgcggc ggtgctccga gcggcgttgc ggggttggag | 37800 |
| gaggcggcgc cctttggacg ggtcagcgtc acgcggcatg gcgcgacgct gctgtgtcgc | 37860 |
| gtggaccatc tgacctggat cagtaagcgc gtaaccacgt acggacacaa aaaaattacg | 37920 |
| cgctacctcg cgcagttccg cggcacgatg gacgacgacg aggcggcgct acccggcgag | 37980 |
| gacgaggcgt ggatcgcgtc caaaaacgtg cagtacgaat tcatgggtct cattttcacc | 38040 |
| gtcaacgtgg attcactatg cgtggacgcg gaacagcgcc aactgctggg caccgtggcc | 38100 |
| acctccttct gtcaccgcgt ctcggacaag atcacggcgc gcaacatgcc gcgcgccttt | 38160 |
| tccttctact tgctaacgag cgcgcagcgc gggtacgacc tgcgatttag ccgcaacccg | 38220 |
| tcactctttt ttagcggcga cgcgctcaac tgtccgcttc tcaacgagcc caacgtgttt | 38280 |
| tcgctcacgg tgcacgcgcc ttacgatatc cacttcgggg tgcaaccgcg gcagacggtg | 38340 |
| gagttggact tgcgctacgt gcagatcaca gaccggtgtt tcttggtggc caacttgcca | 38400 |
| cacgaggacg cctttacac agggcttagc gtgtggcgcg gcggcgagcc gctcaaagtc | 38460 |
| acgctgtgga cgcgcacgcg ttccatcgtg atcccgcagg gcactcccat cgccacgttg | 38520 |
| tatcaaatca ccgagggcga cggtaacgtg tactcgtaca atcaccacac ggtgtttcgg | 38580 |
| cagatgcacg ccgccggagc aaccacgttc tttctgggcg acatgcaatt gcccgcggac | 38640 |
| aactttctca cgtctcccca tccctgaccc tccgtccgtc ctcctttccc gacacgtcac | 38700 |
| tatccgatgg tttcattaaa aagtacgtct gcgtgtgtgt ttattaacta ttcctccgtg | 38760 |
| ttcttaatct tctcgatctt ttggaggatg ttctgcacgg cgtccgacgg cgttttggcg | 38820 |
| ccccccatgc cggcagaacc cggttgcggc cccgtaccgc tcttctgggg cgacgatagg | 38880 |
| tcgaaagcca ccgtttttcat gcccgtcgtg ctcttgacgg gggaacctac ggcggcggtc | 38940 |
| cccgtcgagc ggcgtgattg caaagccgcg ctcgcccccg gtttcaggat ggaggggag | 39000 |
| gccacaggcg gcgcattcga tacgctgctt ttggccgtag acgacggtgg gtaaacggtg | 39060 |
| gttaccgcgg gatacgtcgg cgtggtcgag gcggcccggc tggtgccgga caggcgaccc | 39120 |
| ggcgcgctac cgctcacggg gaccgagggc ggtcgaccta ccaccgcctt gccgcccaaa | 39180 |
| gtaggtttca aagaaggaac accgacgcgg ctgcccccgac ctttcaccgg agacggaggg | 39240 |
| gcactcttgg ccggggacgg agaggctgac gaaaagcatgg acagcggcga cgtgacgggg | 39300 |
| gacacgacat catcctccgt gggcgacaaa acggacgccg aggctgacgg ctgtcgagcc | 39360 |
| gaagcggaag aggttctcgc gccagaagtc acgttccttg atgacgttgt tttagacgaa | 39420 |
| gccggttgag gttgcaacag cgtggcgggt accgtcgacg gcgtgcccga tacctgtttc | 39480 |
| tctacccttc cctgaaccgg tgtcgacgtc accgtctgcg ctcgggcgga cgcgtgcggc | 39540 |
| gtcgcgactc gcttgcccag caccggtttc tggctcgtgg atgtcgtcgt cattggagac | 39600 |
| gataacttag ctttacgtat tctggacggc gtcgactgct cgggcgtctg actgggaggc | 39660 |
| gaaatgacgt cgttgtaatc ggacgacggt gttgtgtgtc ccaggctgac gacggagccg | 39720 |
| gtgtccgagg agtcgtcgtc ttcctcctcg ctgtcttcga ccggtgactc tgcagtttgg | 39780 |
| tcccttaaag cccaaaccctc atcagcggcg ttctgagacg ctgtttgtgt caccgcggcg | 39840 |

```
cgtggagtcg acggcctccg aggggtggtg acacgttgt tttgagaagt cgtggaagtc    39900
gtaggcatcc tgaagggatt gtaagccagg tgaggattct tgagggccca cgcgcgttcg    39960
cgcggccagt tggcggggtt catatccccg ggcaacggcg ccgtcggagc ccagggcgag    40020
ttaccgttga ccggggtttg ggtacccgcg aaggtaggtg tcggggccgg agcggggggcc   40080 gtggaaggat tgacaggcgt cggcgtgagg atggcagcgc cggcgccagc agggacgtta    40140
actccggcgc cgaacgtcaa cgtcggttgc tcgaacttgt acgcggtggt gacgggcggt    40200
ttggcgctcg tctcggtatc cgtgatgtcc accggcgtgt cggtgaaacg cggatcttga    40260
cggttggggg gatagccatc cgagctgtcg gaatcctcgt cgcccgagaa aagatcccct    40320
cttgtctccg tgagcggcct cacgtcccac gcgctgtccc gacggaccct tcccgggctg    40380
gccttggtta cctgcgggga gacgagactg aaagccgcgt gacgctgttg ttgctgcggg    40440
atgttcaagg gaccgctggt cggtttctga ctgcccgagg ataacatgcc gctgaaaatg    40500
ctggaaacac cgttgccact agcggcgccc ttgccgctag ttcccggttt cttgatgggc    40560
gtaaagatgt tttctcgtc atcatcatcg tcgtcgtcct catcggcact ggagccaaag      40620
agcctccggg aggcgcccgg tttacgtgtc ggggcggcg gttgctgctg acgttgctgc     40680
aggttctgct gcctctcctc ccaagccttc agctgctgtt tctcacgctg caccacctcg    40740
tcgtccaccc gtttctgccg ctcgcgacgc ttttcctctt cgtcgtaata gccgacggcc    40800
gccgaacggg cggcgtgggc gtcggcggcc ggtgccagag aaccatgggc ctcgaagcgg    40860
aacggtttgt gtcccttcca gggactggcg atccagctcc agccgtccag cggctgcgtg    40920
gggacatgtt tcttgggtac cgacgagaag gctgaaccgc cgccgagcga gaggagattg    40980
gcgtcatcgt caaactccaa cgacggcggg cgcgcgccca aaaggtgtg cgccgactgc     41040 gggaagctgt ccacgtagat gtcaaagtcc tcgatgagca gctccagcag cgtgtcggcc    41100
gagtcaccgt tttccacggc gtgtttgagg atattgcgac agtagttgga atcaaaggaa    41160
aggcacatgc gcagctcctt gaccagcagc ttgcagcgct cctgaatgcg cgccagacat    41220
ttgcgctcca gctcctccca agacctgcgc acgttcatga tgagacggcc cgtgtacacg    41280
agcttgttga cggcgttgac cagcgccgtg ttggcgtgcc ggtccaggtt aaggtcgagc    41340
ggtttcacgc agaacatgtt acggcgcaca ccctccaggt tttcttcaat gcgctgcacc    41400
tccgtatcct tgaggtgcac aaaagcgatg ggttccgtct ggccgatggc tgtgaccagc    41460
gtctcgcgca ccgacatctt ggccagaatg accgcgctta cgagcgcgcg ctccacaatc    41520
tcagcatcgt ggcgtacgtc cgtatcgaat tcggtacggt ctagcacagc caggtggtca    41580
cgcgccttac cacgatcacc gaacgggtaa gtgtagccgc gacgcgccac ggccgcgcaa    41640
cgcacctcga actcctcgag aaccgaggag aggtcggggt tgtggaaacg cagctcgcgg    41700
tagtatccca accaaagcat gagctcgttg aacagcaccg tacgccggtg caggcgtttt    41760
tcgccacatt ttttcaggat cttggggtgt gcctcgagat ccacgtcggg cttttgcgtg    41820
agatggcgca gaaagttgac cagggccacc acatcgcgcc gctgtagacc gataaactgc    41880
aaactcatgc tggcttttct ccagaacccg gaagcgtcgt cgccccggac tgcgcccgcg    41940
gtctgctatt cgtccacgat ggacaccatc atccacaaca ccacggtgag cgccccacct    42000
agagggaggg ggggtagttt aatagcggag gcggatacgc ggttttcact ctggcaccgc    42060
tgacttgttt cttttgtttt ttgctccgtg tgcttgttcc gcctagaacc gcagtaccag    42120
tactccgcat gtcaacagta cctgtaacat gacggagacg ctatccgcca tccgcactac    42180
```

```
agaagccgtg atcaacacgt tcatcatttt cgtgggcggc ccgctcaatg ccatagtgtt    42240
ggtcacgcag ctgctcacga accgtgtatt gggctattcg acacccacca tctacatgac    42300
caacctctat tccactaatt ttctcacgct caccgtgctg cccttcatcg tgttgagcaa    42360
ccagtggcta ctaccgcta gcgtgacttc gtgcaaattc ttgtcggtaa tttattactc    42420
aagctgcaca gtgggctttg ccaccgtagc cctgatcgcc gccgaccgat accgtgttct    42480
tcataagcgt acctacgcgc ggcagtcgta tcgctctacc tatataattt tgctattgac    42540
ttggtttgcc gggctgatct tttccatgcc cgcggccgtt tacactacag tagtgataca    42600
taatggtaca gatgagaata ccaatgggca cgctacctgc gtactgtact tcatagccga    42660
cgaggtgtac acggtactac tctcgtggaa agtgctgctg acgctagtgt ggggcgccgc    42720
gcccgttatc atgatgacgt ggttctacgc cttcttctat tcaaccgtac agcgcgcatc    42780
tcagaaacaa aggagtcgca cttaaccttt cgtcagcgtg ttactcatct ccttcgtggc    42840
gctacagacg ccttacgtgt ccatcatgat tttcaacagt tacgccacgg ccgcatggcc    42900
catggactgc gaacacctga cactgcgacg caccattggc acgctgtcac gtctggtacc    42960
ccacctacac tgcctcatca atcccattct gtacgcgctg ctgggtcatg acttttttgca    43020 gcgcatgcgg cagtgtttcc gcggccagtt gctggaccgc cgcgctttcc tgagatcgca    43080
gcagaatcag cgagctacag cggagacaaa tctagcggct ggcaacaatt cacaatcagt    43140
ggctacgtca ttagacacca atagcaaaaa ctgcaatcag cacgccaaac gaagcgtgtc    43200
tttcaatttt cccagcggta cgtggaaagg cggtcagaaa accgcgtcca acgacacatc    43260
cacaaaaatc ccccatcgac tctcacaatc gcatcataac ctcagcgggg tatgagcttt    43320
cctgttactt tattcagaaa gcaccagaac ccgtcgccat ttcccctcat atacggtaca    43380 cgtcccctg atctgtcatc acggtacaca gatttcgccc gactgcggac accgacggcc    43440
aatcgcgtgg cgtaggagtg gcgccccggc ttcattataa cgccacgtcg gagcccctgc    43500
gcgccacaac gccgtccggc gcaacttctg tctcggcacg gtacgataaa aacgacgtcc    43560
cccgtcgacg ttgttttctc cgagcggtga tcgttcccgt ccctctcctc cctccgcggc    43620
ccccacggcg gcggccccgct cgcacggacc tatactatta ccgccccacc gccgtcgtcg    43680
tcatgaactt catcatcacc acccgagact tctccaacga cgattcagtc ctgcgagccg    43740 ccagatgcg tgacaacgtg gcaggctcga tttccaaagc gtacaagggt acggtacgcg    43800
ccgaaggcaa gaagaagctg ctgctgaagc acttgcccgt gccgcccggc ggctgctcgc    43860
gccgcaacag caacctcttc gttttctgca ccgagcgcga ctaccgcaag ttccaccagg    43920
gcatcgcaca gctcaagcgc gcgccggccg aactggaccc ccacgagatc cagcaagtca    43980
cggccagtat ccgctgccgc ctgcagccca gtctccgcga gccgcccacg ccggccgacg    44040
agctgcagac ggctgtgtcg cgcgtgtgcg cgctcttcaa ccagttggtt ttcacggccc    44100
agctgcgcca ctactgcgag caccaggaca aggtggtgag ctacgcgcgc gacgagctga    44160
ctaaacgctg cggcgaaaaa tcggcgctgg gcgtggaggt gcatcaactg gtagccctgc    44220
tgccacacga gcgccaccgc gaactgtgcc acgtcctcat cggcttgttg caccagacgc    44280
cgcacatgtg ggcgcgctcc atccgtctca tcggacacct gcgccactac ctgcagaaca    44340
gcttcctaca cctgttgatg aactcaggtt tggatatcgc gcaagtcttc gacggctgtt    44400
accacagcga ggcctaccgc atgctcttcc agatcggtca tacggactcg gtgtcggcgg    44460
ccctggaact ttcacacagc gcggcggccg ggccgcccga ggccgatgag aacaacgacg    44520
aaggagagga ggacgacgac gagctccgtc acagcgaccc ggcgccgctt cacgagtcca    44580
```

```
agaagcccccg caacgcccgt cgtccccgca cacgcgtgcc gcctcacgag caaaagcccg   44640
aagaaaacga ggaggaagaa gaggagctgt ttccctcctg caaggcaacc gcagcattcc   44700
tgcgggcaga accctccgtc tccaacgacg acggcaacgg cggcgaacgc tgcgacacgc   44760
tagcgaccgc cctgcggcat tgcgccgacg aagaagacgg acctctagcc agccagaccg   44820
ctgtgcgggt cgccgcgacc ccctcacctt cagtcacccc agcccttacc cccgtcacgt   44880
cccccataac cccgttgtgt atttaacgtc actggagaac aataaagcgt tgatttctca   44940
agttccgctc tggttttggt ttcgttttca aagggagccc catcatggcc caaggatcgc   45000 gagcccccatc gggcccgcca ctgcccgttc tccccgtgga cgactggctc aactttcggg   45060
ttgacctgtt tggggacgag caccggcgcc tgctgctcga aatgttgacc cagggctgct   45120
ccaactttgt ggggctgctc aactttggcg tgcccagccc cgtatacgcg ctggaggccc   45180
tggtggactt ccaggtgcgc aacgctttta tgaaggtaaa gcccgtggcc caggagatta   45240
tccgtatctg catcctcgct aaccactacc gcaacagccg cgatgtgttg cgggacctgc   45300
gcacgcagct cgacgtgctg tactcggagc cgcttaagac gcggctgctt agagggctca   45360
tccgactctg ccgcgctgcg caaaccggcg tcaagcccga ggacatcagc gtgcacctgg   45420
gcgccgacga tgtgacattc ggcgtgctaa aacgagcgct ggtccggttg caccgggtac   45480
gcgacgcgct ggggctgcgc gcgtctcccg aggccgaggc acgctatccg cgcctcacca   45540
cctataacct gctgttccac ccaccgccct tcaccacggt cgaggcggtg gatctgtgcg   45600
ccgagaacct gtccgacgta acacaacgtc gtaaccgacc gttgcgctgc ctcacctcca   45660
tcaaacgccc gggctcacgc accctggagg acgcgctaaa cgacatgtat ctgttgttga   45720
cgctgcgaca cttacagctg cgacacgcgc tggagctaca aatgatgcag gactgggtgg   45780
tggaacgctg caaccgtctt tgcgacgcgc tttactttg ttacacgcaa gcccccgaaa   45840
cgcggcagac tttcgtcacg ctggtgcgtg ggctggaact tgcgcggcaa cacagcagtc   45900
cggccttcca gccgatgctg tacaatctgt tgcaactact gacgcagctg cacgaggcca   45960
acgtgtacct ctgcccggga tatttacatt tcagcgcgta caagctgcta aaaaagatcc   46020
aatcggtctc ggacgcccgc gagcgcggcg agttcgggga cgaggacgaa gagcaggaga   46080
acgacggcga gccgcgtgag gcccagctcg atctcgaagc cgatcccaca gcgcgcgagg   46140
gcgagctctt tttcttctcc aagaacctgt acggcaacgg cgaggttttc cgcgtgcccg   46200
agcaacccag ccgctacctg cgtcgacgta tgttcgtgga acggcctgaa accctgcaga   46260
tcttctataa cttccacgaa ggcaagatca ccaccgagac gtatcacctc cagcgcatct   46320
atagcatgat gatcgagggc gcctctcggc agacgggcct gacacccaag cgcttcatgg   46380
aactcattga cagagcacct ctgggccagg agtcggaacc cgagatcaca gaacatcgcg   46440
atttatttgc cgatgttttt cgccgtcctg tgaccgacgc agcttcttcg tcgtccgcgt   46500
cttcgtcgtc gtcctcagca tctccgaatt ctgtttcgct gccgtccgcc aggtcgtcat   46560
ccacacgaac caccacgccc gcgtccacgt acacctcggc cgggacttct accacgggcc   46620
tcttgctctc ctcttcttcc ttgtcggggt cgcacggcat tagctccgcg gacctggagc   46680
agccgccccg gcaacgacgc cgcatggtca gcgtaaccct cttttcgccc tactcggtag   46740
cctacagcca ccaccgacgt caccgaagac gacgcagccc gccacccgca cccgagggc    46800 cggcccacac acgtttccag ggaccccgaca gcatgccgag cactagctac ggcagcgacg   46860
tcgaagaccc gcgggacgat ttggccgaaa atctacggca tctctaaacg cggttttcct   46920
```

```
cttttttatac gtgtctgtct caggacgaga cgttgatatc aataaaaata ccgtcaacgt    46980
ggttttctaa cagtgtggtt ttctttattg accagcggag tacacagttt acgagtaaaa    47040
aagacaggga aaggttatat aaaatgctgt gttatataca aaaacatgca cataaacaaa    47100
cgggaccacc gtgctcgtca tcctctcctc aatcagttgt tcatgtaggc gtgtggcggg    47160
gtgaggggcg gcatgccgtt ggcggcgccg ggaataatgt gtcgtcgacc ggcgtcgcac    47220
accttgaaac gccgtcggcg cacgcagcgg tcgcaggacg ggatatccca gaggaagccc    47280
atataggtct cggggtcctc gtcgtgaaag cggtaagaga gttcaaggtg gtgcaatgag    47340
cccgtccgag ctcgcagctt ctggcgaaca ccctccacgt catcggtgca cagcgacagt    47400
gctgggctgt cacacagggc ctgaagctcc tgcggccaca ggtgcgtggc caggggcgag    47460
tccgtcgtca ccagtttgac gcagtgcatc aggttctcgg tgatggcgtc gtacaggcga    47520
ctctcagcct cctcgtgcgt catcacgttc cgaggcagcg acagctcgtc gtcgtcatcc    47580
tcgtcaaaca tgatcatggg gtcagggggtt ttttgggat gttgacaggt gggtgtcttt    47640
tccagacgca cgatggcctc acgccggctg ctgaaacggt ggtttcggtg tcccttcttt    47700
cccatgacgc aggtgaacat aaccacgtcc tcggccagac ggtagacggc gtccatggcg    47760
gggtcgtagc cgtagacgac gccgaaagtg tccaccaaga cgtactggcg tacgagaaac    47820
tctttgcgtt ctggcacctc gtggcccagc gcgcccaaca gctggtgata acaggtgatg    47880
cgcggcacgt acggatcat gagctccatg gtctggatgc tgccgcccgc gcggacaacg    47940
ctgaaggatg tttccttgaa cttcataacc tctgtgttgt gggtccagaa ggcgaaatgg    48000
gtgtcgggac actcatcgaa agggtcgtcg atgctgtagg aagcgtagcc ccgcttggtc    48060
acctcggccg acaggctctc cacgtcaccg cggtagagca tgacggcgtt ccagtagtcg    48120
tcgtactgca ccatgggccg ctggtagtcg cgcatagtgt ggaagtggtc gcagtgacga    48180
aagccatgcc gcagaaagtc cttcatggtg gccgccagct cgtagacgca gtcacgcaga    48240
tcatcgtagc agtagatgcc gccgcgctgc ccgatgagca cgatgagttg gtagcgcata    48300
aagcccggac cctcgacgaa gccaaagggg tgcaggtatt cctgacagca gacgtaagca    48360
cctggtggaa aaataagaaa aatccacaca cgttgaaaac acctggaaag aacgtgcccg    48420
agcgaacgtc ctcttttccag gtgtcttcaa cgacgtgggg cttaccttgc gaacagacgg    48480
tgcccatctt gccacgaagg ccccagggg cgctgcgcga acggagctgg atgaagcagc    48540
gttcgggcca ggccacgtgc agccgggtgc cgcattcctg ctccagaaag tcgttgagac    48600
cgttaaagtc cccggctcgg atggcgatgc agccgtaggc catcaacgtg tcccgtaggt    48660
cgtccatgac ggactcctct accttcgctc gccgacgctg cgcttctcca gccaccgctg    48720
cggtcgacag actcctccgt ccgccttcgg agaactacgg cgcggcgca cggcctttat    48780 agacactatc agcgttgacg tcagacgatc cgatgaacgt cgttttttgt gctggaactt    48840
ccctcgtccc gacaaatgta gcggaaatct tcaagcaaat cgcgacgaag tccgatgagg    48900
aggatgcaaa agaggctgag caacgcgatg ctgcccgccg ccacagtaca tatgctcaac    48960
aacgcccagt gtcccaacgc gcgacttttg gctcggagga gagccgaacg gcggttttc    49020 cacatgatga taacgtagt ccaataccctc catccttcgc attccgatgt ccacatggga    49080
agcgatgtca tgttagttcc cgtaaacgtt gtgttttttt tattgttttt cgtaagctta    49140
acgctcctct tgagaaatcg cggacacatg tcttgtagaa aaatataatc actttccgca    49200
tataccgtta agattgacat cacagtgatg gtgttgttttt ctgaagaagt cacgttatcg    49260
gtgacgttgg tttcctccca atttacggat gactcaaacg gactcgtgcg cgccagtgct    49320
```

```
cgcaatacgt aactgcggcc ggtaaggtta agcgtcagct gtcccatggt aatattagtg    49380
tcatttgtaa aacacgcaac ctccccgtag acctcggtga cgttgatatc gcggctctcg    49440
ttcaggatgc gcaggggaaa ccagccttcc aggtggtact gaaaaccaaa cgtgagcatg    49500
acgctgtgcc actgccgacg tgattgccga aacgttacgt ttaaaggcag ttttgattcg    49560
gctccggcgc aggggccgtt gtagatttgc gtatgattgc acgtgcagtt taaccggcag    49620
ttcatactcg tggcgttgga agtgacgtta atgtccgtac cgtggtacgt acatcggaca    49680
gaaacaccgt atcccgtgct ccaaaacagc gtcaacaaca gccacacaga cacctacgtg    49740
gggacgacac gggacttttt attgacgagg actcatgttt acaccctccc ctttcccata    49800
ggtaaaaacc cacgtttata acacacgttg ttttaccctg aaaccgcgc ggcccgtgga    49860 cgcgacaaaa aaccgcggca ctagaaagaa aatgaaacaa gtatgtttat taagcagcat    49920
gtggggctaa taggggggat aactgaggta tagcaactat taaaaaatac tacaaaaaaa    49980
aaaagctgaa catggtcatc tagcagcaaa gttctccttc tagaccacga ccaccatctg    50040
taccacgtcg ccctccccgg ccgtgtacat cacatccttc accacgaccg gcggcaacgg    50100
cggcgacgag gacaactcgc tctcgacgga ggccgggacg acagaggacg gggggtggt    50160 ggcggcggag gacggagggg tggtgacggc agcggggtct tcttccgaca cgggcgacgg    50220
cagactcggc ggcgcggaca gcacccgttg cgccggagcg tgagaaggct gaaccccggt    50280
ggcctggatg tgggccaacg aattggctcg cagcgaatcg cgatccacga aggtcatagg    50340
aatcttccct tcgcggatcc gccgctcaga ttccaggatg gcgcgcacgt agctgttcac    50400
cgatttggca aaagtgcgcg gcccctccgt attcttgtcg cgacgcgctt ccaacacctg    50460
cttttcgtag tccagctggt ggaagaccat caccaggtcg tccatggtgt gcgcgtgctg    50520
acggacgtgg gagcgcacct ccaccgggaa cagagcgttc caatactcca gcactatggc    50580
accgtgccag aactgcgcca tgctgggagc caggaaaaac aggataccgg agtcgtaggc    50640
gaacacgtcc cacttgggcg tcatgaacaa caccagctga cgcgtgggcc gcctcgaagc    50700
ttcctcccag gcctcgatga ccccgaacat gatgagctcc tggtccaacg ggggcagtg    50760 tcgctccagc caactgatct tgctcaggtt catctgcaga aactcgtagg aggggtcgca    50820
gatgcacacg tagagacccg agtcgtgccg cagcctggct ccgcgcttca tcagtttcct    50880
caccgcgtag cgaagcgcca ccttgcccaa cgccgacgcc tggatcagtc cccccacgtc    50940
catctgcgtc tgtcgccact cggcctcgtc cagcaggctc atgatagcgg cggtgctatg    51000
cgtggtcgta gtcatccttt ctatccttct ctatgaatag cagcaatagc ggtaaagtcc    51060
cttcttatac tatcccggag tctgtggttt ttttgtttac ccctgcttac tggtgagact    51120 gctggggcc gttgtgctgc agcagccgag cttgtcgccg ccgttgccac aggaaccggt    51180
gcctccgcag ggccttttg agggcctcgc aggcttctcg cgcaagtcct gagaggccct    51240
cggcgtcgat ggggttcacc tcgggcgtcc gagcctcgtt ttcttcttct tcatcctccc    51300
tttcctcctc cgtgtcctcc cgctctgtgt cctccgttac gctcctcctcc ccggcctcgg    51360 ccaagagcgc ggccaccaag tccacggacc gctcggtctc cgagttctca ccgtcaatga    51420
cgccatgttg gcgcgtaac cggtgccgag aacgccgggt gagcgcacat gctttttct    51480 ttcttaacca aggcgggaga ggatcttcaa ggcgttttcg ctggatccag cggtagctaa    51540
agtaccaaaa ggccagcagg cccacgctac ctaacagatt cacgtagact ggagacataa    51600
ttaaagaaag aagtgaaacc cgcgtgtggg tctcacgtcg tcttgaaaca ccgtcttata    51660
```

```
tacatgaaga tgccggacat gacgcgccca agacacgtgg ggttttcccc ttaggcgacc    51720
cgatttctta agatgttttt catcttcgca cgcgatgtac tacatcaaag ggtcggctga    51780
ccgaccgcat tgacgcacag tttccgagta cgcgcgtctc ggagcacctg acggtgagcc    51840
acccagctca cgcggatagg gaacaacact gacgtgaggg gcaattcacg tcactgacgg    51900
ctgacgggaa taagacgggt gagggatttc cacctttttc ttaagtgtga ctgtccttac    51960
ggtaaatcgc acctgtgacc tcttaacccc tcctccctgg tacccgataa cagtgaaaaa    52020
cacacaccac acgtcacgac accgatcgat tttctttatt cttagtgtga tgataggtaa    52080
gggcactcgt gaggatgtgc agttatcatt atcaagcctt cttcaaggcg tagtgatgat    52140
cgttgggcag aaccccaggg ctcctagcga tctgggaata aaggaggag aacgagccca    52200 gggccagaat gcccacagtg tacatggccc aggtctccag accgaacgtg gcgggtcgca    52260
gcttcagatg gtaggccacc cgctccgaga gttgtgaatg ctcgttcagg caacaggact    52320
gcagatgggt gagcccaaaa gcgctttcgt ttacgccgcg cacgtgcacc gtctgggccg    52380
gacaatcctg gtgttgcgcg cgaaagtggt ccaggcagga gactccgtct gcgcggcgat    52440
gtgtgttgtt acccacttca atcaacagcg tgttaacggc aagatgacgc gagaacgcga    52500
cgacggtgtt gctggaggtc tggcggcagc agtacaaagg cgcccgtcat gaagacgtag    52560 gcagggaat tcccatattt ttatggcttc ttttaaaagt ctgtgtccga ctccattcgg    52620
cgcttttccc aaaccgtggt ctcctcgtcg tccgactcgg tacccaggag atggtaagtc    52680
ttttgccgca cgtagaaagc tttcaacgtg gagcaaaaga tgagaataaa gaccccgaaa    52740
acgaaacaaa ccacgccgat catgccgatg cagacgttca tgtcgacgta gccggcggtg    52800
ctgttggcgg tgcggcaaaa gagtgtcatg tcgtacgtgc acaaaaaaca ccacacacca    52860
caggccaggt cgtagcgtag ttattattcc gtagcagcaa tgatggtaca gtcaagcaca    52920
tgatctattt cccgttatcc cgatgttgac accgtccccg ttgtattgga attgtcccgg    52980
ttaatcacca cggtgaacac cacggccaag aaaatgatcc ctaatatagc gaccactaag    53040
agagcaaaag tccatttcca gccgttgtca aagtacgccc ccgtggtggg atgcatggtg    53100
gcgggcattt ccatcatatc catgtcgaac gtgtgtcgcg gcgacggcga actaaccagg    53160
cagtacgggg gtcgataggg cggtgggctg cagtcaggtg gtggcggcgg tggcgtggaa    53220
accgtcgtcg ggcacagacc catggcctgc tcgtaggtgg ggggcgcgtc gtcgtgatcc    53280
cggtcgcgga gcatcggcgt gggctccatg tcggtggcag tgacggcgac ggtggtaact    53340
gtggtggaga cggtaccgac ggcgtccgcg gctcaccttc gagcaaagag ccccttcttt    53400
ttgcgcaaac gacggcaaaa cagttctctg ggacagccgg tggcgcggta agcgggtgcc    53460
acgctttcag ggtgtgtaaa acagtcgcgg gcgaagcagt agttgttgca gaaccgcaag    53520
aacccgacgc gaaagaagcc caggagtccg cgcgccagaa agtgcgcctg ccgcgtctcg    53580
ggatgcacgc cgaagacggc gccgctctcg ttcaccagta tggagatgtc caggcgctgc    53640
tgtgactcca ccggcacggc ccgcaccaca aatacctgca gcacgttcag cgagcacgtc    53700
tcttttaacc agttgccgtg ggccggatcc tcgtaagtct ggctcccgtt caagacgacc    53760
gtcgtcagcg cctcattacc gtctcgccag ctgaagatgg aaccctcgcg cttcatgcac    53820
aggcgccaca gggccagcag gtcgcgcgcc aacatgaact cgcgacccac gtcgccgccg    53880
gtctcgaagc ggacatagcc cagttcttcg cgcagcggcg cgtagttgcg caggccctcc    53940
tgcacgaagc cgcggaaacc ggaccgcgac accaggtaca gcgattccac cacggggcag    54000
tagacgtaga cgcggccgcc ctcgccgatg agtatgggta gcggtgggcg gccgatggct    54060
```

```
tcgcaacgac tcacagtgcc caccggcagc aggaacttgt cgcagcacag gaaggtcttc    54120
tccaaacctt taatattgag atgtccaaag tagccaacgc gtaacaggtc gcagtaggtg    54180
aagaaccaac cgttcggcca gttgagacgc agcaccgtgc cactgacgcg acgaaccagc    54240
ttctgcaggt ccttgcgggc gtcggcggtg acagagcagc ggaaggtctc gttgaccagc    54300
tcgacagcca gcgcgtcctc cagcgtgcgt tccttcatct cgtcgttaat gctctggcgg    54360
cgccgccgga tttcgtcgaa acgggccgcg gaggcggcga ccgacgcgga ggtcgtccga    54420
acgccctctg tgacgctgtc gtccggccag tcaagaaagc taaggctggc gctgcgccgc    54480
ctaaagtgtc cgatccgcgc gggacgtcgc tgaggaacgg tggctggtct gctggggcgg    54540
gtacggccgc gggtgtccgc ggacacgtta gttatacacg ggattgagtc acgtggcacg    54600
ttgccagctg aaaccgccgt cgtctccgcc ggcgttttct ccatcgcggg accgcgccgt    54660
gcgcgcaggc cgcgtgcccg ggcacgcgct ctagccgcac ttttgcttct tggtgttagg    54720
gacgaactcg aacgttacag aatcctcgct gtcgctctcc tctttcgcgt cgttgaagta    54780
attgccggag ttgcgatcca aaccgccgcc tcctcctcct ccgccgccgc ccgatccacc    54840
tttggacgtc aggtaactgg tgatcttgtg ctgctcgtat ttttccttgg aggaaagacc    54900
gtgatcgtga tcaccgccgc cgccaccgct gctcattttc gcgtaccgg aaccaccgcc    54960 gccaccgcgg tcgtgcttct tgccgccacc gccgccacct cctcccagac cgccgagacc    55020
catgggctcg ttcatgagat cgttatccag acccgggccg tcgtcgtgca gaccgccggc    55080
attggccagc gaagagaggc tgccgccacc accgccgccg ccacgcgact tgccgctgtt    55140
cccgacgtaa ttttttgtcga agggatcgcc acgctggaaa ggttcctcgg tgagaaagtt    55200
ctccacggcg aacagaccgt tgcggctggc cacgtacaac agcgtgtcgt gctccgtaac    55260
tatacgcagc gtgcacggta gtttggtgac ggcgcaattg agcagcgtct ggtagaagtt    55320
cttcagctgc acgttgatac gcatgttttt tacgccgtgg aaactgacgc ggttattggc    55380
cgtgaattcc agctcgctgc cgttggtcag gatgaacttg atggccggcg gaccggcgtg    55440
caccagaatc tgcacggtgc ccgtagggca gggcgctttt ttaacgttac gcttgacgcg    55500
ggtatgcggc ccgatccact taagcaggtc ggccaccacg ccgaaatcga gatccacgtg    55560
cacggccgaa ttctcgcttt cgcgcacaat gtcttgaccg tgcacgcagg ccgagctgaa    55620
ctccatattg aaatcgggcg cgcacatgga gatcttggcc gacaggtccg agatgtcctg    55680
cacgtagaac ttggtcaggt ccttgctgga ggtcaggtac ataaaattgc cgagcagcgg    55740
cgtggaattg ttaatggtct tgggctgaaa cgacttgtcg gtgatgtaga ggcatgagct    55800
gttaaaagtg attttttgaca cgcaatgact gcgtaccgtt tgcaagataa gcgacggcgt    55860
gggcaagaag gtaaccgtgg tgttctcctt gagcgcacgg atcacagatc gcagctgctg    55920
gatagccgtc ttgtacggct tcagccgcag cgccagcgtc ggtggctccg agaggcgcgt    55980
cttgcgatcc atcccggaca gcgtgcaagt ctcgactaag gagcgggcgc gagcgagcga    56040 aagtttttata gagagcacac acgacgaccg ggaacgctgc gaagacgccc ggcgtctaat    56100
aatacagccg cgccgagcca gcgggccccc gactaagagg cacagtactt atatactccg    56160
accttaaagc gccagtggta ccacttgagc atcctggcca gaagcacgtc gggcgtcatc    56220
cccgagtcat agtagaaaac cagggccacg cactggtcca caaacacgct caggttcacg    56280
gccgccattt ccacgtcgtt ttggatcgcc ggcgccgcct ggaacagaca ctgcgtcgcc    56340
ttgccctcct cctggtgctg ctccaaccac gcgtaattca ccacgggcac gcgcagcggc    56400
```

```
ctccgcacca cagtggggaa gtaacactca cggttgggcg ggcacaatga ccacaccgtc    56460
tcctcctcga acacggtgcc gcgcgaagcc catactgacg gcgtcacgcc ccacagatgc    56520
gccacctcgt cgtcgggacc caccgccaga aactgacagt tgcgcaatcc gaactcgagc    56580
atgtcggcgc gcagcgcttc ccagcgcgcg ctggcgatgg agagccgcgg caaccgatac    56640
aattcgaaaa tgaatttgcc ctcttgatag atggtgcgtt cgaaccattc gcagcgtggc    56700
aaacccgact tgcacaaatc gacgctagcg cgcaccgcgg caaagtacat gtgctcaaag    56760
atgcgctcga tcaagtccca agaggcaaag tacgtaaacc ctaaccgcat aagcgcagtg    56820
tgcaggccag ccacgccgat gtgcagcgga cgcagttttt ccagcgcgct ctctacccac    56880
cattcggacg ccgacattag cgcgtccaag cgcgcgttgc cccaaaccac cgcctcggtc    56940
accaactcgc gcagcacgct caaatcaaag taacgtcgcg tgttcccaa aaccacgtcg     57000 ggtagatgca gcttctgctc gtcgctacgc gcaaacacgc agcgagccac gttcaccgtc    57060
agccgctgca ccggcatgtc acactcgcca aagtggcacg acgccatatc gggactcaag    57120
cacggcggca ggcacacgct gtcggccata atcgagtact tgactacgtg atggacaaag    57180
accaccgagg cacggccctt gagcgcgcac agcaacatct ttttcagaaa atcgtccgtg    57240
ttcacgacca ccttggggca cgattgctcg cagcgcgaat actctttctc gaaagccgac    57300
tcctgaccca gatccgagag ccgccgggag acaggccgcc cgaacagcga gtagcgctgc    57360
tcacgcgcac ggtagcgctt cattaacacg ctaggcacgt tgaaagcgta gcaaaccccc    57420
gtcaactccg acgtgctttc tttgagaata aagttaatca cgcggatagc ggccacgtcc    57480
cacatgtcca caaacacacg taccacgggt cgatgcacct ccttctcgcg tatcaaatcg    57540
cagtatcccc ccaggcaacg aatcacgctg ttcacatcgg cgttgagtcg cgttacgttc    57600
accgacacag aaacgccgca actcaaggta ctcatccact tgcacatggc cgcccaactg    57660
gcgtcacgcg agaaagggtc ggccgagatc agaaagtcgt actgcggcac gcgatcgaaa    57720
cccacggtag acatggtgaa ggtagacagc gacagctgcc catcgcgaca gcgcttcaac    57780
accgagtcca acacttcgcc ctcgaaacgc gcatccagat ggaaacgata gatgcgcgag    57840
tgcctactgt tctcgatagc ggccgtcaac gccacggcga tgcgcaaaaa cacgccgccc    57900
gggctctcgt cctgtccatg cagttggcga cacaccttat ccaaacacaa aatagccgcg    57960
tacaagcccc agcaaccggc caattccaca aaacgcgccg tctcctcggc cagcttgggt    58020
agatcctcca tgtgacgcag cacaaaacgg cgcaccgact catcgcacag ctccgaagcg    58080
taacacagtg gcgtgcggct ttcgcgcgcc cagttggctt tgaaataaaa gcgacccaac    58140
agcagatcgc aacgcggcga gtgacgaatc agacagggac cgtggcgcat gatgagctga    58200
aacagcctga aactgcccaa accggcactg tgtcgcgaca cggtgtccat ctcgcgccac    58260
agcgcgttcc tgtcggacgg cagctcccgc gccggctcct gtacgccaca aaagcgaaac    58320
ttgccccagt agccgtgaca atgacacttt ttgcccatca acatgcgcgt agcctgtatc    58380
ggcggcgata ctttgcagag tgaagccccg aaatcgtcct cctcctcgac actgtccagc    58440
tccatcctgg tcgcgccggc cggattgaag gtgctcagac cgctactcac acgtccaccg    58500
cgactgggca cggcgggacc gctgtcacgc gtcaacgaca gcagacacgg cgtgccgtcg    58560
ggagacggcg actcgggacg ccaactgacg acgccgccac cactcgtaaa acccgctaca    58620
cacgctacgc cgctcgatac gttggtattt ccagcggacg cttccttgtc accccgggc    58680 agcggcccct cctcgagctc gctgtcatct ccccgtag tatcagcggc ggcctctgcc      58740
gacgattcct ccgtctcggt ttccgagccg cggcttggaa tcctacctgg ccggcaccga    58800
```

```
tgtgcgggca ccgaggacac ccgctgttcc tcgtccgcgt cagccggatt cataagttta    58860
cgaggaaaat aacaaagaaa tcaggtagat ttcaataaag tgagtctaga tggcgccgat    58920
aactacggtt tataaagtct gtgtgcgatg tgtttatttt tttcttctgt gtctcctccc    58980
cgtatgctgt cagcgccgct cagacgaatt ctcgaaagtc tcccaattcg acgctaaagt    59040
tgtccaaacg gacgacggac agtttgagtt ctttgtgtac caggaacgag gtgtgaatgt    59100
cgtcagccag gcaccagccc agcttttgta tgacccggt acacagaggg atctggcgcg    59160
ggcgcgtgat gcgacggttg acaaagctac agcgctcgcg ggcgaacttt ccgcgtgcaa    59220
cgtcgaccag ggtctgccag tgtgcgatgc tggaggtgag cacgtagatg ccgggacgtg    59280
tttcgggccc gtcatagtca tagacgatga ttaaatacac gtattgcagc cgtccccggg    59340
tctcttccca cgtcaggtac atgtctttcg gtatcatcaa cgcgaacacc tccgttttga    59400
gcgtgttgta aaggtagccg cgcatgacgc aggtgagcaa cgaggtgatg cccagcgaga    59460
cggtcttaac gcagcccagc gtctcaaggc ggcggtgcag cagatgcggg cccaggtcca    59520
gccactgcag cgcggcgcgc gcggccgagg ccgtgtacac gctttcgagc aggcagcgcg    59580
tgctggccga gacgttggag gcgcgaatgc ctaacaggta gaggctgatg tagaggtgtc    59640
gcggcgagtc gcaacccgtc tccatgcgga tgagcagcgc gcccggctgc gcctcgaact    59700
ctaccaggcc ctcgggcacg aagaaacgcg ccgtgagcgc ctggtgatcg gcgtggtaga    59760
ggtagcgcac cgatatagta tttacctcgc gtttggcttt gagcgccgtc actagttcat    59820
tgtcctcgtc ggccgggtcg cgcggccgtt tggccaccgc gcgcgcgtcc atgatggcga    59880
ggcgcacggt agatttcaaa aagttgatag agcagctgcg ggcacgggcc acggacaaag    59940
cggaggcgtt aaataccgtg agccaattgg agatcggcgc ggtggatgcc caggacgtga    60000
ccgcgagcgc cgtgcgcgcc ttcgtgggtg cgttgccgag ctcgggctac cactttggct    60060
tcgtgcgtca gaacgtggtc tttttacctcc taagccacgc cacggtacag acggcgcgcg    60120
acccgctgta cgccgccgag cagttgcacg aacagctgga ccgcttcctg cgacaccagc    60180
acgacggcgg cggggacgag gaccggttgc cgttctacca caacggggcc acgctgacgg    60240 cttttccagaa gctgttgcag accctgcgcg agatccagac cgtaatagcc gaacagagcg    60300
gcggcaccgc ggcggcggcg gacttgatcg ccagtaacaa cgcgtcggcc gagcgccgcg    60360
gcaagaaggg cggttcgagt tccgggggcc agcagccgct ggtccgccgg tgatcacgc    60420 agctggaaac ggctgccacg gaggcgcggc cctacgtcaa ttgtcgcgcc gtggccgaac    60480
tcctggacct gacctaccag cggctcatct actgggcctg cacgctcatg ccctacgtgt    60540
tgtttcggcg cgacaccgac accgaactgg acacggtgct tctgatgcat ttttttttaca    60600 cacgctaccg ttcggttaac ggcgatttgg ccgtggagtt tcaaaactac gtcaagaaca    60660
gcgtgcggca catgagctct ttcgtcagtt ccgatatcga cggcgaccag aagcccggtg    60720
ccgaacacat gcgtgacgtc agctacaagc tgttcgtggg taatctgcag gcgcgtgacg    60780
ccagcggcct catgtttccc atcattagca gcgcatctc caccgtgaac ctttacctgt    60840
cgcccgaacg tatgttttc cacccgggtc tgatctcgcg tctgttgagt gaggaagttt    60900
cgccgcgcgc caacctagac gcttacgcgc gcgtgtgcga tcgcgtgctg gaagaccact    60960
tgcatacgcc gcgacgcgtg cagcggctac tggatctgac gcagatggta acgcgactgg    61020
tggaactggg tttcaatcac gatacctgcg cggcctacgc gcaaatggcg ctgatccagc    61080
cggccagtca gaagagctcg ctctttgtca gcgagattcg cgagaaactc atacagatca    61140
```

```
tctacaatttt ttacacgtttt ttcatgtgcc tctatgtgta cagccccacg ttcctgttcg    61200
accaccggcg gcggttgatt ttggagcagc atcgatccac gttgatcggc tccaaggagg    61260
aactacagca cgtctggagc aacgtgacac tgaacgtcaa tacgcactttt gcggttcagt    61320 acacggaaga agactttgag gcacatacga agggtgccac ggaggcagag cgcgagtacc    61380
tgtatcggga cctgcacagc aagtggggcg tgcacctgtt taccttgcgt ccgtctcgcg    61440
gcgcggccgg cgcggcctcg cctttgcctc cgcttgacgg cgtcacacgc tccgacatct    61500
tacgcgaatg cgcgctcgtt aatctgaacg aaggccgcgt caactacgcc tccctgctag    61560
ccttcagcca tcatcccgag ttccccagca tcttcgcgca gttggtggtg gtaactgaat    61620
tttcggagat ctttggtatc ccgcagggcc tgtttcaagc cgtgggttcg ccgcgtcttt    61680
tcgcgctcat tcagctgtgt cgtgtattgt tgcccgagca ggtgacgctg taccagaacc    61740
tggtctccat ttacaacctg accacctttg tcaagcacat cgacgccgcg gtttttaaga    61800
cggtacgcga ttgcgtcttc gacatcgcca cgaccctcga gcacctcagc ggtgtacccg    61860
tcacgcccaa tgtggacctg ctggccgagc tcatggcgcg ctccgtagcg cataacctgt    61920
acaccaccgt caacccgctg atcgaggacg tgatgcgcag cagcgccggc agtctgagaa    61980
actatctgcg acacacgcga ctctgtttcg gtctggcgcg cggccgggcg cgcctctcgg    62040
aggacggcgt gacggtgtac gtggaggtac agggtcagta cggactgcgc gtacctacca    62100 cgcgttttcgt agaacagttg cgcgaactgg ttcgccgcga tcggctgttg gccgagaatc    62160
tgcgcggctt aaacgagcgc ctgctgagtg ttcgcgtgcg cgtacgtcag atcagcagcg    62220
acacagagga agtaagccga cacgccaagg gtcaccgcac ggtggcccag atgagcaagg    62280
cgctcaaaaa gacggcctcc aaaatcaaag tgttggaaac acgcgtgaca ttggcgctcg    62340
agcaggcgca acgttccaat ggcgccgtcg ttaccgcggt gcaacgcgcg ctagccgtct    62400
ttgacgtact aagtcgcgag aacttggaac gccgcggcgc acagctctgt ctgacggaag    62460
cgacgagcct actgcaccga catcgcgcgc tagcgccgat gacctggccc gcgggcacgg    62520
gcgttgcggc ggcggccgaa gcggatcgcg ccttacgcga gttcttggag gcgccctggg    62580
aatcggcgcc ccaaccgccg cgactccgca tgacgcccga caccgatcac gaagaatcga    62640
cggcaggcgc gacgtccgta ccggaggtcc tgggtgcgcg ctacgaaccc gcacacctgg    62700
ccgcgagcga cctattaaac tggtacatcg tccccgtaag ccaggcgcag caggacatct    62760
tgtcttcgat cgacccgccc gccggctcga catcggtgtc cctgccgccg gcctcgccat    62820
gaaagtcacg caggccagct gccaccaggg cgacatcgct cgctttggag cgcgagcggg    62880
caatcaatgc gtctgcaacg gcatcatgtt cctacacgcc ttgcacctgg gtggaacgag    62940
cgccgtcctg cagaccgagg cgctggacgc catcatggaa gagggcgcgc gtctggacgc    63000
gcggctagag cgcgagttgc aaaagaagct gcccgccggc gggcggctgc cggtctaccg    63060
actgggcgac gaagtgccgc gccgcctgga gtcgcggttc ggccggaccg tgcacgcgct    63120
ctcgcggccc ttcaacggca ccaccgagac gtgcgacctg gacggctaca tgtgtccggg    63180
catcttcgac tttctgcggt acgcgcacgc caaaccgcgt cccacctacg tactcgtcac    63240
cgtcaactcg ttggcgcgcg ccgtggtctt caccgaggac cacatgttgg tctttgatcc    63300
gcacagctcc gcggaatgtc acaacgccgc cgtgtatcac tgcgagggtc tccatcaggt    63360
gctgatggtg ctcacgggct tcggcgtgca gctatcgccc gctttctact atgaggccct    63420
ttttctctac atgctggatg tggcgaccgt gccagaggct gagatcgccg cacgtttggt    63480
ctccacctat cgcgaccgcg atatcgacct caccggcgtc gtccgagaaa gcgcggacac    63540
```

```
ggcggcgaca acgaccaccg ccgcaccttc cttacctccg ctgcccgacc ccatcgtcga    63600
cccgggctgc cctcctggcg tggcgcccag cattcccgtc tacgatccct cgtcctcacc    63660
caaaaaaaca cccgagaaac gccgcaagga cctcagcggt agcaaacacg gaggcaaaaa    63720
gaaacccccg tccacgacgt ccaaaacact ggccaccgcc tcctcctcct cagcgatagc    63780
ggcggcctct tcttcgtccg cggtaccacc gtcctacagc tgcggcgaag gggccctgcc    63840
ggccctgggc cgctaccaac agctggtcga cgaggtagag caggagttga aggctctgac    63900
gctgccgccg ttgcctgcca acaccagcgc ctggacgttg cacgcggcgg gtaccgaaag    63960
cggcgctaac gcggcaacgg ccacggcgcc gtccttcgac gaagctttcc tcaccgatcg    64020
tctccagcag ctcatcatcc atgccgtcaa tcagcgctcg tgtctgcgcc gccctgcgg     64080 tccgcaatcg gcgcgcagc aggcggtacg cgcctatctg ggcctatcca agaaattgga     64140
tgcctttctg ctcaactggc tgcaccacgg cctggatctg cggcgcatgc acgactacct    64200
gagccacaag accaccaaag gcacgtactc gacgctggat cgcgcactgc tggagaagat    64260
gcaagtcgtc ttcgatccct acggacgtca gcacggcccg gcgctcatcg cctgggtgga    64320
ggagatgcta cgctacgtgg aaagcaagcc cactaacgaa ctgtctcaac gactgcaacg    64380
tttcgtaacc aagcgaccga tgcccgttag cgacagcttc gtctgcctgc gacccgtaga    64440 cttcagcgt ctgacgcagg tcatcgaaca gcgacgtcgg gtgttgcaac gtcaacgcga     64500
ggagtaccac ggcgtttacg agcacttggc cggcctcatc accagcatcg acattcacga    64560
cctagacgcc agcgatctga accgacgcga aattctgaaa gcgctgcagc cgttggacga    64620
caacgccaag caggaactct ttcgcctggg caacgccaaa atgctagagt gcagatgga     64680 cctggaccgt ctgagcacgc agctgctaac gcgcgtgcac aatcacatcc tcaacggctt    64740
tttgccggta gaggacctga agcagatgga acgcgtcgtc gagcaggtac tgagactctt    64800
ttacgacctg cgcgacctga aactgtgtga cggcagctac gaagagggat tgtcgtcat     64860 acgcgaacaa ctgagctacc tcatgacggg cactgtgcgc gacaacgtac cgctactgca    64920
agagatcctg cagctgcgac acgcgtacca gcaagccacg cagcaaaacg agggtcgcct    64980
cacgcagatt cacgacctgc ttcatgtcat cgagacgctg gtgcgcgacc cgggcagccg    65040
cggctcggcg ctgacactgg ccttggtaca ggagcagcta gctcagctgg aagcgctagg    65100
cggcctgcag ctacccgaag tgcagcagcg cctacagaac gcgcaactcg cgctaagccg    65160
cctctacgaa gaggaagagg aaacgcagcg tttcctcgac ggactctcgt acgacgatcc    65220
gcccaccgaa cagaccatca agcgacaccc acaattacgc gagatgttac gtcgcgacga    65280
acagacgcgt ctgcgactca tcaacgccgt actgagcatg ttccacacat tagtgatgcg    65340
actggcgcgc gacgagtcgc cgcgaccgac gttttttgac gccgtcagtt tgttgttgca    65400
gcaactgcca cccgactcgc atgaacgtga ggatctgcgt gccgccaacg ccacgtacgc    65460
gcagatggtc aagaaactgg agcagatcga gaaagccggt accggcgcat ccgaaaaacg    65520
cttccaagcg ttacgggagt tggtttactt tttccgtaat catgaatatt tctttcaaca    65580
tatggtcgga cgactgggcg tcggacctca ggtaacggaa ctctacgagc gatatcaaca    65640
cgagatggaa gaacagcacc tggaacgcct ggaacgtgaa tggcaagaag aggccggcaa    65700
gctcacggta acttctgtgg aggacgtgca gcgtgtcttg gcccgggcac cgagccatcg    65760
tgtcatgcat caaatgcaac aaacgttaac caccaagatg caagactttt tagacaagga    65820
gaaacgtaaa caggaagaac agcaacggca gctactggac ggctaccaaa aaaaggtgca    65880
```

| | |
|---|---|
| gcaggatttg caacgcgtgg tggacgccgt taagggcgag atgctctcca ccatcccgca | 65940 |
| ccaaccactg gaggccacac tcgagctgct cttgggccta gatcaacgcg cccaaccgct | 66000 |
| actagacaag ttcaaccagg acttgctgtc ggcgctgcag cagctgagca aaaaactaga | 66060 |
| cgggcgaatc aacgagtgtc tgcacggcgt gctgacgggt gatgtagagc ggcgctgtca | 66120 |
| cccgcaccga aagcggcta tgcaaaccca agcctcgcta aaccacttgg accaaatttt | 66180 |
| gggtccgcaa cttctgatcc atgagacgca gcaggccctg caacacgccg tccatcaagc | 66240 |
| gcagttcatc gagaagtgtc aacagggcga tccaactaca gccatcacgg gcagcgagtt | 66300 |
| cgagggcgac tttgcacgct accgcagcag tcaacagaag atggaggaac aattacaaga | 66360 |
| gactagacaa cagatgaccg agactagcga gcggctagat cgctcgctgc gccaggatcc | 66420 |
| cgggagcagc tccgtcacgc gtgtacccga gaaaccttc aagggtcagg agctggcggg | 66480 |
| tcggatcacg cccccgcccg ccgacttcca gcggcccgtt ttcaaaacgc tgctagatca | 66540 |
| gcaggccgac gcggcccgga aagcgctcag cgacgaggcc gatctgctga atcagaaagt | 66600 |
| acagacgcag ttgcgacaac gcgacgagca gctgagcacg gcgcagaacc tgtggactga | 66660 |
| tctggtcacg cgccacaaaa tgagcggcgg actggacgtg accaccccg acgccaaggc | 66720 |
| gctgatgaa aagccgctgg agacacttcg cgagctgttg ggcaaagcca cgcaacaact | 66780 |
| gccgtacctg tcggcggagc gcacggtgcg ctggatgctg gcttttctgg aggaagccct | 66840 |
| tgcgcaaatc accacggacc ctacgcaccc gcatcacgga agcaggaccc actaccggaa | 66900 |
| cctgcaacag caagccgtcg agagcgccgt gacgctagcg catcaaatcg aacaaaacgc | 66960 |
| ggcctgtgaa aattttattg cacagcatca agaggcgact gccaacggcg cgtccacgcc | 67020 |
| gcgggtcgac atggtccagg cggtggaagc gatctggcag cgactggaac ccggacgcgt | 67080 |
| agccggcggc gccgcgcgtc atcaaaaagt gcaggaactg ttgcagcgct tgggtcagac | 67140 |
| gctaggcgac ctagaactgc aggaaacgtt ggcgacggaa tactttgcgc tgttacacgg | 67200 |
| catccagacc ttcagctacg ggctggactt tcggtcgcag ttggaaaaga tccgcgatct | 67260 |
| gcggactcgt tttgcggaac tggccaagcg acgcggtaca cgtctctcca acgagggagc | 67320 |
| cctgcccaac ccacggaaac cgcaggcgac gacttgctg ggcgcccttta cacgcggtt | 67380 |
| gaacgcactg gaacgacacg tccagctggg tcaccagtat ctgctcaaca agctcaacgg | 67440 |
| ctcatcgcta gtctataggc tggaagacat tcctagcgtg cttccgccaa cacacgagac | 67500 |
| cgaccccgcg ctgataatgc gcgaccgcct gcgtcgtcta tgcttcgcgc gtcaccacga | 67560 |
| caccttcctt gaagtggtag acgtcttcgg catgcggcaa atcgtcacgc aggcggcga | 67620 |
| acccattcac ctggtcaccg attatggcaa cgtagccttt aagtacttgg cgctgcgaga | 67680 |
| cgatggccgg cccctggcat ggcggcgccg ctgtagcggc ggaggactca agaacgtcgt | 67740 |
| caccacacgt tataaagcca tcacggtagc cgtggccgtc tgtcagacat tgcgcacttt | 67800 |
| ctggccacag atctcgcagt acgacctacg accctacctc acgcagcatc agagccacac | 67860 |
| gcaccccgca gagactcaca cgttgcataa ccttaagctc ttttgttatc tggtgagcac | 67920 |
| cgcctggcac cagcgcatcg acacgcagca ggagctgacg gccgccgatc acgtaggcag | 67980 |
| cggcgagggt ggtgacgtag gggaacagag accgggccgc ggtaccgtgc tgcgcctgag | 68040 |
| tctgcaagag ttttgtgtac tcatagcagc tctgtacccc gagtacatct acaccgtcct | 68100 |
| caaatacccg gtgcagatgt cactacccctc cctcacaact cacctacatc aggatgtgat | 68160 |
| acacgcggta gtcaataaca cacacaaaat gccccccgac caccttcccg aacaggtcaa | 68220 |
| ggccttctgt atcaccccca cccaatggcc cgccatgcag ctcaataaac tgttttggga | 68280 |

```
aaataaactg gtacagcaac tgtgccaggt aggcccgcaa aaaagcacac cgcctttagg    68340
caagctatgg ctctacgcca tggccacgct ggtctttcca caagacatgc tgcagtgtct    68400
gtggctagaa ctgaaacccc agtacgccga gacatacgcc tcggtgtccg aattggtaca    68460
gacattgttt cagattttca cgcaacaatg cgaaatggtg accaggggt acacgcaacc     68520 gcagctcccc accggagagc cggtgcttca gatgatccgc gtgcgacgtc aggacacaac    68580
caccacagac acaaacacga ccacggagcc gggactttta gatgttttta ttcaaacaga    68640
aaccgcccta gactacgcgc tgggctcctg gcttttcggc ataccgtgt gtctcggcgt     68700 gcatgtagcc gacctgctga aaggccaacg tatactagta gcgcgccacc tcgaatacac    68760
gtcgcgagac cgcgacttcc tccgcatcca acgctcccgg gatctcaatc tcagtcaact    68820
gctccaggac acgtggaccg aaacgccgct ggagcactgc tggctacaag cccaaatcag    68880
acggctacgc gattacctgc gtttccccac ccgcttagag tttattcccc tagtcattta    68940
caacgcacag gaccacaccg tcgtacgcgt gctgcgaccg ccctccacgt tcgaacagga    69000
ccacagtcgg ctggtgttgg acgaggcctt ccccaccttc ccgctgtatg accaagatga    69060
taactcatcc gcggacaacg tcgctgcgtc tggcgccgct ccaacaccgc cggtaccttt    69120
caaccgcgtg ccagtcaata ttcagtttct gcgtgaaaac ccgccaccca tcgcgcgagt    69180
tcagcagccg ccgcgccgac atcgtcatcg agcggccgcg gccgcagacg acgacggaca    69240
gatagatcac gtacaagacg atacatcaag gacagccgac tctgcattag tctctaccgc    69300 cttttggcggg tccgtctttc aagaaaaccg attgggagaa acaccactat gccgagatga    69360
acttgtggcc gtggcgcccg gcgccgccag caccagtttc gcctcgccgc ctatcacggt    69420
gctcacgcag aacgtcctca gtgctctaga aatactgcgg ctagtgcgat tggacctgcg    69480
acaactggcg caatccgtac aggacactat tcaacacatg cggtttctct atcttttgta    69540
accgacactg acagtagcgg gtaataaaaa caataggctt tttatcgttt tttatgttac    69600
aaaacaacgt atcactttta cggtgattta ttcttgctat tctttttccc cttgggctgt    69660
cagcgccggg tgcgcgacac ggctaccatg cgcaacaggt ccagcttaaa ggcgcacttg    69720
tcattaaaca ggctggacat gcgcgtgtac ttgctcagca tggtgccaa caccgggtgg     69780 gtggcctctg atatctcggt cggcagctcc aaaacgacgt tgacgacgtg acggtgtttt    69840
tcgtcccgct tgttggccac cgtgggtccc ggcgcggtgt tagacatggg gcaggccgtg    69900
gggggaggac gaagaggaag ccgctgctaa accgccgcgc gcctgctgca caatgtggcc    69960
gccgacgtgg caggcggtct gtttaaccag cgcgcagccc cgacacagcg gggcgccgtc    70020
ttcgctttcc aaacagctgt cgcggtactc gcccgtctga cagcgcgcgc acagcaggcc    70080
gtgcccgtgc gaagtgaggc gcaggagacg cgggaccgtc acgccgcgta ccaccacagt    70140
ggagtcgcag gtgcgtgccg cgcagggcag aatgacgtcg aaagccagcc ggtgatcgta    70200
cacggcacaa gccgcgttga ggcccagcac ggctttccag cccacgcgta cgcagcgctg    70260
tccaaagagc gtctcggaga cgagctcgta gacgcgctgc cgcaccaccc gctgactgcc    70320
gcagagcgag cagtgcacga gctcggcgtg cgtgttgaag atgacgctct tttcttgacg    70380
gtcccgataa tagaacatcg agttgagcgg aaagttttgc tggcagtgta gcttttcctt    70440
acccaggttg aggcagtgtc cgcactgccg acagaccacg gccaccagcg agcgcgcgtc    70500 cagatgcgc tcgcacttga gtcgacacag acaccagagc ggcaggtcga tgacgctgcc     70560
gatgaggccg ccgcgcagcg cggcgctgag tgcaaagagg acgatcttgg tgggctctac    70620
```

-continued

```
gtgacgcgcc tgctgtccgg cgcccgcgtg tcctaccgcc gcagctgccg ccgtcgagcc   70680
tcctccgcgc gtctcgtcgt gcagacccag tgcccgcaac ggcaccaggt atcgcggaca   70740
cgtgtcgcaa aacgtctgca ccgcttgtcg ggccagtacg tagagcgggt ttccgcaggg   70800
taccttcccg gcgtgccggc gcaaggctgc gatgaggccc cgcagctgcg gcgaccgcgg   70860
ctgccgttgg tgacaccact ggttacggtg gtatacggcc aaatcagcgc gggcgtcgaa   70920
gcgcttggcg cgtagtagtg ctaggcacgg cgagctggtg gggtgaagca cgggcagccg   70980
aaggtccacc ccgaaaagga aacggtgaag gtcacctagc agcgaggagg tgacaccgtc   71040
caacaacgcg tgcagccgct cgggcgggta gagccgcaga cggcgcagca ggtagtcggt   71100
gtcgtagcgt tcgaaacgca gaaaggccat cgtgcggacg gccacggtgt gcagacagtc   71160
catgctgtag acgtaagcga gaaacacaaa gtagggcttg gtcataacca tacgctgaaa   71220
aagcgccgtc accgcctccc gctcggcctg ccgacacacc agccattcgc gcaggaagcg   71280
ttggtagaga cggtcgccca gctcgcgatt cagaaagcgc ttatccgtca cgaagagatg   71340
aaggacgcaa gaacgtggca cgtgatgcac cagctgctgc tggaggaccg ccgacgtctg   71400
cgccgcaaac tgcgccggtg gctgcgacgt ttctaccgcc gcttcctccg gctgcagcgc   71460
accgcggccg atcaccagct gcacatggaa atggtcctcg tgaacgcaga ggggcgcgaa   71520
gagacggcgc agagcctggt ggaactcctc agtcgcggtg tgcggagcgt gtcggagacg   71580
gcgattggcc atgaccgcgc cacagcagag ccagcaccag caggagagcc agcaccagcg   71640
ggcccagagt cgcgaagcgc gcgggcagcc acggcccaga ctgcggtcgc gatggcccgg   71700
agcgcgctcg ccaccacgat gacggtgccc aacgataacc agtccgctcc aaggacggcg   71760
cgcacggcgg agacggcgga tgacggtgat gggtcgacac ccctcgccga cgactcacgt   71820
gctcctccag aggccgacgc gcggaccctc cgacatcctg gcccgccgct gccgctgccg   71880
ccttcccttc tcccgccaga gccagcaact cctcctcctc ttcatcagcg tctccctcgc   71940
ttgcgcatcc gcatcgtccc atacaggcct cacaacgaca cagccgccac gaccccgccg   72000
ccatgggtgg cggcggcggc cgaggcccgg cagcggcgcc gccagcggcg accatggtgg   72060
gagagcaact cggatgacga ggaggaggag gaggggagga tgcggtccga gaggaccgct   72120 ttccccgccgt tcgcgtgagc gcggccgaca tgcgggcgcg ccacagggac ggaccgctgc   72180
cgctgtgact gcttacggtg acgtggttcc ggaccgccaa cgacgtcgac gcggcttttct   72240 tggcgtacag ctcgcgcagc agattctcgt actcgccctc gttttcgggt ccgaaggcga   72300
tgagctcgat gttgaagacc gacgccgaat tggatttgcg caccacgcac ttcgtcagca   72360
ctccgtaggc cgagggcttg atctcctcga tgtccttgag cgtgacgatg agcgactcgt   72420
tcaccttaag cacattgaac tcacctacgt ggcgcgccgg cgagacgagc ttgacgggcg   72480
ctcgcacaaa acagcagagg gagacggcac agccagtgtt tttaaagata aacaaggca   72540 cgtggtctgt gcggctctcc cagtagctga gcagatactc gacacaatag accgtgtctg   72600
tcttgagcat ggcgtcgcac accgagtaat tggggttttt acagatgagg ccggcgtcgg   72660
tgacgcgcag ctcgctggga cccaacttga ggatacgccg cgtggcctgc accagatcct   72720
gatggagaac cttgttcatc tccatcgcac cgacgccacc gccgatttat ttacccggcg   72780
ccggctcgtc ttttccctcc aggattccgt taatgtccat gagcttgctg acgatcgccg   72840
ttaatagttg cgtcttctca cggaggatct ctccgtgact gcaggtcgcg cagtcgccgt   72900
gcacgtactt gaggaaggcg gcgtacttct gacccgcgtt cacgaaattt aagcgcgcgt   72960
ccagagaggg cagcaacaga tcgtagacgc gcggcagcat cggctcgaac tgtaatagca   73020
```

```
gatcgtcgtc aagatcgggt agcgcgtgcc cgtcttcacc gtcctcgtcg tcaccacctc    73080 cccctcgag cccaccgctc gtaccagccg cgggctccgc gtcctcgtcg atcaccagcg     73140
gtcgcgtcgg caccggagaa tccacgtcat cctgcacgtc gttttcctcc tctccgtcgt    73200
catcgtccga aaacggcacc cgctgcttag cccaggacat tcttttccg cgtcctcaat     73260 cagcggcgcc gatcgccatg aatccgagta cccacgtgag cagtaacggc caacgactc     73320 cccctcacgg gccccacacc acgtttcttc ccccgaccag cccggcccg tccaccagct     73380 ccgtcgccgc cgctaccttg tgcagtccgc aacgacaggc cgtttcacgt tacagcggct    73440
ggagcaccga gtacacccag tggcactcgg acttgacaac tgagctgcta tggcacgcgc    73500
acccacgtca agtacctatg gacgaagcgc tggccgccgc ggcggccgcc tcataccagg    73560
tgaatcctca acaccccgcc aaccgttacc gtcattacga attccagacg ctcagtctcg    73620
gcacctcgga ggtagacgaa ctgctcaact gctgtgcgga agaaaccacg tgcggcggca    73680
cgcaatccac cgtactcacc aatgcgacca acaccactaa ctgcggcgga gccgtcgccg    73740
gcagtagcaa cgcaggaccc gccggcgctt cggccgcctg cgacctagat gcagaactgg    73800
ccggcctcga aacctcggcg gccgactttg aacaactgcg gcgactgtgc gcgccgctgg    73860
ccatcgacac acgctgtaac ctatgcgcca tcatcagcat ctgcctcaaa caagactgcg    73920
accagagctg gctcctcgag tacagcttgc tgtgcttcaa atgcagttac gcgcccgtg    73980 cggcgctcag cacgctcatc atcatgtccg agtttacgca tctgctgcag cagcactttt    74040
ccgatctgcg catcgacgac ctgttccgac accacgttct cacggtcttc gatttccacc    74100
tgcacttctt cataaatcgt tgctttgaaa acaagtggg cgacgcggtt gataacgaga    74160
atgtcaccct gaaccatctg gccgtggtgc gggccatggt catgggcgaa gacacggtgc    74220
cttacaacaa gcctcggcgc caccgcaac agaagcaaaa accaaccct tatcacgtcg     74280 aagtgccgca agaactgatc gacaactttc tagaacacag ctcacctagc cgcgaccgct    74340
tcgtgcagct gcttttctat atgtgggccg gcaccggcgt catgagcacc acgccactca    74400
cggaactcac gcacactaag ttcgcgcgac tagacgcgtt atccacgacc tcggaaagag    74460
aagacgcaag gatgatgatg gaagaagagg aagatgaaga aggaggagaa aaaggaggag    74520
acgatccggg ccgtcacaac ggcggtggca ccagcggggg gttcagcgag agcacgctaa    74580
aaaagaacgt gggtcccatt tacctatgtc ccgtacccgc ctttttacc aagaaccaaa     74640 ccagtaccgt gtgtctgctg tgcgaactca tggcctgctc ctattacgat aacgtcgtcc    74700
tgcgcgaact gtaccgtcgc gtcgtctcgt actgtcagaa caatgtgaag atggtggacc    74760
gcattcagct ggtattggcc gacctgttgc gcgaatgcac gtcgccgctc ggcgcggcgc    74820
acgaggacgt ggcgcgctgt ggactcgaag cgcccacctc gcccggaggc gactcggact    74880
atcacggcct gagcggcgtc gacggcgcac tggcgcgacc cgacccggta ttttgccacg    74940
tcctgcgtca gcgggcgtc acgggcatct acaagcactt tttctgtgac ccgcagtgcg     75000
ccggcaacat ccgcgtcacc aacgaggccg tgctcttcgg acgcctgcac ccccaccacg    75060
tccaggaggt gaaactggcc atctgtcacg acaattacta tataagtcga cttccgcgac    75120
gtgtgtggct ctgcatcaca ctcttcaagg cctttcagat tacaaaacgc acctacaaag    75180
gcaaagtgca cctggcggac tttatgcgcg atttcacgca gctgttggag agttgcgaca    75240
tcaagctggt ggaccccacg tacgtgatag acaagtatgt ctagcgtgag cggcgtgcgc    75300
acgccgcgcg aacgacgctc agccttgcgc tccctgctcc gcaagcgccg ccaacgcgag    75360
```

```
ctggccagta aagtggcgtc aacggtgaac ggcgctacgt cggccaacaa ccacggcgaa    75420
cgcccgtcgc cggccgacgc gcgcccgcgc ctcacgctgc acgacctgca cgacatcttc    75480
cgcgagcacc ccgaactgga gctcaagtac ctcaacatga tgaagatggc cattacgggc    75540
aaagagtcca tctgcttacc cttcaatttc cactcgcacc ggcagcacac ctgcctcgac    75600
atctcgccgt acggcaacga gcaggtctcg cgcatcgcct gcacctcgtg cgaggacaac    75660
cgcatcctgc ccaccgcctc cgacgccatg gtggccttca tcaatcagac gtccaacatc    75720
atgaaaaata gaaactttta ttacgggttc tgtaagagca gcgagctact caagctctcc    75780
accaaccagc cgcccatctt ccaaatttat tacctgctgc acgccgctaa ccacgacatc    75840
gtgcccttta tgcacgccga ggacggccgg ttgcacatgc acgtcatctt cgaaaacccc    75900
gacgtgcaca tccctgcga ctgcatcacg cagatgctca cggcggcgcg cgaagactac    75960
agcgtcacgc tcaacatcgt gcgcgaccac gtcgttatca gcgtgctgtg tcacgccgtc    76020
tcggccagca gcgtcaagat cgacgtgact attttgcaac gcaagattga cgagatggac    76080
attcccaacg acgtgagcga gtcctttgag cgctacaaag agctcattca ggagctgtgt    76140
cagtccagcg gcagcaacct atacgaggag gccacgtcgt cctacgcgat acggtctccc    76200
ttaaccgcgt cgccgttgca cgtaacttcc accaacggct gcggcccctc ctcctcgtcc    76260
cagtccacgc cgcctcatct ccatccgccg tcgcaggcga cgcagcccca ccactactct    76320
caccaccagc ctcagtctca gcagcattat caccgtcccc agtcaccacc gccgccgctg    76380
tttctcaaca gcattcgtgc gccttgacac tgtacggcag aaaagccggc tccaagtgca    76440 agcgccgcg cagcaccatg tgcaaaaact tgtccttgcg cgcggtttcg ccgccgggaa    76500
agacgggcga cagcacgttg gttacagcct tgagaacctg ctcaaagtac ttgtcggcgt    76560
gaatgggcac gccgtgctcg cgcacgtagc tcggatcttc ggctacctcg tagttgcaca    76620
cggccgacgg tggtttccgc gccctcttct ttggcggctc tcctcctctc ctgttgctct    76680
cctctacccc gccgccgtca gcgtcgtcgt ccgtgccatc aatcgcgtcc gaccgggaaa    76740
ccacgccggt ggttacagaa tcaccgttgt cagaggaacc ctgcggcgcc gtccggacac    76800
cgggcgccgt cagtacgtaa aagacccgat ccccgaccga gggtagctcc tcagaacggg    76860
ccgccagtcg cttaatgacg gcaatgtgcg gcaggttaga ttgacggtac aacgagatgt    76920
ccttagaaag caccgacgaa agcaccaggt cctcgacacg cacacggtgc aggtacagat    76980
cgtcgcgggc ctgcaccagg cggcgcaaga tacgccagaa accgcgtggc acgccgtatt    77040
tcttgacttc atcgagtgag aggcgcgaca ggcgcacggc tgcttccgag acctcgcgat    77100
cctcaaagag cagcgagagg acgtcacgcg taacgcccctt gacgaactcg caagccgtct    77160
tgcgcaccag atccacgccc ttcatgctca gacccgaggc gccctccact ttgccgatgt    77220
aacgtttctt gcagatcatc ataagagaga cgaagacctt ttcaaactcc agcttgacgg    77280
gctccacaaa aagacaggcc gtcacgtagt gcgccaggct gggcccacgc gccaccagag    77340
cctgcggcgt cagaccacga aagcggacaa acacgctgtc cgtgtccccg tagatgaccc    77400
gcgcctccac ccgccgttcg tccgagcccc ctgacgatgt tcgagccccc tccggtaacg    77460
tgctgctctc ctccgaatcc ccctcccgcg ttcccaccac ataatcttct tgattaaaaa    77520
aattgtgcaa aaacacggc tctgaaaagt tgtctttgat gaaccgcgcc gtgcgctcta    77580
gcatgtcgcg accgatgcgc gtgatgctgg cggcgatggg cagacacggc atcatgccgt    77640
tgaccacgcc ggtaaaaccg tagaaagcgt tgcacgttac tttgagcgcc atctgttcct    77700
tgtcgagcaa catacgacgc acagggtctt gacactcgcg catgcattcg cgcacggcac    77760
```

| | | | | |
|---|---|---|---|---|
| gccgctgcga | aacccacttg | ttgagcagtt | ccgaaagcac | cgagacgcgc accgaagcgc 77820 |
| gcacaaagcg | gtgggtcacg | ccgttctcta | gcgtgacgct | gtatacgtcg gcagggtcca 77880 |
| cggggtactc | gccacccggc | accaacaggg | tggagtagca | gaggttgtgg gccatgatga 77940 |
| tggaagggta | gaggctggca | aaatcgaaca | cggccacggg | gtcgttgtag taacccacct 78000 |
| cgggctcaaa | caccgtggca | ccttggtacg | aaaccgccgc | ggtaccgccg cgccgtgac 78060 |
| tgtcgttgga | aacgccgacg | ccgccactac | tgccggagcc | gacgctgaaa acgccgacgc 78120 |
| tgctactact | gttactacca | gagccgggtg | aaacgccgtc | ctgactcgac ggcgcagatt 78180 |
| gcaagggcgg | cgacatctga | aacatagccg | ccacagaacc | cgcgtcgccg ggcacggcgg 78240 |
| cggtagagat | gatagcggcg | ttaggtgaca | cggcaacgct | attcgtttcg ggcaccgtcg 78300 |
| tacctttgct | gtagtggttg | ggcaagataa | aatcgcggca | ggcgcactcg tctagcagcg 78360 |
| aggtgtagat | acggatctgc | tgtccgtcaa | agatgacacg | ccgcaacgga attttagcca 78420 |
| gccgcgcgat | ggccccggcc | tcgtagtgaa | aattaatggt | gttgaacaga tcgcgcacca 78480 |
| atacggcgtc | ctgcagacag | taacggccta | cctgggcgcg | gccctcggca ttagccacga 78540 |
| aacaacgcgg | gatgtccttg | taggacaggt | catccttgcg | ttccgcagg taaagctcgg 78600 |
| ccatagtgtt | gagcttatag | ttgggcgagt | tagtcttggc | catgcatacg gggtacatgt 78660 |
| cgataaccac | cgaacccgca | atatacacct | tggtggcggc | cgtgctggcc ggattattgt 78720 |
| gagaagccga | gggaaaggcg | gcggcgtact | gccgcttaaa | acccacggcg gggctgtgta 78780 |
| aaaaaaaacg | gccgccctgc | gccgtgggca | acttgcagaa | gcgctgcgag tccaccttat 78840 |
| acaggtactc | gaggcgcgtg | aggatgtact | tcaagtcaaa | agagttgatg ttgtaaccgg 78900 |
| tcacaaaggc | cggcgcgtac | cgttgaaaga | aaagcataaa | gcccagcagc agctcgtatt 78960 |
| cggaagggaa | ctcgtagacg | tctacgtctg | ggcccacctg | cccgcaggtg ccgatcgtaa 79020 |
| agagatgaag | acccgagtgc | ccaaagatca | cgccctccga | ggtgcagccc cgaccatcgt 79080 |
| tcccgtttgg | gattccctga | tccacggcgg | tgtttcctcc | cgtctcgtag cacacgcacg 79140 |
| agatctgaat | gacaatgtca | tcagacttct | cggcgcaggg | aaaaccaccc tcgccgctca 79200 |
| tgcactcgat | atcgaaggac | aggcaccgat | aacgcggcca | cgagctgtcg tcgggcacgg 79260 |
| ccaccaggtc | ggagacatcg | cagtcgacct | cgatatcaca | agtcgacgcg cgaccctgct 79320 |
| gccgccagtc | gtaacgattc | acggaacacc | agccgaacgt | ggtgatccgc cgatcgatga 79380 |
| ccaaacgcgt | cagcggatcc | acacggacct | cgtacacggg | aaaaccctgc tccagcagat 79440 |
| actcgccgat | ctttctagcc | atggtccagt | tgctgataga | cacacactgc aaatcgggca 79500 |
| cgggtcgcgt | cccgtacccg | tagatggagg | tcttggtggc | cggcgtgaca gacacggcgt 79560 |
| atggcgtccg | cggttcgggc | actagttcgc | ccacgctggc | aatgacctca cgcagcctat 79620 |
| cggtgtcgct | gtactcacag | taaaagtagc | tgcgctgccc | gaaaacgttg acgcagatac 79680 |
| tgtagccgtg | ttctgtggcc | ccgaagaaac | gcaacacgtt | ccccgaaggc accagatgct 79740 |
| gacgatagcg | cggcgacacg | ttttcgggcg | agtcgaagaa | gagcacggcg tccgtttgat 79800 |
| cgtaggtgtg | aaaacgaata | ggtcccacca | cgcgacccac | cagggtctcg cgccaaggac 79860 |
| acggccaaac | catgtcatga | ctcaacaaat | gtttaatctc | tcgatagaac atgagaggca 79920 |
| accgtcccgt | cttatgcttg | atcaaccccg | tctgaccgtc | gaacatgacg cctcgcggca 79980 |
| cgatctgcaa | aaactgtttc | tgtggcggcc | gcttgcccga | gccctgcgcg gagcggct 80040 |
| gcgaacgctg | acgccggcca | cccgcaaccg | caccgccggt | cacgccgccg ctcagatacg 80100 |

```
ggttgaaaaa catagcggac cgtgagaggc tgacagctta cgaagcaaaa tcacaaagca    80160
aatacacatg cagcacctag atgtccagtt taaccccgta tatcacaagt ctctgtcact    80220
ttttttgtct agttttttt tctcctcttg gttcagacgt tctcttcttc gtcggagtct    80280
ttcaagtgtc ggtagccgtt tttgcggtgt cgcagtcggt ctagcaggtt gggcttctgt    80340
cccttgtcct gcgtgccagt ctgtccgtcc aaagaatctg taccgttctg ctgcgctcgc    80400
tgctctgcgt ccagacggac cagggccaga agcatctggt aagcctgctc gttggtgtaa    80460
ggcggagccg ccgtggatgc atcagacgac ggtggtcccg gtcctttgcg accagaatta    80520
taaacacttt cctcgtagga aggcggagcc tgtaacgacg tgtctttggt gttgcccgac    80580
gtcacggtgg tcccgtcggc ggacaccaga tagggaaaga ggttctgcag cggctgcatg    80640
cagagacgcc gctgtcgagt atagatcaaa taaatgataa tgacgacggc tatgccacg    80700 aggatgatgg tgaaggctcc gaaggggttt ttgaggaagg tggcaacgcc ttcgaccacg    80760
gaggccaccg cgccacccac ggccccaatg gctacgccaa cggcctttcc cgcggcgccc    80820
aggccgctca tgaggtcgtc cagacccttg aggtaggggcg gcagcgggtc gactaccttg    80880
tcctccacgt actttacccg ctgcttatac gaattgaact cgcgcatgat ctcctcgaga    80940
tcaaaaacgt tgctggaacg caattctttc tgcgagtaaa gttccagtac cctgaagtcg    81000
gtgttttcca gcgggtcgat gtctagggcg atcatgctgt cgacggtgga gatgctgctg    81060
aggtcaatca tgcgtttgaa gaggtagtcc acgtactcgt aggccgagtt gccggcgatg    81120
aagatcttga ggctgggaag ctgacattcc tcagtgcggt ggttgcccaa caggatttcg    81180
ttatcctcgc ccagttgacc gtactgcacg tacgagctgt tggcgaaatt aaagatgacc    81240
actggtcgtg agtagcagcg tcctggcgat tccttcacat tcatatcacg cagcaccttg    81300
acgctggttt ggttaatggt cacgcagctg gccagaccca ggacatcacc catgaaacgc    81360
gcggcaatcg gtttgttgta gatggccgag agaatagctg acgggttgat cttgctaagt    81420
tccttgaaga cctctagggt gcgccgttga tccacacacc aggcttctgc gatttgcgcc    81480
agcgcccggt tgatgtaacc gcgcaacgtg tcataggtga actgcagctg ggcgtagacc    81540
agattgtgca ccgactccat gttggataaa tgagttgcat tgttgccatc tgtacttctt    81600
ttggttctat tatgagtaag attcagactg gagcggttgg ccaaacgttc gagttccacc    81660
agagattttt gcttgatacc ttgccagaac accaccaaac caccagtggt ttcaaagacg    81720
gacacgtttc catattttc atatgtttga ttgtatgaag tattgaaaat ctgctgtaac    81780
ttatttatgg cctcatcacg tacacagtcc agcgcagagt cggacatgtt cacctcttgc    81840
ttcttagata agaaagtggc ggtcattttg gcagaagaaa agtgatacga gtcctcggct    81900
tcggaacgaa tggtgcgttc cgaggcttcc cagaaagtga gttgacaagt aacattcttc    81960
tcgtcctgta tatcccagga gatcactgag tccgcacgtt caagaaaagc caccaacctg    82020
tgggtctcta acgcagaatt cggtcttcca aagtcggaga cgatagtgta gttcggaaaa    82080
atgaaaaact tgtcggcgtt ttctccaaaa tagctggcat tgcgattagt tccgttgtag    82140
aaaggagaaa tgtcaaccac atcacccgtg gaagttgcga aaaaatgata gggatacttg    82200
gagcgcgcag tagtgatggt caccatacaa ttcagattac aggtctcacg atagagccag    82260
gtgctgccgc ggctgtgcca ttgatccttg accgtcacgt aacgggtact gtgggtgttg    82320
gaataatcgt cgggcattaa ttgcatggtt ttgttttcat agctgtccct atgataagcc    82380
acgaaaaccg tgcctgctat aacgcggctg taggaactgt agcactgact gtgactgttg    82440
atatgatgaa tctcccacat aggaggcgcc acgtattccg tgttgctgcc cagcagataa    82500
```

```
gtggtgtgga tgtaagcgta gctacgacga aacgtcaaaa ccttctggta gactcgtacc    82560
ttaaaggtgt gcgcgacgat gttgcgtttg tagaccacca tgatgccctc gtccaggtct    82620
tcattgatgg gcttcatcga ggtgcagacg atattacgtt caaagcgaat aagatccgta    82680
ccctgtgcca tagaacacac gcgataggggg tacttggtgg tgttgacccc caccacatct   82740
ccgtacttga gggtagtgtt gtagatggtc tcgttaacac catggctgac cgtttgggaa    82800
gaagttacgc gttgagagac tgaaccggat cgagaatgag cagcagacgt cgtatgagag    82860
gaatggtgac tgtgagtagc agaagttcca cgagtagaag atgaggaaac cgcagcaccc    82920
agacagacga tacacaagtt aacgcagact accaggcacc agatcctgga ttccatgttc    82980
gtcgcgggcc aaatccagca gcgatgaggc gcgtcgtggt ctcttgcgtg ttgcgcggac    83040
cctccgggaa acgcccgcgg tcgaggagga ggggtacgga cttggcagcc aaggtcggtc    83100
cggctccctg aaggcacccg agacggccgc ggcggccgtc agggtggagg gcttggccgc    83160
gggagctgtt ggcacgtcgc cactctcatc cggtctggac agatgcctgt agaggaggag    83220
atatagatct ttggacttat aaagacttcc ttcgtgacga agcagcagcg gccactcttt    83280
gttatacgtg agaatcacat ctctgtccgg gtgcagttcg tcgcgcaggc acgcgatcga    83340
gagttgtttc ccgaaagttt cattatatag tgcgacggag agcacgagct cccgcacgtg    83400
catccacatc tccttctgca gcacgtttag atcctgacag tccgaaaaat tgaaaaaacc    83460
catgtacttc accaccatcc actcactggg atacacggta ccttccgcgc atttgaccaa    83520
atcgtccttg acgtggggta gtacgcccgc gttgtcgcag cataggcca tgtccacatt     83580 gtgagagagg ggatagcgat cggtgcagtg tgtgaagagg ggcccgttac acaactcgta    83640
gatctgctga cccagtagcg ggagggattc cacaggcaga ctcttgtgga tcaggttatt    83700
gaccacatac aggtgctcat cgtacgtgaa ctgatccccc acgtccacca cgtcttggtc    83760
ctggtggtat tggctgcggt atagaaaccc attcatgagc ttagagataa agtccagaca    83820
caagggcccc actaggttga catcgatgag tttgctagtc agacgctcct gcgttttgat    83880
gcaacggatc accttgccat agcccacctc cgaaaccttc tgcaggtagg cgcgtttgcg    83940
cacgttcacc tcgcgggtga cgttgtggat gcgggaacgc gcgtccacca agtcgagagc    84000
ctcgtgttcg tcgcagttgc gcaccccgtaa gccgttctcg ctgccgtcgc cgtcctgccc    84060
attcgcccct cccctaccg cttcttgcc tcctccacgg gccggccgc cgccaccgtt        84120 attcctctga ctgtgagtac tgctgttgct gctgttgctg gccgtcatca aagtcgtacc    84180
cgtccccgac atcgcctccc gtccacgcag gtgaatagcc tcgccctcgg ggccgtcgcc    84240
ccccgtgcca tcgggcagcg gacgtcgaat ctcctcgaga atatgcttga ttttggtgta    84300
catctcgttg ctttcgtgga gcttgttgaa caccgggttg tcctcgaaag cttgaatgct    84360
gagggatgtg atgaggtcga tgatcctgtt gggggcggca aagaccgacc ccacgaacat    84420
gcgctcctcc ccgtccaacg ccttttcccc gagcacgaag atgtcctcca cgtcctcccc    84480
gtacagatgg cgactgatgc cgttcatgag cgcccggcac agctggtgat acacatttag    84540
ctgctggatg gtgatgccca cccgcttgac gataacctcc gaggtacggg accagtaggt    84600
aaaatccgac aaggaatata ttcgttccgg tatatccgta aacaggttgt actccctcag    84660
cgcctcctcc gcctcctgga tgtagctgtg gtaggccgat gaagaagaga ataggctttt    84720
gagggccgaa aggactccag ccaagtgggg gatgcgcgtt gtcaggtcca gcaggtcctg    84780
ctccaccgtc tggatattca catcggactg gcttgacgga cggtggaccg ctatatggtt    84840
```

| | |
|---|---|
| gcacagcaag ccctgcagcc gcttgttcaa cgagcggccc tgattcggga tgatggtcag | 84900 |
| ctcctcgtag cattgggcgc atgtcgtccc ttcgacgtac acttcctgac gcgccaccgg | 84960 |
| cgagatgccg cataggcgac ggagaagctc cagcagctgc gcgcagacct ccaggccggc | 85020 |
| ctccggcgcc aggatcccgt acacgtagtt catcttgcac aggaagcgct cgatgtcgtt | 85080 |
| gagtgtggcc agactgacgc tgaaacggac gttgtccgta aactggagct ccacggtgtg | 85140 |
| atggcgatcg cagcgatcca aacggaggac ggtacggtag aaggccgccc ggtccggctg | 85200 |
| gcgcgagtag gccatcagcg cccggtccag caaagccgta cctcgtgca cgcgccttcag | 85260 |
| cagcatctcc agatagagcg tcagcagcga actctgcgta cgattctgcg ccaccacctc | 85320 |
| cgggtagatc ttccggtaca gatacactat agccgccgcg tttctcttga acggcgtgga | 85380 |
| ctccgccagt aacacgttcg gatcgcagta ctttagacac tccagctcca tggcgtattc | 85440 |
| gttgcatttc gaacacacta cgcatagttt ctgtaacaaa ttcatctcca tgactcgact | 85500 |
| cgctcacgta cgagacgctg tcgtccggtc tggcgccggc cagagacatg gagtcggtgc | 85560 |
| acaaataact cgcgggccgc tcgctatgcc gactgacgtt gacgttaata tataacgacg | 85620 |
| tcgtcgacga cgcgggttct gctcccgacg ctgttgccgc cgcctgcggc gcaacctcct | 85680 |
| ccaccaccgc cgccgccggc tcctccgcct cgggcgacgg gggctcggag atgaccggct | 85740 |
| gtgtctgaca ctcctcccct tcctcaggcg gcccgggcgc cgacgcgaat gtcggagctt | 85800 |
| gccagcgcgg cggcggtctc tgtctctggt gccgcggcgc caaccttcgg ggctgttgct | 85860 |
| gctgctgatg atgcgacgcc gtctgtcgcc gctgttgcgg cggtagctga tacggtgtcg | 85920 |
| cctggtgctg ctgtgtcggt ggctgctgtt gttgctgctg ttgttgcggt ctgaaaagcg | 85980 |
| gccacggggg ctgcgactgt tgctgctgtt gttgcgatgc tcgtggctgc ggcggccgtt | 86040 |
| gtcgcggcgt ctgctggcgg ttacaaccgg ctgcgtttgg ccggcaataa cccgctgccc | 86100 |
| ccgccgcccc cgctgctccc gccgacgccg ccagcctcgt cttcgccggc gttcacgaga | 86160 |
| aagcagccac ctcccgtctc gccgggcacg ccgaagcaaa tggagttgcc cgtgacggac | 86220 |
| tcgccgagaa gaagaccgcc accccgacg ccggacgccg cgccgacgcc actgggcgcg | 86280 |
| aagagcgccg acaggtcgtg cacctccccc ccagcggcgt ccgtcaatcg ctgggcgtcg | 86340 |
| gcgtccagca cgcgtcgcaa gttctccagc gaaaagtcct ccacgccctg ctcctgcaac | 86400 |
| gcggcaaact tgtccatcag cgacgcggcc agcgcctcgc agccatccac gaagaagagc | 86460 |
| acatcgtcgg acgcggggat ctcctcgcgc acgctcagaa tctcgtacac ggccattact | 86520 |
| tcggggtcgc aatccaagtt ctcggcgtcc agcgccagca tgacgcggtt ttttataaga | 86580 |
| tccgcgtcaa aaagcacgtt ctcgcggcgc gagcgtttaa tgagcacgtc ggccagacgc | 86640 |
| gtagccaaga ggtagcgctg gcgcatgaaa cgataatctt ggccgctcat agagctcacg | 86700 |
| ttaaggctgc gttccacacc gttgcccgaa aagtagccga tctgcccaaa ctgatagatc | 86760 |
| tccttgctgt tgttgatacc cgcatatttt tccacgctca cgggcacggt caccaaggaa | 86820 |
| cgatgctcaa aaacgctccg tactaacgat tcacgcgcca cagtggcggc catgggcgcc | 86880 |
| ggcacgcctg cggtcttcaa gcccttgaca tgcaacgcaa attcggcggg cgacgagaaa | 86940 |
| cgcggactag cacctaacac gtgaggaaac tgcgcgtggt tctgcgtcgt taagcgcgtc | 87000 |
| gttaacccgt gcagcgagcc gatgtagtct ttgaagccgt agtagcagag gaatttgtta | 87060 |
| tggaaacggc tttccacgta actcagcaca cagtctggcg ccacatccag cagatcgtgc | 87120 |
| tcctgatagt cagccgtcac agccaccaga aatttgacga aagcattgaa ctcgcccatg | 87180 |
| tcacctatgg gcacattctt gggcaacgcg ttggaacaga ccttctgcca aaactgtaag | 87240 |

```
caggggagac cacattcagg aaagagtcgc tcgtgatgtc gatacagcag aaatcccaag   87300
cagcccttag ccggattacg acgcggaacg tgatcgcggc gaaaaaacac gctacccgcg   87360
ttgcccttgc ccgcgcggta gatgggtcgg tttttcaccc gcaccatgat caacgtgggt   87420
accgacagcc gcgagagctt gatctccatg ggcaccacgg cgtacgtgcc ctgcgcgtac   87480
agcctaaagt ccagcaggcg gtcgtgatcc gaattcttgg acgacttgat ctgcttggtg   87540
aagagaaagc ccttgcgcga cgacgtggta gagaacgcgc cgtggatgga ttgaaagtgc   87600
tgcgtcatcc atttggatac caagttggtg gtcaacggat tgtccacaat gtacgaggta   87660
gcggtaataa gcgccacgtt ctggatcacg taaaagacga atctgaaata ggcgtaggcc   87720
agcagcggct ggaaggccac ggcgtaggga ttcagatcca ggttgaaggc ctgcgtggcg   87780
cccgccacct cgtcgcggct gctcttgagg cgcacctccg aaacgaaacc cagggcctcg   87840
tcgtccacaa acttgttgag cgccgaaaag acggccacaa agtcgctttt gccgtgcgcg   87900
ctaaaggtat cctcgcccgt cacggggtcg atgagccgca tcttgcggca gtaatccaag   87960
atgcgattga gccgataggt acggtccacg ctagcgccca gcatgcgacc gccgcgcccc   88020
atcattcccc cggaatcccc gccacccca ccaccgac cgccgcccag accgtcgctc   88080
gggcccccgc tcacgtctcg tccaccaccc ccgccagcac cgccgcccgg agcccgtcg   88140 tcacctttgc cgtccaaacc cccgtccttg gcgtcgacgt tgtaacgccg accgaagctg   88200
cccaaaatat ccacgtcgtt gagaaaacgc gactgcacgg tgatcacgca gggctccttc   88260
ttgggctgct tgggcaccac gggcaagcgg gtgcgcaccc gcacgaaggc cgtctgataa   88320
cacgtgtggc aacaagtacc cccacaggcc tcgcacaacc ccgcggcgca gcccaccagg   88380
tgattcgtga gcgtcgacga acccgacaag cccgtgttat acaccgagac acgatttaga   88440
taccagacga agcccgaaac tagctgcgga cacgtgccac acaccaacgc caaatgctgc   88500
ggcccatagc gttcgtcctt gagcggcgcg ccttgaaact tgagcacctt gcgcgcgtcg   88560
ttgtagacgt cttcgcaggc cgccgacaac ccgttggtga actgaatagc cttgagcaac   88620
gtctcctgac tggccgtacc gccggcgctg ggatgccgcg ccgacgactg gagatacacc   88680
agcctgtgct ggtagagcac cgaattagcg ctgaagacca aggcggccac gtgcgtcgag   88740
agatgcaact tgagctcggt cagcgcgcgg atcagatcgc ggtgatcggt tgcgttggtc   88800
actaaaggcc actcggaaaa gagcatagac tcggcaggtt ggtaggccga atcgaaaaat   88860
accgaggcaa aactgaaggc caactcgcaa accaccgcgt cactcagcat cagatgatcc   88920 tttttccagac tgctgagtcg ctggctcatg taccccaagt agcgcttatg tggcgccagc   88980
ttcaccgact gctgactgtc gtgcacaaac tgccgcaacg ccgcctcgat cagcacacgc   89040
ggctccgaga agcgcagcga ttgacaccat gacgtgtaca cgtagtagaa aagcgtctcg   89100
cttacggccg gcacgtagag ccctcgcgcc tccacaaaag cgctgcgcgc atccagcgag   89160
acctcgtcgg cttcggcgtc aagctgcagc gaattaaaga gcgtaggcgg gtacaacggc   89220
acgcgcaccg ccctcgccgcc gtgcagtcgc accgtggtcg cctcctccac gcatggaatc   89280
agctgaccgg caaagagaaa ctccttcaag ccgttgccca ccaccacgtg cacagtcgtc   89340
tcggacgcct gacagcccac cgccgcgcac aacgccgcca gatcggtagg cacgcgatcc   89400
gcctcgggcg tgtaggcctc caacgcgtac ttctggcggg cgtcctcgca cagccgatgc   89460
acgtctccgt gatcctcggt aaaagccacg atgccttgcg tatgatgaaa gtagagcgca   89520
aaaggacaga aggacgtgac tttcgtgagc accccgccgt cgtaacaaag cacaggcgta   89580
```

```
cgcacagaga cgccgaaatc cgcctccacc gtgagcccg ccaacagagg agcgatcacc    89640
acgctcgagg aacggtcgca taacgagaga gtggccagaa tctcctgcgt ttctgcgttc    89700
aacctgctga agtagagaaa agccgcgggc cccaccggcg ctagcgcggt tagttcctcg    89760
tggctcatgg tggatgaacg gaagacaatg gctacgccgc cactgagtga attttatacc    89820
aaggaaaagt tcagcacgtc atgtttgacg cacgacgtct gagacaccac cgtggccacc    89880
actgcggtct ggctgcggtt gcggaccacc aaaggcgaca accgcaacga tcccagcaat    89940
tcgtaagaaa agctaaccgc tacggtcggg tagcctctcg cagccagacc gctagccgac    90000
gcacccgccc gcgaaaatag cgtgatgttc gggacggctt tgcgtcaccg ccaactaacg    90060
tcggtagtcg agcacgtcgt ttatcctcag cacaccgtcc gatcacaatc cgttttccca    90120
ctcagtcgca caagcagcac ataaaaaccc cacacagggc acgtgaaaac accgtcccta    90180
gaaaacggtg ttttctgtcc taccgtcacc ggtatacaca ggcaaatccc aagcccgatc    90240
cccgaaaaca ccgtacggtg tttgtgacct ccaaaatcac atcagctaac aaaccgtgaa    90300
aagtcacgtt tcacgaacac ggtgttttta aatcacaaag aaccgcctga cggtttacaa    90360
gcagaaacac cgcaccacgg tggtacaagc gcgatgaatc tggtctcgca acctcaatcg    90420
ccgctatcac caccgatttt cgctgcgctc cgccgacaaa acgccgtaca agctacacac    90480
cccaaaaacc cgcgcgccta cgggcgccaa acctgtgtat tatcccaacg tcacaacacg    90540
acacaaaccg cgtaacgtgg tttcccgaac acgtacgcgg cacagacccc cgacacgtac    90600
tcgaagacct tacagtttac gagtcaataa aacaggaaaa gatccgaact ttaaaattgt    90660
gtatttttat tttcccatcc ccctcttttt accaaaaaac acattttcg tcttgtaaaa    90720 agtaactttc gcccattgcc atgaaacacc gtgatgggga acggtgttgt gtgtcgactg    90780
acgtcactac ggcgatcagt atcgacgtcg tgtatacata acggtgcccg gtgttttat    90840 tcggggcgtt gtcgcgtctt gatgtaatgt aacctgaaac cgccgtgccc aagaatgcgg    90900
aagccagcgt gtactcataa cggggttttg ggtacaatct gacgacatct ggcggcgagc    90960
gtacaccatc gaatgtggcg atcgccggct ctacgtcaca atgacgcaaa acacactgt    91020 aaaacccgcg tagacagctt tcctggtcaa cgagcgccat ctggtgtcgg cataagaaca    91080
ggaatcaacc ccgtggccgg cgaggcggtg agcacttttc ctggtcacgt gaccatcagc    91140
gcaggaagcg aggcccgtag aaccgcccaa gaggcggtgc cagatgccaa cgtcataatc    91200
acaaggtgat ttgttacgtc acgcgtgtgc gcacgcacgc gcgcacgcgc gcggtagaat    91260
acagcgatcc ctagtgaagc cacacccatt acgtgtagcc atatccgctt acgtatacag    91320 ccacaccct aggtacgcca ccttatctac caatcacaga aacggatata caatgacccc    91380
tccctagact ccacccttg tacgaaatt tcagataggt ggaacccgtt agggttccac    91440
cgtcctcggt gtacgtacag gcttctccgt ctaccggaaa tatacacctg ctgacgtaga    91500
cgctactccc ggatacgcgt cataagctac tggaccctag gggggagtg tctcagggc    91560 tacgtgcacg ccccccttacc tagggtatcc gcccccttcc tctgttttga cctagtaaac    91620
ttaacgccgc cgcttctcac gtgaccctg acaagcctac gtcacactcg tcgtaaccac    91680
acccattccg gatatacgtc atcctgtgga attccggaca tacggtgacg tagcgagcgt    91740
agcgagctac gtcacgtatg cgtgcgtcac ctccggcgga aatcatctct gatgacgtag    91800
cgagcgaagc gagctacgtc atcagtccgt tctacgtata ccggatgcta ggcgacgccc    91860
cgtaggggcg gagcctagct tccaccccta ggatgcatac cctatatagc ataattcttc    91920
taacgaaacg ttctacgaaa acggactggc ggaacgggaa ccaccgtaac cccccccct    91980
```

```
cacccccccc cttctcctcc ggaaccgggg ggggcaaatt tttaccaaat ttgggcaacc    92040
atgatttcca atgggacggc gtttccgtgc gcatgcgcag tcggggcgaa ttttcggtta    92100
ccagggcgtt accacgcgga ttatgggatg gggactcgag tgcgcatgcg ccggggatgc    92160
cgtatggaga gcctatatat aaagaggggt gaaccagggg ccccggtgcg catgcgcggg    92220
tcctggtccg cgggagggtc gtcctgcgca tgcgccggta aaattccact gggtgtgtgt    92280
cgtgcgcatg cgccagtatt tttccactgg aggcggtcag tgcgcatgcg tcggtaaatt    92340
tccattggat gcgcgtcgtg cgcatgcgcc ggtatttttc cactgggcgg ccgcacctag    92400
ggagcgcgag ccccgtgccg gcatgggcc gcggcggtgg aaaattaccg ctccgcccac    92460
ctaggcgggg cctctgaaaa cctataaaac ccggcgtgcc cgtcgccccc cggcgcagtc    92520
cgcggcaggg ttccggccgt gctgcggtcc gcacgctgcg cccgctcccg cctgcctccc    92580
gccctacccc ccaccctccc cggccgaggc ccggcgccgg tccgtccgcg ggcccgtccc    92640
accgccctgg agcaccatcc ggggccgtgg gccgggcacc gggcgcggcc cgctccggac    92700
ctcggccggg ggtccctccc ctcccccgc tcgaccccc catccgacgg cccggccggg    92760
ctgggacccc cgcaccgggg tcccggttcc cgtccgtggc ccgggggac ccgagcgggg    92820 gcttcccacc cccacccgc tcctccccgg gctccggccc gggatccctc gctgctcccg    92880
gcgacctccg ccggcttccc ggtccacccg ccgcggaatg gacgggaccc ggggtccgcg    92940
cccttcccct cccccacgg ggggctgggt cgcggacccc ggttcctagg ctcgttccgc    93000
ggtgggcgac cggggatccc ccacccagct ccccttcccg gccgccttg ctggcttttg    93060 ggccctgcg ggcttttttt ttccggctgg gggtcgcggc ggtcggccga cgttaaagct    93120
gattgatctc acggtggtgt ggacgggcga accccggct cgacggcagt cggcccccgga    93180 gggttggggg ctgggggccc ggtcaggagc tccgggagcg gggtcgaccg cgacggcttc    93240
cgggtctcgc ggcggctccc tctcggcggc tccggttggg ctcccctccc ccctctcgag    93300
ggtccggtcg ccggttgtgg tcgggggtcc ctcggcctag ccgccggctc tcggtccgcc    93360
ttaccctggg cgttggccgg tcccgtgacg ctcccctccc ccgctgctcc caaaaaactc    93420
cgcccgaacc gtcgcggttt gctggccctg ggcgtggtct ccccactccc ctccccccat    93480
cggccgccca gccggggtcg gcgcctcgga ccccaccagg ctgtggcgtg tgtgctggcc    93540 gatgcggcg cgaggttggg tgtggccgga agcgctcggg gtcgacggtg ggccgccatg    93600
acacctcaat tgccgtcagt acgcccctcc acaatcaccg tccccacacg atgggcccgg    93660
cagttcaccc aacgttggtt caggcccagt cgggttttc cccggtacga acgcacgtcc    93720
ccgtgggctc cacgcgtttt ccacccttc ctggagggt ccggaacacc gtgaatccac    93780 ggggaggtc ccggcacggg ccgaggagac cacgaccgtc ccaccggcg tgtcgactcg    93840 tccgagaccc gggaagggaa caggccccac cttttttccc ttctccgatt tgccgtggaa    93900
aacccgtgaa ccgatacggg tgcagacggc cgaaaaaatt cgagacggca atacgacggc    93960
agggcgtgat tttctccccc acccgacaaa accgtgtccc tcaaaattcc ccacctttct    94020
ctgttcaaat ggccccgaaa ctgtaaaaca ccgtttgacc gcaccccaac cggcgccatc    94080
ttggtgacct tctcgacggt tctctcgctc gtcatgccgt tctgagctcc gacatggcgg    94140
acgagagaaa atggcgtcga gagccgagga gcgttttcgc tccaggcggg taaaaaaata    94200
gcacgataac ttttctgtgc tttttttgaga cgttttttgaa gagctttttt tctgctcaga    94260
gcgaaaaaat gatagccctg aaaatctcga cgagtctggc cgagcggcgc catcttggag    94320
```

```
gaggggcgag tcgcgggcac cgcctcggta cccectggce gaggcgagtc cgcggtcgce    94380 gcctgttccg tgatgctacc tagagggcgc cgtcgaggcg actcttcctg ttttcgccct    94440
gagggctaac ggtcgctgac gtcaaaccat ctcgtgctcg ctgagtcaca tccggttgtt    94500
gacaagcgat ggaggaccgc acccaaagtg cgccctctag tcatcgcgcc tgacccettt    94560 tataaactgc tcgaagaaaa gaacaccta tgtgaaaaaa tacagaatga tgacaagttc    94620
attcaacaca accgctcaac aacgccatat ctatcagtgt ccaaaaacta tcttctatcc    94680
tttgaaacta taaatgctgc ctatatacat atttagtatc caagactctt accacgtaga    94740
cgaaaagaag tgatacaatg atcttgacgt gtatcgtcta tatcgtgcta gatatattca    94800
gataagacgc gcaaaccata gatttctcat cagtatcatg aaagacctat agctctatat    94860
acgaacctag tcattttagg acagccgccg gagaagccga cgagggatcg ggcgggtgca    94920
gccagaacct cacgcccgat cccgcctccg gtaggcgatt tgcatctgtt tggtaaaaag    94980
ctcataagtc tgtatgtgac ctatatatat attatacgct atgtacaccg aactgtcgct    95040
gttgtataag aagaaaaaac tctccatatt tatatcgtct gaattttgc ttgatagaca     95100 cgtgttgga actctgtccc cccacgtttt cactgtgtat aacaaaaata tgtgtttctc     95160
aaaagatctt gaggtgtttg aaaacggggg aaacctgcgc ttgggtgcgc taagccccgg    95220
actgggacgt agccggcgtc cggcacctat atttttctat tttttttta caaaatatat     95280 gatgaaccaa gaataaaact ctagctctcg tctattttta atatgctcta cttagaacct    95340
ttttaatgac agaatgaact ccatgttata cgctctttat atagtttctc tgcactaacc    95400
tttaaaaccg tatccttccc tgttgtacaa atcatcttt gatacacaat gatgacctga     95460
tatccctcca tatatatgat cggatattat tccgttagac ttgtcctcct ttttttttcct   95520 catctcctgt atctggagat atatgttgac caccaccgcc atgaccacca aaagctagc     95580 cgtcacgact agaaatgtgt aggattcgga cttteegttt gagaagaaag agaccgcgtc    95640 tctgacgct cttttgtcg gtctgaatcg acccgggata cgtaagagag cggccctaca      95700 tcgggggcg ctcgagaccg acgacgttcc atctgaccag aaaaaaaaag gcaccectcg     95760 gtggcgacct ctcaccatcg tttgcccgtc cgcccgtcct tcgtagccat catcatcatc    95820
tcaggctcta tcggtaccat cgttgtcatc tgaaaaaaaa aactgcctca cccacctgcg    95880
taaaaacacc atctttccgg aggtgcggta agacgggcaa atacggtcgt gccgaggcaa    95940
aaaaacgcac catcgacacc acaccctcat gagcaccacc tgtcggtgtt ggtcgtcctc    96000
catcgttctc tacgaacatc tcgacgcccg ggtgacggac gacggcaaga cgtcccggag    96060
aagacggtgt tctctcgggc ggtacgctct ctggatctat aatatctata gtagctaaac    96120
gagactgtga gtacgacgaa ccacatcatc ttttttttat gttgcttctt tagaaaatga    96180
cttatgtcga cgacactcgg catcagccat ctcgtgaaac acgctcgctt tcgtctctc     96240 caaggaacac tgggtccgct gaaagggacc gtgtaccgac caaagcaaaa aacacacacg    96300
tagtaacatg atcaaccacg tctgaatgac acgaaaacac aatcgtataa cgctctattc    96360
atggaacgaa cttggaataa aaaaccatc gcaggccaga ggctaagccg aaaccgtccg     96420
gggaagcggg cgcgagtttt ccgacttagt ctctggtgct cgttgagcct ctttttttt    96480 tcctgattct ctgaagaatc accgtcacag ccctatgacg cgaaatcaat tgctagaaca    96540
taaacgttct caacaggtat gaaatgaaca aactagatga tgctataacc ttatattgtg    96600
tgtatataga taggtgtgaa atttgtagga taaaaagtgt cgttgtatga tgcacaacga    96660
tcgtgaaact ggagactgta gctctctacc gaatgcaaat acacaaatga catcgattcc    96720
```

```
cgtccccaca taaagaaatg tgctttactg tgaaagaatg aagaagattc ttgttcctcg    96780
tacgacgggg ccctcgctcg tcgtgcctct tcccccctcc gggagagggg acgtcggggc    96840
cctccgtcgc accgggccga agccagtgaa atgtttacta cactgtcatc agaatatatg    96900
atgtatatta tttcctccaa actcctcacc atagccacca attcgcatca cttaagaaag    96960
tagtagcaac cgcggcggcg gcgaccggcc ggtcgtcgtc tcctcgtcct caaatgttgt    97020
acatgtgcag aaaaatgtgt aaatacgtgt tatttatccc atgcgtcttg tacatagata    97080
tatgttttta tatacgctat ttatacttta tatatccttt tgcataacca tagacagtca    97140
aggattttaa tgatttgctc atccgccttt gagccatcgc ttaggagtta gttcctctat    97200
gttctcggcc caccttttcg actacagtag caaaccttg tactaccacc ccgataaaaa      97260
ccacatcatc atcgtcacca cgacctggaa acgacacacg ttccccccca atcttgggca    97320
tgtgtatata taaaaagaat gggagggaga ggacgtgggg ctcgagaaga aataaacgcc    97380
aagctcgatt cgaaccaaaa aaccacatgt gtattgtgct tttttttttt tttacggtgg    97440
gggaaaagga gggggccgtc attaacggaa accgtgtatg gggtccggac acgaacagta    97500
cacagcttat ggggaaaaaa gctcacagag agaaaaaaac accaagctca ggcacgcgta    97560
catcattatc atcatcggat atctcaccac gggtcatagt agtaccaagg agtgtgtaac    97620
accatttttt cttttctttg taacgggata agggacagca atcatcacgc acaacaccct    97680
tcactctctt tttagtcatc catatcatcg ctgtaacaca gcatgtcctc gtaatcgggc    97740
gtctggcagc gcattaccac cgagtcgtct tcttgcggta ccggtggtgg tggcggcggc    97800
ggctgctgct gctgggttgc cgtcgtactg tgattaccgt tggcggactg cacagggatg    97860
atgggctgct tgtggggaac ctgggtgga ctgccgccgt gagaaggcga cggcgtcatc      97920
aagttaagat caccacggtg actccggaca ccggcgaggg gcgccggggg actgggaggg    97980
accgcggtcg tcttgtagac gacggtgtcc ccgtgtcgat ccgtggctcg taccagatct    98040
tgactgctag cgtcgtcact gtcttcgtcc tcttccagct cgccctcaga gtagtgctgc    98100
tgtggttgcg acgtggctg ggcgggagga gcggcggcgg cgatcattgg agagggatgt      98160
cgatgactcc cttctctgtc tttttatcg taggctgtca gcgttgctgg gtccgtcctg      98220
ctttccatat ttgtgtattg ctcatcggtg ggatgaattt ggtctcctcc ccgctgttgt    98280
ccgccggcag tggcatggtt gctggcggtt gtcgttgtcg taccggcaaa gacggtgaga    98340
tccaatagcg actgctcgtc gaagggacag tacgctatca tgaaacgata gggtgccaac    98400
gcgcgttgga tgcgcagttc gcacatctcg ttctgacact cgtggcactg cagggcgcct    98460
aggatcaggt ccgagacagc gccgcagcgg taggtaccca tggcgttgtt agtatcgaac    98520
tggtcaaaaa attggggcgt accggtgact tgcaacgcgc gacggcgtag cgagacggcc    98580
acgcgcgaga aagagcacac gtaggccatg gcgcggtgca tgggttgcga aaggtctcg      98640 ggcggacgct tctgcagatc gcagacgtcg tcgcgtagcc aggcgctcat ttgacccggc    98700
ttcttgacta accgtttgag cgtgctgcaa tggtcgcccc agccgtcctg gtggtccagg    98760
atgcagccca ggtccaggtt gttgagtttg ttgaagagca gctgacgcat gccgcccacc    98820
gtctccagat agggatcgtg cgggttgacg ggtagcccgt gcaggtggtg gtacttcatg    98880
tagctgagcg tttcgtcgat gatggccagc aatgtgtgta agttgggagc gttgtacacg    98940
gcgaagatct tttccaccac cagccttgcgc agcaacggtt cctccagcca atcgaactgt    99000
tgacggatgt gcaacaggta gtcggtgtgc atgagctcgt cgtgtgacag caggatgcga    99060
```

```
ccgcgcggct gatgatcttg cgggaaggcg gtggggacct tgagatcggc ggggtagggt      99120
gccagacgta gactctcggc cgtgtagcgc tgaaggtcgt agacgggcga ggtagaactc      99180
ggtgaggtac ccgacgaggc ggcgccgcgc tgcagacgcg ctctttcttt cttttcgatc      99240
aaacggctga gttgctgtag ttcgtcctcg tccatggcgc ccagttcgtc gtcaataagc      99300
gccagcatct gttgttgttg cggtccggcg gacgatccgt gatgattatt ggctgaggag      99360
gggtgagaag aaccgaaagt cgtaggacaa ctgggaactc ggcgacgaag atgcgtcgaa      99420
tcgccgccgt gatggtgcgg ttcgccgtca tcgttgtcgt aagacttacc gtagtggggg      99480
ttaaggggca ccgaggcgga cgcggccacg cgtcgcttga aagaggagga cgccctatgt      99540
ccgccacgga agcccgcggt gcccatgatg atgtgtccgc cggtgccccc gagtgcgtgg      99600
cgggaggagg gtggaagggg aggaggatag tggtccggat cgccttcggt atcatcgtct      99660
ttgctgtagc ggggtcgtcg tgcggggacg cagggtcggt gatgatgcga ggcggcgccg      99720
acggtatctt ccgcgagatg gtattcgctg gcggctgctc cgttccgtgt cgacggcgag      99780
gttggacttc gctcgcgtcg gaacttccgt ggcacgggtt cgtaatccag acagaagcgc      99840
cgtgcgcgac gggcgcggcg ttcgcgctcg ctcagggaag ataacgacgg agcgtcgtga      99900
cggccgcgtg agtgcagctc catggccgtc gtcgctagga aggtcacgtt cgggcacgct      99960
gatgtatata tagatgagac cgctgccggg gggcgggtca ccggcgccgt ggaaagtgag     100020
gctcagacgg cggtcgccgg cggcatgggc gcgtcgggcg gtctgatttt gatggaaatg     100080
tggacgtttt tggcgttgga gtgacacttt ttggtgaaac agcggctcca gaggctggcc     100140
cagagcgcgt agctgtgctc ggtgcgcagg tcgatgaaca cctgcacggt ctcttgcggg     100200
ttgcggtgcg tgtagttgag acagcgaaaa tcccgcgtgc gcgcgccgtc gcgccgcttg     100260
acggccacgc agcaggcgcc gtgggggctga aagaggagga cgtggggcgc ggtaaactgc     100320
tcgctgacgt gcggttcgta gtgttgcgtg aggtgctcga gcagcggcgg ccacacgcgg     100380
gtgacgacga gccgctgcaa gtccgtgtcg gaaatcgcag cggcagtggc gccgtcgcca     100440
ccgtacaggt gataggcgag cacctcggtg agaccgcggc gtcgataacg cgtcacgtta     100500
agcgagcgcg tttcgatgaa gttggcttcg gtcgaggggc agattttgtc gcgcacgctg     100560
agaatgacgc gcggcggcgg cgacagggcc aacgcgggca ggtcgtgcgg cgggtggtgg     100620
tgaagcaggt tacgcaggtc cagttgggcg cgcacaaagc ctagcgggtg ttcgcggtag     100680
gcgtcgggca cgatgaacag cggcaacaga cggcgatgca tgaaatagcc gtcgtcttgg     100740 tccatttat acatgtaggg cagacgtaca gagcgtccat ggtggtagat gcctgtgtct     100800
aggctgctct cgggatgcga gatggggtcc agcagcgtgt gcagttcggc gtcgagacag     100860
acggcgtgat tgagcacctg cgccacggcg cgtaaaacgc tggggtgtac ggcgacggtg     100920
caggcgggga acggcgtgat gatgcgcagc cccagtttgc ccttgcagcg gcagtaaggg     100980
ggtgacgtgt caacggagga cgttgttttt tgaaaacgc cgttatccgg gacgttattt     101040
ttattctctt tcccgtcttc gtcttcctct gtgtcgcgct cgtcccggta atcgagatag     101100
tcgtcgtcat cgaaaggcgc gccggccgcg tctacgggca cgctgttggg tgggcacgcg     101160
cttttgaaga aatagaccgg gtgccggtcg gggtgcgtgt agccaaagag gctcgcccat     101220
acggtcatcc agacgcgtcg tagtccgcga cataactcaa agacggtgtg tcgcgccaga     101280
ccggagacgc cgtcgcgcag ccgtaaatca aagtcggcca caaaattgaa gacgggcaga     101340
cgttcgttga agacttcgtg tcgcgtgtag tagaactgtg tctcggggct ggtgctggcc     101400
acgtcgtcgt cgtgtagcca cacggtctcg gtcagggcct catccgagaa acggctgtcg     101460
```

-continued

```
ggtacgtgac ggagcaggtc gcgcggaaag aggctgcgat gccaggtttc ggaggccacg   101520
gcgcagaaga cgtgctggtc attgggcagg tgtacgcgt  agacgggcag cggtcgctcc   101580
agcagcggtg ccagcgcggg ctcgggtagc aggtagcgac gttgcgagta acgcgttagc   101640
gtgccggtgg tgtaggtctg ggctgtgcgt agcgaggcgc atagacgtaa caaaccggac   101700
agggagcgtt ccagcgggga gaagacagac tcggaaagcg tgttgatgcg ttcgagctgg   101760
cgcgccagct gcgtggaggt gccgaagaag cccgccaggt gcgtgccgtc gatgcggccg   101820
ccgtagccgg ccagccccag gccgtgcggg ctggtcgccg agtgggggga ttcgtcgagg   101880
cgcagtaggt gcgtctccac gtagtcgtgt agaaagttgt cgagcgagaa gtattttgc    101940 atgacgtcca gcagctcggt ggaaagccgg cggcccagaa aacccggttc gcgcgtgcac   102000
tgcgcttcgg gcgccgcgtc agcgtcgtaa gccaccacgc gccggtactc gagcaaccgc   102060
gcgcgtgcca gcgccgtgcg gtaggccagg tagacgtagt gcacgcagac cgtgtcgggc   102120
agacgcgcac gttcgcggaa cgcgttgatc tgcgtgtcca cctgctctag ctcggtgtag   102180
tcgcggcggt tgcgcgccac ggcgtacgcc acgaaagcgg acacgcgctg acggaagggc   102240
gagcccagta gcagacgcgc gaactcgccc atggaggcgt gcgtggggat gatggtgccc   102300
aggtcgcgcg tgcagaagct gcgcacgtac tcctccacgg tggagatggt gctgtactgg   102360
ccctcgaata ggtagtaggc catggtcagc agcacctggc cctcggtgtg cccgaagacg   102420
ctgatgaacc acgagggcga ggtggggcag aggaagacct ggttgagatg acgtagcacg   102480
gccgcgtggt gaaagtacac caggtgcttg aattcgcgca cctcgccgcc gtgttcgggc   102540
gagagcacgg gcgtgcggaa gagatgccgg tagagcggct gcgtctcggc ctcgtccaga   102600
ctggcgataa gcgccgagag ggggatgggc tggcgcgcgg ccaggtagcg cgagagctgc   102660
agcgtttcgt tgttcacggc gaagacgggc gccacccgcc gcgagtccga gcactttgt    102720 gtctgtaggc agaaataaac acgtcgcgag acctggtgtt tgaccagcag ggggaagacg   102780
cagtgatccg tcggtgtctg cgagagtacg ttggcgacta tatgagcaga atcatactct   102840
gttgcgaaca gaacgagcgt catcgtcgcg ccggcacgat gcagctagcc cagcgcctgt   102900
gcgagctgct gatgtgccgt cgcaaagccg cgcctgtggc cgattacgtg ctgctgcagc   102960
ctagcgagga cgtggagctg cgcgagctgc aggcgtttct ggacgagaac tttaagcagc   103020
tggagatcac cccggccgac ctgcgaacct tttctcgcga cacggacgtg gtgaaccacc   103080
tgctgaagct gctgccgctc tataggcaat gccagagcaa gtgcgcgttc ctcaagggct   103140
atctctcgga gggctgtttg cctcacacgc ggccggcggc cgaggtggag tgcaagaaat   103200
cgcagcgcat cctggaggcc ctggacattc tcatcctcaa actggtggtg ggcgagtttg   103260
ccatgtccga ggccgacagc ctggagatgt tgctggataa gttctccacg gatcaggcct   103320
cgctggtgga ggtgcagcgc gttatgggcc tggtggacat ggactgcgag aaaagcgcgt   103380
acatgctcga ggcggcgtg  gctgcgacgg ttgcaccacc gacgccaccg gcggtcgttc   103440 aggggggaaag cggcgtccgc gaggacgggg aaacggtcgc cgccgtgtcg gcctttgcct   103500
gtccctcggt ttcggactcg ctgatccccg aggaaacggg ggtcacgcgt cctatgatga   103560
gtttggctca cattaacacc gtctcctgtc ccaccgttat gaggttcgac cagcggctgc   103620
tggaagaggg cgacgaggag gatgaagtga ccgtaatgtc gccgtcaccc gagcccgtgc   103680
aacagcagcc gccggtcgag cccgtgcagc agcagcccca gggacgtggg tctcaccgtc   103740
ggcgctacaa ggagtcggcg ccgcaggaga cgctgcctac gaatcacgaa cgcgagattt   103800
```

```
tggatctcat gcgacacagc cccgacgtgc ctcgggaagc ggtgatgtca ccgaccatgg    103860
tcaccatacc tcctcccag ataccctttg tgggttccgc gcgtgaactc aggggcgtga    103920
agaaaaagaa acccacggcg gcggccttgc tgtcctccgt gtgaacagcc tggcacgttt    103980
tggaaaacgt acgtgatcac ggacacgacg agtacggggt ttctcataga cgtactttat    104040
taggtcaggg atgacgggga ggtttcgggc cgacgtcaaa ataacgtca ctcgtgttga     104100 cagggctttc tgcgtcggag ctctttcat cttcttctgt ctcgtcgacg tcatcgtcta    104160
ccggcgaggg tgtccgttgc aacaacgcgt gctcgggcgt gtgggtgaaa ccgatgtcgg    104220
gggtgggcgg cacgatcatc tgtcctaggg ggtgactgcc caccggcaga taggtaaagc    104280
ggtgggtggt aaaaccgct ttggctacgg tggtgtgtgg ggagatgcag acggtggtgt    104340
gcgaagtgtt gaccaccgtc acgccggccg cggtacccgg gagccagatg gtgggtcgga    104400
tgatgagatc cgactgacta aactggcgca cgcccactat gagggcgcag ataccgggcg    104460
cgtgcacgta ggccgcgtca aaatagacgg tttgcgtgtg acccggaccg atcaccagcg    104520
tctgacgggt acgtaatgaa agaaacggt gttcgttggg cggcggcaag ttcatggagct    104580 gccaaggttc tggcacaaaa caggggaaaa cgccgatatc gccttcgatg gtgcctggaa    104640
agatggactg aaaagtgtcg ttgaggttga caacatccaa ctgcgggact gcagcccgg    104700 attccagcag ctcgggcatg caaacgaatt gcgcgtccag gcatttgtaa aggtaatgc    104760 cgaaaaaacc ttcggggata tagaggctga cgcccagcga ggtgggcact ttgcgctcgc    104820
gtgatagcca aatgatgtgt ttattgtaaa aggccagctg cgtgtggcat tgtttgacga    104880
tgaaactgga aggcatccac ttgtaggaa ctttgagcgg cgacggtaat ggcgacgacg    104940
cttcatcttc tcccggatgc tgctctttgt cgtatttctc ctcggtcgat tggggcagcg    105000
taaatgtggt ttgaaaatcg ctatcgctag cgaaacgtac gcagtaacgc atgttgacgg    105060
atttctcggc taggatgatg gagcctgatg acggtgcgga ctcttccttc attattaacg    105120 tagggggtctc ccagaatcgc tgaaaacggg agcgcggcag ccgcgacagt accagttgag    105180
agtcgattcg atcggtaaac atcgtaagca tcgtggcggt ggtgtgatgg agtggaacac    105240
actagtacta ggtctttgg ttttatcggt agcggcaagt tccaaccata cgtcgactgc    105300
tagcacaccg agtccctcta gctctactca cacctcaacg accgtgaagg caacgactac    105360
tgcgacaact agtacaacta cggtgacaag tacgacttca tcaacgacta gtaccaaacc    105420
cggttccacc actcacgacc ccaatgtgat gagaccacat gctcacaatg attttacaa    105480 ggcgcattgt acatcgcata tgtatgaact ttctctgtcc agctttgcgg cctggtggac    105540
tatgcttaat gctctcattc tcatgggagt tttttgtatc gtactacgac attgctgttt    105600
ccagaacttt actgcaacca ccaccaaagg ctattgaggg tggacaggtt cacagcccgg    105660
cggtgttccg gcgggtaag gtttccatat gtggacgact gtaggctgaa gttacggatt    105720
tcacttaaaa acagcagcga gtctagataa tcccacatgg gatctataaa cgttctctga    105780
aacctcgtcg atggtgacgt aggtgtagtt ttgttattat cggaagccgt ttcgtttttcc    105840 acgggcatgg tgtcgttgta atataaggag ctcatgtcaa gagtaccgta aatagtgtac    105900
ggtgtttcgt tgcgaatcaa tacgtgcgta ttttctcataa attctgatac ggcggtccgg    105960
ttacggtttg gtttacaaaa aggttcatct cgatagcgca gagtagtata cacccacgtc    106020
gctagatctt ttaactgcgt ggtcagaatg gatttcataa agttttcgtc aggacgataa    106080
ccaattgtag atgtgggaat ccgagttggg acaataggac tataagttac attagtactg    106140
acgttaaaaa tagttgacgt gtaggaagaa tatggtgtgg tggtgctaac acgacttttc    106200
```

```
ttactgatcg atttgacagg cgcttgttta cgtttaagct ttcgcatagt gttcttcagc    106260
ttggtgctgt taatatactt gggaacgcgg aatatattcc ggctcatggc gttaaccagg    106320
tagaagctgc gtgtacagtt acgttgcgcg taacgtagaa gcagggcggc taaacctaaa    106380
aaataaattg tttggctatc cacattgact ttactcggac ccacgtacag tttggtgttc    106440
caacgtggta cgttaaaaaa cataggatta aatgtggtaa aattgccaca gttttcctcc    106500
ccggtgttgt tacgccggga tacatttagc atttcagaaa ggcaagtcat ggaaggtatc    106560
gtaccacagg atgggggtcg aaatgttatt ttttgccctg tatgattata ttccgaatac    106620
acatatttgg ccggtttacg gagttgggtc gtgtgaaaat cgaaccagag gtgggtaatg    106680
ctatgattac gaataggtcc tgctaaaatg gaattcgggg gaaactgttt catttctaca    106740
gttatgttat acaactttg ctgactagga aatgtgaaaa acttgtaata atcacctgtt    106800
tttgacgcta gttcttgcag tatacgtaat tttagttgcc tctcttcctc ttttgctttc    106860
tgactcttta ctcgaaaacg cgctaccgtg atcttacagt ttatgaaaga gaatagcagg    106920
aaagttagcg acataaggaa aaataaatta aaaacacctc tcatctctcc ctttctcccc    106980
atgacagagg aggagacccc gcaccgtccg tctgccttgt ggtttggctt gcctgcgtgt    107040
actcactgct gattctggtc gttttgctgc tcatctaccg ttgttgcatc ggcttccaag    107100
acgacctagt ctcccgcacc ttggctgtgt accgagcttg tatccaaggc ccgatatgta    107160
accagaccca caacagtacc tcgtaaataa agacgcacag acctcacaca tatagtacca    107220
tcacaccgtg tggcgtgtac tttattacaa cgagcaagag tgcccctaag tattggggcc    107280
cgtaccgttt tagaagattt tgtgtgaatg tctttaactt tctctgtccc ttttctcata    107340
aactgtcagg ttctacagtc agcatgtctt gagcatgcgg tagagcagat agatgccgat    107400
gatggccgat agcgcgtaga cggacatcat gaggagacga ctgtcggtag cgtccacgac    107460
gacgtcagtt acttctagga ccgtaccgtt tttcaaaagc atgaggtagt gagttcgcgg    107520
agatgagacc accacttcgt tgtagggatc cagggcgaaa aggacgtcgt ccgagtcgtg    107580
catgtacatg atgttgatga cgccttgcgt gtcgtcgtat tctagtaggg cgctttggca    107640
aaaggcgcag ttttctaggg aaatgttgag cgccgctgtg atgctgtgtg tggtatgcat    107700
gttgcgcgtc agttcgcatt tagtttgact gtccgtctgg gtgatgatga ggctctggcc    107760
tacgacggtg gtggagacag ggtaggagat acctttgatc aggtactggt ttgttacgac    107820
ataactgacg tgttcggaga cggtcagcgc ggagaaggat tcgccgagcg gcagacaaaa    107880
caggtcgggg aaggtttcta gcgtgcttgg ttgcatggta gataggatgg agagggcggc    107940
gggaacggta gtggggacgg tggcatcggg gaagagacgt gtgaggcgtt cgagcgagtg    108000
atcgcgtcgc ccgctactgg aacagggtgt gtacaggtcg ctgaggtatt cgtggtgcgg    108060
atgagctagc aactgcgtaa agtgtgatag ctcggctaat gaacagaggc ccgtttctac    108120
gatgaagatt tcgcgtctct ccgtcgtatg tactagcatg gagtggacga ggctgcccat    108180
gaggtagagt tcttgacgcg cgaaggctga agaaaagag gccaggtgcg ttttgtgtag    108240
ttttagggca aagtcggcga tctgtcgtag tgcccactgg gggatgagat gttgctgatt    108300
ctgtttagag agtatgtaga ccaggcgtac gaggctggtg atgtcggtga tctgattcgg    108360
tgtccaaagg gctcgtttgg ccaggtccac ggccgtggga tacagcagca acgtggtgcg    108420
tggtggtgtt tgtgagaggc aggtgatcat aaattcttgt atttgtaaga gtgcggcctg    108480
gcggtctagg gcccgtggga cggagacttg ggcgccggcc tcttcttgtc gggctgctgc    108540
```

```
gaacagtgct aatgcgtagg cgaaggccat ttctaccgtg cggcggtcca gcatctgaca  108600
tcgaccgctt ttgagtacat ccacggcgta acggtgaaag ctgttacgta gtagtgcgct  108660
gaggtccagg tagttgaagt caagtgcggc gtcaagaaag tccgggtctt tgagataaga  108720
gtgacggttc agttgatctt tcttaactag caccaggagc tcgtgttttt cagtttgtcg  108780
tagtataaag ttgtcgcgtt gatagggcgc tttaaagagt acgcgtggaa gatggccgaa  108840
gataagcagc atgggtgtgt cgtcgtctat ggacaccgta actacgaaga agtcctcggt  108900
cagtgttatt ttaacgtaac gtagttcgtc gatgaggtaa aagccttggt gcaaacaagg  108960
tgtgacggtg ctgaatagta gatcgtgtcc atcaaagagg atacaggtct ggttaaagtg  109020
tggtcggtgt agtcctgagg tggtatgtga ttctgtccag ccgtgtggag tggtttgcgg  109080
tggcatccaa acgtgaggta ttgacaggtc aatgggtggt ggcacagtgg tgggctgttc  109140
acctaggctg tcctgtgcct ttagctgctg cgaaaaagat cggtagctgg ccaggtcttt  109200
ggataccagc gcgtaagtgt taagtctctg ttggtatctt tccagggttt cggtcagatc  109260
tacctggttc agaaactgct ccgccagagg acccgcaaaa agacatcgag gcatatgaa    109320
tacatagtat tgattatagc tttggaaaaa gttgaaactg atggcgtttt ccctgacgac  109380
cgtgctgtta cggaggctgc tattgtaggt acactgggtg gtgttttcac gcaggaagcg  109440
gatgggtctc ccgtaggtgt tgagcagtag gtgaaacgct ttgtccagcg gttcggatat  109500
ggcttctgcg ccatatcgtg acgaaagtag gtggctgagg agacagacgg cgaggacgat  109560
gaggtaggag gggaggcctg ccgcatagc gcggccgcgc cgctgggttc agcggcgtga   109620
tccaggtggt ggttggcgtt acacccgaga gaaggagaga aaggatccca ggaaggagca  109680
cccgggtgcg gcgctacggg ttacaaaagt cgcgtctccg tctatttaat acgatgtcat  109740
tggccgctgc gaaggagaa gaggggacac gcgagtaagt catgccgtcc gggtgtgggg    109800
acgacgctga ttcgaagggg aacgctctgc ggagattgcc tcacgtgcgt aagcggatcg  109860
gtaagcgcaa gcacctggac atctaccgtc gcctgctgcg ggtctttccc tcatttgtgt  109920
cgctcaaccg cctgttggga ggccttttcc cacccgagtt gcaaaagtac cgtcgccgtc  109980
ttttcatcga agtacgatta agtcggcgga ttcccgactg cgtgttggtg ttttttaccgc 110040
cggactctgg gtcgcgcggc atcgtgtatt gctacgtgat tgagttcaaa actacgtact  110100
cagacgccga cgatcagtcc gtgcggtggc acgccaccca cagcctgcag tacgccgagg  110160
gcctgcgcca gctcaagggc gccttggtgg actttgattt tctgcgtctg ccgcgcggtg  110220
gcggtcaagt ctgagcgta gtgcccagtc tggttttttt tcagcaaaag gccgatcgcc   110280
catctttta ccgggctttt cgttcgggcc gtttcgacct gtgtaccgat tctgttctgg    110340
actatctggg acggcgtcag gatgagtctg ttgcacacct tttggcggct acccgtcgcc  110400
gtcttcttcg agccgcacga ggaaaacgtg ctgcgctgcc ccgagcgcgt gcttcggcgg  110460
ttgttggagg acgcggcggt ggcaatgcgc ggcggggggct ggcgcgagga cgtgctcatg  110520
gaccgggtgc gcaaacggta tctgcgtcag gagctgaggg atctgggtca cagggtgcag  110580
acttactgcg aggatctcga agggcgcgtg tccgaggcgg aggcgctgtt gaaccagcag  110640
tgcgagctcg acgaaggacc gtcgccgcgg acgctgctac aaccaccgtg tcgtccgcgt  110700
tcgtcgtccc cagggaccgg cgtggcagga gcttccgccg tcccacacgg tctttatagt  110760
cggcacgatg ccatcacggg acccgccacc ccgtctgacg cggcgaccgc gtcagcggcc  110820
gccggtgctt cttctacctg gctggcgcag tgcgccgagc ggccgttgcc cgggaacgta  110880
cctagctact ttggaatcac gcagaacgat cccttatcc gctttcacac cgattttcgc   110940
```

```
ggcgaggtgg tcaacaccat gttcgagaac gcctctactt ggactttctc ctttggtatc  111000
tggtactatc ggctcaagcg ggggttgtac acgcaaccac ggtggaaacg agtgtaccat  111060
ctggcgcaga tggacaactt ttccatttcg caggagctgc tgctcggcgt ggtcaacgct  111120
ttggaaaacg tgacggtgta tccgacgtac gactgcgtac tctccgattt ggaagccgcc  111180
gcctgtctgc tggccgccta cggacacgcg ctttgggagg ccgcgatcc gccggactcc  111240
gtggcgacgg tgttgggtga gctccctcag ctgttgccgc gtctggccga cgacgtaagt  111300
cgtgagattg ccgcttggga aggccctgtc gccgcgggta caactatta cgcgtatcgc  111360
gactcgcccg atctacgtta ctacatgccc ctaagtggtg ggcgccacta tcacccgggc  111420
acttttgatc gtcacgtgct ggtgcggctt ttccacaaac gcggcgttat tcagcatttg  111480
ccgggctacg ggacgataac ggaggagctg gtgcaagagc gtctgtcggg ccaggtgcgc  111540
gacgacgtgc tttccctctg gagtcgacgt ctgctggtcg gcaagctggg tcgcgacgtg  111600
cccgtctttg tgcacgaaca gcaatatctg cgttcaggcc tgacctgcct ggctggcctg  111660
ctgttgttgt ggaaggtgac caacgcggat agcgtcttcg ctccgcgcac gggcaaattt  111720
acgttggccg acctgctggg ttcggatgcc gtagccggcg gcgggttgcc tggggggcgc  111780
gcggcggcg aagaggaggg ctacgggggg cggcacgggc gggtacgtaa ctttgagttt  111840
ctcgtgcagt actacatcgg gccatggtac gcgcgcgacc ccgcggtcac gctgtcgcag  111900
ctctttcccg gcctggctct gttggccgtg accgagagcg tgcgcagcgg ttgggatccc  111960
tcacgtcgcg aggacagcgc cggaggtggc gacggcggcg cgccgtgct catgcagctc  112020
agcaagagca ccccgtggc cgactacatg ttcgcgcaga gctccaaaca gtacggcgat  112080
ttacgtcgct tggaagtaca cgacgccctg ctctttcact acgaacacgg gctagggcgg  112140
ctgttgtcag tgaccctgcc gcgtcatcgt gtgtccactt tgggctcgtc cctctttaac  112200
gtcaacgata tttacgaact gttgtacttt ttagtgttgg gttttcttcc gagcgtggcg  112260
gtgttgtaat ttccaccacg tgtcgcttgc tgcataaagg gcgagcgtcc ccggagaggg  112320
tatattcgtt cggcgagagc gggcggcggt ggtgggtatg tcctcttctg cggagaagac  112380
tacctcagtt accgattcca tcatgctcgc tatcgtgaat ttcaaataca tgggcccgtt  112440
cgaaggctac tctatgtcgg ccgatcgcgc cgcttcggac ctgctcatcg gcatgtttgg  112500
ctccgttagc ctggtcaacc tgctgaccat catcggttgc ctctgggtgt tgcgtgttac  112560
gcggccgccc gtgtccgtaa tgattttttac ttggaatcta gtacttagtc agttttttc  112620
catcgtggcc accatgttgt ccaagggtat catgctgcgt ggcgctctaa atctcagctt  112680
ctgtcgctta gtactctttg tcgacgacgt gggcctatat tcgacggcgt tgttttcct  112740
cttctgata ctggatcgtc tgtcggccat tcttatggt cgtgatctct ggcatcatga  112800
gacgcgcgaa aacgccggcg tggcgctcta cgcggtcgcc tttgcctggg ttctttccat  112860
cgtagccgct gtgcccaccg ccgctacggg ttcactggac taccgttggc taggctgtca  112920
aatccctata cagtatgctg cggtggacct caccatcaag atgtggtttt tgctggggc  112980
gcccatgatc gccgtactgg ctaacgtggt agagttggcc tacagcgatc ggcgcgacca  113040
cgtctggtcc tacgtgggtc gtgtctgcac cttctacgtg acgtgtctca tgcttttgt  113100
gccctactac tgcttcagag tcctacgcgg tgtactgcag cccgctagcg cggccggcac  113160
cggtttcggc attatggatt acgtggaatt ggctacgcgt accctctca ccatgcgtct  113220
tggcattctg ccgctctta tcattgcgtt cttctcccgc gagcccacca aggatctgga  113280
```

```
tgactcctttt gattatctgg tcgagagatg tcagcaaagc tgccacggtc atttcgtacg    113340
tcggttggtg caggcgttga agcgggctat gtatagcgtg gagctggccg tgtgttactt    113400
ttctacgtcc gtccgagacg tcgccgaggc ggtgaaaaag tcctccagcc gttgttacgc    113460
tgacgcgacg tcggcggccg ttgtggtaac gacgaccacg tcggagaaag ccacgttggt    113520
agagcacgcg gaaggcatgg cttccgaaat gtgtcctggg actacgatcg acgtttcggc    113580
cgagagttcc tccgtcctct gcaccgacgg cgaaaacacc gtcgcgacgg acgcgacggt    113640
aacggcatta tgagcggcgg cgttgtacgg cagcggggag aaaagtggca gataaattac    113700
gtcaggttca cacgtcgtta gccagcgtcg gcatatgaag ggcgcgggcg gccagtacgg    113760
cctctgggtt gagacaggac gaggcagggt gagaaagagg aggatggggg ggaccggggt    113820
ggtggtgctg ctgctgttgt gggtgcggac ggtgcgggtg ccgggacagc gtgccggcga    113880
acgttctgta atcttccata ataaaggtaa aaatgcccgt tcgtgtcga ctccgctgga    113940 tctcgaaggc gtcggggta atgcgcatct tgccggtgcc gatgagataa agtaccaca    114000 ttttttgaca gatgatgcga atcaagggtt cgtacgcttc ggcaccccag tggcgtgtga    114060
agaaggccgc cagacgaaac aggcggtgtc cgtagagcgt gcctagggag aagaggatgt    114120
tgccgttgcg cgccaggtct cgggggaaaa cgaccggcag gccggtgtgg cgctgcacaa    114180
agcgcgtcag cagtccgccg ctcaagcgcg ggtgacacag gcgctggctg agacgggcgg    114240
cgcgtgtttc atcgaacacg gccgcctcaa agtccagccc cgggaaggcc tggcgcagtt    114300
cgcggtacag atgaggccag tagggttgcg gcgtcttgcg gctaagcacg gcgtggtccg    114360
agacacccag gttgttcata gtttcgcgca gtagcagcgt ttcgagaccg cggtgaaaga    114420
ggaggacgca gatgaggcgt acgattttga gttcttccaa acgcagcgag ctcagcggct    114480
gtccgcgcga catcttctcg ctaatctgta atattagatg attggcgcaa gtaaaggaga    114540
atttgcctgt gcggacccgc gggacggcgg ggttctcttc gtcgcgggcc atcatcgttc    114600
gctcggtgag cgggtagcga cggtgacgac aatgacgatg gacgagcagc agccgcaggc    114660
tgtgacgccg gtctacgtgg gcggctttct cgcccgttac gaccagtctc cggacgaggc    114720
cgaattgctg ttgccgcggg acgtagtgga gcactggttg cacgcgcagg ccagggaca    114780 gccttcgttg tcggtcgcgc tcccgctcaa catcaaccac gacgacacgg ccgttgtagg    114840
acacgttgcg gcgatgcaga gcgttcgcga cggtcttttt tgtctaggtt gcgtcacttc    114900
gcccaggttt ctggagattg tgcgccgcgc ttcggaaaag tccgagctgg tttcgcgcgg    114960
gcccgtcagt ccgctgcagc cggacaaggt ggtggagttt ctcagcggca gctacgccgg    115020
cctctcgctc tccagccggc gctgcgacga cgtggaggcc gcgacgtcgc tttcgggctc    115080
ggaaaccacg ccgttcaaac acgtggcttt gtgcagcgtg ggtcggcgtc gcggtacgtt    115140
ggctgtgtac ggacgcgatc ccgagtgggt tacccagcgg tttccagacc tcacggcggc    115200
cgaccgcgac gggctacgtg cacagtggca gcgctgcggc agcactgctg tcgacgcgtc    115260
gggcgatccc tttcgctcag acagctacgg cctgttgggc aacagcgtgg acgcgctcta    115320
catccgtgag cgactgccca agctgcgcta cgacaagcaa ctagtcggcg tgacggagcg    115380
cgagtcgtac gtcaaggcga gcgtttcgcc tgaggcggcg tgcgatatta aagcggcgtc    115440
cgccgagcgt tcgggcgaca gccgcagtca ggccgccacg ccggcggctg gggcgcgtgt    115500
tccctcttca tccccgtcgc ctccagtcga accgccatct cctgtccagc cgcctgcgct    115560
tccagcgtcg ccgtccgttc tccccgcgga atcatcgccg tcgctttctc cttcggagcc    115620
ggcagaggcg gcgtccatgt cgcaccctct gagtgctgcg gttaccgccg ctacggctcc    115680
```

```
tccaggtgct accgtggcag gtgcgtcgcc ggctgtgccg tctttagcgt ggcctcacga   115740
cggagtttat ttacccaaag acgctttttt ctcgctactt ggggccagtc gctcggcagc   115800
gcccgtcatg tatcccggcg ccgtagcggc ccctccttct gcttcgccag caccgctgcc   115860
tttgccgtct tatcccgcgt cctacggcgc cccgtcgtg ggttacgacc agttggcggc   115920
acgtcacttt gcggactacg tggatcccca ttatcccggg tggggtcggc gttacgagcc   115980
cgcgccgtct ttgcatccgt cttatcccgt gccgccgcca ccatcaccgg cctattaccg   116040
tcggcgcgac tctccgggcg gtatggatga accaccgtcc ggatgggagc gttacgacgg   116100
tagtcaccgt ggtcagtcgc agaagcagca ccgtcacggg ggcagcggcg gacacaacaa   116160
acgccgtaag gaagccgcgg cggcgtcgtc gtcctcggac gaagacttga gtttccccgg   116220
cgaggccgag cacggccggg cgcgaaagcg tctaaaaagt cacgtcaata gcgacggtgg   116280
aagtggcggg cacgcgggtt ccaatcagca gcagcaacaa cgttacgatg aactgcggga   116340
tgccattcac gagctgaaac gcgatctgtt tgccgcgcgg cagagttcta cgttactttc   116400
ggcggctctc cccgctgcgg cctcttcctc cccgactact actaccgtgt gtactcccac   116460
cggcgatctg acgagcggcg gaggagaaac accgacggca cttctatcag gaggtgccaa   116520
ggtagctgag cgcgctcagg ccggtgtggt gaacgccagt tgccgcctcg ctaccgcgtc   116580
gggttctgag gcggcaacgg cagggccttc gacggcgggt tcttcttcct gcccggctag   116640
tgtcgtgtta gccgccgctg ctgcccaagc cgccgcagct tcccagagcc cgcccaaaga   116700
catggtggat ctgaatcggc ggattttgt ggctgcgctc aataagctcg agtaagagag   116760
acgctatatt tagggcttcc ctctcttttt tttctacacc gtgatacccc taataaagcac   116820 accgcggtta ttatcaacgt ctctgttttt attatttaga aataaataca gggaatggga   116880
aaaacacgcg ggggggaaaac aaagaagtct ctctctagat gcggggtcga ctgcgtgggg   116940
tgctggaagt ggaagcggtg ctgatgggcg agggtcgtgg cgcgggcacg gaccgcaacg   117000
tgctgctgat gtctgctgcg gtacgcacgt cgccgtccat gtcgctgcgc agataagagg   117060
taggtcgtag tgcggcgtgc tgcacgctca ccgttaatgg taccaggtcg tccaagctcg   117120
caaagacgtg ccacgagggg atgacgagcg tgagagcccc gttgttaccg cttcggcgtc   117180
tttgtccggt caggatcagt gcccgggaca gtccggcttg ggtgtccgag tcctcgtcgc   117240
cgctggcctc ctcgaagccg gcaaacatgg cctcggacag gggggtcggt gtcggtgtgg   117300
aggagaggtc atcttcgtcg tcctcttcct cttcttcctc ctcttcctcg gtgggtggta   117360
atcctggcga ttgcgggaga aactcggaga cggcgccgcg catgacgttg ctccgtgaa   117420 agagaccggc gcgcagctgc acctgggac gcttgatctt gtccggttta ccgggtgtga   117480
gagtccaaaa cccacggcgg aaaaagtgga tgccggctag cggctgtcgg tgttccaaat   117540
gaacggcctg atcgccggtc agcgtgacgc ggagggtgat tcgcacacga tcgggtagcg   117600
ggccggcttc tatggagacg cccgggatgt tttccgggaa aaaatggtg tcgtgagtct   117660 gattggtctc gaaagcattc tggatctgca cgatgtactc gggatgtatg cgcgttagcg   117720
taaaactttt gggaatcaac agctggaagc cgttgtccgg caagcgtcgt aggtgcgggt   117780
acggattgtg tcgcgccacc acctcggcgc gatgcgtgta aaccgaaaag tgcagaaaca   117840
cgctggtcgg cgggtgcggt gagtcgtgat gcagaaacag catgatccat tggcctcgct   117900
cgtccgtctc cgttttgtgg atgtacgtgt tagggtccga acaggccagc tgctccaggg   117960
cgtctaccag cgtcagcggg atagcgccgg cgcgaaaggc gaactggctg acaaagatct   118020
```

```
ggccggcctc caagctgctg tcggttctgc ggcgccagtt cggcgttacg gtcagtcgca  118080
cggcccagta gtgagccgtg cggcggatga tggcgcgcgc ctccactcgc ggccgatttt  118140
cttcgccgcc gcgccgctgg ctctgaaaga ggtgcagtcc gctaacgggc acgcggtcca  118200
gcggcagtgc aaaggccagt accgagaccg tgttgttttc tgagcctggc gtcaggcgtc  118260
gtgggccaaa gttgttgagg tccaccagca gtcggtcctg ttcgcccacc acgcagcggc  118320
ccttgatgtt taggtcggtc aggtctacgg tgtcgtgcgg agatttgttc tcctgaaaac  118380
agcagagaac cgagggccgg ctcacctcta tgttggtacg caggtccagg agtcgcagac  118440
gaccggcttc cagcgagccg ccttccacgt tggtgatgag ccgaagcacc tggcagtgca  118500
ggcgaccaaa gcttccgctg gcggcttcgg cctcgctgat cgcggccgct tccgacgagg  118560
gtccctcacc gggcgaggac gatgcctgag acatcgcgaa ggcgggatga ggggggggt  118620 caggggatgc gcaaaggtga acgggtcttc gtgggaggtc gggaagggtt ccggcaactg  118680
tcgcaaatat agcagcggcg acaggtgtgg cggccaaaag tcgcgtgtct gagtggacgt  118740
gggtttttat agagtcgtcc taagcgcgtg cgcggcgggt ggctcaacct cggtgctttt  118800
tgggcgtcga ggcgatgcat ggcccgggca aggcgtcttg ccggtggcgg cgacgtttgg  118860
gttgcgcagc gggctgccat acgccttcca attcggcgaa gatgcggtag atgtcgttgg  118920
cgtcccagaa gaactcctgg tacttcagat tctgaccctg aaccgtagcc accatgggca  118980
ccaggttgcg ggccaggatg ccggcctgcc agggcggcca ggtgaacacg gccggattgt  119040
ggatttcgtt gtcggaatcc tcgtcggtgt cctcttcggg cgcgacggtg gactcggcct  119100
taaggcggcc gcgtgtcata acgcccgccg tgcacgccgt cgccgaggat gctgatttgc  119160
gtttgcggcc cgcggaagtg gaggcgcccg ccatggcgcc gccgccggta acgcggggcg  119220
tcttgcgctc ggtggttacg agttcctcgt cggagtccga tccgctggtc cagacgtcgt  119280
cgtcgccctg gcggcacccc tcgtcgtgcc ggtcccaggt gtgtcggtac tcaagcttgc  119340
cctggatgcg atactggctg gtgaaggtgg ggtgttcgct gtactgaggc ccgcgctgca  119400
gcagcaagtc gatatcgaaa aagaagagcg cagccacggg atcgtactga cgcagttcca  119460
cggtctcgcg tatcgcttgc acctccagga agatctgctg cccgttcatc aataggttac  119520
ctgagatgct caggcccggg atgctcttgg gacacagcag cccaaaatgc tcgtgtgagg  119580
taaaagccac atccagcatg atgtgcgaga tcttgcccgg tttgattatc atattttttgg  119640 gacacaacac cgtaaagccg ttgcgctcgt ggggcgcat gaagggttgc gggttgcggg  119700
tcatcgtcag gtcctcttcc acgtcagagc ccagcgtgac gtgcataaag agcttgccgg  119760
agggcacgtc ctcgcagaag gactccaggt acaccttgac gtactggtca cctatcacct  119820
gcatcttggt tgcgcgcgtg ttctccatgg agcaaaccag ctcgtgcgcg cacaccacgt  119880
gccgcagtgc cacgtccttg gtgggaaaca cgaacgctga cgtgtagtag acgtcgggct  119940 cttccactg gttctgctga cgcgtccagg ccagtcccga gccgtgaga cgcgcctgcc  120000 acatctgctt gcccgacgcg tgaatcacag cgtcagctac gggcaggtgt cggtgtttgc  120060
gctcggccgc cgacgggtag tggtgcacgt tgatgctggg gatgttcagc atcttgagcg  120120
gcagcgcgta cacatagatc gacatggcgt cttggctggg gcagatgctc cggcccgtgg  120180
ggttgtgcac gttgaccgac acgttctcca cctcgctgcc cgtaaagtac gtgtgctgca  120240
cctgcagctg attgtcgccg cggtggcatg gcgtcgagtc gggcgtgtac tgcgacacca  120300
ggatcagcga gggctggctc acgcgcacgt ggatacccgt ctgcaggagt cgcgtctcgt  120360
gcggcagcac cggcgtgtcg ccgcgactaa acacggcttt cagcacgtgc cccgaaatgg  120420
```

```
gacccagtac ggatatcatt tcgggacaac ggcgaccgcg cgactccatg ctgcctgcgc 120480
gtacgggtgt aggcgactga gcggcgcgcc ctctgcggcc gccgcttac ataggcaggc 120540 gaccagacgc ggaacccgaa ataaaaacgt tctacacaga gacaaccgcg gattattgag 120600
tgtctttttt tattaaaaaa aagaggcaaa gccccaccgt caccacaccc catcacacac 120660
caccaccgat ttttttgttt taaccccgta tcgcgcggac gcctagtgtc cgtttcccat 120720
caccagggtt ctctgtttag agatcgccgc agaccatggc taaagtgaca ggactcgttt 120780
tctctgtcgt attttccgta agcttacagt cttgcggttc cgtctccggg gacgccagcc 120840
gcatgggcag caggtcctcc aacgcgatgg aagcgcccag caccgagagc tgctgttgcg 120900
acggcgaatg ggacgtggac cgcgagtgta gcgtggattt gacttggtgc gtcattgctg 120960
acaggcaacc gcgattcagc gtatgctttg acgagataaa atagaggcgt cccaggagcg 121020
cgtcccgtgg gaacgtggcg ccattctcgt cgctcaccag tacggttaat tccaaccagg 121080
agcgcggtag ccagaccgta acgggcattt tgagtccctg acggttgtgt ggtacaaaaa 121140
cacccagata aggcccgtaa aagcggcggt agatacgtaa cgtgtgcgag ttcttcagcg 121200
tcaattcgta agggacgcgc acctccagtc cctcgtccgc cgcgccagag cgtggcggta 121260
caaagtaagg cagtggcgcg tccgaaaaga agggtcgtcg caccgtttcg cgtcgcagcc 121320
gcaggcgaaa cgccactggg tcggctggcg cctcggtgcg gtcgcaggtc acgttgaaac 121380
gtaacatgcc gtcttggtat agcgtgagtg acgacagcgt caggtccggc ggtgattcgt 121440
tcgggtctag ctccaatcgt ccaaagacgg agggtcccaa tgtcttggcc gtggtttccg 121500
agaggcgcgc cgagatacgg ctggtgagtc cacgcggccc cgagatgccg ccttccactc 121560
gatgccagca cagcgcgtgt cgtacgcgca ccgtcagcgt gggcgtcaga tccgcgtccg 121620
ttgactccgc ggcatcggcg acggaagccg cgttctccgt tacgttgttt atatccagcg 121680
tcgactcgaa cgtgagttct ggcagatgca gcgccagaca gtcgtgtaac gccgtgtgat 121740
gcgcggcttt acgtcgtagc ggtagccgtt tcagcagcgg cgtgatgata cggagcgcga 121800
agagattgag tgataagcgc acgatggcca tgcgcgtcag ttgttggtcg attaccgagc 121860
gcaggatatg gcagcctggg cgtgcgggaa agagagagaa ggccgggcgc acgtcagaat 121920
cctcgttgga gaccacgcat agaatgccgc gttcacgatc gtcgttgcgg tcatcctcgt 121980
cctcttcttc tttcttctct tctttttcct tttttttctc gagctcgtgg gaagccgccg 122040
tttcttcttc ttgcgacgtc gcggggggcgg tttgagactc gccgttcgct tcccccaatt 122100
gcagcggcgt agagagcaga atctggaagg gatcccgcaa ttcttcgggt cggaggtcga 122160
ggtgcaactg gattagatgg taagttccgc ggtgcacccg aggctgacgg atgtcgtgtt 122220
tatccgtcaa tgtaaggatg gtctgcgcg agccgctgtg cttgtccagc tcgtccggcg 122280
ttttcaggag gaggctgtcg tcgtcggtac tggcgacgcc catcatggtc gtggtggtag 122340
tggtggcgag gaaagtgagc ggcggcgccg acagagctcg gcgttggcgg cggcatttgc 122400
cgctgtgtcg gctgctattg ctgccaacgc caccgccgcc gcctcgtctg gctcgtggcc 122460
ggcgggcccg attccgaagg ttggggtcgg cgcgtggcat gcttggtgtc tgcgggcgcg 122520
agagggccgc ctcagccttt aaatatgcag gtcgcggatt tgttatcggg tgaaacgtca 122580
cacaccgtga agacgacctg ttcgcggatg aggtcatcca gctgtcgcag catgacgaaa 122640
agcgccgaca gccgcgcgat ctcgtcgtcg ggcgacacgt gctgcggccg cgcgggcgtg 122700
cgcggctcgc cgacgctgcg ctcgcggtcc agccgcatca gcagctcctg gcacttgacg 122760
```

-continued

```
agcagcatgg agctgtcctc tagcgccaac ttgcgcacgt aggtcatggt cagctctgag 122820
gctagattgg ccaccatgga catggagagg caggcggtct tcatgtcgat cagcaggtgc 122880
tggtcgatga ccggatcggg gatggtgaag gtggcgtcgc gaaaagtaat ggtctgcagc 122940
tgctgcacgg cagcctttac ctcctcgtac gaacggtcga gcgagaagag gcccatgatg 123000
agtagtcgct ggttgatttc cagcgccagt ggcatgggca cgatccaggg cagcaccagc 123060
tcccactggc ccagcgtcag caggttctcg cgcgccagcg gtccgtggaa gagcggcggc 123120
agcacgcata gcgcgtcgcc cttctcccaa gtcacgggtc ccgtgttgag gacggtgtag 123180
agcagtccgt gcgtcggtac gtgtaggagg atctggttgc cttctacgcg ccgcatcaac 123240
gtcagcgtca tattgcgcag caggccgcgc agtcgcacgt agccgcgggt gtgatctacg 123300
aactggtgta ggcccagctg gtagtgcttg atgagatgta gacgctgcgg aatgggcacg 123360
actgccgcta ctagcttggt cagtttgcct acgtcggcga tgctgagctt gtggtcgaaa 123420
gtgcagaaga tgttggcctc catggccgcc atagcggcgg tgaaatcgtg gccgcgacgg 123480
aggagaagcg gagacgaaca acgtctgcac cgggcgcggc gtcagagcga gcgtggcgcg 123540
tccgggcccg cgtttgcgtc taggtgactc gccgctaacc tgcggtcgtc gccgtcctcc 123600
tcaccggacg gcctcacgag ttaaataaca tggattgctg cagcgggatg atttcgccta 123660
cgacgtagtt accaaagtgc gtctcggacg tggcgaaagc cccggcgcca cccttgagtt 123720
tggtctccat cagcgccagc gtggtggtgc tgagaatcgg caacgcttcc tgcgtcaggc 123780
ggcacgggtt ttcgatgagt tgttccgtgc cttcgacgca gacgtactgc gtgtccgtgt 123840
cgccgcggat gcagtccttg gcgcgtagta ggtactcgtc gatggttttg aagagcgttt 123900
tgttggccgc gataatctct tctgtgttaa agtactgcgc acaggggctg tagaatttgg 123960
agttgtagcc caaacgttcg cgatgtcggg tgttgtacag tacgtcgctt agacagccgg 124020
cttgcgaggc ccaggggttg tgtgtggccg cgaaagtctg tgcgtcagct tcgcgatgat 124080
cgtagatggc cttggtggcg gcctccgtgt cgtacggatc gacgcccagc atgcaggagg 124140
cgcgtccgcg cggggttgttg gtgattttga agtaattaac gtccatcgtt accggcgtga 124200
ggatgagttc gcacacggcc ttttgtccgt gcaccgtggc ggcggcgttg cgctcggaca 124260
tgctgccgaa cgtcagcatg gagatggtct ccgtatctaa cagttgcggc cgttccacgc 124320
cggccgcgtg ccggatccag cggtccacct cgtcgtggcg gtacacgttc atagggaaga 124380
cgcgaaagag gtcttgcacg cggacgccca tgtcggtccg cacgcggttt acgtaggcta 124440
cgcaggtatt tgacgtgtaa cccagaccca tgtctacggt gttaatgttc tgcgtgacgt 124500
ggtacgtggt gctgatgtcg cgttcctcct tggtcacgat gggattgttg atgataactg 124560
acgtgcatga tttgccgctg tagagcagca tgtccacctc gaaggtgtcg gtgcgtacgg 124620
ccgtgagtgc gaatcccggg tggatgtgcg ccttggtctg cagcaccagt gaaactggtg 124680
agattttgta taacatggcg gccagcgtca taactgagtg caaacgttgg gacaggtgg 124740 ccgagtagcg cgaaagggc gagcgtagcc agttgtggta ctcgtgtgcg aaggctgtgg 124800
gtagcggaaa accaccgtcg tgacggtgat agtgcgggaa ctcggtcacg tagcgtttaa 124860
tgtcgtcgct caacgccgcg cagatggtgg ggtttgagta gaaacggtgg aaaggtacgg 124920
gtaggctgta ctcgatcagc gtcttaggcg ccgtcacgac gcagcagccg ttgtaaagca 124980
cgtgctgacg tgagataaag tccggcaggc cctgacgttg cgcgtgatcc agaggcgcgc 125040
gcacttcgag caccttgacg tgctcgccca cgaattgcac ggccaaaaac agctcacgac 125100
aggcctgcag cagcggcgta tgcgcgtcgg tggcgacgtc ctccaccagc tcggtcagca 125160
```

```
tctcgcctac ggcttgacgt tgcgccgcta ccgagtcttc gggggtgacg ccgcttgtgc 125220
tctctttcga cgtcgtacct gacgtggaga ccgcggtggc ggccggcatc aggagaaacg 125280
ccggtcggta aaagaggtct actagcagcg tcttgaggtt gagtcccagg ccgcaggccc 125340
ggttgttggt catggcgggt atgaggcaga gataaaagac cttttgtaac gtccattcgt 125400
cgtcggtggc acggtaatcg tccacaaaca gcggctcgtc ggcatccatg gcgcccaaac 125460
gcggtacgtc agaaacgccg tggtgtcgcg cctcgatgtt ggccgggttc aacgttgcc 125520 ggtcggccac tacctgtacg ccttccatat tacgcggcag gtgcgtaacg aagggggcc 125580 acagccggtg gtcgtgcagc gcgttcacgt aagccgatag cggttcctcg gccagttgac 125640
cgttgttaag ccccggcagc gctgagatgc gcgttaccag acgcagcacg gcgactagat 125700
tgcggtagtg aaagagcaac tgcggtggta gggcgccatc ggccaggtgt tcggcgatca 125760
acgtcaccag cgcgtagctg tgtgcaaaaa ccagcagctg acgtgtgtga acatgttga 125820 cgatacaacg tgctatgaaa gcgcggatta gcaaaaaagc gtcggcgttg ccgtgtacca 125880
gtacgtcgac caggtagcag agctcggggt aattggggct ggtcacggtg ttttgaaaa 125940 gtcgcaacgt ctcttcgtag tcgggtggtg gccgcagtcg catgtgttcc atgatctccc 126000
aggtgcgcag ttcgtggaag gggcccggtg ccagtccatc tggcaaatta ccgatgacga 126060
tacgcggcgt acacagcgcc accgtttcgc tgtttttcctg gcagtgcgta aagtcgaaga 126120
aggggtgcag ctcggtgtag agcgtgatgt tgcccacctt gtagaagtcg gtgaccacaa 126180
aatcctgctt catttcgttc accgtgcgcg ggacctcacg ccgtacgcgg taaaaatgtg 126240
gtatgcggcg cgccgcaccg cccatgggct cctgctgaaa acgacattcg agcagccgtt 126300
gcatggcggg ttccgagggc ggtccgcgtt ccgtgaaggc ctgcagacag ggcgcgggtt 126360
catgcagcac cgggtggcac agcgtcttaa gcgcgtccac aaagtctatc ttttgcacgg 126420
cacggtcccg gtttagcagg taggccgtgg tgggcagcgc gttgcggacg gtgtcgttga 126480
gcttaacttt gctttccacc gtggtgtaac cgcgatcctc gggcagatac agccctacgg 126540
ggaagaaaaa cgtcaggtcc acgttacgtt ctagcggatc tttggtatcg gtgttttgt 126600 agacgcgccg caagttttcc ataatcaccg ttttttcgcc cagtcgaatc acatccatgc 126660
ttagtggcgt taggctgtgc gccccggcct gcgaaagcga tcgttgggc agatgcggtt 126720 gacccgaagt cagatgggcc ttgtatgagt tgaaatcggc caggatcgag tgataggaaa 126780
tggcggtgac ggcgttttcg ggactgagca caaagttgcc gtaggtggcc ggcgccgaga 126840
ccgtctcttt ggtgatgtgg cttgagagca gcgacatgat gatctgcata acgttggccg 126900
tgcttaccat cacgccgctg atcttggccc ccgagctcgt ggtatacgtg gtggggttgt 126960
ctaggatgct atcggtggcc gcttcggcca gacgcgtgag gaacttgagc acatagtcgc 127020
gatcgcgcgt gcgattcagc aaaaagagcg tggccagcat tttggccttg aagctctgca 127080
agatgttgct tcgctggatg cggttcaatg cctgtcgcgc cagcgtggcg ttttctacca 127140
gcgtctgcac cacaaagtac ggcggcgcct tgcgtagcag tgtctgtaaa aagctgtgaa 127200
tcaagccgcg ctccatggcg tcggccgtgt ttttaagcgc gcgcagcacc gtgtgcatgg 127260
cttccacgtt gaggatcttg tccaagatgg tgccctcgaa tgtctcgcgc agatacgtga 127320
ggcaggctgc gctgagctcg aaggggatgg tgatggggga ttttcactg tatttggtga 127380 ccataatggt ggtctgacga ctggtgggca aaccggcgcc gctggccaca cgcggcacct 127440
gcacgtggaa cagcattttg cccgtagtca gtttattgag gtcgtggaac ttgatggcgt 127500
```

```
gcgccgccgc ggccaagccg ctggtcaaaa aataaaccca ttccaggcga ttgcagaagg   127560
tgccgaagat ggcttcgaag tgaatattgt aacgctcggg gtcgtcgccg tagtagatgc   127620
gtaaggcctc gaacatctcc tcgccggcgc tggtcttgac gtgcgtcaga aagtcagtgg   127680
gaatgcctac tttaggcagg agctcgagcg ccgaccagtt ctccatcgcg gcggcggcgt   127740
gagcgcgagg cgtcggagct cggggaaagc agcgcgaccc ggagaatggc cggcgctgcg   127800
ccgcgccgcc tcggctgcga cgctctaata gtcgtcggcg gctccgctac gccgcgccgc   127860
gttttacacg tccccgtgca cgttcgcgcc tgcaacctca cccaagagct atcgacgggc   127920
gaggacgccc gcttctgtcg tccgcgaccc gttaacgtcg aacgggtacg cgctgttttc   127980
gcggctctct accgtgcctg tcccgtacac gcgaggaccg agtccgagcg tgtcaagctg   128040
gtactgggtc gtctgttgct gggacccgtg gccgtaccct gttttgcga cggtgaagtg   128100 gagggccacg gcgagcatct ggtacccacg acgcagtttt gtcgcgggcc gctgctctac   128160
gtgcaccgac gttgttgttg cggatccgtg accgccgggc gcgcgctgtc ctaccacgtt   128220
ctcgaaaacc acgtggccac gcatgtgtta cgcggattgc tctcgctgac ggaatggaat   128280
cgagagttgc cgggccttt ttgcgactgt cctggcagcg gtggcgcctt gggaaccgag   128340
gaacgctacg ccatggcctg cttgccgcgc gacctcagcc tgcacctgga cgactatcct   128400
tacctgatgg tggaaatcgg acgcgtactc agcgtcagcg aggtagacga ctacgtaacc   128460
gccgtctccg gctacctggg cgaggccgcg gcgccgcgca ttcaggttca ctacaagctg   128520
ctctttggac tcaacgtgcg tccgcaagcg ccgtgcgcgt tggacgctac acgcgacttt   128580
tttctgctgg agctgcaaaa gctttggctg gcgttgaat atcaccacga agtcacgtcg   128640 gagttttcg gtcgcgtact ggctcagctg catcgcgacc gcgcccgcgt catgatggca   128700
cttcgcttgc ccgagcagac ggtgtgccac ctaagcacct tcgttctcag tcgcttcaag   128760
cgacaggtac tgtacttcaa gttacaggtg agctacggca agtgccggac tggccacgct   128820
gacagaagtg ggggaggggg aaacggtgga agtcagggac accacaacct actgtgttat   128880
cgacgtctta gcgtcacgtt tgccgacacg gacacggtgt ggagaaacct tttctacgtt   128940
tattatgaac tagctcggga tctggggtcc catgggacag aggaccgatc cgtaagccgc   129000
ggttacggtg tttcttgcgc tccgaggacg tcgcggctac caccgtcaga accgacggtg   129060
gtttcagcca acggacacgc gctgtcttcc accgcgctcc cgacgacgag cgcgggtcac   129120
aagctgtcgc tgccgcgcga cccggccgca gatcgcgttc gacgttacgt gtgcattatc   129180
tcgcgtctca tgttcgcccg gtatggggag agatggcgta acaccgtcg acggcggtcg   129240 gagacgggag aagaggagga ggaagagacg gtggaatcgg gggagactga cgccacgccg   129300
ccatttgact ttacggggca gcagctgcgc cgggcctatc aggaacaccg acgtcgtaaa   129360
catctagccg tgcagcgtta cgcgccgtgc cgtcgtaagc tcatcggcgg gatggagttt   129420
gccgaggtga cgggcgttag tctggaccgc atcgccgtca acgctttcaa caccaaccgc   129480
gttatcaata tgaaggccgc actctcgtcc atcgccgcgt cgggtctcgg cgtgcgcgcg   129540
ccgcggcttc ccaagaacat gacccacagt tttgtgatgt acaagcacac cttcaaggag   129600
cccgcttgca ccgtcagcac tttttgtttcc aacgacgccg tctacatcaa ctcgctcaac   129660
gtcaatattc gcggttccta tcccgagttt ctgtactcgc tgggcgtgta ccggctgcac   129720
gttaatatcg atcacttctt tctgccggcc gtggtgtgca acagcaactc ctcgctggac   129780
gtgcatgggc tggaggacca ggcggtgatc cgctcggagc gcagcaaggt gtactggacc   129840
accaactttc cgtgcatgat ctcgcatact aacaacgtca acgtggggttg gttcaaagcg   129900
```

```
gctacggcca ttgtgccgcg cgtctcgggc gctgacctgg aagccattct gctcaaagaa    129960
ctctcgtgca tcaagaacat gcgcgacgtg tgcatcgatt acggtctgca tcgcgttttc    130020
acgcaactag agctgcgcaa ttcgtaccag atcccctttcc tggccaagca gttggtgctg   130080
tttctgcgtg cttgcctgct caagctgcac ggtcgagaga agcggctgca gttggaccgc    130140
ctagtatttg aggcggcaca gcggggtctc tttgactaca gcaagaacct cacggcgcac    130200
accaagatca agcacacttg cgcgctcatc ggcagtcgtc tagccaacaa cgtgcccaag    130260
atcctggccc ggaacaaaaa agtcaaattg gatcacctgg gccggaacgc caacgtgctg    130320
acggtgtgtc ggcacgtgga agcccacaag atccctcgca cgcgcctcaa agtgttagtc    130380
gaggtgctgg gcgcgttgca gagtatcagc ggtacgccgc acacgcgtga agtgatccac    130440
cagacgttgt ttcgattgtg ctcggcggcc gcagccacct cgggcctgtg ttcatcccct    130500
cccccattgt gtgtgtcctc atcttcctcc gcccctttctg tcccaacctc cgtcagcgtt   130560
gacggcagtt ctgaacccac gtcgccgcga gcgcggtttg catcacgatg atggaagccg    130620
cggccgctgc cgccgcggcg tttcgtccgg aggagcgtcc gacgccgggt tggcacgacg    130680
cagcgttgtt aatggacgac ggtacggtgc gcgagcacgc gtttcgcaac ggaccgctgt    130740
cgcaactgat tcgccgtgtg ttaccgccgc cgcccgacgc cgaagatgac gtggtttttg    130800
cttcagaact gtgttttttat tgcagcggtc gttttaaccg caggtcgtcc gtcttctcca    130860
tctattggca gaagcatagc gatctggtat acgcgcttac gggcattacc cattgcgcta    130920
agttggtggt ggaatgcggt cagttgggga gtggtaggct acggtggcgc gacggtgacg    130980
tgggtggtga ggagcgccgg ggagacgacg acagcaggga cgagctgtac gacgtgccgg    131040
gaatttacat gatccgcgtc aacgacggcg gcagcaccgg ccccaggcac gttatttggc    131100
cgggtaccag cgtgctttgg gcgccggacg tggtgatcac tacggtgcag cgacgaatct    131160
cggcggcgcg cgccctggtg aacacgttcc gccagtattt ttttttgctg aacggcgct    131220 cgcacgagga gctggttctt tgtccgcccg agatggagga gcgtctagcg ccgttgttgc    131280
agagtgccac gcgtggtgat tcggacatgt ttgacggtgt ggtggccagc gcttatcacc    131340
gtttgcgaat aagtaatatt ccgcgttcat ccgcccgtct gctggagcac tgcgtggggc    131400
tggcaggtgc taagaagctg ctcttgctcg acgtgccgcg tctggagaac tattttctttt   131460 gtcaagtctg tctttacgag ctggacgagg acagatgggg cgaggagatg ctgggtatgt    131520
tggccggaaa gcccgaggac gccgccgtct cgggcgcaag cggcggtttt ctgctacatc    131580
gcaagacgat gaagctggcc gcctgtctat gtttgctgct caattcgctg catttgcacc    131640
aggaggcgct ggaggccttg gatcctccgc cgccgcgcgt cgaggagaac gaccttgtca    131700
acgtggtgct gcgccgttac tatcgcagtc acggcggcgt gcaggcgcgg acgttggcgg    131760
cggcccgggc tttgttagcc gactacgccg aaacgttttc gcccttgggg agttttacgc    131820
gcctgggtta cgatcgtctc gtttctgccg atgccggcgt cagtcgccgg cacctggtgg    131880
ctctgctgcg tgcctagctg accctgaaac ggatggcgtg tatctcgtca cacaggtagg    131940
tggccatgat gacggctatg ataagatcgt ccgagatacg attctggcgc ttggccgagt    132000
agcgtgccgt cgtgccttcg gccagcgtga cgcggtgcag gttctgaatc tgctccagaa    132060
gatactcgat ggggtcgtgg ctcagcttga tggtgtagga gacgagctct gcgaggctt    132120 tgatgtagcc cgagttgaaa cgcgagatga actgttctac ggccagcgcc ttgtcgcggc    132180
ccatgaggta gaagggctgt tcgatgtggt tctggtcggg cgtgtggtag aagagcacgc    132240
```

```
ggatgagcgt gctactctgc acgctctgtc ggatgaggca ggcgatgcgc acggccgccg  132300
cctggttagt gttgccctcc acggcgatac gcagttcgtc caggtaaggg tgcaggctca  132360
gcaccgagat gatcatgtgc gccgcgcact cggcgatggc tacctcagaa ctctcggaga  132420
ggtcgcgcaa aaagaaatgc tctaggccgt aaatgagaaa ctggtgtcgg taggcgccta  132480
cggccgccac gcccgtgccc gaggccttgc ggttggtggt gaaggccggg tccagatata  132540
cgtagagcgt cttgccgaaa taatcgtagg cgttggtgtt gagcgtgctg taacgcaaaa  132600
tatcgaactc ttcgcggctc tggtccgtga tgagcacggt gttttgcgag atcttattgg  132660
taccgccgat gatctcgtcc atgaaggcgc ccggcataaa catgttggcc gtcttgcgca  132720
cctgcgagtt gaggctgatg aaggtgggct tgtgcagtcg gtagcaagga caggccgtgg  132780
cgtcgccctt ctccgtgaag ctgtgcaggt gctcttcgca cacgtaagag accacgttga  132840
gcatgtcaaa gggcgcattg ttgaggcgcg tcaagaaaca cgtggcgtca ctggtagtgt  132900
tggtggacga tatgaagatg atcttggtgg tattctgtgc caggaacccc agaatggtgt  132960
tgaaggcctc tttcttgatg aagtgcgcct cgtccaccag cagcaagtgg aagttttgtc  133020
ctcggatgct ctgtgtagag aggagacaga aaagggactc ttatgattac gcacgctcgg  133080
ctggaagcct acagagtcgg ggtggggccg acaggtgagc caggtgagc cgccaggtga  133140
ggcgggatcg ccgtgtgcca accgggctgc gacctgaaaa ccggaaccaa tccgccgaca  133200
ccggcgccgc gtgacgcgcg cccataaaaa cgaaagtgtc gtcgtcgcga cccgccacag  133260
ccgccatgaa ctcgttgctg gcggaactca accgactggg ggtcgcgcac gccactacgg  133320
aggatgtttt tatctttgtc gaccgcctct ttcaacactt ttccttcctt ttccaggccg  133380
aggagtcagg cccgcgccgc ttggaactgg tcgcgtccgt gttcgagcac ctgacggtgg  133440
agtgcgtcaa cgacatcctg gacgcctgca gccacccgga cgtgaacgtc gcggagacaa  133500
gcaacacctg tcgtccctgc ccttctcctg ttccctccgc ccccaaaact gtcagcgacg  133560
ctcagacgtc atgtgcgacg tctcgggcgc ctgtgacatg aggcacgtcc agaacgcgtt  133620
taccgaggag atccagttac actcgctcta cgcgtgcacg cgctgctttc gcacgcacct  133680
gtgtgatctg ggcagcggct gcgcgctcgt ctccacgctc gagggctccg tctgcgtcaa  133740
gacgggcctg gtatacgagg ctctttatcc ggtggcgcgt agccacctgt tggaacccat  133800
cgaggaggcc gcactggacg acgtcaacat catcagcgcc gtgctcagcg gcgtgtacag  133860
ctacctcatg acgcacgccg ccgttacgc cgacgtgatc caagaggtgg tcgagcgcga  133920
ccgcctcaaa aagcaggtgg aggacagtat ttacttcacc tttaataagg ttttccgttc  133980
tatgcataac gtcaaccgta tttcggtgcc cgtcatcagc caacttttta ttcagcttat  134040
catcggtatc tactcaaagc agaccaagta cgacgcgtgt gtcatcaagg ttagtcgtaa  134100
gaagcgcgag gacgcgcttc tgaaacagat gcgttccgaa tatggaaacg cacctgtatt  134160
cggatctggc gtttgaggcg cggttcgctg acgatgagca attgcctcta catctggtgc  134220
tcgaccagga ggtgctgagt aacgaggagg ccgagacgct gcgctacgtc tactatcgta  134280
atgtagacag cgctggccga tccgcgggcc gcgctccggg tggagatgag gacgacgcac  134340
cggcctccga cgacgccgag aacgccgtgg gcggcgatcg cgcttttgac gcgcgagcgg  134400
ggacttggca gcgtgcctgt tttcgtgtac taccgcgccc actggagttg ctcgattacc  134460
tacgtcaaag cggtctcact gtgacgttag agaaagagca gcgcgtgcgc atgttctatg  134520
ccgtcttcac tacgttaggt ctgcgctgcc ccgataatcg gctctcaggc gcgcagacgc  134580
tacacctgag actggtctgg cccgacggca gctatcgtga ctgggaattt ttagcgcgtg  134640
```

```
acctgttacg agaagaaatg gaagcgaaca agcgcgaccg gcagcaccaa ttggccacgg   134700
ccacgaatca ccgtcggcgg ggcggactgc gtaacaattt agacaatggg tcggatcgcc   134760
gattgcccga aacggctatg gcttctttgg agacggccgt cagtactcca tttttcgaaa   134820
ttccgaacga agcaggaacc tcctccgcga atggcggcgg cagattcagt aacctggagc   134880
agcgggtagc gcgtttgttg cgcggcgacg aggaattcat ctatcacgcg ggtccattgg   134940
agccgccttc caagatacgc ggtcacgagt tggtgcagct gcgcctggac gtaaatccag   135000
acctcatgta cgccaccgat ccgcacgacc gagacgaggt cgcgcgtacg gacgagtgga   135060
agggcgccgg cgtctcgcgt ctccgcgagg tttgggatgt gcagcatcgc gtgcgcctcc   135120
gtgtgctgtg gtacgtcaat tccttttggc gcaatcgcga gctgagctac gatgatcacg   135180
aagtcgaact ataccgggcg ttggacgctt atcgggcgcg cattgccgtc gagtacgtgc   135240
tgattcgcgc cgtgcgcgac gagatctatg ctgtactacg acgggacggc ggcgcgttgc   135300
cacagcgttt cgcctgccac gtgccacgga acatgtcctg gcgcgttgtt tgggaacttt   135360
gccgtcatgc cttggtgctc tggatggatc gggcggacgt gcgtagctgt attattaagg   135420
cgctgacgcc tcgtctgagc cggggtgccg ccgctgccgc tcagcgagct cgtcgccagc   135480
gcgagcgccc ggcgcccaaa ccgcaggagc tgcttttcgg gccgcggaac gagagcggtc   135540
cgcccgccga acggacttgg tacgctgacg tggtgcgctg cgttcgcgcg caagtggatt   135600
tgggcgtgga agtgcgcgcg gcgcgttgtc ctcgcaccgg gctttggatc gttcgtgatc   135660
gccgcggacg cctgcgacgt tggctctcgc agcccgaggt gtgcgtgctc tacgtcacgc   135720
cagacttgga cttttactgg gtgctgccgg gcggctttgc tgtgttctcg cgcgtcactc   135780
ttcatggctt ggcgcagcgg gctttgcgag accgattcca gaactttgaa gcagttcttg   135840
caagaggaat gcatgtggaa gctggtcggc aagagtcgga acaccgcga gtatcgggcc   135900
gtcgcttgcc gttcgacgat ctttagtccg gaggacgaca gctcgtgtat cttatgccag   135960
ttgctgttgc tctaccgcga cggcgaatgg atcatctgtt tttgctgcaa cggccgttat   136020
caaggccact atggcgtgaa tcacgtacat cggcgtcgtc gacgcatctg tcatctacct   136080
accttgtacc aactgagctt cggaggtcct ttgggtccag ccagcatcga tttcttgccg   136140
agctttagcc aggtgaccag cagtatgacg tgcgatggta ttacgcccga cgtgatttac   136200
gaggtctgca tgttggtgcc ccaggatgaa gccaagcgta tcctggtcaa gggtcacggt   136260
gccatggacc tgacctgtca gaaggcagtg acgctaggcg gcgccggcgc ctggttgctg   136320
ccgcgtcccg aaggctacac gcttttcttt tacattctgt gttacgacct gtttacctca   136380
tgcggcaatc ggtgcgatat ccctccatg acgcgcctca tggcggcggc cacggcctgc   136440
gggcaggcgg gttgcagctt ttgcacggat cacgagggac acgtagatcc cactggcaat   136500
tacgtgggtt gcacccccga tatgggccgt tgtctttgtt acgtgccctg tgggcccatg   136560
acgcagtcgc tcatccacaa cgaggaaccc gcgactttt tctgtgagag cgatgacgcc   136620
aagtacctat gcgccgtagg ttctaagacc gcggcgcagg tcacactggg agacggcctg   136680
gattatcaca tcggtgttaa ggattctgag ggccgatggc tgcccgtcaa gaccgatgtg   136740
tgggacctgg tcaaggtaga ggaacctgtg tcacgtatga tagtgtgttc ctgtccggtg   136800
cttaagaacc tagtgcacta acggggtctg acagttcacg gggagaagaa acaagaaaca   136860
acaaaaaaag gaggacatgg actcgccacg gtttgtggca aggcgtatgt tatcatcatg   136920
gagctactca cgttggtgtt gtagcaactg gcaaaaagcg ccgtgctctt ggcgccgcgg   136980
```

```
tggtcgatgc tgatcacgtt gtccttgttc tcgaccacgt agtcgcgcgc gaaggtgtgg   137040
cggcagcgga actcgacctc tttgagcaca aactgcgaca cgtgcttttg gtgcgccacg   137100
tagccgatgc tgatgccgat catgtgctta agcagaaacg agataatggg gatgatgaac   137160
caagtcttgc cgtgacgtcg cggcaccagg aacacggtgg cttctgctt aaagatgtcg    137220 atggaggtct gcgagaggaa gtcgatctgg aaggcgtgga tgaggtactg cagcacgcga   137280
ttggccagca cggggatctt ggtcacggct ataaaaaaga tgacgtgtat caataaattc   137340
ttttgaaacg gttcgagtcg gatggctttt gcgtcgccct cgacggcggt actgaagccg   137400
ccgtcgagcc acttttaaa gtcggtcatg aagttgttga tctgctgaaa ctgcggatcg     137460
cggtagagct cggtcaacgc gtccagcttc tggtaggagg cgcgctgctc ctcggagcac   137520
gggcgaaacg tcagttcatc gagcgcgctc ttgaggcgct cgtgaaacag cagctcgcgc   137580
tggctttcct cgggcgagtt gtagtcgcgg tggcggccgc agaaggccat gagcggcagg   137640
aaggcctcgt tgcacgagtg ggccagcccg agttcggggt gcatcatctg gtagcgcttg   137700
cggcacagcg ccgccacatt ggtgaaggcc gtggagatgc aggaggtggg gtggctcttg   137760
cgcttctgca gctccgcgta gcgctcctgg atcttggcgg ccgagtctcc gcgcaacatg   137820
atggcggcgg cggtggtgcg agcggaggtt aggcggcagc ggcgagagga gaggaaaaag   137880
atggcggccg cgaggacgac ggaggatcca cccgaaaacc acgttgttgc ggacgtggct   137940
tgtgggacgg gcgccgtcac tcgttcgtct tcgtcgtccc tagtggtgtc gtcttcctcg   138000
gcgtcaggct cggacgaacc ttcctccgcc tctcctctca gtttcccgt ctgctccccc    138060 tcaactgccg tcaggtctcc gggtccgcc ggggtttcaa cgtccctgtg ctcggtggaa     138120
cggatggtcg agctgtcggc gcagtctccg gccgccgatt tctcggtctc cgaggcttgg   138180
cgcttcgagg aggccgtaaa tatgcgctg gtggcctgcg aggccgtgtc accttacgat     138240
cgctttcgcc taattgaaac gcccgacgag aatttcttgt tggtcaccaa cgtaattccg   138300
cgcgagtcgg ccgaggtgcc ggtgttggat agcagtagca gcggtggcga tagcgggccg   138360
gaggacaaaa agaaaaacgt cgggaataaa accgcggggg aaaagaacgg cggtgggtct   138420
cgggccaaac gccgtcgtag acgacgcgct ccgaaaaacg acgccgccac gccgtctttt    138480
ctacgtcgac acgacgtgct ggagcgtttc gcggccgcgg ctgagccttt gccgtcgctt    138540
tgtgtgcgtg attatgcgtt acgcaatgct gaccgtgtta cctacgacgg cgaattaatc   138600
tacggcagtt acctgttgta tcgcaaggct cacgtggagc tgtcactctc cagcaacaag   138660
gtgcaacacg tggaagccgt gctgcgacag gtgtacacgc cgggcttgtt agatcatcac   138720
aacgtgtgcg acgtggaggc cctgctgtgg ctgctgtact gcggaccgcg tagcttttgc   138780
gcgcgtgaca cctgtttcgg tcgcgaaaaa aacggttgtc cttttcccgc gttgttgccc    138840
aaactctttt acgaacccgt gcgggactat atgacctaca tgaatctggc tgagctgtac   138900
gtctttgttt ggtatcgcgg ctacgaattc cctgcgccga cgccgcaggc gacgacggcg   138960
ggtagtggtg gcggcggcgg ggccggcgct tgtgcggtcg agacgagcgc gtcagcaggc   139020
cgggtcgatg acgccggcga cgaggtgcat ttgcctttaa agcccgtctc gctggaccgt    139080
ctcagagagt gttgcaggc ggtgcgcggc cgcttctcgg ggcgcgaggt gcccgcctgg     139140
ccggcctcgt cgcgcacctg tttgttgtgc gcgctctaca gtcagaaccg tctctgttta   139200
gatctcgcgc gtgacgaggc gcggaccgtg agttatagcc ccatcgttat ccaagactgc   139260
gccgcggctg tcaccgacgt cactttgagc cacatcttgc ccggcagag caccgtctcg    139320 cttttccccg tctaccacgt cggaaagttg ctggacgccc tctcgctgaa cgacgcgggt   139380
```

```
ctcatcacgt tgaatctatg acgtcggtca acaaacagct cttaaaggac gtgatgcgcg   139440
tcgaccttga gcgacagcag catcagtttc tgcggcgtac ctacgaccg cagcaccggc    139500 ttaccacgca gcaggctttg acggtgatgc gtgtggccgc tcgggaacag acccgataca   139560
gtcagcgaac gacgcagtgc gtggccgcac acctgttgga gcaacgggcg gccgtgcagc   139620
aagagttgca acgcgcccga cagctgcaat ccggtaacgt ggacgacgcg ctggactctt   139680
taaccgagct gaaggacacg gtagacgacg tgagagccac cttggtggac tcggtttcgg   139740
cgacgtgcga tttggacctg gaggtcgacg acgccgtcta acaggtatag caatccccgt   139800
cacgcctctg ttcagatttt attaaaaaaa aaaaacacaa cataacgaca gtgtcggtgt   139860
ggtagctagt gcagctctag gaacagggaa gactgtcgcc actatgtcct ccgcacttcg   139920
gtctcgggct cgctcggcct cgctcggaac gacgactgag ggctgggatc cgccgccatt   139980
gcgtcgtccc agcagggcgc gccggcgcca gtggatgcgc gaagctgcgc aggccgccgc   140040
tcaagccgcg gtgcaggccg cgcaggccgc cgccgctcag gtcgcccagg ctcacgtcga   140100
tgaagacgag gtcgtggatc tgatggccga cgaggccggc ggcggcgtca ccactttgac   140160
caccctgagt tccgtcagca caaccaccgt gcttggacac gcgacttttt ccgcatgcgt   140220
tcgaaatgac gtgatgcgtg acggagaaaa agaggacgcg gcttcggaca aggagaacct   140280
gcgtcggccc gtggtgccgt ccacgtcgtc tcgcggcagc gccgcagcg gcgacggtta    140340 ccacggcttg cgctgccgcg aaacctcggc catgtggtcg ttcgagtacg atcgcgacgg   140400
cgacgtgacc agcgtacgcc gcgctctctt caccggcggc agcgacccct cggacagcgt   140460
gagcggcgtc cgcggtggac gcaaacgccc gttgcgtccg ccgttggtgt cgctggcccg   140520
caccccgctg tgccgacgtc gtgtgggcgg cgtggacgcg gtgctcgaag aaaacgacgt   140580
ggagctgcgc gcggaaagtc aggacagcgc cgtggcatcg ggcccgggcc gcgttccgca   140640
gccgctcagc ggtagttccg gggaggaatc cgccacggcg gtggaggccg actccacgtc   140700
acacgacgac gtgcattgca cctgttccaa cgaccagatc atcaccacgt ccatccgcgg   140760
ccttacgtgc gacccgcgta tgttcttgcg ccttacgcat cccgagctct gcgagctctc   140820
tatctcctac ctgctggtct acgtgcccaa agaggacgat ttttgccaca agatctgtta   140880
tgccgtggac atgagcgacg agagctaccg cctgggccag ggctccttcg gcgaggtctg   140940
gccgctcgat cgctatcgcg tggtcaaggt ggcgcgtaag cacagcgaga cggtgctcac   141000
ggtctggatg tcgggcctga tccgcacgcg cgccgctggc gagcaacagc agccgccgtc   141060
gctggtgggt acgggcgtgc accgcggtct gctcacggcc acgggctgct gtctgctgca   141120
caacgtcacg gtacatcgac gtttccacac agacatgttt catcacgacc agtggaagct   141180
ggcgtgcatc gacagctacc gacgtgcctt ttgcacgttg gccgacgcta tcaaatttct   141240
caatcaccag tgtcgtgtat gccactttga cattacaccc atgaacgtgc tcatcgacgt   141300
gaacccgcac aaccccagcg agatcgtgcg cgccgcgctg tgcgattaca gcctcagcga   141360
gccctatccg gattacaacg agcgctgtgt ggccgtcttt caggagacgg gcacggcgcg   141420
ccgcatcccc aactgctcgc accgtctgcg cgaatgttac caccctgctt tccgacccat   141480
gccgctgcag aagctgctca tctgcgaccc gcacgcgcgt ttccccgtag ccggtctacg   141540
gcgttattgc atgtcggagc tgtcggcgct gggcaacgtg ctgggcttt gcctcatgcg    141600 gctgttggac cggcgcggtc tggacgaggt gcgcatgggc acggaggcgt tgctctttaa   141660
gcacgccggc gcggcctgcc gcgcgttgga gaacggcaag ctcacgcact gctccgacgc   141720
```

```
ctgtctgctc attctggcgg cgcaaatgag ctacggcgcc tgtctcctgg gcgagcatgg   141780
cgccgcgctg gtgtcgcaca cgctgcgctt tgtggaggcc aagatgtcct cgtgtcgcgt   141840
acgcgccttt cgccgcttct accacgaatg ctcgcagacc atgctgcacg aatacgtcag   141900
aaagaacgtg gagcgtctgt tggccacgag cgacgggctg tatttatata cgccttttcg   141960
gcgcaccacc agcataatct gcgaggagga ccttgacggt gactgccgcc aactgttccc   142020
cgagtaaccg ggacgcggaa cgtgacggtt gctgagggga aaggcgacag agaaggtaca   142080
aacccaccgg cggggaaaat accgaggcgc cgccatcatc atgtgggggcg tctcgagttt   142140
ggactacgac gacgatgagg agctcacccg gctgctggcg gtttgggacg atgagcccct   142200
cagtctcttt ctcatgaaca ccttttttgct gcaccaggag ggcttccgta atctgccctt   142260
tacggtgctg cgtctgtctt acgcctaccg catcttcgcc aagatgctgc gggcccacgg   142320
tacgccagta gccgaggact ttatgacgcg cgtggccgcg ttggctcgcg acgagggtct   142380
gcgcgacatt ttgggtcagc ggcacgccgc cgaagcctcg cgcgccgaga tcgccgaggc   142440
cctggagcgc gtggccgagc ggtgcgacga ccggcacggc ggctcggacg actacgtgtg   142500
gctcagccgg ttgctggatt tggcgcccaa ctatcggcag gtcgagctct tccagttgct   142560
ggaaaaggaa tcgcgcggac agtcgcgcaa ctcggtgtgg catctgttgc gtatggacac   142620
ggtttcggcc accaagttct acgaggcctt cgtcagcggc tgtctgcccg gcgccgcggc   142680
ggcggacggt tcgggtggcg gcggctcgca ctacacgggc tcgcgcgccg cgtctcgcc   142740
aggcatccag ttcggtatca aacacgaggg tttagtcaaa cgctggtgg aatgttacgt   142800
gatgcacggg cgcgagccgg tgcgcgacgg cctcggtctg ctcatcgacc ccacgtcggg   142860
gctgctgggc gcttccatgg acctgtgctt cggcgtgctc aagcagggca gcggtcgcac   142920
cttgctggtg gaaccgtgcg cgcgcgtcta cgagatcaag tgccgctaca aatatttgcg   142980
caaaaaggag gacccctttg tgcagaacgt gctgcggagg cacgacgcgg cggccgtggc   143040
ctcgctgttg cagtcacacc cggtgccggg cgtggagttt cgcggtgaac gcgagacccc   143100
gtcggcacgc gagtttctgc tttcgcacga cgcggcgctc ttcagggcca cgctcaagcg   143160
cgcgcgcccg ctcaagccgc ctgaaccgct gcgcgagtac ctggccgatc tgctgtatct   143220
caataaggcc gagtgttcgg aagtgatcgt gtttgacgcc aagcacctga atgacgacaa   143280
cagcgacggg gacgccacga ccactattaa cgcgagtctc ggcctagccg cgggcgcacg   143340
cgctggcggc ggcgctgatc accacctgcg gggcagcccg ggcgattcgc cgccgccgat   143400
acctttcgag gacgaaaaca cgcccgagct gctgggccgg ctcaacgtgt acgaggtagc   143460
gcgcttttca ctgccggctt ttgtcaatcc gcgtcaccag tattactttc agatgctcat   143520
tcagcagtac gtgctcagcc aatactatat aaagaagcat ccggacccgg agcggatcga   143580
tttccgcgac ctgcctaccg tctacctggt ctcggccatc ttccgcgagc gcgaggaaag   143640
cgaactgggc tgcgagttgc tggccggcgg tcgcgttttc cactgcgacc acatcccgct   143700
cctgctcatc gtcacgcccg tggtctttga ccctcagttt acgcgccatg ccgtctctac   143760
cgtgctagac cgttggagtc gcgacctgtc ccgcaagacg aacctaccga tatgggtgcc   143820
gaactctgca aacgaatatg ttgtgagttc ggtaccacgc ccggtgagcc cctgaaagat   143880
gctctgggtc gccaggtgtc tctacgctcc tacgacaaca tccctccgac ttcctcctcg   143940
gacgaagggg aggacgatga cgacgggggag gatgacgata cgaggagcg gcaacagaag   144000
ctgcggctct gcggtagtag ctgcggggga aacgacaata gtagcggcag ccaccgcgag   144060
gccgcccacg acggctccaa gaaaaatgcg gtgcgctcga cgtttcgcga ggacaaggct   144120
```

```
ccgaaaccga gcaagcagtc aaaaaagaaa aagaaaccct caaaacatca ccaccatcag   144180
caaagctcca ttatgcagga gacggacgac ctagacgaag aggacacctc aatttacctg   144240
tccccgcccc cggtcccccc cgtccaggtg gtggctaagc gactgccgag gcccgacaca   144300
cccaggactc cgcgccaaaa gaagatttca caacgtccac ccaccccgg  dacaaaaaag   144360 cccgccgcct ccttgccctt ttaacccata aactttcagg tctcgcgtac gattcgcgag   144420
tcgggaatgg gacaccgtg  ggtgtttctc cgtgtgtata ttattttttt tttgtgtgtg   144480
tttgcgcccc cgtgtgtcta atgtgctgtt tgaaacacgt aaagtagctg gtggaagaac   144540
agataaacct ttaataaaaa aaaaagtatg tgctcccgac ccacggtctg cgtgtctctt   144600
ttttatgtcc atgtctccaa gtctggtgcg ggtggcggcg gggtcaagcg tcctcgaagt   144660
cttcatcatc gtcgtcgtcc tcttcttcgc ggaggcgacg gctttccaag ctgtcgtggt   144720
gactgagtgc agcgacttct tcgccggagg ctgtggccag cgcctggtac ttaacactgc   144780
cgctaccgcg tccgcgaaag taacggacgg cgcgacacgt cgtaaacatg gcccatatga   144840 aaagagcat  gccgaacgac cagctgatgc cggtgcggta ttcgttgctg aggaaggtat   144900
cgtactgcac gatggggtag atgaggccgc agagtccaaa gaaggcgccc aggtggtagc   144960
cgaattgcac cttgacgtat tgaaaaaaga cggcctcgat cagtaaaaag tagatgatgg   145020
agatgatagc gtagaccacg aagacggcta acaccatgtg gcctgtacgc acgaaaaagt   145080
tgtttctgaa gccgtagcat agggccatgg ctaccacggt ggtgttgaaa ccaagcgcta   145140
cctccaccag gttgacgatg agcgtgcgga actgcaccgt acctttgagc ttggggtgca   145200
gacgcgagaa gaaaaagagc gagcgtttgt agctgcggta ctgcgtgacc atgctcacgt   145260
tgaaaatggt caggcagaaa aagtgcacgg cggccatgaa ggcgatcatg ctgggcagcc   145320
gaaatgacat ggtcagtgtg aatagttgga atgtgtccat gctgaggatg aaaaggaagg   145380
ctgtgaggct gtcgcccatg tacgagatgt cgcgtgtcga ctggtttagg ctcatgcctt   145440
tgtccttgcg catgctgatc ttgatccagc ataccaggta gtagatggtc acggctaaaa   145500
agacgagctg catgaacacg gcgtagcaca ccagctgcac cgagtctaag aaaagcatag   145560
gcgtgtgcag gtgcattacg ttgtaggccg acatgttgag cctttcaaag tccacgacgt   145620
gatagtagac gcaggggtag cccaggtgcg gaaaattgct cagcaccaga tgcacgctga   145680
cgttgacaaa agtcagcacc atgaaaacga tagaagcgct ccatgtccgt gtattcacct   145740
tatccacgtg cgagggggcc atggcgatag cggcggcccg ctcgctcggg aggcgatggg   145800
ggcgcgccga tgacgacagg ctcgcgggtc gttaaatact acgatgggag ccgccgcggc   145860
tcacgacgcg gtttgagcgc gtccgggcgg tcggcgaaaa aagacccgc  gggccttcgc   145920 gactctcttc tgtccgagga tgaccgctca gccgccgctg caccaccgcc accaccgta   145980 cgccctgttc gggaccagct gtcatctcag ctggtacggc cttctggagg cctcggtgcc   146040
catcgtacaa tgtctgtttt tggatctggg tggcggccgt gccgaaccgc ggcttcacac   146100
gttcgtggtg cgcggtgacc gtctgccgcc ggctgaggtg cgtgctgtgc atcgcgccag   146160
ctacgccgcg ctggcctcgg ccgtgactac ggacgccgac gagcgccggc gcggcctaga   146220
gcagcgtagc gccgtgttgg cgcgcgtgtt gctagaaggc agcgcgttaa tccgcgtgtt   146280
ggcgcgcacc ttcacgccgg tgcagattca gacggacgct agcggcgtgg agatcttgga   146340
ggccgcgccg gcattgggcg tggaaaccgc agcgctgtcg aacgcgctta gtcttttcca   146400
cgtagccaag ttagtggtca tcggctcgta tcccgaagtg cacgagtcgc gtgtggtcac   146460
```

```
gcatgccgcg gaacgcgtct ccgaagagta tggcacccac gcgcacaaaa aattgcgtcg    146520
cggttactac gcctacgatt tggccatgtc gtttcgcgtc ggcactcaca agtatgtgct    146580
ggagcgcgac gacgaggccg tcctggcacg cctctttgag gtgcgcgagg tgtgtttttt    146640
gcgcacctgt ctgcgtctgg tcacgcccgt cggtttcgtg gccgtggcag tgaccgatga    146700
gcagtgttgt ttattgctgc agtcggcctg gactcacctt tacgacgtgc ttttttcgtgg   146760 tttcgctggg cagccgccgc tacgcgacta cctgggggccg gacctctttg agacgggcgc   146820
tgcccgttct ttcttttttc ccggtttccc gcccgtgccc gtctacgcgg tccacggtct    146880
gcacacgtta atgcgcgaga cggcgttgga cgcggcggct gaggtgctct cgtggtgcgg   146940
cctgcccgac atcgtgggct cggccggcaa gctggaggtg gaaccctgcg cgctctcgct   147000
cggcgtgccc gaggatgagt ggcaggtctt cggcaccgag gccggcggcg gcgccgtgcg    147060
tctcaatgcc acggcttttc gcgagcgacc ggccggcagc gatcgtcgct ggctgttgcc    147120
gccgctgccg cgtgacgacg gcgacggtga aaacaacgtc gtggaagtca gcagcagcac    147180
cggcggtgcg caccgccga gcgacgacgc cactttcacc gtgcacgttc gcgacgccac    147240
gctacatcga gtgctcatcg tggatttggt cgagcgcgtg ctggccaagt gtgtacgcgc    147300
gcgcgacttc aatccctacg tgcgttatag tcatcgactc cacacttatg cggttttgtga   147360 aaagtttatt gaaaatctgc gttttcgctc gcgacgcgcc ttctggcaga tccagagtct    147420
gctgggctac atctccgagc acgttacgtc agcctgcgct tcggccggcc ttttgtgggt    147480
tctgtcgcgc ggccaccgcg agttttatgt ctacgacggc tattcgggtc acggacccgt    147540
ctcggccgaa gtgtgcgtgc ggactgtggt cgactgttat tggcgcaaac tttttggcgg    147600
cgacgatcca ggtcccacct gtcgtgttca agagagcgcg cccggcgtgc tgttggtctg    147660
gggcgacgag cggttggtgg gtcccttcaa cttcttctac ggcaacgcg gcgccggtgc    147720 tagtccgctc cacggggtgg tgggtggttt cgcggcggga cattgcggcg gcgcttgttg    147780
cgcgggctgc gtcgtcactc accgccattc tagcggcggc ggtggtagtg gcgtgggcga    147840
cgcggaccac gcgagtggcg gcggtctaga tgccgctgcc gggagtggtc ataacggcgg    147900
tagtgatcgg gtttctcccct ccacgccgcc cgcggcgttg ggtggctgtt gctgcgcggc    147960
cggtggcgac tggctctcgg ccgtgggtca tgtcctgggc cggctgccgg cgctgttacg    148020
ggagcgcgtg agcgtgtccg agctggaagc cgtgtaccgc gagatcctct ttcgcttcgt    148080
ggctcgccgc aacgacgtgg acttttggtt actgcgcttc cagcccggtg aaaacgaagt    148140
aaggccgcac gccggggtga ttgactgcgc gcccttccac ggcgtgtggg ccgagcaggg    148200
ccagatcatc gtacagtcac gcgatacggc gttggcggcc gatattggct acggcgtcta    148260
tgtggacaag gccttttgcca tgctcacggc ttgcgtggag gtctgggcgc gagagttatt    148320
gtcgtcctcc accgcttcca ccaccgcttg ttcttcttct tccgttctct cctccgcctt    148380
gccgtccgtc acttcgtcct cttcgggcac ggcgacggtg tctcctccgt cttgttcttc    148440
ttcgtcggcg acttggctcg aggagcgcga cgagtgggtc cgttcgctgg cggttgacgc    148500
gcaacacgct gctaagcggg tggcttccga gggcctgcgg ttttttccggc tcaacgctta    148560 acgagtcacg tagggaact acgtgggtaa gtgacgtgga tactagtaaa aaaaagtgcg    148620
tcaaagctct cagcgtgtga cgtggatact agtaaaaggg acgtcaaagc tcactacgtg    148680
ttgcgtgttt tttttttctat gatatgcgtg tctagttcgc ttctcactct tcctctcccc    148740
gttcccagcg cggtggcagc ttgggggggtg agggcaaatt ggggtagttg gcgttgagca    148800
cgtctagcag gcccaggccc acgggccaac cgtccacggt cttacgctcg gtcagcttga    148860
```

```
ggctgaacga gtgtgcctcg tcttgaccgg taaggcggaa aaagaagcgt gctaccagct   148920
gcaggcaggt atgctgcgtc tgctggaaga gcacgaaggt agcgggtacg tactgcacaa   148980
tgtgcggttc ttttcctca aagagtaggt agagcgcgct gcagatcagc cgccgggcgc   149040
tgtggtgcag cagccggccg aagctttcgc gcacgttcac cgcgtccagg tactggagca   149100
ggtcgtgcag gcacttgcgc gttaagttgc aatttccac gcatgaaata acggtacaga   149160
gcgcgaagtg cagcaggttg tcggccttga cgatgccgca gcggtgtttg agccgcagat   149220
ccgagagcct cacctgcgtg acggcgtctt cggtctcgag caaaaacacg gcggagtagc   149280
ccagaaaggc cgaggtgcac agcagctcgc tgcggtactc ggccatggag accagcagcc   149340
cgtgctccgt gtgcagccac agcttgtcgc cgcgcaccgt aaagtcgagc acttgcggct   149400
ccatgatcat cacattctgt ctagtgaaat ccgtatggac ctccagcacg ccgcggatca   149460
tcagggcctc catttcgaaa tcggccgaca cgctctgggc cgcgccgctc ctcgtctgcc   149520
gtgatcaggc ggcgcggcgc ggaccttca agcgttcctg ggccgccgct cgaggcagtt   149580
cccctttctg gcactccgcc cgccgcttcg cggctcattt ggcgtcggcg cgccttctcg   149640
cggctgcaaa tcagctccac gtatcggcaa aacttgctgt cgtcgtaggc ggcggccacg   149700
atctcgccga aggagagctg caggtaggcc tcgggtacgg ggtccagcgt gcccagcgcc   149760
aggatgtgac acagatagg cagggtcacg cgctctaccg tgtaattgga gtagacgatg   149820
gcctcttcgg cccctgatg cgtgaccaga cgccgcaggc gaaaggtgcg gaaatactcg   149880
ttttcccaca gctgcgtgag gaagcgttcc agcgactcgg tgccgggcac gaactgcgag   149940
aagaagctgt tggccaccag gcggttgtcc tccaccgcca acggacggaa aggcgccgcg   150000
tcgcgcgcct tgcgcacggc ctccaacacg ggcaggtggt agagttcggc gtcgcgcgcg   150060
cccaggctca tggagtcctc gcggcgcgag gcgtagcgcg tgagcaggtc gcgcagttcg   150120
cgcacgcgat tctcccaggt ctggttgagc gtgcgcaggt cctggatctc gtctacctgc   150180
gactggatct gctcctccag gcacttgatg acctgcttct taaacaggtc gcggatgtcc   150240
cgctcgggcg ccgccgggcc gggtggcggc ggcatcagcc cgacgtggcc cgcgggtcct   150300
cccaccacgg caccgccggg ccccaccacg ccgggtccac ccggaccacg cgcgggtagc   150360
agacggtttt ggtccaccag cgaaggggtc aagtcctgca ggaaggactc gacgctgtcc   150420
tcgatgccga tgcgcgattt gctgtccgag acgttaagca aaaacttcat aatgggactt   150480
ttggcgtcgc tgccccggtc gtgctgctcc atcatctcca ccagcttctt gcagttgagc   150540
tcgtggcggc tggcggtcac cactttcaca ggaaaggtat tgagcaactg gcagatcttt   150600
tggtggcggc agagcccgtc gtagcgcaga atctcctcgt gcaggtgtgc caccggcgtg   150660
gtgaacagca gcttgtcgcg ctcataagcc agcggttcgg tcgccacgta caagcggatg   150720
tgcttgccgc gcagctgcgc ctccagccgc tccgagcgca ccttcttgaa gacgcgtacc   150780
tcgggcgcgt tggctacgcg cacagctccc aggcgctcgg ccacctgcag cagcagcgcc   150840
aggttagcct gcagcaggtc ctgcgccagc gggtgtgtct cggtggctcg ctgcacggcc   150900
gcgcgtacaa attgcgcccg ctcggccgcc tcgctcggct tggtcttcac gtccagcagc   150960
ggtaccagtc ccaccgttac gcaccaatcc acgtagagac catagtcgtc gttatcggcg   151020
tactgatata aaatgtcgcg gagcgcgccc agcacgcccg tttgcacgct ctggcgcaac   151080
gaggcgctcc acaccaacag atactgctcc aggtcctctt cgtccagcgc gcggtaggga   151140
aacagcgccg cgtgcaactt ccactcttcg gccacgcgcc gcaccgtgat ggtgtcaaag   151200
```

```
agcgttttgc acactccgta gagcagctgc ttgcgcagca cgcacgggtc gcgcagcact   151260
tggtgcatgc tttggccgcg acacgtcccc agaaagccgt gcagcaaccg caggaagctc   151320
atcgtctggc ccgtggggaa aatgtcgatg acggcctcgt catccacacc gcggcccacg   151380
cccaagtacg acgacgcctt gatcctcaac ctctcgtcgg ccgccaagat cgaacggatc   151440
gtcgacaagg tcaagtccct ctcgcgcgag cgctttgcgc ccgaggattt ttcgttccag   151500
tggtttcgct ccatcagtcg cgttgaacga acgacagata acaaccctc tgccgcaact    151560
accgccgcgg caacgacgac cgttcactcc tccgcctcct cttctgccgc cgctgccgct   151620
tcgtccgagg ccggcggcac gcgcgtgccc tgcgtcgacc gttggccctt ctttcccttc   151680
cgcgcgctgc tcgtcaccgg cacggcgggc gccggcaaga cttccagcat ccaggtgctg   151740
gcggccaatc tagattgcgt gatcaccggt accacggtga tcgccgcgca gaacctcagc   151800
gcgatcctca accgcactcg ctcggcgcag gtcaagacca tctaccgcgt cttcggcttc   151860
gtcagcaagc acgtgccgct ggctgacagc gccgttagcc acgagacgct ggaacgctac   151920
cgcgtgtgcg agccgcacga ggagaccacc atccagcgcc tgcagatcaa cgatctgctc   151980
gcctactggc cggtcatcgc cgacatcgtg gacaaatgct taaatatgtg ggagcgcaag   152040
gccgcttcgg cctccgccgc ggccgcagcc gccgcctgcg aggacctctc ggagctgtgc   152100
gagagcaata tcatcgtcat cgacgagtgc ggccttatgc tgcgctacat gctgcaggtg   152160
gtggtgtttt tttactactt ttacaacgcc ctgggcgaca cgcgacttta ccgcgaacgc   152220
cgcgtgccct gcatcatctg cgtcggttcg cccacgcaga ccgaggcgct ggagagccgc   152280
tacgaccact acacgcaaaa caagagcgta cgcaagggtg ttgacgtgct ctcggcgctg   152340
attcagaacg aggtgctcat caactactgc gacatcgccg acaactgggt catgtttatt   152400
cacaacaagc gttgcaccga cctggacttt ggcgacctgc tcaagtacat ggagttcggt   152460
atcccgctca aggaggaaca cgtggcctac gtggaccgct tcgtgcggcc gcccagctcc   152520
atccgtaacc cctcgtacgc cgccgagatg acgcggcttt ttctctcgca cgtcgaggtg   152580
caggcttact tcaagcggct gcacgagcag atccgcctga gcgagcgcca ccgtctcttt   152640
gatctgcccg tctactgcgt ggtcaacaac cgcgcgtacc aggagctctg cgagctggcc   152700
gacccgctgg gtgactcgcc gcagcccgtc gagctctggt tccgccagaa cttggcgcgc   152760
atcattaact actcgcagtt tgtcgaccac aacctttcca gcgagatcac caaggaggcg   152820
ctgcgccccg cggccgacgt cgttgccacc aacaactcct ccgtccaggc tcacggaggg   152880
ggaggatctg taatcgggag caccggcggc aacgacgaga cggcgttttt ccaggacgat   152940
gataccacca ccgcgcccga tagccgtgag acgctgctca ccttgcgcat tacctacatc   153000
aagggcagtt cggtgggagt caactctaag gtgcgggcct gtgttatcgg ataccagggc   153060
acggtcgaac gtttcgtgga catcttgcaa aaggacacgt ttatcgaacg cacgccctgc   153120
gagcaggcgg cctacgccta ctcgttagtt tcgggcctgc tcttctcggc catgtactac   153180
ttctacgtgt cgccctacac gaccgaggag atgttgcgtg agctgcgcg cgttgagctg    153240
cccgacgtga gttcgctttg cgccgctgcc gccgccacgg ccgccgctcc cgcttggagc   153300
gggggagaga atccgataaa taatcacgtc gacgcggatt cttctcaggg cggccagagc   153360
gtgccggtat ctcaacggat ggaacatggc caagaggaga cccacgacat cccctgcctg   153420
tccaaccacc atgacgactc ggacgccatc acgacgccg aactcatgga ttacaccagt    153480
ctgtacgcg atcccttttt tctcaaatac gtcaagccac ctagcctggc gctgctttct    153540
ttcgaggaga cggtgcacat gtacactacc ttccgcgaca tttttctcaa gcgctaccag   153600
```

```
ctcatgcagc gtctcacggg cggtcgcttc gccacgttgc cgctcgttac ctacaatcgc   153660
cgtaacgtgg tgttcaaggc caactgtcag atcagctcgc agaccggctc cttcgtgggc   153720
atgctttcgc atgtgtcgcc ggcgcagacg tacacgctcg agggctacac cagcgacaac   153780
gtgctcagtc tgcccagtga ccgccaccgc atccaccccg aggtggtgca gcgcggcctt   153840
tcgcggctgg tgctacgcga tgcgctcggg ttcctctttg tgctcgacgt taacgtttcg   153900
cgcttcgtcg agtcggcgca gggcaagagt ctgcacgtgt gcaccaccgt ggactacggc   153960
ctcacttcgc gcacggccat gaccatcgcc aagagtcagg gcctgtcgct cgagaaggtg   154020
gccgtggact tggggacca tcccaagaac ctcaaaatga gccacatcta cgtggccatg   154080
tcgcgagtca cggaccccga gcacctcatg atgaacgtta acccgttgcg actgccctat   154140
gagaagaaca ccgctatcac cccctatatc tgtcgcgcgc tcaaagacaa acgcaccacg   154200 cttattttt gacacaacac cgtgtaagga aaacgtgact ttattgagca gggtaaaaac   154260
cacgtacaag aaccacgttg tctatcccca aaaaaacaca caccgtcagg gaacacatcg   154320
cctatagata gcggcacttt acataaaacc accgtacctg catcacggtg gctcgataca   154380
ctggaaattc aataaaaacc accgtatctc cgtgacagta cttatcgggt cagcgtcttt   154440
ctcttgagat ttctgttcgt aaacttatcc gtttccccgg tccgcggtgt ctcctcgcga   154500
ggctgacagt ctacgggtgg tacctgcaag agaagaaacc cgggtgggag cgacgccgtc   154560
gctgggtatc aaccccgcgg ctgaccgtcg tccggtaaag gaacgacccg tcgtcgcaag   154620
ccgggttcga ccaagagaaa aaacccgggt gcggggggag acgggtcgtc ctttggttgt   154680
tcgcggacgg cgtacatgcc gcgtgggtca gtcgacggcg tcgctccgtg cggtcggtca   154740
tcattctgct tcacatatat gggttgtttg tgttttttt ataatgaata cgcactgatc   154800
ctatccgtga ctgcgcgtgt ggcagagagg atgccttata acatgtattt tgaaaaattg   154860
ccaacagcta taatttctct catgtagcag aatagagacc ttttgtcgtc tttttgtttg   154920
tcattacttg ttttccaggg aattagagag agggaaccgc gcctccggcg gcggtgcccg   154980
cggaccccgg ccccttctcg cgtgcgcggt gtgactggtt gagcgaatga gcagctaggc   155040
ttggtggtgc tccgcgtgcg ggggagaaga cgattaacaa caaaaaataa gtggaagtgg   155100
ccggtgggtc tttgtccgcg tgcgcgccca tccgtcgccg ggaccgagca gaaagtgatg   155160
tggtggtaca ttgattttt ccttgacagg aaagaaaaaa aagagttttg ttttcctatg   155220
tgagaggaga aaggtatgtg aggagatgtt cgatgatcgt atgttacagt tatgctgtaa   155280
ggaagctttt atcgtgcgtc ctgttttca tttgatgtat atgacacaat tgaaacctat   155340
cgataggcgt atatcgagga ttcatcaatt cttagaatcg tcgtcttttt ggctaattgg   155400
actttgccca tgttggttgt cattcgtggc ctgaggtcat cgtcgtccac gacgacgtgt   155460
ctatagcgtg cggtgtgatc attgtgtcga gccagagaaa gcgcgcctcg cacgacgttt   155520
gcggatcggc tcgcgggtgt gtggaattcc taagaacata atcagctggt cgtctttctt   155580
tgatgtgttg ttgtcgtcga ggtcttgctt cgttttcttt tttctttta gtcgatggaa   155640 cttttcttcg gtacgggttc ttgttatgga agcttgtgtt ttcgaacatg aattcgaaaa   155700
aataaaaagg cctatcttcg tttcaaaaaa aggacagata tcaatcttct taacttatat   155760
catggtaaat tcagaatcct atggtgtctt attatctcta aagtagtcaa cattatggtc   155820
taacttgtat ttccctgacg agatatatat gatccttata acctggctac tatcatgaac   155880
aacaatatcc ttacttacag tcatcttcgt gagttaatga agtataatat cggtcatcta   155940
```

```
tcaacttatc tgctatgtaa cgtacccttt taggtatttt gcgtttctta acgagtgtac  156000
ccgcctgtgt gaggcgaaac tctgagaagt ctaccgagtc gagttacaag tcactaaaac  156060
acttacacga gttatctata ctaaaatcac tatctatgtt gtttgcttac ctaattatta  156120
tcctacatga cgaagctacc tcccaacgta aggtagggg agaggagaca gaacaataaa  156180
aagtaactaa tgtttcttag aacttacccg ctaaggactt accaaactat attcaccaaa  156240
aaacaacagc tacgtgtttc atttgtttta atctaccgaa gtaaaaaaa aaagatgat  156300 tagctatcca gaacctactt acttcttaat gttttaacta aggatgccta tgggattgga  156360
aaaaaaatca cagcaacttg ctactaatca gttgacagcg aagagactca taacaaagat  156420
ttctgggtaa tacggttata ataatgctta tggactaaag gatacttgga aaaaagaac  156480 gggctatgac tatagagatt cgtcgagata tcaaacttca aataggcggc tatcattcat  156540
ggttgtggtg actatatcgt ggagaaaaaa tgtgatcgtt agttagctag gtgagactta  156600
cagctatcca tccgtctagt ttttcgttgt aatgatgata gtacgtctat ggtggtgatc  156660
gattttggtt aacaatttgt tcgtttaaag gcttaatgta cttatgctac atgatgtatt  156720
attctttgat tcatcgttcc tcctaagggg gtgtatgtat gtatgtacta gtcgtatagt  156780
gttcctaaca tcatgactat tcagactatg gcttcatcta tcgtgtctaa agttcactta  156840
ttctactatt actatatata tgcactacta tgtaactagg atatggtcct ataaggtgtc  156900
ttctatcacg gtggcttgtt tatcgcttgg cggttacgag caagagttca tcacggacca  156960
gccgtgaggc agggcacacg cgggtcggcg gcgataatgt ccctcgcgaa ggggacaacg  157020
aaaacaagag gccgccggcc gcggccacgg acgcgtagcg gttacacaat gtttggttga  157080
gcgttttgtt tcatcgtcgt ggtggttttg ttgttctctg tatatatcgt gtggtggctt  157140
tatcgtcatc attattatca tcattcttgt ttccatcatc acgatgagtt ttctccgttt  157200
tcctctcctc cagtggtagt cgtgtatcat catcaatcat cgtagtgacg tcgttgctgc  157260
tgctgctctt gccttcatgg cggtatttct cttcctcccc cctaacccca tattaactcg  157320
tgagtgtgat ggttagagtg gctgcttgtt ttttttttct tttctctttg gaacaacaaa  157380
agaggataaa gatggtcggt gaatgtatta ttattattat catcattatg atacggtcgc  157440
ggtcttcttc tccgatgacg aaacctgcgc acatcgaaga aaagacgagc gcgcgaaccg  157500
atagccgtcc gtctgggacg aaggagaaga tgatggggag aggaggagag ccccagaagc  157560
cagagcgaga ggggagacga cagacatacg tcgtcaccgt cctctggagg aggcacggcg  157620
gcgctgtttg ttgtttggat gcttgattat atcctgttct atggggtaga ttattatcaa  157680
taggcttggt tttcaaaggt cagcctgtgt attgtcgtgt cttttttttc gttctcatga  157740
tcgcggagac cacacagacg tgcgcgtctc ccaatggcta ggcgttcttt ttaggtagta  157800
attttttgat cttttttttt cttaacaagt ctggcttgat ttcttttatc tatgatcgat  157860
tcttcttttt ctcggggggtt gcatcttccg tgaaagtaaa gtgacactac tctaaatggt  157920
aaccatatta tctgttgatt aggagaaaaa ataattttt cgcacgaaat cgatcctaag  157980
tgaggtgatt tacttgctat cacacgaaat gattatcttt tgctgctaac gtactgaatt  158040
ttttaacaga attgcttctc cgtaactatt tccgcagatt cagacagatt gtcaaaaaaa  158100
aatacggcac agaaatagtg ggtctgtggc ttttggttcg tgtacattcg cgtttgcgtg  158160
tcgagatttc tacggtatgt ttattcttcc tgcgatgatg tagggtcctt ggtgtaagta  158220
ggatttcgag tatctctctt agagcgaaca aaataatcaa aaaacaacag ctaggaaatc  158280
gagggttact ctacgataaa gtgtctctac aaagtgaaga atgttacgtt gtggtggaat  158340
```

```
aataagactc gcgtgatcga tgagtgatcg agagcggctc gaaccttctt taagagcttt    158400
gtttagtgca actttaaatt acaaggagta gaaagctgaa atgaatctat gaaggtgcta    158460
ttctttgaat atcttacttt gtacgcttca cattcgttat ttggatagag agttgtctag    158520
agaaaatctg tgattctcta tgagtgttat ttttattatc cttttgggga ctacgatttt    158580
tcttcttgtt ctacatacca ctactactcg taatcacata catggacgaa aaaaaaattc    158640
gtcaggcagt agataccaga ttctccgacg ttacggcgtc ttttttcttt ttgagagagt    158700
atctgctgag attgtccgtg gtgtatctag tcgctatttt tgttgttact agtagttttg    158760
cacacagttt attcagtata gttttctttc ttgccatgat caattgagcc caccacctttt  158820 tttttaagag aggaggaatt cgtcttgat ctccagccgg agataacggc ggtggtggtg    158880
gtggcgggag agacttcaag gcaatgaaaa aaaaaaattt cgttttgcca tcaagtggtg    158940
acgataaccc gtcagattga taattggttc ctacagaaac tattctaacc gcggaagaaa    159000
gaaattgaaa aaaaaaaatt gacaaaaaac atcataacat aaaggaccac ctacctggga    159060
cgcgcagttg ggcggcggac tggggcggca tgctgcggtg atgctgtcgg tgatggtctc    159120
ttcctctctg gtcctgatcg tcttttttct aggcgcttcc gaggaggcga agccggcgac    159180
gacgacgacg ataaagaata caaagccgca gtgtcgtcca gaggattacg cgaccagatt    159240
gcaagatctc cgcgtcacct ttcatcgagt aaaacctacg ttggtaggtc acgtaggtac    159300
ggtttattgt gacggtcttt cttttccgcg tgtcgggtga cgtagttttc ctcttgtagc    159360
aacgtgagga cgactactcc gtgtggctcg acggtacggt ggtcaaaggc tgttggggat    159420
gcagcgtcat ggactggttg ttgaggcggt atctggagat cgtgttcccc gcaggcgacc    159480
acgtctatcc cggactcaag acggaattgc atagtatgcg ctcgacgcta gaatccatct    159540
acaaagacat gcggcaatgc gtaagtgtct ctgtggcggc gctgtccgcg cagaggtaac    159600
aacgtgttca tagcacgctg ttttacttttt gtcgggctcc cagcctctgt taggttgcgg    159660
agataagtcc gtgattagtc ggctgtctca ggaggcggaa aggaaatcgg ataacggcac    159720
gcggaaaggt ctcagcgagt tggacacgtt gtttagccgt ctcgaagagt atctgcactc    159780
gagaaagtag cgttgcgatt tgcagtccgc tccggtgtcg ttcacccagt tacttttaata   159840 aacgtactgt ttaaccacgt tgcgtcgtga cgttgtttgt gggtgttgct aggcgggctg    159900
gaaagatgat gtataaatag agtctgcgac ggggttcggc gctctgccgg ctgcggcggc    159960
actcgctcca cggcctccga cgagcgttgc gctcgcgctt tgcgccgccg cgtcatggat    160020
ctgcctacta ccgtcgtgcg aaaatactgg acttttacga atcctaaccg catcctgcat    160080
cagagcgtca atcagacttt cgacgtgcgc cagttcgtct ttgacaacgc ccgtctggtc    160140
aactgcgtgg acggcgatgg caaggtgctg cacctcaaca agggctggct ctgcgctacc    160200
attatgcagc acggcgaggc ttcggccggc gccaagacgc agcagggctt catgtccatt    160260
gacattacgg gcgacgggga acttcaggag cacctctttg tacgcggcgg tatcgtcttt    160320
aacaaatccg tctcctcggt ggtgggctcc agcggaccca atgagagcgc gctgctcact    160380
atgatttccg agaacggtaa tttgcaagtg acttacgtgc ggcattacct gaaaaaccac    160440
ggcgaatcct ccagcggagg cggtggttgc ggcgccgcgt ctactgcctc cgccgtctgc    160500
gtgtcctcgc tgggtggcag cggcgggact cgcgacggcc cttctgcgga ggaacagcaa    160560
cggcgaaggc aggaacagcg tcacgaagaa cggcgcaaaa aatcgtcctc gtctgccggt    160620
ggtggtggag gcggcggcgc tggtggtggc ggtggcggcg gcgggagcgg cggtcagcac    160680
```

```
tcctcggact ccgccaacgg actgctgcgg gatccccggt tgatgaaccg gcagaaggag   160740
cggcggccgc ctccctcctc cgagaacgac ggtgagtccc ggccctcctc gcgtcacggt   160800
gctttccgag tggactcgtg agcccccgt agcgcacgag cgagcaggcg agcggtgttg    160860
gtgcgctggt ggttgtgtgg atgataacca tgtgcttttt cgtgcgctat gtgtcgtccc   160920
gtctgtaggc tctcctcccc tccgggaggc gaagagacaa aagaccaccg cacagcacga   160980
aggccatggc ggcggcggca agaacgagac ggagcagcag tccggtggtg ctggcggtgg   161040
tggtggcggc ggcagcggcc gcatgtcgct gccgctggac acgtctgaag cggtggcctt   161100
tctcaattac tcgtcctcat cctccgcggt ctcttcttcc tccaacaacc accaccacca   161160
tcatcaccac cataacgccg tgacggacgt ggccgccggc accgacggtg cgttacttct   161220
acccattgag cgcggagcgg tggtttcgtc gccgtcgtcg acgtcgccgt cgtcacttct   161280
ttcgctccct cgacccggca gcgccacag cgcgggcgag acggtgcagg agtccgaggc    161340
ggcggcgacg gcggcggctg cggggttaat gatgatgagg aggatgagga gggctccggc   161400
tgaggcggcg gaggcaccac cgcagtcgga ggaggagaat gattccacca ctccagtctc   161460
taactgccgt gttcctccga attcgcagga atccgcggcg cctcagcctc ctcgcagtcc   161520
gcgttttgat gacattatac agtcattgac caaaatgctc aatgattgta aggagaaaag   161580
attgtgcgat ctccccctgg tttccagcag actcttgcca gagacgtcgg gcgggactgt   161640
cgtcgtcaac cacagcagcg tcgcgaggac cgccgcagct gtctccacag ccggcgttgg   161700
ccccccagca gccgcatgtc cgccactcgt caccaccggt gttgtaccct caggttccgt   161760
cgccggtgtc gcgcccgttg ccgccgcagt cgaaacacca gctgctcctc cccggcccgt   161820
gtgtgaaatc aagccctacg tggtaaaccc cgttgtcgcc accgccgcgg ctgccagtaa   161880
ctcttcctcg tcttcttcgg ctccgctgcc gccgccgcca ccaccgccgg gcggacgtcg   161940
gggtcgggcc cggaataata cccgaggagg cggcggtggt agaaacagcc ggcggcaggc   162000
cgcatcgtcg tcgtcctcct cctctcggag atcgcgacgg agaaacaacc gccacgagga   162060
cgaggaggac aacgaccctc tgctccggtt gtcgcaagtc gccggcagcg gccgccggcg   162120
agggccctcg ttcctcgagg acggactcga aattatcgat cccagcgagg aagctgcgat   162180
cgccgccgcc tcgatcgcgg cgttttttcga cgattaaaaa accgagccga gaccggaaaa   162240
attatgaaac aggacgcgct tggacattg ggttccacc ccctttggtg tgtgtctata    162300
tatattggtc actgatttt tttacaataa agagatagac atcacagttc accaccttgt    162360
ctccccggtg tgtctattat catcaatcac ccacagagtc gccagtccat ggtctctcgg   162420
taatgcgtgt ccagatacgc gttggccagt ataaaatggt cgttgcccac aaaggcgcgg   162480
gtggtgttgc gcggcgacgg gtggcaggac ttgagtacca agtgccgccg tcggtcgatc   162540
aggtactcgc aggtgtgcgc gtcggcgccc catagcatga acaccagatg ctcccggcgc   162600
tctgacagcc tccggatcac atggttactc agcgtctgcc agcctaagtg acggtgagat   162660
ccaggctgtc cgtgcaccac ggtgaacacg gtgttgagca gcagcacgcc gcgtcgcgcc   162720
caggcgtcca ggcaacccga ggccggacgc tgaaacccgt ccaccgtacg cgccagttcg   162780
cgaaacacgt tgttgaggga gggtggcggc ggtcggcccg ccagcgtgcc gaaggccagg   162840
ccgctggcgc tgccgtcgca gtacgggtcc tggcccacga tcaccacgcg cacctgctcg   162900
ggcggacaca gatagctcca gcggtgtacg tgctcgggtg ccgggtacac catctcgagt   162960
tgccgcgcgc cctccaccgc cgccaccgtg tcgcgcagca gcaccgtgtc gtggtcgggc   163020
aagctgagga agcggatcca gtcggcgctc agacaaaaca cgcgagcctg ctcgtcgggg   163080
```

```
gttaacagag agcctttatt atcagcaatg ttagcgagca tccactgctt gagggccata    163140
gcgcgagtga gccggcaggt tgacgcgcgt ctgcttcagc tcgggcggca gtccggcgta    163200
gtatttatct aggtggcgta gcagcggcgg gtccagctgg tgacgcaggc agaattcctt    163260
cactgcgttg tacaggccgt aaaagagcgt gatgccctcg ggcgcggcag cggtgctcac    163320
gggcagacgc acggcgcggt tggtacgcgt ggcttcgttg cgtatggcca ccaccacgtt    163380
aaagagagac ggtggcacca gctcgaagcc taacacgtgt tccgtgaaga tgctgcgccc    163440
gtatgacagt cgcgtgaggt cgtagccgcg gcacaggtcg tccacgcacg tgtacacggc    163500
cggcgagcca tcgccgcact cgctgtaacc gcgcatcacc gtcatccagc gcggcgctgt    163560
gtccgagctc aacagcgtca gcaaggcccg caattgatcc ggattgttgt acagcagggc    163620
cagagtgtcc aggaaagcat cgtccaacag cacggagttg gcggcctccg gcgtaacggg    163680
acggtaacga ataagttgcg atagcgggcc atcgcgtctg gtaacattca ccaacgggcg    163740
cagccaactt tcatacttgt caccctgaaa cacctcaccc aacaggcatc gacgcgttag    163800
ttcggggcac tccgcgggaa cttctcggc gacggtagga gcgacgctga cggtggctga    163860
ggaaacgatg ggcagcagaa ggcaacacca cagcagtgcc accggtccag gtgagaaaga    163920
gaagccgcaa tccgggcggc ggcacatcaa gtctgcggca cgatgagagt gtgacggtaa    163980
ggagccagtt ggcgccgaaa gttggcgctc aggtcttcga tccctaaaac gttatatatt    164040
gcatccagca ggtgagccag gctaaacgga ttcacgtacc aggtttggtt acccgcgacg    164100
ataacggcca gaccgtgggc gctacagttg gagaggttcc tgggtacgaa ggtaactgag    164160
tcgatgtcgc gccacggggg gaatgagaca gacgactggc gcacgctgta atcacaactg    164220
tgattgacgt attgtagcgt gtaatttagg ttgcactcag cctcgaagta gaggggaac     164280 cacagttcgt cgtactcgtc gtcgtcctcc agttctggct cttcttcatc caccgcaatg    164340
tctacgctgc tctgagattc ctcttcgtac aggatgattg acaggttatg gctacaaagg    164400
tcctgggcgg gaggacgcgt gggagcgcgg gtggtggtaa tgttttccag atcgtcaaaa    164460
gtcggagtgt agtctgacgc cgtgacgaca ccgtcgacgg agatagtaga agttgcggcc    164520
ggtgtcacgg tggtaagtat ggatacagaa ggggagggg aagtagcgtt cgtaccgatg     164580
gttgtggtat tattattcct tgtatttctt gtttcagaaa ccgttgacgt tgagatggga    164640
atcgacgtgg cgctggacgt cagattgctg accgaggaaa ccgtggtggg agtggtgacg    164700
gtgttactcg tggttgaagt gacgttaggg gaggtagtag tggtaccggt ggtggcgacg    164760
gtagtgtttg tcgtggcggc ggcagcggtg gtactggtaa cggtggtcgc gttggtttcc    164820
accgcttcac acagtaagca aaagcacagg gccaggaaaa gcaaccagcc ccgccatcgc    164880
cgccgccgct tcatgaggtg ggcaggcgaa agctggtgaa ttcgttgtac agcggcaagt    164940
ggggcgccgc gatcgaaggg tacgtcaaca agctgacgtt gatattaaat acgtctggct    165000
gcttttctac gatggaagcg cacagggtta cggcgtcaaa caggtctttc ttggtggcgc    165060
ccgagaccca catctggtat acacccgtct cgtggtacga agtagagcgc ggcaccaccg    165120
gacggatgca gtccagaacg cggttgggat cctggtgaaa gaatttgaac gtggctacgg    165180
cctgtggcgt gtgcggcatc gtctgcgtga tgagctgctg gcccgctaac acggtgacgt    165240
tgtgcaactt gagcagggca ctcttgaggg cctggaaagc gttgccgcac gaggcgctga    165300
tctgcagctg cacggccgtg gagtcgtgca gccgcatgag acgtgatacc tcttcgaaga    165360
cgtacttgta tttgctggca aagagtggcg cgtaccgaca gtcggccggc aaaatgtagg    165420
```

```
tggcgttacc gccgttggtg gccacggcgg gcgcagcggc cgcggaggcc ggcgtaaaca  165480
gcgtcagcgg ccggtggtgg ctggtaaggt cgatcatggg cggcgtggtg accgtggcgg  165540
tggcgggcat gacggggttt gcggcgacgg gcactccggc cacagcggcg gcagcggcgg  165600
ccacggcggc gctggccgag cccacacccg ccggcagtcc tccgccaccc atgacgccgc  165660
cgggcagagc gtcgcccaga cagacttcca cagtggcggg cgcgctctcg gcggtcagta  165720
cggtttgccg atcgacctcg cgacgaaagc tggtgaggaa ctcactatga tccatggccg  165780
cagggcccga gatcccggga ttctgcgggt gctgaccgag tgcgggccga gttatatgga  165840
agacgattag cttggagcgg agttttgcgt ccctagctga cctgcggatc agcgacgtgc  165900
catagggata gactgtgagc ggcggccgca acggcggggt cggccgccgc tcgtcgtcac  165960
ggggcggcgc gagggaggag gaggtggtgg gtacgatctt gacgtggttg acgtcctgcc  166020
cgtccggggg aatacgcaaa aaaccccgcc gcggcgctac cacgatggtg cgatgggtct  166080
ttctcttgtt ggccgggcc agggacttgc agatgcgtgt ggagccgtag acgatctgga  166140
cgtggtcctg ggagaacatg accatcgccg ccaacgctca gcggggggac gggttgggaa  166200
cacagaggct gagggggaaac cccgtagaag tcagcgaaat aaagacaaca cagcagccgc  166260
tcctctcgtt tctggcccta ccactgcttg aagtagggca ccggtgtttt cttttcctca  166320
acgggctcct ccagtctctt ataggaccag tcccgccggc gcgccagcat gtaggtcacg  166380
tacaaaagaa taattaccat gaacaccagg aaagccagca cgccgtaggc cagcagccgg  166440
tcctcgaaca gcgggtcgct cttgataaac acgtaggtgg tggtaaaact tcggcccgcg  166500
atctgaacgt ggagacgcac gacagtatac gtgccgttga ggtagaagac aaactcgcgt  166560
aaccgttgtc cgttatacgt cacgttacta atattccacg gcggaatgag ctggtcgccc  166620
tgatgcagat gcacggtgct gtttgggtga tagaggctgc taccgttgag caagcagtgt  166680
tcgtgttcct gaagcagcac gcggacccgc atcgtggtag cgttcaagcg agtcccgtac  166740
acggcgtaga tgggataggt gaaaaggtcc caagtggcgt tgtgatggcg gccccagctg  166800
aaaaaagagc acgtgtactc agtggtctcc tgcggcctga gtcccgagat aagcagctct  166860
tgagcagtag cgttgtagga gagatgtagt tttcctgtgg ataaaattca tatgctgttt  166920
attctgttag caggttggtg ggggaggaag gggaatagaa cagaggcggt attacttacc  166980
tttatcaccg ggcgcaaaag cgctaagata ccccacctga gtgaagggac ccttgcagtc  167040
tgtccgtgca taacaggtaa tggacaaaat gtcgggattt acggtgttgt tcaacaggga  167100
cactttacag gtggcgttga gagacacctg gtcgtagctg tagctggctt cgcaattcac  167160
agtatacagg tgcccctctt tctgcgtcgt ggctgccacg gaggtagcgg cggatgtgaa  167220
ggtagagccg gacgtggaaa tagaggtttg taccgtggtg ctgacggcag aagtgacgtt  167280
attagaggta cttattgacg tagtggacgt gacggtggta ttaatggggg aagtgacggc  167340
gcttgtggtg ctactttcca ctcccgggtg cgtgtcgcct aagagcgtaa ccatgagcgc  167400
gatcgccagt acgggacaca tgttgccgtg tgacgagacg gagtgtggac gagctatatg  167460
tggcaggagg ccgcgtcacc tcttatgacg cttaaacgtc cagctccaga taaagaggc  167520 gttaataatg aacactacaa aaaccacttg cgtcaatatg acgatcataa aggctcggtg  167580
atcgctgcgc ctaaagtatg cgggattctc caccagctca ctgtctttga caaagtggat  167640
agatgtacta gtgttaccgg ccgtttcgtt gaccatggat tgtactatga aagtcccggc  167700
gccaaaagtt ccattagagc cccagcaagt aacgctgccg tttacgtagg ttcccggctg  167760
gcctgtcagc atgtatgtca gttggtgggt ataattctgt ttaatgtttt ccatgtcctc  167820
```

```
gctgtagttg acttttctag tgagaaattg cgtacgatgc ggaaggacga tcatcatccc  167880
tgaggccaaa aagggcgaat cataagctgt cgtgttacaa aaaatagtca ggttagtatc  167940
gttgtgctca tagatataag ccatttttac ttgaggttca taccaccacc ctaccctaat  168000
tgtagttgcc accgtcaccg agtcccatct cccgaaacct accaccgcca ccactaatag  168060
cgtcaccccc gcacggtaca tagttaccct ctcgacgtcg ccggctgtca atgacgtgcc  168120
tgcgtcagtg gctatgattt atagcttttg gacacaaccg caacggatct gtcgtaatct  168180
accttccaca gggccgccgc gacgatgctg aacgacagga tcagacagac ggcgtatagg  168240
agtcctaggt cggcgtcgac gcggcaggtg cggatgtctc gcagggtggg tagatgggcg  168300
atgcacaact ccttctcccc ccgcccgtac attccatccc gtatcagcag ccgtagcgtg  168360
gcattgatgg tcagcggggt aaccaaagaa atcacatagg gatgtgtaca ggaagtcag  168420
tgacgggtat ccgtgagatg taagtcatca ccctcatcac cctcatcatg aaagaccagg  168480
actcgggtga gacgacccga tgaatactgg atctcccacc acagtctttg gtccaacacc  168540
gagagggcgc aggagattct aagtctccct gggttggggg agcagatgta agccccgtgt  168600
gtgcccttg ccatcaaagc catacacatg aggggggagaa ggacaagtat ccggaccac  168660
ccgcaccccc acatcacgag accagagacg gagatgtata aaaaaagcta cttttattaa  168720
acagcattct caccacacgt taatactgtc acggggaatc actatgtaca agagtccatg  168780
tctctctttc cagttttca cttactgaga cttgttcctc aggtcctgga tggctgcctc  168840
gatggccagg ctcagggtgt ccaggtcttc ggggagggtc tcggtgggct gctcaaactg  168900
ccccacggcg taggccttcg tggccgtctc gtagataggc agcatgaacc caccctggtt  168960
ggtggagaag atgcgcacca tgacctgttt gggaaacttt tgcatcaggg gcaggcacag  169020
gttgagagcg cccaacaggt ccacggggggt ggcagcgtgg atgatcatgt tgcggtaatc  169080
ggaggaacgg gggcataatt ggtgggtgtg caattctttg aggctccacg cggccttgac  169140
gccttcgtta caagcatcgg ctgtgcgctg cgccactttg ggtggatgtg tcacgggcat  169200
ggtgtgctcc atgaggaagg gagtggagag ggccaggttg cacatggtgc ccaggcgaca  169260
ccgcaccgca tccacctcac tcttcacctc atgattgcgg gtgtagataa tctggatgcc  169320
cttgttgttc acctgcatgg ttttgcaggc tttgatggcc tcatctaaca cctggtgcat  169380
actgggaatc gtgaagggca ggttcttgta ctcaagagag cgattggtgt tgcggaacat  169440
gcggctcacc tcgtcaatct tgacgcgacc ccgccgagtc tgcacgttgg gtgtgcagaa  169500
ggggggtgttc ttatctttca tgatattgcg caccttctcg ttgtccaact cggagatgcg  169560
tttgctcttc ttcttgcggg gtccggtgct cgccccgccg ctgctctgat ggccgcagct  169620
cagcagagag gaggaggccg cgccaccaaa accgccgcgc ccatggtggc tcgaggtcac  169680
ggatgctcct ccgccactgc tgcatttcat ctcctcggac tcactctccg agtccgaagc  169740
cgaactgcag gaggaagacg aagaggaact atcttcatcg ggccggccca agggatcggg  169800
aagaggaggg tggttcatct gggagagcgg gtgcgtggga gaggtcactc gcggcgtgcc  169860
gctgccggtg aaggggaag acgcggtagc accgcgggtt tcgacttctt caccctgttc  169920
ttcctcgcta tcagagatca cgatacagcc ggcggtatcg ataatcttgt tgcggtactg  169980
gatggtaaag tcgggctcgg gcttgatgtc ttcctgtttg atgagggca gcatgatagg  170040
cgcgggaggc acgggcggtt taataatcac cttgaaagga cgcgtggttt tgcgcggttt  170100
cttacgcggg ctgagctcgg gagtagcgga tgccccgggg agaggagtgt tagtaaccgc  170160
```

-continued

```
gacgctggtg ggggtcggct tgttaagagg ggcgctgcta acgctgcaag agtgggttgt   170220
cagcgtgggg ccggtgctac tggaatcgat accggcatga ttgacagcct gggcgaggat   170280
gtcacctgat ggtgataaga agacacggga gacttagtac ggtttcacag gcgtgacacg   170340
tttattgagt aggattacag agtataacat agagtataat atagagtata caatagtgac   170400
gtgggatcca taacagtaac tgatatatat atacaatagt ttactggtca gccttgcttc   170460
tagtcaccat agggtgggtg ctcttgcctc cagaggcggt gggttcctca gcaccatcct   170520
cctcttcctc tgggcaact tcctctatct cagacactgg ctcagacttg acagacacag    170580
tgtcctcccg ctcctcctga gcaccctcct cctcttcctc atcactctgc tcactttctt   170640
cctgatcact gttctcagcc acaattactg aggacagagg gatagtcgcg ggtacagggg   170700
actctggggg tgacaccaga gaatcagagg agctggcacc agcggtggcc aaagtgtagg   170760
ctacaatagc ctcttcctca tctgactcct cggcgatggc ccgtaggtca tccacactag   170820
gagagcagac tctcagagga tcggccccca gaatgtactg ggcaaagacc ttcatgcaga   170880
tctcctcaat gcggcgcttc attacactga taacctcagg cttggttatc agaggccgct   170940
tggccagcat cacactagtc tcctctaaga catagcagca cagcacccga cagaactcac   171000
ttaagagaga gatgcccccg tacatggtca tcatacaagc gtcactagtg accttgtact   171060
cattacacat tgtttccaca catgtagtga ggatatccat aaatatgtga tcaatgtgcg   171120
tgagcacctt gtctctctcc tcatccaaaa tcttaaatat tttctgggca taagccataa   171180
tctcatcagg ggagcactga ggcaagttct gcaatgccgc catggcctga ctgcagccat   171240
tggtggtctt agggaaggct gagttcttgg taaagaactc tatattcctg tagcacatat   171300
acatcatctt tctcctaagt tcatccttt tagcacgggc cttagcctgc agtgcacccc    171360
ccaacttgtt agcggcgccc ttgctcacat catgcagctc cttaatacaa gccatccaca   171420
tctcccgctt atcctcaggt acaatgtagt tctcatacat gctctgcata gttagcccaa   171480
tacacttcat ctcctcgaaa ggctcatgaa ccttatctaa gatatctaag gcattctgca   171540
aacatcctcc catcatatta aaggcgccag tgaatttctc ttccgtctgg gtatattttt   171600
tcagcatgtg ctccttgatt ctatgccgca ccatgtccac tcgaaccttt atctgtttga   171660
ctgtagagga ggataacaac acatataagt atccgtcctc ctgactcatt tatcgctatc   171720
tcgatgcccc gctcacatgc aagagttaat ctttactcta tctgacatac acaagtaaat   171780
ccacgtccca tgcaggttag tatacatcac atacatgtca acagacttac cgagttctgc   171840
caggacatct ttctcggggt tctcgttgca atcctcggtc actcgttcaa agttttgag    171900
ggattcttcg gccaactctg gaaacagcgg gtctcccaga ctcagctgac tgttaacctc   171960
cttcctcaac atagtctgca ggaacgtcgt ggccttggtc acgggtgtct cgggcctaaa   172020
cacatgagaa atagagtcat aagcacatgg gtcacataca ggagatatgt atataacatt   172080
aatacaattt tataaaaaaa agggggggca caaaccccga cacgtaccgt ggcaccttgg   172140
aggaagggcc ctcgtcagga ttatcagggt ccatctttct cttggcagag gactccatcg   172200
tgtcaaggac ggtgactgca gaaaagaccc atggaaagga acagtctgtt agtctgtcag   172260
ctattatgtc tggtggcgcg cgcggcagca acgagtactg ctcagactac actgccctcc   172320
accgttaaca gcaccgcaac gggagttacc tctgactctt atcagaatac aacaactcag   172380
ctgcctgcat cttcttctgc cgctgcctta agtcttccat ctgcgtcagc ggtgcgagcc   172440
caatctccga gctcattttc agacacatac cctaccgcca cggccttgtg cggcacactg   172500
gtggtggtgg gcattgtgct gtgcctaagt ctggcctcca ctgttaggag caaggagctg   172560
```

```
ccgagcgacc atgagccgct ggaggcatgg gaccagggct cggatgtgga agctccgccg   172620
ctaccggaga agagcccatg tccggaacac gtacccgaga ttcgcgtgga gatcccacgc   172680
tatgtttaat aaaaactgcg ggcacggggg acggcgttgt tgtatatgtg aatttgtaaa   172740
taataaatgg gaccccatcc tgtaaaaata cagagtccgt gtcagtctct gaaggacaga   172800
gtattggcat atagccaata gagatagttg tggcaaagag ccatgttatg gattagtaat   172860
ggaaagtatc gtcaccaata ggggagtggt caataatggt caataaccca cacctatagg   172920
ctaagctata ccatcaccta tagcataagg aagcgggggt gtataggccc caagccaaaa   172980
acagtatagc atgcataaga gccaaagggg tgtgcctata gagtctatag gcggtactta   173040
cgtcactctt ggcacgggga atccgcgttc caatgcaccg ttcccggccg cggaggctgg   173100
atcggtcccg tgtcttcta tggaggtcaa aacagcgtgg atggcgtctc caggcgatct   173160
gacggttcac taaacgagct ctgcttatat agacctccca ccgtacacgc ctaccgccca   173220
tttgcgtcaa cggggcgggg ttattacgac attttggaaa gtcccgttga ttttggtgcc   173280
aaaacaaact cccattgacg tcaatggggt ggagacttgg aaatcccgt gagtcaaacc   173340 gctatccacg cccattggtg tactgccaaa accgcatcac catggtaata gcgatgacta   173400
atacgtagat gtactgccaa gtaggaaagt cccgtaaggt catgtactgg gcataatgcc   173460
aggcgggcca tttaccgtca ttgacgtcaa taggggggcgg acttggcata tgatacactt   173520
gatgtactgc caagtgggca gtttaccgta aatactccac ccattgacgt caatggaaag   173580
tccctattgg cgttactatg gaacatacg tcattattga cgtcaatggg cggggtcgt   173640 tgggcggtca gccaggcggg ccatttaccg taagttatgt aacgcggaac tccatatatg   173700
ggctatgaac taatgacccc gtaattgatt actattaata actagtcaat aatcaatgtc   173760
aacatggcgg tcatattgga catgagccaa tataaatgta catattatga tatagataca   173820
acgtatgcaa tggccaatag ccaatattga tttatgctat ataaccaatg actaatatgg   173880
ctaattgcca atattgattc aatgtataga tcgatatgca ttggccatgt gccagcttga   173940
tgtcgcctct atcggcgata tagcctcata tcgtctgtca cctatatcga aactgcgata   174000
tttgcgacac acagaatcgc ccaagtcgcc aaagtcgtct atcgccatcc cccgtaaacg   174060
atataagcgc tatcgccaga tatcgcgtat gcccaaaaat cacttttgga aaaatggcga   174120
tatcagttac acagaaactc acatcggcga cattttcaat atgccatatt ttcaaatatc   174180 gattttcca atatcgccat ctctatcggc gataaacacc actatcgcgc gacatgaatt   174240
tagtcggcga cagaaatctc aaaacgcgta tttcggacaa acacacattt tattattcac   174300
tgcagcatat agcccatttt agcgcggcac acatccagcc gtttgtgttt cttaacgctc   174360
tccaggtact gatccaggcc cacgatccgg gttatcttgt cgtattccag gttgatccat   174420
cgatagggaa cgctgccagc ggcgcccagc aggtactgcg ccttgtcgtt cactttgccg   174480
cagcgtattc gcccgtcagc ttcgagatat aacctacaac acgagggga aggggggtac   174540 aaaacgtgaa attagacttt tttttaatga tgttttgtcc ctctctgtct tactctccca   174600
taggctgtaa ggccctcgag gaagagactt acggattgta gttgcagctc gtcagtttgt   174660
tgtgtacgac ctggcgtgtc aatgaatggg tcatggtggt gacgatcccg cgaatctcag   174720
ccgttttctc gggactgtag cagacttcgc cgtccggaca ccgcagcctg tggattcatg   174780
aaaatctact ctggcattcc cgaggatcgt cgatggaaca tggctatcag aaacgtcgag   174840
agacagatcc agacgcacca cagaacgcag acaatcatga aaatacgtac gcgacggtga   174900
```

```
agcgattgca catttttgaaa tcgtaacagc gttccggcgg gtggttgacg tttatgaatt    174960
cgcaacattc ttctgcgcgc acccgcggca cgcggctgtg acccaatagc agccacaacg    175020
ccgtcaagaa cggcgtcagg tttttgggac tcatgacgcg cggttttcaa aattccctgc    175080
gcgcgcgacg ggctcaaacg atgagattgg gatgggtgca gaaggtgtaa aagtctggtt    175140
attggcctcg gtgaacgtca atcgcacctg aaaagacacg ctgtagtccc ggaagacgtg    175200
agcccagctc tccagcttca tcacacacat ctgataacgt gtgccatcgt tgacgacgaa    175260
gcgtagcagc ttggtctgct tgggcaccat gtgcgctcca aaaatcttgg cgtcttccac    175320
gctgatctgc acgtttccgt cgctcggttt cgaagccgtt cggggcatcc gttgaaggat    175380
ggtctggttg cgaccgctca ggtaccagat caccttttttc acccaggtgg agcttctctc    175440
caccaaggtc tggccttccc ggttatacag cagatacagg gtctcgttgc gacactcggg    175500
acccgttaat acccgctgga accccgagaa ttgcaagggg gaccgtgggg gcgagggata    175560
gagaaaagga cagtaaaacg tcgccgcgtc atgccggttg gaatacgtca gtttagacca    175620
tggcggggac ggattctggt ttgccgttag cgtcgaccag ggagacgcca gacagggcgt    175680
tgcccaaacc gcgcacagaa gcaggcagtg aaagtggtga cgaagcagaa gccgcagcat    175740
attatttccc gtgacgcagg ctagttggca aagagccgca cgctgaactc gaggctccgg    175800
gcgtgtggcg ccagcgaacc ggcggcgttg aacgtggtcc ttttgttggt gccgccgcga    175860
cggttctgac gtctaaagtc gctgatgagc aacgacacct cggtcacgtt gattctgcaa    175920
gcacaggttc caaacgtcat ttcatacccc atgcggttac ttagccgtta cccgttcgct    175980
cttaccttcc cgttgtcatg cacctttagc gcgtaccctc acctcttgag cacgtcaaag    176040
ttgtccaagc cgtggctcgc atcgtagtgg tagttcaacg tgaggtccac gagctgttcc    176100
acatacttgt aacgggtttg gtcgggcagc gcgcgagagc acgcgtccca gtaatgcggt    176160
actcggtaat aatcgttttt ttccgcggtt tcccgctggc actgacccag caccacggcg    176220
cacagacaaa cagacagcca cacccgacac agccgcatgt tgcagactga gaaagaaagc    176280
tttattatga gacatcatac acatagtata ggcgaggtga tggggcgggg aaagagttgg    176340
aaccgaaaga caaaaaaaaa agcctagtcg tactcgggat ctctgagcga gacgggttgc    176400
atggcaactt tcattagttt gggaatctgc cagctggtgc tgttcgaagg ttcttccatt    176460
tccgaggcgg tcagttcatc gtacaccgaa acgtagtacc tgatgggtcc tcctcattg     176520
tccgagaggt gagattcgat ggtcaaaggc gagcctctcc cataattggg attcacgaac    176580
gacgtgtcca agttgccatc ctttctgaaa tagatgacgt tctcaggatc atgtttcatg    176640
cgctcgcggg ccgcggacgc ctcctcctcc tcgtcccagt cccgagtttc caaccgctga    176700
taagggctcg aggaacaaaa tccggcgggg atctgagaac ctcgtcggga accgctgcca    176760
aacgggctgc tgccgccact gtcgtccgtg tcgtccaaca ggttgacggc ctcttcgtcg    176820
gcgaaacgaa agcggcccgg gtgcttgcaa cacgaggagt aaactaccgc gatcagtacc    176880
gctatgaagc tgaaaatgga ggtgcctgtc acgatgtaga agaggatagc cagcactttc    176940
atgatttcgt cattgcgcgc gtcgtgaacg gaagattcgc gggcggtggt catgttggtt    177000
tcggttgtag gttcgctact cgtggtgctc tcgacgtgat ttctgctgct ggtgctagta    177060
gggacgtttg tgctgctggt catatttgta gcgtcgctga agtcgatgtg aagcagcaac    177120
ccgaacgcga ccaggaccag gaatgttgcg cgaaggagac cccgcggggc cggcattctt    177180
gagacgtggc gacgtggatt tctcgttatg tccgcgaacg acgtgtgacg aggacgtggt    177240
ttccgcaagc ctctaccgac gccgcgacac caggtaggtt atcaaaacgc gagcccatat    177300
```

```
cgccgccatc attgtaatca gcaatgtgtt gaggtactgc acgatgaatc tgtctagtga  177360
caccagccaa ccctctgctt ttgcgggcaa gcgcgctttc ggtgacaggg tgtatcgtac  177420
gtagccgcgg gtcaggcgcg cgttgtagcg gtacacgcag aaatctatcc acaggccaac  177480
gcccggctgt agcttaggat ggtggataat agcgcggtga cgtacgccac ggggctttag  177540
aatctccacc tgtaaggcca tctcctccag gtagtgggtc tgactgcgac gcagcgtcca  177600
gttcatgtaa aagtcggtct cgccgtgtcc ggccacgtag aggctgctta ctaaatcggg  177660
cgccagagct agatcaggcg tatcaaattc cactgccagg cgacctgatt ctaacggttc  177720
cacgatccgg gagagcgttt ctagatatag agcaaagcgt accacgtcta cctgcggtgt  177780
aaaaaactgt tgtgggcgtt caccgtcgtt gaccacgtaa gccacgtaga ggccaacatt  177840
ttccaccacg ggttctagct gcaggcggca cgtaaagctt agaaacgacg gctgtacggt  177900
ttggttcccg tgaagctgaa gcgtcacttc cttgccgggg ctcaccgtgc tgtaacgccg  177960
caccgagtcg gtcatctgct ccagatcggt agaccagaag ggcgtgcaat gcatactgtc  178020
ccagtcgcga cacgcagccc agcctagctc ggtgaagggt cgacgcacac ccgaaaaagt  178080
gtgcttgaag accaggggt cgcctcggta gctcagtagc cgaacatgca catagtcgcg  178140
gctagcgttg acagacggcc cgtagagggc cagcaggaca agcgtgaaca gcaagcgcaa  178200
catgctgcgc gggttagaaa atgcggcgtg ccggccaccg cccgactcat aaacgctacc  178260
agcatgacgt ctcagatcac acaagtgacg aggagcgtac cgcaaatcac tagggaaaag  178320
gccagcagag cccgatagtc ttgctcttcg cgaacgatct cgtccggttc ctcgcagtct  178380
tcgtggtcca cagaagatga ggagcaggat tcttcgttaa tttctgccag gatactagtg  178440
ctgtaccaca ccagagcgct cagcgtgccc agggctaccg cacggtaaaa tagggacatg  178500
atcaccagcg caatctgaag tggtggtagt tcagtttctt ggcgtatttc cagagaaagg  178560
ctttgtaggc cgtagggact ggccaggcac cgaactcaat attggtagac actacgtcgt  178620
aaatgcgttg ttcctcgtct aagattaacc gaaaaaatag ccggttgatg tgacgacgca  178680
cggcttgcgc gttaggattg agacacttgg tgcccttgtc ctttaaaata gccagcactt  178740
cctgacgatt gcagctttcg ctcgccgcga ttggcttaag caattcagtt ccgattggca  178800
gagtattcaa cagaatttgg ttgttacaac gacagcgttt gtcgtaatct tccaattcta  178860
aaagatggac ggctagggga catacgacaa ataacatgta tgcagtcaat tgcatatatc  178920
gtaccgataa aatgttagtg tgcggattca gaatcggatg atgcaaccgt cttagcatca  178980
tatcgaaaaa gtatacatat taccgattca ttataattag ggaattattt ccaacgcgga  179040
cgtttgttag tgacagcgtt ttcttctaca tgcggtccat tactatcctt tacttttacc  179100
aatactctgt gccatgagtt gtctttttta ccatccagcc atttggacaa atgatgatcg  179160
ggagctaaac atacaggttt acctcgagga ggcaatagat aatgttgagg tttgtcacac  179220
tcaggaggat tgggagggtc acgaccaacc caaaataagc cacctatagg atgatgtaaa  179280
gctttgtggg tacacggaca acgcaattct ctactgtgaa ccccatggta atacataaat  179340
gccatcaaaa gactaatcag cgaaccaaaa attaatcgca ttctaatttt attaactacg  179400
tcactatcag taattcgtaa tatccggtat tcccggaaaa tcactcaaaa ctgcgtccat  179460
gacacatcaa ttcccgataa gtaccccct ttgaaatcgg atcccccac ataccaatca  179520 atcacacaac acacaggttt aaaaatcgat cacacgtcaa ttaggtttca aaatcgatac  179580
tgtttattat caggaatcta gactaattct acaatgacag ctctgaattt ctctctcgtc  179640
```

```
tttcttgtca ggttctcatc atcaatcttc acttccaccc atcgaggagt catcgtcgct  179700
ccaaaaccct tgggggtcgc tggttggaaa agtctctgac acgatccagg caccccgtac  179760
ccagtccgac tgatctagct tacggagcat ctcaacaggc atgagctgca gggccacggc  179820
tgtcacggca gggattatta ctaccgttca ggtaaactgt atctccctga gttaccgtga  179880
tgggtctttc tacatgttga ctttgcgtaa aaaatcgccg gtaaatgtt ttttcttgtt   179940
catgtaaaag taccggaact aaaatgctag ttagaatggt tgcagttgct attagcgcgg  180000
ctagtaacag tagtttagtg ttacattgta tacccatgtt tttaataact atgaatattc  180060
tgcttcacac cataagtgct taacccacaa aaaccacacg gagacattat tggctaaaaa  180120
taaaaacaaa agtttattga tgtgcatgtt aggttttagt ctaaaattca tctgggtcgt  180180
atttgggaag ttttgtataa cgcggtcttc tggggacgcg acggctaccc atgtataagg  180240
ctataagtgc cacagatacc actatacccg cccatacagc atgaattccc aggggaatgt  180300
tagtgttttt tacagttttt attacattgt cccacgttct gctattatgc tggtctgatt  180360
cctcttttgt tttacattta tcaggtatag gagacgatgt tgcagttcct gataacacgg  180420
ttaaatagta gttttccttt ttaccgtcac tgtaacgttg caaaacgtat tttccagcgt  180480
gttcggtagt tacgttgtat atagtgagag aggtcttatt gcagtctaaa cacatgccgt  180540
tcagtgggga agttgaataa taatgtccaa tgctgcacag ttggtgtgcg cgaggtccat  180600
attttatcca ttctatatcg tgccatacat ccgttctact gcagttttc aaagtgacgt    180660
atccaccgac atatcctgtt acattaatta cttcgtaatt taaattagag tgtttataaa  180720
cggtgtacaa actgccattg caagttatgt tgctggtatt caaccaggga gtagtactat  180780
gaatggtaga aaacgttaat gttggcgtag cgcttgacga tgattttgaa agcgttgaag  180840
tggttgctga tgcgactgaa gaagcggtag agggtttgtg cgtggttcca tttgcgatag  180900
ctgaagtgct gttagcatcg gtgacagagt tagaagaatt tgtgatagtg gaggcggtgg  180960
aggtaaaggc aattgcacgg acaggagcac gtgtcattgc aaccttcaga tatcgtaatc  181020
atcagtaacg tccacttaac cgtaaatctc cagtccataa cgttattaaa tttcggttaa  181080
cgggcattga tgtttcttcg gacgttgttg atctttcttg cccgtttatt ttctgatatg  181140
gtctcataag acatttatcc ggaaacgttg cttagtcctc gtgctcagga ttgtatcgaa  181200
ctatgaattc tgattcactt tatcgtcac ttaatggatg atatttttta tttagagctc    181260
gtcggacgaa aaataggaga atgcaggcta cacaaattaa tgctaacgtc cacgtagtgc  181320
gtctgccgtg tgatgtgtta gaatgattgt tatagcggta taaatgatct atagatgatg  181380
tggctgtatt gtcttcataa ttggtcggtt tatgagaagt gtcccattcg tgctttggtt  181440
cttcacatac ccagggattc acgtgtgtcc cgtttgtgtt gtttctagga tgtatttgca  181500
gattaaagtt ttgattttgt tcggagggat gcccagtttt ataacatcga aagctatatt  181560
taccagaatg agtaaaatta agaccgtaca gagataaaga taaattacga tcgcatgtaa  181620
aacataaatc atagtgatgt tttagataat ttgtgtgcca ctcacatagt atacgcgaat  181680
ggaggatttt caatgaatgg ttatgatatt ttccatttct tatgttggga tgggtgtatt  181740
ttccgtgtgt ggatatatta aaatgtctaa gccaggctgt tttgtagcac gatgtgatgg  181800
ttaggttgtg tgttatagta atattgtctc cttgtgccgc ctccaataat gtttcagatt  181860
cttttgatat cgtattattt gtactgttag gcgatgagca agttggaagc ggtgtagtga  181920
cgttttcatt tgcatttatc atagtagtag tgttggttga taatgatata gtttgcaaag  181980
tcacagtact atcggttaca tgctgtgtcg atgaattcgt gtcgccgttt ggtgaagttg  182040
```

```
ttattacagt tacgttagtt gtagatgttt gggtagatat ggtggaaata gttgaggtca  182100
cgtctgtgcc ttttacagag cttgcagtga atcctgtgga tgtgttgacg ttgccattgg  182160
aggatgtgaa catagtggta gacatttcgg tggtttgtaa cgtagatgtc agttgtgtag  182220
tagatattaa gcttgtgggt gtaatcgacg tggaagtatt ggcgatagtg gtgttgttac  182280
acttgctttt ctgcagaatc caaaaaataa taaacatgca tattatttgc gtatatgatg  182340
acttgttcca ccgtcgatgt tgtgtgcgca tcttttactc caaatccccg tccaccgtca  182400
acaacagagg ttccgtatct aggtccgtcc gcaaccgttc agcgtcctgt tccccgattc  182460
gttgcgaccg cagaaagcag atgaccagtg cgccaacaaa gatcatcagt cccgaaaccg  182520
aggcgcaatg gagtgagagg ccggaccact ggcgttttaa atccgagata attgctcggt  182580
ctgcctcttg ggaatccgta accacaactc tccctggtcc cggataaaag catcgacgcg  182640
tttccaaagc tcggcagaag ctacgtgggt ggatgatgag gtaaaaagcc tcgacatcac  182700
cggtatactg atcctgcagg aggtagactc ccgtatcttt aaccgtaaga ttgtacagcg  182760
tgagattttg gcgcgtgcac gtgaaagttg cgccaccctg atgcgtggtt tctttatagg  182820
cgtctgtaat gatgcaaagt ggcggcatac gacgcatgta tctgctgtag atatcataac  182880
gttgccagac tacgctgtga tggctagtgt taagcctggt aaccagagta cgtgtacggt  182940
cctcgcaggt ggcgcggtaa ttggcgagct ttaggggttt tttggttggt tcgacggcgt  183000
tcgatgaact tccctgagtt gtgaacaaaa acagcgacgt gactatgaca agcgtgaggg  183060
gggtgctgta ggtctgcatg gtgcaaaaca cgttctcgcc ttccttgtca gacgtcgtcg  183120
tcctcgtcct cttcgtcgtc tgtgcccgtc ggttcgatca acggggagtt atctttctgt  183180
ctggagggtc ggtatggaat ccgttcgtag atgttctgct ttttagccgc gtgttgttcc  183240 agcttttttgc gtgtcaggct ccgataggcc agacattgat ctacctcggt gcccgtgttg  183300 ttttctcct cctcgcgcgc gtaaattacg aagaagacca ccagcaggac tatcagcgtg  183360
gccacgaacg agcccgcgcc ccaggccgag tatgcgccta gcattgtaat gggttctgtg  183420
acccggcatt tgcacatcgc gtggcacctg ctgccattgg tagatgtgct attcggattg  183480
cacttacatg ttaggtgggt attttctgtt ttcacgagac aattggtggt aaccgtgttt  183540
tcggcgcaaa cggccacgta gcttatcaaa ccgagtgcta aaaagcacac cgcgtgcatt  183600
acacgcggat acatattaaa acaccgtgtt ccacaagcac cgcacacgtc gatcctcccc  183660
gcacggtctt cagcccgccc atgacatgat ctccctcacg ttacccttca acactctgta  183720
gtactctgtc tcggcttccg gtccccatgt cctaatcata acaaaacacc gtgtcactgt  183780
ccatctccct gtcttttcgc gccgccggtc cccccaaac catgtctcta gatgccgcca  183840
gccaccaacc ggcggcacgg cggctcttgg attcggcatt ggtgcgccgc gtcttggcct  183900
gcatgatcat cgtcatcatg atcgccatta gcatctggat cctgacctac gtgctgtttt  183960
tctaataaga accccggccc ctgacggtaa ttttcctttc ttctccgttt ctcctcagct  184020
gccgtacgtg atgcctcacg gccatctccg acaggccctc tccccgacct cctggacatg  184080
tgagggcttg ttgctcctcc tgggattgct ggtgctcttc tttcaccacc acaaccagtc  184140
ggccgtagag aggcgtcgcc gcgtctcgtt cgtcgaggtc gatcgactgc cgcatgagag  184200
cggatggtat tcttccgatg acgacggaga ccgggatggc gatgaggaaa ctggagagag  184260
ccacaacaga aacagcgtgg gactgtccgc tgttttttagc tgagactggc gtgcgacctg  184320
taaaccgtta ctcgggtctc aagatggttt ggaagttgtg actcatcttc ctgtgggcaa  184380
```

```
tgcccaaccg gacgcgagtg tcccataaaa gccgggcgct ccggcgagac catgccatcc   184440
tcgccttcgg acgccccgct cctcttctct ctcctctcct ccccgctgcc gcggccactg   184500
ccgccgccgc ccataccatc ggcatgtcgg ccgacaaatc gcagctgtcg tcgtcgccgc   184560
cgcagctgta gcagttaacg tcgccggcct tcaggaggag atggcgctct gcgtcgtctc   184620
ttcgtcccgc ctccctctgt ggtcgtgggt ggtgcgagag tacacgatgg gtggctctcg   184680
tctcggggga ccacaggggg aggggggtaa tttattattc gtattactgt aattttgtat   184740
cgcttaattt gtttagagcc gcacgcttga caacgccttg tatagcctta tttatcccga   184800
tgactttttt ctccgtacaa gaaatggacg tcacttgagc agacacagtt tcatcgacca   184860
cgacagtctc atgatctgac tacctctgac ccgccaatga gaaaaccgaa agtaaaaga   184920
tgaccgcgcc ctcggagtcc ttttttcctt ttcaatcatg aaagcaagag gcagccgaga   184980
gaatgccagt aagagacgac catcgcagac acagtacgat actcatctta gaacgaacca   185040
gcgaataacc atcacacgta cagcagaatc tcatgaacta gtcaaccaac gtcataaaat   185100
cttcacacaa tcgttttttgc gaacttttag gaaccagcaa gtcaacaaaa gactaacaaa   185160
gaaaaaccat cttggaatta aaaaagtag catcgttacc ttatgaacca gcagcattca   185220
gtatatacac cagatataat atatttatta atgtatcctc tctttctcct gatgtaattt   185280
tgttttttgta aattcaattg ttgaaagtct ctccctgggg gaattgcata tcttattgat   185340
gaagaagaaa tccctgccat atgtgttgtc aaactatcat tatttctcta tatgggtatt   185400
ttttttctaa gaagcaaaag actagcagca gccaaaataa acctgatgaa atctttaact   185460
gaactcccgg tggtctgtgt gtatatttct gttggtggtc ggttgtctga acccgggtgg   185520
gttgttcgga aacggcggga cggggaaacg ggtggaaaca gcgtcgctat atacgtgact   185580
tttgatctaa acgacgtcg ctaggctgac agtttacgaa ttgctaaaca aggtggtcag   185640
gaacacaaca agcggggctt tgcctggtag gatttcctgt ggaaacaatc accggatgtt   185700
atcgtggctg gtacataagc tggttctggc tgcaagcgct ttttactgca ttaggttcgg   185760
cgttagctct tgcttaggaa cgccatggct ataacgggaa ataaccggtt tggcagcatt   185820
ccattgtggg ggggggggta cttatagcgt gttttcatgac ggtgtttata catgaaggtg   185880
cgggtttcaa taaagtagag gttaaaagtg gtgacaatgt aaccattgaa cacaaaaacg   185940
acccgatgac tacgaaatgg agccatctga atcaaggatg gttatgtaat gtaacaggga   186000
gacatgcacc tctagtgaat aatggatcaa gcgtttgtgt aacgaattgt actcatacat   186060
ctttagatct gtgcaatatc acgaagggta acgatgcgt tgtcgacctt ggtcgttggt   186120
tcggagagaa taaagacgag tacagcggtg aattatggta tttgactact aaaaattagg   186180
tttagagagt gttaggttac gttgacctag ttagatttcc tgtgtagaac aatgaccgga   186240
cgtgcttgga ctggtacata cgcaggggct ggacgtggtt accggtcact ggactcggtt   186300
tcgctgtagc tgtggttcaa cctgaacatg gctcccagag ctgctaggaa ccggtccagt   186360
cacatttttt ggtgggtggg gggtactaaa aaagtgttta atattgggt ttaatgataa   186420
aatccaggtt atggatatga ggaaactgaa tacctcgcag ggtcgaaatc ttaccacagt   186480
tgatgataga agacggtttt ccatcgggtg ggaaacatgg gatgacggtg gagagtctct   186540
atacgatgtg actaataatg gtacaacggt catcaataca acagcctgtg tttcaagttg   186600
ttcgcatacg tcgcttgtgc tttgcaatat gacgcagcag actgattcgt tgtacggagt   186660
gggtcatcgg ttgaatgacg aagaagatgg tgaactgtgg agagtttcgg tttcttaata   186720
atcccatacg acatgtgttc atttatatct gaattttagg atgatgacta tagtataact   186780
```

```
ctggggaaca aatatcatac gttaatcact ttaagttacg ccgttaggaa aagaaaatca  186840
gtccgaatga agcatagtca gccgaatgat acagcaatag cttgtttaca acgtgttctt  186900
ttttacatta tgaacgtgcc ttgcttttta tacacacatg gagacagagg tccctcagcc  186960
cttgtcacga caactcccct tttctaaacc gtatgtgctc caaaccgcat ctcctcatcg  187020
tcacgtgaaa taccatggga ccccttttcg tcacacacgt cttccgctt actcaacgcg    187080 tcagcccgcg ctcggcagag ctaccatata aaaacgcagg ggtttagcgg cttccccaga  187140
tcgctgctgc cccggcgttc tccagaagcc ccggcgggcg aatcggccgg ctggtcggtc  187200
ggcgctcgga cggatgggga gaacggcggt gacttagccg cccgtggccg ggagaagatg  187260
gaggagccga gatgacaacg gcagtcgtgg aagggtcgcc aagccccggt ccttctcttc  187320
tgtctggtcg aatctcgttt tcttttttca accgctcttt ttatcacctt tttatgtgag  187380
tttctcttcc gcgtctcccg gccgtaccat ccacccatgc agcatgcacg cgtgtatgta  187440
tgcatcgtct ctcctccgtc ccgactacca tcagcagcac cactaccgcc accccagcg   187500 ccaccaccgc tgccgtcgcc accgcgttat ccgttcctcg taggctggtc ctggggaacg   187560
ggtcggcggc cggtcggctt ctgttttatt atttttttt attttttatc ttctcctttc   187620
cttaatctcg gattatcatt tccctctcct acctaccacg aatcgcagat gataaacaag  187680
agggtaaaaa gaaaaagct acagacattt gggtacctca gctttccgat aactcgaaga   187740
attcaaagtc gacgattccc aacgagagaa aacagaacaa aaacaaggtc atttttattt   187800
atcctcatcg tcaacaacaa ctaccgacaa caacgaaaca ccaccaagaa tgtcaatccg  187860
caagggtgtt cctgccccct cgacgcgcct gtcgcgatcc tcatggcgag gaccgcgatc  187920
tccgtatagg tagatgaaat tatcccgtgt ccggtcctga ttccccgcat gccctgcaca   187980
tcctgacgcg tcggtcagca gccaaacaat cataggaaat gaaccagaag aacaaaaaga  188040
tcatctctct cggtgtatag caacaccaac aacaaccgca tcgcaacatc ttcatccgca  188100
agacggaaag aaaacaacaa taatgagaat gaaatcacca caaccaagcc agatttcacg  188160
tccatgagtt tttattatat tattatcaaa acgaaaaaca gaaaaactgt catagataaa  188220
tataaaaaaa aatagaaacc acaaacgact actagtactc caatcttaga tgtatatgct  188280
cctagataag atttagtatt accataatca tcgaagaatg aaagacgacg atgattcctt  188340
accgctcctg ccacccggtc tgtatgtaga gagagaagag agaaaacggt gaatccaaga  188400
tccccgggtc ggcgtcggca tgccgctgat cgcagtggcc ccacctcggc atgccggcgc  188460
cgggcgagga attgctcatg aaaaaagtat ctttctgtaa aaaagaaaa caatacatga   188520 ttaaccgaaa agaaccaac aaaaagaacc cgagatcagt cgatttcgat cactacgata   188580
aacacatgga agatttcttg aaaaaagaaa agagaaagag accaccttcc cggcggcgga  188640
cacgctcctc tccgtcgccg ttctgcacca tgattcgatc aataacaaca tcatcatcgg  188700
agaccatctt ttaatcaatc agcgttgcag tagtcgactc cctggacacg aaggagtcat  188760 ccattttat cctcgcactt cttcgctctc aaagccgcct ttaaagttga atgaaagga    188820 tggaaacatg gaatacagtt ttaattgcac gtatcaccat tttactacaa aaagaaaaaa  188880
aaacaactta cacatagtat taccttaggt ttacggataa gtagagtgta ggcgttttg    188940 aaacagttca gccaatgcaa tcttgtctcg gcataatcac tctttctgca tataatagta  189000
gtagtagatt tattcacatc aacacagcga aaaactccag catcaaagta cacctagaga  189060
cagcccttaa aatatagttt gcagctttta gatgtactta caccaaagaa gattaccgtc  189120
```

```
cttacgagaa aacagatact cggatatagg aatcaagaca gctctgcact gaaaacacac   189180
tctcctgtca cgacaccgcg ccacaccaga ggcgtacgcg tgacttcatc gcaacgatcc   189240
atcgtgatgt ccctcgcaga acctaaaaag accaaaaaaa aatcttggac cacagttgtc   189300
gattcttgaa gacaatattc tcgtgagaac tttgagattc gcacttgaaa cctcttagga   189360
tccacaaaaa caacaacctc tgtatggaaa atgcgctatt ttatctcagc ttttctccca   189420
aacctcggtt tcttcctatt cttaagtttt ccctagtata tttgcctcct tataacaaaa   189480
gaagcacaag ctcggtcgca cggattattc cttctgctaa tctattattt tgttccttt    189540
tttttttgttt gccttcaccc ccttcactcc ctgtagcaac acagagtagt agacacaata   189600
aatgagaagt ttgcatgcat ttgccgtgtc cgtggtctgt tatagcgtgt ggagtgctcg   189660
ggatggatgg acgtggggac ggattcctga ggctacaaag atacgcgag acgtcgtggc    189720
gaggggatgg gtttattgga tatcggtgaa gcagcgtggc ggcgaaatac gcgatccctg   189780
ggctggtaga tccccctacc ccgtctaccg gggacgttta tccttgggac atgtaaatgt   189840
ttcggccggc atccacgcgc cacgttcacc gcgtcgtgcc cagcgccatg tgcgggtcgt   189900
ttcggcgtga agttggacgg cgtggtttcg gggattgtga accgtggctg agggtgtaga   189960
agggatagga aagagcgtgt catgtgggcg agtcgtagca tgtgggtgcg atgcggtgga   190020
tatggtgggc tggggtggtt ttgggcgtgg agatgtggag atgggggtga tccggatgcg   190080
tggcaatagg cctcgagctt gggcttctcc cgcggatgga cgttctaact gtacacggcg   190140
gccgtggcct ccgagtaaaa aaaccaggtg ctgacgccag acacagacgc cgtcctcgga   190200
atcgtgtgcg cgaaagcctg tgccgcggca gcgtacgacg ttccagtcag cgaggccgtc   190260
gcgttggcgc gccaacagta aggtcacgat aggttggcgg cccatggttc cgaagcgtcc   190320
ccacatgcac cagcagtcgg cgtcgaagtc gcttgcgctg tcggcccggt cgccaccgcc   190380
gcggcggatt tccgcgcggg ggacggggta gccgagcgct gcgccttcgc caatgttgtg   190440
aagtagatgc gtcagttgat ggtgatgttc tgtggaaaaa tgagcgcttt cctgagggtt   190500
ggcgtcgggg tatgcgtgta gttggggttg tgttggagcg tagaggtgtt ggcgggcctg   190560
cgcgcaagcg gcgtaatccg cggcgtcgag ctccatctgc gtgcggtgtt cttcgttggc   190620
gtgtttgtcc gaggtttgga taggcggttg tgtgttgctg tggtgtaagg gtagcgtgtg   190680
ttggtactgt gggtgaagcg gcgtggtgtg ggtgctgttt gtggctgtgg ctggcatgat   190740
tgtgcggcag gtgtgtgttg aagtgggtgg aggttaaata ggcgagggcg agtccccgtc   190800
cccgcacacc cgcgtcctcg ccgcaaacac ccgcgccacc ccgtccctc ggtccggacc     190860
cgcaacaccc gcgtcgccaa cgtaaccccc gtacccgcaa cgccccggcc ctaccgccgt   190920
cacgcacacc ccccggcccg cagcccggta cccagcgcgc ccaaaaagcg ccgtggagac   190980
acccgtacag agatccctca gcgcgatgac gccccgcaaa cctcacgcag tccggtcccg   191040
cgaacagata ccgtgggacg acacgcaccg gtagtgcgca caaaggcagc cgcgcttacg   191100
ggcctcaaag ttccctcagc cccgtcccgc gccggcgtcg ggttgggtgt gccggggcg    191160
cggctgggtg ggtgcgtgcg tgccgggtgt gtcgcgggcg tgtgtcgggt gtgtcggtcg   191220
ggtgtgtcgg tcgggtgtgt cggtcgggtg tgtcggtcgg gtgtgccgcg ggtgtgtcgg   191280
tcgggtgtgt cgcgggcgtg tgtcgggcgc gtggcgggtg tgtcgcgggt gtgtcggtcg   191340
ggtgtgccgc gggtgtgtca ggggtgtgtc agcggtgtgc gcggcttcgg ggtgcgtgtc   191400
ggcggccgga gggaacaaca agtgtgcccc ggggcccgcg agcccccccc cctcccctcg   191460
gccggacgcc tcttctgcgt gtgtcctcga cgcgggtcgc gccgtacttt gcggccgttg   191520
```

```
cttccccgc ggtccccagg gtcgcgcggc gccgcgcgct tcctcttttc cgcgcgcggc    191580
cgtcccccg gggacttcct cttttccgcg tcgtttccgc gtcgctggcc cctgggaggc    191640
gttcttcgtg tgtccccggg gacccgcgct gccgtcgtcc cctgggact  tcctccgttc    191700
cccggggaat caaacagaca cagacacgcg tcttcttttc gccgtgcgcg ccgcacgccg    191760
cttttatgcg ccgccgccgt cccaaccgca ccgcaacgcg actccaagac tccaaatttc    191820
accccccgc  taaaaacacc ccccgcccc  acggggaccc aacacacggc ccggaatgga    191880
tgtcaggcgt ccacctagat gacagcgctc gagtgctgcg ggcctgtctc gcgtcttcct    191940
tcgggcgtct gcctttccca gtcgagtgcg tcgtcgcctg ccgggtggtt ttccacgggc    192000
ttccagactg cgcgtcgcca aggcggcgcc agcaagcgcc gtgcacggcg ctgcctataa    192060
aagccaggtg cgtgtcggcc gtggcacacg acaacggag  acgtccgcgt gtgtaaacgg    192120
cgtgctcgct gacgcgggtt gtgttgctat atagtggacg tcgcctcgac gtcggaggtg    192180
tccggcggcc atggcccagc gcaacggcat gtcgccgcgc cccccgcccc tcggtcgcgg    192240
ccgcggtgcc ggagggcctt cggggggttgc ttcctctcct tcttcttgtg tgccgatggg   192300
agcgacgtca acggcgggaa ctggtgcaag tactgcgggt tcggcgacgc cgggccacgg    192360
cgtccaacgg gtagaacccc gcgggccgcc gggcgcccct ccgggtagcg gcaacaatag    192420
caacttttgg cacgggccgg agcgcctgtt gctgtctcag attccggtgg agcggcaggc    192480
gctgacggaa ctggaatacc aggccatggg cgccgtgtgg cgcgcggcgt ttctggccaa    192540
cagcacgggc cgcgccatgc gcaagtggtc gcagcgcgac gcgggcacgc tgctgccgct    192600
cggacggccg tacggattct acgcgcgggt gacgccgcgc agccagatga acggcgtggg    192660
cgcgacggac ctgcgtcagc tgtcgccgcg ggacgcgtgg atcgtgctgg tggcgaccgt    192720
ggtgcacgag gtagaccccg cggccgaccc gacggtgggc gacaaggccg gccatcccga    192780
gggtctgtgc gcgcaggacg gactgtacct ggcgctgggc gccggattcc gcgtgttcgt    192840
gtacgacctg gcgaacaaca cgctgatcct ggcggcgcgc gacgcggacg agtggtttcg    192900
gcacggcgcg ggcgaggtgg tgcgggtgta ccgctgcaac cggctgggcg tgggcacccc    192960
gcgcgcgacg ctgctgcctc agccggcgct tcgacagacc ttgctgcgcg ccgaggaggc    193020
gacggcgctc ggacgggagc tgcgccggcg gtgggccggc acgacggtgg cgctgcagac    193080
gccgggcagc cgactgcagc cgatggtact gctgggcgcg tggcaggagc tggcgcagta    193140
cgagccgttc gcgtcggcgc cgcacccccgc gtcgctgctg acggccgtgc gtcggcacct    193200
gaaccagcgt ctgtgctgcg gctggctggc gctgggcgcg gtgctgcccg cgcggtggct    193260
gggctgcgcg gcggggccgg cgacgatgac ggcggggacg acggcgatgg cgacggggac    193320
gacgttgccg gcgggggcga gcggcacgga gacggaggcc gccggcgggg acgcgccgtg    193380
cgcgatagcg ggagccgtgg ggtctgctgt gactttacct ccgcagccgt acggcgccgc    193440
cggcgggagc gcggtttgcg taccaaacgc ggacacgcac gcgtggtcg  gaacggatgc    193500
ggcggcggcg gcagcggcgg cgccgacggt gatggtgggt ccgacggcga tggcgggtcc    193560
ggcggcgtcg gggaccgtgc cgcgcgccat gctggtggtg gtgctggacg agctgggcgc    193620
cgtgttcggg tactgcccgc tggacgggca cgtgtacccg ctggcggcgg agctgtcgca    193680
ctttctgcgc gcgggcgtgc tgggcgcgct ggcgctgggg cgcgagtcgg cgcccgccgc    193740
cgaggccgcg cggcggctgc tgcccgagct ggaccgcgag cagtgggagc ggccgcgctg    193800
ggacgcgctg cacctgcacc cgcgcgccgc gctgtgggcg cgcgagccgc acgggcagtg    193860
```

```
ggagttcatg tttcgcgaac aacgcggtga ccccataaat gatcccgtcg catttcgtgt   193920
ttcggacgct cgaactctcg gtctcgacct caccaccgtc atgacagagc gtcaaagtca   193980
attgcccgaa aagtatatcg gtttctatca gattaggaaa cctccttggc tcatggaaca   194040
acctccaccc ccatctcgcc aaaccaaacc ggacgctgca acgatgcccc caccgctcag   194100
tgctcaggca agcgtcagct acgcgctccg atacgatgac gagtcctggc gcccgctcag   194160
cacagttgac gaccacaaag cctggttgga tctcgacgaa tcacattggg tcctcgggga   194220
cagccgaccc gacgatataa aacaacgcag actgctgaag gccactcaac gacgaggcgc   194280
cgaaatcgac agacccatgc ctgtcgtgcc tgaagaatgt tacgaccaac gcttcactac   194340
cgaaggccac caggtcatcc cgttgtggca aacagaggat ggctaaccgt cgttgcatgt   194400
tccaggccat gagccaggct aggcccgtac accagacgca gagcatggat gacaggacat   194460
aggcctggat taccacggtg cgatcgaaac acagcccgat ggtggacacg gatatcgtag   194520
tgagggtggt ataccatg accagcatca gggtcccggg tcggcgccga cgttccagcc   194580
agtacgcgtg gcaacgcaga gcgcagggta gcagtgtgct ccagaagggc agtgtatcgc   194640
gcaggtaggg ggtcgtcacg cgccacggta tgagcatgaa aaggatggta gtggctatgg   194700
tagcgctggt ctggaacacg acggtgccgt agagacgtac catccagaga aagtgttgaa   194760
cgctccgcag ggtgtcttca tctttggtga ttacggtgac tcgacggatc ggcggtggtg   194820
acggcggcga cacgggtggg ggtttctctt tcttatggcc gagtggctcg ccttggtgaa   194880
actggatctg taccatgacg ggtgctcgac gaacagtcgt cggggcttca ggtacccggc   194940
aagtttata gagaaagggg gacgatgggt ggtggctacg agccaccgcc accttcgcaa   195000
tacgaggatc tgaaggcggc aaagacggtc gtccagggca ggcgccagag gttgggactg   195060
agcacgatca gcgtgatttt aaacatggtc accagtccta cgtagatcag cagcgagccg   195120
cgtaacgtct gagcggccgg cagttcgtcg cggatgtaac gcgtgccgta gaaagtcacg   195180
gtcatcataa ggaagacgat ggcgccgtag ccgtagagta gaatacgctg atgatggaac   195240
acggtctggt cgccgataac ccagagcgtg atgaaaaaaa cgctggtgag cacccgtgag   195300
catatgagct cccaacgctt agcgcgaaaa ctgtccccaa ccatgacagc gccggtgcaa   195360
gctatccaca gcgtgaggac cagtgtgtag tcgatgagga tggcgggcag gtcggagcac   195420
caggtgtaga aaaccgtggt aacggagagg aggcctacgt agcccatggt caataccacg   195480
tcgtcgggt gcctttcgcc ctgtatcaag accaaacacc agagaaggga ggggcaaaa   195540
accagcagca gagggaaga ttcatgttga catatgttgt gggaatcggg gatacccagc   195600
caaatcattc cgcagaaagc cgtactgatg gcgatgtgaa agaccactag ggcgtagacc   195660
cggacgagga cagcaaaacg cgcagccac ataaggccgt ggtgcagctg caggagggaa   195720
gcccattgcg gcgaatgtag cgacggcagc ggcgggtcca tgaggcgggt gatgcgcccg   195780
agtgaacggg tgagcgtctc ggtggagtct tcttataaac cagcggagct caggcagcct   195840
tgctctggaa cgtcgcggtg gtggtgttga ggatgacgct gagcgtgccg ttgtcaatca   195900
ggtaatgatg ataggtgccg agcttggcca ggtagctgaa catttggtcc cagcgtgccg   195960
accacaccac gggcgtgagc attaggagtg tggtgtgata aatgagtgtt tcggtggcgt   196020
aaagtatcag cgagctgcgg atgatgtggc tcacgggcat tttggtggcg atgtagcgca   196080
cgtcttggaa aagaacggcc aggatgcagc ccacgaacac ggtgtagaga cacagcgag   196140
tcttatgcaa ccaagtgtaa gtagaagcca ggacgctgac catcaccgtc aaaagtggg   196200
aggtaaaaag cgcgtcacgc cacacggagc tgagacggtg ctcccaagcc acgccgttgc   196260
```

```
aggccacgaa caacgtccac gttaagatga gactggaaac gccaatgggc gctgtggcgc    196320
acaggttgag cccggcggtg gtgaacgaca gaagcgccac atacagcgca aacaccaggc    196380
cgttgctggg gtgtctgtga tcggtaagct ccagcgcgcc cagaaccaac accggtgtgc    196440
agctaagcaa taacggcgaa ggatcgtcgc ggcactcgta gcccagcgag gggtaaccca    196500
gccaaaccag cgcgctaatg agcacgctga aagcggtttc cagcgtcagc aatccgtaga    196560
cacgcatgac gatcgcggtc cgccgtagcc aacacaccgc atcttcggaa gctgtggacg    196620
ctgtttccga ataccgggag gagatcgtgc ttccctcttc taaggatcgg aaagtagcgt    196680
ccgtcgtttc cgcggacgcg gcttccctgg tacgctccgt ttccgacgac gcggtttccc    196740
gctgcgtgga aactgtctcc atgtcgggac cgcagcgccc ggcggcgtat ccgcaaggtc    196800
tcgaagctac agcttgtcag aggaaaagta ggtttgcaaa aaggtgcgca gggtcatgat    196860
tctcagcacc atcagcagag tgaaaaccag gctgagaaac accttgacgg ccgccaaaag    196920
cgcgcgttcc agcggcgtct cgtagcgtac agccagggcc gcttcgtgga aatgcgagac    196980
ggctagacag gtaatgagca cgctgaagga caagacgatc ttaaagcacc aggaccaacc    197040
acgcctcaag atgaccacca cgattgccgt gaaggtcaac gtgatcaaag catgacgac     197100
cacgatctga cggcggacgg tacgttcggg agccaacaac gctacgccgg tgcagctgag    197160
aaaggccagt aaggtgaaca acgcggccga gatgaccaac gtaccgtcca ggcagagaca    197220
tatcacgatc aacggcggca cgtgaagcag cgtgtaaaag agcagaacgc cgatattgct    197280
gggatgcgat gtttcgtaac agtgaatgaa gatcaccgac gtgacgggta tgacaaagac    197340
gaggctgggc gaggactccg tgagacacag acgggaatgg tgaaaccacg tcgcgggcgc    197400
cgcgtagcag aaggcgctca acaacgcggt caagccggcc agctgccaac ccacggcgcc    197460
ataagtgtgc agcgccacgc ggcaacagtc gacccaagcc agactgcggg tcgccagccg    197520
ggtctcttgt atcccggggg gcacgtagat gaccgtgcca tcggtgggta cttgaaaccc    197580
ttttctctt ctcatggtgc gctgcgttct ctggaaacgg ctgctctgtc cgaaaaccag     197640
ttccgaacga aaatctaggg cgagagggtg gacaacggcg tcgacgacga agcatgggac    197700
aggtcgttcg gcgttaacgt catcgcgtcg gacgacggta gttctaagag acgtagatcg    197760
ctcagcaggt cctgacagtt gcggattcgc aagatcagaa aaaaagggga aatgaacgta    197820
ataaagagct gtagcgacgt atgcgccaca tcgcgtggca taagaacgtg acggacgaaa    197880
aggacctgct gcgaaaagtg gccggcgaag ataaggccca ccgtgctgta gaagcccaaa    197940
agcagccgca ggggccaagt ccaggccgc gtgaagacga tgagaacgtt agccagaaag     198000
accacgaccc agacgccgtt gatgagggta aattgatcgg acagggtgca gttgtcgcga    198060
cagatgaaga ctacttccgc gcagagcaag gtgatgacca acgtgagcac aaacgacgtc    198120
aacacctcgc ggggctcctg gcaggcacac gtgacaccta gcgccgggat gtgcgccagg    198180
aggccggcga gtaatagcac cagctgtcgg aacggacgac ggcagcgcgg gtgccggttt    198240
cgctgagcga gaaccggtcg ctcatagcgg aaatacacga agagcgcgga ggccacaggc    198300
accaggagga gcacctcggg cgcccagaca acgtgacaag gaaagcccgg acgcgactta    198360
agagtcgctg tagggaagac cagagagaag ctacccaaga cggccaccgc cgcggagatt    198420
tggaagagga gcaagccggc gattcggacg acaacctcga agcgatgcac ccagcccagc    198480
acggccacca cggccgcttc atcatagtcg tcgttgttgc cgctgtcgaa cagccgccga    198540
aacacgatct gtcgctgggt cgcggtggga aagcgcagac ccatgacagc cggaggctat    198600
```

```
atgaccgtgc gtctaaggcg cgagatccgt gggggggactt ttagatgttt gggcggcccg    198660
cggttctaac aggcttgatt ggtggagacg gccggcgcgg cgggtggggg aaacgacgag    198720
tttttccgtt acgccatggt tcgcgtgagg tttctctgta cctcccgcaa aaggtcacag    198780
cccgaaatgg aggccgcgtt ggtggccccg gtggcgcgtg acgataacca ggtcatccaa    198840
gcgatgagtt tgtctaatga gtcctcggtg gtgaagagga taagaatgag caggtacagg    198900
tacaccaggt tctcatagag acacaaggtg agcaggtcgg cctcggacca cgcgatctca    198960
aacaggcgcg tggtgtcaaa gaccgtgacg accagcatga agctgagcgc catggcgtaa    199020
tagcccaaaa aaagtttgtg ccctaacggt acggggttgca ggtaaagtgc gatcaagaac    199080
gcgataacgc cgatcacaaa cagcgtgatg atgacctgcc atcgacggtg attatgggcg    199140
gctagacccg tgacgcagct gcagaggcta aaaagcacgc aagccaagag gcccgagaag    199200
gtcaccagcg tagaggagga gcaggcgctg gccacgatca ccgaaagcgt cgtgagcacg    199260
ctgtaaatgg tgagcaggcc cgggctcggc ggcgacgtga acgatccctc gtcgcgtttg    199320
ccgtgcagca gagccagaca gatggtgggc accaccaaac tcaaaggcgg cataaagcca    199380
gtgcaacaga gaaagacggt gcttttgaga tgcggaaaag ccagcaccag gcccagacag    199440
agcaagaagg tgcaggtgcc ctgcacggcc acggtgctgt agacccgcat acaaagcaaa    199500
aagcgacgta cgtcgttcgt cgagacggag gaaatcataa tgactccgcg cgagggtcgc    199560
gggggtgggg gcgcccaggc cgtcccggtg gcctctgagt tcggagacat gacggcggtg    199620
gcgatcaaaa ggcgcgtatg aaaaaccgtt tatagagtgt aatagaatca ccgtcatccc    199680
cacacggcgt tcccccataa agtcacgtca cactcgagta agcgtgaaaa agctttattg    199740
ttgaataaaa aacacgagta caacaccgag ttgcggtgtc ctgtctgtct actgggtggg    199800
ggaggttcat cgtctgtctc tggagggaag gtggggaacg tttaagcgag caggagcgtg    199860
tcatctcccc catctttta taacaagctg aggagactca cgccgtcgat gcgtccgccg    199920
tgtttctcgg cgtactgctg cacccagacg tggccgctaa agatggcgac gctcatgttt    199980
aggagactca tgacgatggt gtacaacacg acgctgacac agacgctgtt tttagacagc    200040
gttccacgct ggtagatgag atccagggtc tcgtaaataa gcacggccga agcggcggtc    200100
accaccagga cgtagagtcc gctgtagatc ttgctgaccc acaacacggg cgaaaagtaa    200160
agcaataggt aaaagacgat gacggaccag ccgtaaccaa tcccgatgac tttccagcgc    200220
gtgggattgt tgccggccag gtaggtgaga ccgctgcaga gaacgaaaaa gaccatcacc    200280
agggcaaacg acagaccgat gacgcgcctt tctccgcaaa agcccgtgca cacggtgatg    200340
ccggtgttga tcagcaggca cgccaccgtg agatgagcaa aattggtggt gtgtgggcga    200400
aactcggcga aaccgcgtag catagccagc gtggacacgg gcacgatgga ggacagggct    200460
ggcactatgc cgttggcgca ctgtccctgc acatcgggga aggcgagcca agccagcagg    200520
cagaccgtga gggtacaagc cagctgccac acgagcccgt gatagacctc catgagcagc    200580
ttgaagcgtt tcaaccattg gaagagctgc tgttcggcca ccagcgcgtg gctgcgatgg    200640
agcggcacga tggtaaccgt cggcgactca tggtgttcgg aaaccgaggc ggtgtcgccc    200700
atgctgccgc ttacgaccgc tgtcggtcta aggtaggcgt cgatgaaaca gtccgtctta    200760
tcagcacccg gttaccgcgg atttgattga cgtcacgagt gtggtcaaac cgtggcgcca    200820
ccctgtatcc gacccgtcgt catgggctcc acaaccagag cctcagaaga tggtacatgc    200880
cgatgaataa agccacattt tcgacataga ggcgtagcga gggctgaaaa ctctccggga    200940
aagaactctg acaggtgatc agggacagat cgtgaattag catcagcgtc accgtcaaca    201000
```

```
gcgtcgtcgc gtgtaaaccg agaaagaacg gggccgcggc ccgcagcagc caaagtccca   201060
gcgccgtagc gcagagcaga gacaggaccg acggtagcca cagccgccgg agagacgcgc   201120
caggatcgca acccaaaagc gaggccccca ggcagctgag atctaccgcc agggcgagaa   201180
gagccgcgcc gacaaaggcc tgcggcgacg gctggcacat cagcaaggtc agaaaggcta   201240
gcgcgtgcgg caggcagtaa gccaacagga gtgggagttt gcggggacaa cggtcgatcg   201300
acggaccgcg tagcagcagg aacaggcagc cgacgggcac gacgaggctg agatgagaaa   201360
gcggcggtgg gtcgtcgtcc cgtccccgct cgcatagctc ggccaccggt ggcggcatga   201420
gccaccagct gagcacgctg agggcgacgg tggcggtaag ctggaaggcg acgaggacga   201480
aggcgcgcag ccataccgcc agcctctcta ggtagggac tacctcctcg acggtccatt   201540
ctagcgggac gacatgaagc atggcgacaa gcgcggctgc tgtgaaaacg ggcgcggttt   201600
tataggcatt aggacttccc cgtcgtactg gcggctgtca aagtcccgtt gtccaaaggc   201660
acgccgtccg aaagactaat ccaacgggga cccgagagca tgagcaacaa cgtgagaaag   201720
atggccatgc tgtccaggta gagacagacg gcgtgacgga tgcattggtt aggtgggcag   201780
aaaaagatga ccatgagact gtcgtaggcc agaatacccc aaaagaagct gatagagaag   201840
gcgcacaacg tcaccactat cttctgcagc caatcggcgt cgcttagcag agcgagcgtg   201900
aggaacgaaa gcagcatcac cacgtagacg cagctgatgc atttccagcg acgtcggtca   201960
cggccaccta gaaacgccag ccccgtaaag gagataaaca acgccagggt catcacgtag   202020
gaacctacta gtacgcggct ttcagagcac atctggaaga tggccgccgt caggctgttg   202080
gccaacagat agatgaaaag caccgtggcg ttactagggt gttcgttgcc caacgtgtac   202140
gtgatgaaca tgcagacgat gggcacgagc acggtgagaa agaagctgta gttctcgacg   202200
caaaagttgc ggttttgtgg aaccccaac caaaaaacgc ttcccaaacc gaagctgaaa   202260
gccagctgaa agatgaagat ggcgtacacg cgcagccata cggtgaactt tttgaaccac   202320
tcgagagcct ccatgcggga gagcagcagc gcgttagcct cctgcgcctg catggtggcg   202380
acggtctcgg cacaaagccg ctgcggcgca cctaccctcc tcttatacac aagcgagcga   202440
gtggggcacg gtgacgtggt cacgccgcgg acacgtcgat taggagacga actggggcga   202500
cgccgctgct gtggcagcga ccgtcgtagc gaccgtcgtc tgagcagtgt gggcgctgcc   202560
gggctcggag ggcatgaagt agagcacgga gacaaagagg tacatgaggt ccatgtacaa   202620
gcagagcgcg cccgggatat aactctcata ctcgatgtcg tgcaggatgt cctgcgtatc   202680
gcacaccacc gaggtcacga tgacggccaa accggctatc atcaccagga tctcacttac   202740
cgcctcggga aaagagaaa atacggcgaa cagtaataga atcagcgtgg atgcgcccgt   202800
caatagggaa cgctgtaatt ccacgtcgcg ggcaaacaga tacgtagcga gcgtaaggaa   202860
acaaaatagc gttactgtgg ccaccatggc ataaatgact gaacgatgac taaagtggaa   202920
gcctgacgcc gtgacagcca cgctggtaag caacgtgtac gtcagtaaga tccatacgtt   202980
tttgggaaag ttgggctcgg cccaacgcaa cagacctagg cacacgatgg agatcattaa   203040
gcaagacagc gtcagacgca cgctggaaaa gagctgctcc agccggtgcg gcaacaccag   203100
ccagcaaaag gcgcagacgc tcataaggat gaggcattgc acccagataa ggatgtagat   203160
gcgcagcagg aagaccgacc gggctatctg gacctgaccg cggagcgaca tgcggcaac   203220 gccgcggtt atcgccgaga ttcgtctaaa tacacaaagc gaactagaaa acgcacacac   203280
gtgatttgca aaagaaagc agctgccggc ttattatttt attaaaaatt tatctgtgca   203340
```

```
gaatcataag tttatgatga ataaaaacgg ggaaagggaa tctgctttta gggacccggg    203400
tctggtccgt cgtctcccat ctggtcgggt tcggggatgg ggacctgttt cagcgtgtgt    203460
ccgcgggcgt gcatggcttt tgctcgccgg ccgcgctgta accaggcctc tttctctgtg    203520
gtcggcgagt cttccgacgg gtagggagtc tgggagtcca tcgcttcagg cccaccgctc    203580
gctccctcga ccgtcgtgtc gtcctcgttt tcgctattac acggggtttc tggagtatcg    203640
cctatacggt tggcgattct ccgggggcgg ccgctctcgt cctcgtcgct gctatcgccg    203700
cccggtaatt cgacgccgca ttcgttgtac ggagcgcggc acatgggcgg cggaaagaac    203760
ttgggcatgc gaaagcagcg ttgtccatcc acggtctgcg tggtttcatc gttatcctcc    203820
cataatcccc cctgtagcgc cggcagcgtt tcgacgctgt gagagggaa  ggcccagttc    203880 tggttgtctt gcagcgcgcc cgtgggcagt aggtccgtgc ggccccaggc gctgctgttg    203940
ttgggtacct tgtcagtgcc gcgagtaggt cgcagaaacc agtccagagc gctctctaac    204000
tgcgagcgtg tgatggtgcc cagtgcgccg tgccagcgca gcacgtctct tttcagcgtg    204060
tggtgacaga cgggcagctc ctccaaccga cactcgccgc gcaatccgcg gtcgaagcgg    204120
cagagaccac gcagtttaag cagaccgcac ttgagaaaca tgtgaaaatt atcggcaatg    204180
cgatacaggt ctgagtcctc gatcttgtgt aggtagacca cgccaaactt gtcgagcagc    204240
accaggccgc tgggcacaaa aggcccgtag gccaggtaat agcccacgag gccgacgacg    204300
taccactcgc agcataagcg ttgacgaata aagttcagaa gatcgcgaaa gtccgcggcc    204360
ggcatgtggt caaaggccg  gcaggcgcgc aggccctcga tggagcccag catgagcaac    204420
ggctccacct cggtgcgacc cggcgtgcgg atgaccaggt tgagaccgct catttcgcgg    204480
gccgtcttgg ccacggccgc agcgtcagtg gggtcggtgc agaggaattt ttgcacatga    204540
tagcgcggtt cggtggtggc gaacggcgtt tgtgggtgcc gatacacata ttcgcaccag    204600
agtaggccgt tcttggaaaa ggctttgata tcactggcca cctcgtagag cccgtcggtc    204660
tcccagtcgt agacgtagac ggtgccgtaa tgacttagca tgagcacaca gggcagttcc    204720
tgcgcctgct tggtgtttcg tgttagatcg ctgtcgggtg gacgtacggc taatacaccg    204780
acggcttcca gggtgtcatc gcagcagaga tagtcggcgg ccagagaacg tgcgtaaatc    204840
tgcgggatgg cgacctgttc gcgcatcact aggaaccagt tggcggggtt gcgcagtgct    204900
acggtggttc cttggtggcg ctgcacgtag gttctcagcg ccggaggatc gtactggcgc    204960
agatagaggc cttgcagcat cgataacgtc ttttgaaaga cggtgtttct aaactgaaaa    205020
acgccgtagt cgcagcggat agcatcttcg cagcgctcgt cgcgctgtcg gagataggtg    205080
ccccaggctt cggcggcggc tttggtgagt agggacatgc cggcggagcc gtctcgacag    205140
cgagtcggat aaagcgcgct gcgcgaaagc ttaatatagg agcagcgtca gacgaatcgc    205200
ggctggtggc cctggggtg  ggacgcgccg cctacacaaa gtgctcccga aaatcgaaac    205260
tcttgaccca ctccggagac aaatccgtat tcagattgat gcgtcgcgct tccacttcgg    205320
cttccgaaac ctcggcctcc gtccggtagg cgttaacgat acgctgaccc aggtgccaac    205380
gctctttctc tgccaaacgc cgttgctcaa accattcgtc tacgtccttg aggtcaaaga    205440
cagtgtcctc ctcaaggtca aagcctaggt cttcccactc gtcgtcatcg ctctcgtggc    205500
cggcggccat acgcgcggca accgcgtcct cccctcctct tctttcaacg ttgggtacca    205560
cgttattttc ttcgggttcc ataggttctg cgccactgtc gtcatcatcc tctccctgct    205620
cctcatcgtc cgccaaggcg tcgtggatta tctccaggtt ctgattgtcg ggtacgacgt    205680
ggttatcttc gtcgtcgtcg cgtggcatgg gcggcggccg acgcggacg  accggcatgg    205740
```

```
cgcggccgtc gtttccttcg tcttcctctt caccgtctcc caaggaacgc ggtcgacgac 205800
gttccgcgaa gtcgccgcgg actacgcgcg cctgccaaat ggtaaacgcg tcccaaccgt 205860
cccagttatt gagcatttcg gcgcgaaaac ggtcgcctcg acagagccag cgaaactgcc 205920
gcgcgtagtc gcggtctacg ccgctgtcga acatggtaaa gtgcagacgc gccgcctcgc 205980
ccatgtgtac gcagcctccg ttgcgttcca gcctggccgc gcgccgtaga ccgtgttcgt 206040
agcggcgacg cacgtacacc ttcatgaggc cggcgcgaaa aagttcctct aggctgtcgg 206100
ccagacggta gatttcaccg gctagacgct gcagaggcgg cgagcggtcc agatgcgatt 206160
tgacaatcac cacgtaaaaa cgacagaaac ggtcgaagat gatgaggaag gacgtgtcaa 206220
aaaaaccacc ggcgcggtag gagcccacgg cgcccagcag gtaccagcgg caacgcagtt 206280
gcagcgtgac gtacatttcg cactcggcca agcgggcggc tggcgctacc tcgaagggcc 206340
aacagtccgt caagcagccg aaactggtca ggagtttcaa cgttttggca tggcgtccag 206400
gtgtatgaaa gttcacgtcg cgtccgtgat gttcgccaac gcaggcggcc aacgcgtcgg 206460
cgtcatgacc gtgacgcagc agcatcgcta ccacgtcgtg cggtacccgc gtagcaaacg 206520
gcgtctgtgg ctgacggtat acggcttcgg tgtacatcat accgtaacgc gccagctcgt 206580
ccagatgacg cgcgcacagc agcagaatct cttgcgaggg ttcgtagatg tagaggcgcg 206640
taccgccacc catgcagagc accagctccg tctcttcgta gtgatcttcc accatgatca 206700
cgcacttgcc tagcacgata aggcgttcgg ggcaacaaat cacgtcgtcc agcagctggt 206760
cgcgtagctc cggcatggtg ctgccgggcc gtacctgcag gaaccagttg tgcggaatgc 206820
cgagcgacag cacctggtcg acgtggttac ggacccagtc gcgaagcacg tcggcgctgt 206880
actggcactc aaagatgccc tgaaagtcgc ccatgacccg cagaaaagtt tcgtagcgcg 206940
tgtggcaata gaggaattca tcgtttcgcg taaacgtggg agctccgtct tcccaacgtg 207000
tacgccacat gtcaaaagag gccgccagct agacacccca gaaaagaagc agagaaagag 207060
acttctttgt gcgacacgtt ttattccgcg ttctccgctc gacgttcaaa tctggatgta 207120
ctcgcgcaca cccgtcaggc tctttaaggg aaaagggtcc gagtacgtca ctaaccgcga 207180
ctgatgcacc agggcggtaa tcacccgctc cgcgccctcg cgcgtcgacg aacgcgtcgt 207240
caccaggcag tgcagccgcg ggcccgtatc gtcctgatga ccagcggcct cgcgctcggc 207300
tgcttccaca ccgacaatgt cgggatccaa cacgtagctc tgcgagttgg tatcgtagcg 207360
gtgtagcacc aacgtgttgg ggtccagacg ctcccacgcg ccctcgtgcg ggtcaaaacg 207420
ctccgttaaa cagagccagt catactgctg ctgcagaata cgccgctcgc gctcgcgtcg 207480
ctcatcgggc aacgcggcgt cttcgttgaa gagaatgtcc cgcttgtggt ctacggcacg 207540
ctcgtggtga tgcgggcaca gatgacggtg ttccatacgc gtctgacgtt gacgctcgcg 207600
ctcgaaacgc cggtgtcgaa agaccatttt cagcaacccc atgcggaaaa actccgtgat 207660
ggtgttggca acgcgccgca cgtagtggtt ggggtcgtcc atctggatgg cgtacacggc 207720
accgaaccag tccaacagta ccagcacttc ggccacaaaa ctgcgtcccg gtcgcggacg 207780
tcccgtcacg cctagcacat accacggcgt ggccagatta gcacggacag cccaccacca 207840
acgacggctc tccacctcgg tgagcgcaca aaagggccaa atgcggtgta actgctgcac 207900
cgttttcatc agccgcataa tcaccgtgcc gtaacccggt gtatgcaact tcacgtcgca 207960
acccaggatt cgttcggccg tggcgtacga gccctcaggt gtggtgtcat tgagaaacaa 208020
aacatgcatg gtacgcgcgc ccttagggta tcgtcgcgga acaggtaccg tcattctccg 208080
```

```
cagagtggtg tgaatcacgt cgcgatacgc aatctccgaa cgtgacacac cgtaacgtgc   208140
cagttcgtcc aggttgtgcg ataccaacac catgtacttt tcacgagtgt cgtaggcgta   208200
gacgcgagaa aagcgaccca taaaaaccac gtacggggta gccaccatgc catcatggtg   208260
atcgcgacgt ggctcgggca acaaaataac agcgtatccc aacggcgtca gcggctcgcg   208320
gcaacagatg agctttgacg ccgcctgttt ggcggcggta atgatcccgt cctccgtacg   208380
taacatcaca tgccagccct tgggggggacc caaggacaga cagcgtccct cgttacgatg   208440
aacgtaacgc gtgatttcca ttggctccag gcaaaagaac agttccttaa aatctcgcaa   208500
cacttgtcgg tataacgcca tgggatcctc ggccgccaca ggcagcgcgg ggagctccgg   208560
cggcacaact gcagcgccgt cggggccaga acccgcagcc ggatccatca ttgcgcgaca   208620
ctctcagccg gacaaccggc gtcactgaca gaagccgagc caaatacaga gaaagcaacg   208680
ccacaccgtc accccgctcc caagcgccgc ggaaagtgct ccgattttc accgtcgttc    208740
acgacgttga tttgcctcgg tctgagaacc gacctagcgt tcggaccggt gcgcagaaac   208800
agccggcggt ccgagccact gagcggttca cagccccggc cgccgatagt tatcggagag   208860
acgttcgagc tgcaggtaca tcggcgctcc ccgcttcgcc accccgcgcc cgccccagtt   208920
tatactctcc gacgcccctt ccaacgcgcc tgtggagggc caatcggacc gcgggagctc   208980
tccaagtgga tgacaggcac agccgggtgc ccgaccgtga agagccctca tccacctgaa   209040
cagaccgcta accgaaggac cccgagtcgc gtccgtcagt cccgacgtcc gtcgccatct   209100
ggctccctgc tgttggctac ctctcggatt tcaaaaaaga gcacgtgccg atgacggtgc   209160
acaggaaaga gccaaagtgt cacagcgtct tttttattt gtattccttt cctgttttgt    209220
actcgtaaac tgttgacgtt gttttttacat ccaaagggc aagtaagaaa caggatgagg   209280
catggtaggt ttgggcgtgg ggcggccctc cagcacggcg gccgggccg cccggcgggt    209340
gagcacccgg cgttgcgccg tgtctatctt gtgtttcttc tgtgtcttt cctatcttg     209400
ttccgcgacg gcctctttca tcacgttcag catgcgttcc tcgacgccct ccagggatcc   209460
tggggaggag ggagtcctag tgaggcttcc aatgttgttt tgtggatttt cggtttcctc   209520
ttcttggtcg tcatcgtcgg acgtgtcgtc ttcctcttga tcctcttctt cgtccgagta   209580
gtagacgcat agtccttggt tcatcaggct gggattcatc aggttctgac ggggaatccg   209640
ctgttgtaga cgtttaaccg cccgttccag gcgagagctc atgccgcacc agacgctgta   209700
acgccgcacg ggcccgtagc gggctgtttg ttcgcgtaca tgatcgttga gctcttgcca   209760
atattgtttg gcacactcca gatcggaggt ttgtggatag tcgggtcgga tccgtggatc   209820
ccaactgaca tcggcggtgc cggagacttc gtccagactg ttacgcatag agcaccagtc   209880
gggtcggacg ataaacctgt ccttgcggat taaccattta taacgtagtt cgtgatggcg   209940
tgtagaggcc cgtacacgct ccacggtccc aaagcggtcc cagaagggaa agttttcgtg   210000
ggggcagcga cccggcactt ccagacgttc ggcgtcgtcc acggcgtagt gaaaacgccg   210060
gccggcctgg taaattttga gcagacccac tgttaacaac atatccacgc tgtcagccaa   210120
ccgccagatc tcgcggcgag acacgtcaaa atagaaaaat tcgcaggctc ggtcgaccag   210180
gatcacgaaa tcggcgtgaa agacgccgga gggtagcgat tcgcccacca cacccattat   210240
catggtttca cagcataagc ggtccacaaa gaacttcaac aggtcgttga attgctccgt   210300
ctccatacag atgaagggcc agacgccttt gaggttctcg gcctggccgc agagcagtag   210360
cggacgtgtc atctcgcccg gagtgcgcag aggcacgcat tcgccgcgat aacgacaggt   210420
cacacgctgt agttcgctga tgctgttgtc gtgcaggcga aggtcgcaga taatatgatc   210480
```

```
cggttgcgtg gttagcagcg gcgtgcgcat ttgctcgccg tagatggcct cgcagtgcaa   210540
cagcccgtgt cgcgcaaaat cgtccagact gtgcgccagg tagtaaagca ccccgcgatc   210600
gcggtctaga caccacacgg tttcgtaacg tcctaacagg agcaccagac gggcctggct   210660
aggtggctca atttcctcta catacacgaa aaagtcgtca tcgtccgagt cctcgtcctc   210720
agaagaggac cgcggcccgt gtactctggg caacacggtg gtagagaact gcaggacgcc   210780
cagagactcg agcgactctt cgcagcagat gagctgaccc cagggcgttt cgggcccgtc   210840
ggtgacagcc gcgctgccaa agatgtcctc aaactctaca aaatctagac gccatccggg   210900
tggcgctgaa atgggaaggc taatgttcat atcagcataa ctacgaacta agtggcggat   210960
gtcctgccgc aagtcttggc agagaatgag ctttcgtaaa cccttgaggg tcctccgaac   211020
aacgccccca gacgcgtagc gataggactg gcgcatggtg ccgcggcgtg gagcggcact   211080
tggcagccta ttttatggag tttcttcagt gacgtggctt gttcacgtcg ttcgtgggct   211140
gcggttggca gctccggtct gtaaaccacc cgaaaagact gacatcgacg tcaaagactc   211200
acgtaatttg gaacatgtgc gaccgcaaag tgcgtcagaa tagcacgtgg ctttaggaca   211260
taaaaagtac cgtgaggtct agacgtggtt tttgtgattg acacttacac caggtaagcc   211320
aagggacggt gaaactgtat gtgaggaacc tgggtgctta gacaactaac gtgtaatgct   211380
ttttacagga ccgttcaaca ggtgatacta cctgcaaggt aatgactaca tctactacaa   211440
ctaccactaa tatcatgcta caggtgagca acgtaacgaa tcacaccctg aatagcaccg   211500
aaatttatca gttgttcgag tacactcggt tcggggtatg gttgatgtgc atcgtgggca   211560
cgtttctgaa cgtgctggtg attaccacca tcctgtacta ccgtcgtaag aaaaaatctc   211620
cgagcgatac ctacatctgc aacctggctg tagccgatct gttgattgtc gtcggcctgc   211680
cgttttttct agaatatgcc aagcatcacc ccaaactcag ccgagaggtg atttgttcgg   211740
gactcaacgc ttgtttctac atctgtcttt tgccggcgt ttgttttctc atcaacctgt   211800
cgatggatcg ctactgcgtc attgtctggg gtgtagaatt gaaccgcgtt cgaaataaca   211860
agcgggctac ctgttgggtg gtgattttt ggatactggc cgcgctcatg gggatgccac   211920
actacctgat gtacagtcat accaataacg agtgtgttgg tgaatttgct aacgagactt   211980
caggttggtt ccccgtcttt ttgaacacca aagtcaacat ttgcggctac ctggcgccca   212040
tcgtgctgat ggcgtacacg tacaaccgta tggtgcggtt tatcattaac tacgtgggta   212100
aatggcacat gcagacgctc cacgttcttt tagttgtggt tgtatctttt gccagcttt   212160
ggttccccctt caacctggca ctattttag aatccatccg tcttttagcg ggaacgcaaa   212220
acgagactct ccaaaccgtt attactttct gtctatacgt cggtcagttt ttggcctacg   212280
ttcgcgcttg tctgaatcct ggaatctaca tcctagtagg cactcaaatg aggaaggaca   212340
tgtggacaac cctaagggta ttcgcctgtt gctgcgtgaa gcaggagata ccttaccagg   212400
acattgatat tgagctacaa aaggacatac aagaagggc caaacacacc aaacgtaccc   212460
attatgacag aaaaaatgca cctatggagt ccggggagga ggaatttctg ttgtaattcg   212520
atcctctctc acgcgtccgc cgcacatcta tttttgctaa ttgcacgttt cttcgtggtc   212580
acgtcggctc gaagaggttg gtgtgaaaac gtcatctcgc cgacgtggtg aaccgctcat   212640
atagaccaaa ccggacgctg cctcagtctc tcggtgcgtg gaccagacgg cgtccatgca   212700
ccgagggcag aactggtgct atcatgacac cgacgacgac gaccgcggaa ctcacgacgg   212760
agtttgacta cgatgaagac gcgactcctt gtgttttcac cgacgtgctt aatcagtcaa   212820
```

```
agccagtcac gttgtttctg tacggcgttg tctttctctt cggttccatc ggcaacttct    212880
tggtgatctt caccatcacc tggcgacgtc ggattcaatg ctccggcgat gtttacttta    212940
tcaacctcgc ggccgccgat ttgcttttcg tttgtacact acctctgtgg atgcaatacc    213000
tcctagatca caactcccta gccagcgtgc cgtgtacgtt actcactgcc tgtttctacg    213060
tggctatgtt tgccagtttg tgttttatca cggagattgc actcgatcgc tactacgcta    213120
ttgtttacat gagatatcgg cctgtaaaac aggcctgcct tttcagtatt ttttggtgga    213180
tctttgccgt gatcatcgcc attccacact ttatggtggt gaccaaaaaa gacaatcaat    213240
gtatgaccga ctacgactac ttagaggtca gttacccgat catcctcaac gtagaactca    213300
tgcttggtgc tttcgtgatc ccgctcagtg ttatcagcta ctgctactac cgcatttcca    213360
gaatcgttgc ggtgtctcag tcgcgccaca aaggtcgcat tgtacgggta cttatagcgg    213420
tcgtgcttgt ctttatcatc ttttggctgc cgtaccacct aacgctgttt gtggacacgt    213480
taaaactcct caaatggatc tccagcagct gcgagttcga agatcgctc aaacgtgcgc    213540 tcatcttgac cgagtcgctc gccttttgtc actgttgtct caatccgctg ctgtacgtct    213600
tcgtgggcac caagtttcgg caagaactgc actgtctgct ggccgagttt cgccagcgac    213660
tcttttcccg cgatgtatcc tggtaccaca gcatgagctt tcgcgtcgg agctcgccga    213720 gtcgaagaga gacatcttcc gacacgctgt ccgacgaggt gtgtcgcgtc tcacaaatta    213780
taccgtaata aaaaagcgct acctcggcct tttcatacaa accccgtgtc cgcccctctt    213840
ttccccgtgc ccgatataca cgatattaaa cccacgacca tttccgtgcg attagcgaac    213900
cggaaaagtt tatggggaaa aagacgtagg aaaggatcat gtagaaaaac atgcggtgtt    213960
tccgatggtg gctctacagt gggtggtggt ggctcacgtt tggatgtgct cggaccgtga    214020
cggtgggttt cgtcgcgccc acggtccggg cacaatcaac cgtggccgc tctgagccgg    214080 ctccgccgtc ggaaacccga cgagacaaca atgacacgtc ttacttcagc agcacctctt    214140
tccattcttc cgtgtcccct gccacctcag tggaccgtca atttcgacgg accacgtacg    214200
accgttggga cggtcgacgt tggctgcgca cccgctacgg gaacgccagc gcctgcgtga    214260
cgggcaccca atggagcacc aactttttt tctctcagtg tgagcactac cctagtttcg    214320
tgaaactcaa cggggtgcag cgctggacac ctgttcggag acctatgggc gaggttgcct    214380
actacggggg ttgttgtatg gtgggcgggg gtaatcgtgc gtacgtgata ctcgtgagcg    214440
gttacgggac cgccagctac ggcaacgctt tacgcgtgga ttttggccgc ggcaactgta    214500
cggcgccgaa acgcacctac cctcggcgct tggaactgca cgatgccgc acagacccta    214560 gccgttgcga tccctaccaa gtgtatttct acggtctaca gtgtcctgag caactggtta    214620
tcaccgccca cggcggcgtg gtatgcgcc gctgtcctac cggctctcgt cccacccgt    214680 cccggcccca ccggcatgac ttggagaacg agctacatgg tctgtgtgtg atcttctgg    214740 tgtgcgtcct tttattagct ctgctgctgt tggagctcgt tcccatggaa gccgtgcgtc    214800
acccgctgct tttctggcga cgcgtggcgt tatcgccgtc cacttccaag gtggatcgcg    214860
ccgtcaagct gtgtcttcgg cgcatgctgg gtctgccgcc gccaccgtca gtcgcaccac    214920
ctggggaaaa gaaggagcta ccggctcagg cggccttgtc gccgccactg accacctggt    214980
cactaccgcc gtttccgtcc acgcggatac ctgacagtcc gccgccaccg taccagcttc    215040
gtcacgccac gtcactagtg acggtaccca cgctgctgtt atatacgtca tccgacatcg    215100
gtgacacagc ttcagaaaca acgtgtgtgg cgcacgctac ttatgggaa ccccggagc    215160 ccgctcgatc gacggctacg gttcaggaat gtgccgttct taccgcccca aattgcggca    215220
```

```
tcgtcaacaa cgacggcgcg gtctctgaag gccaagacca tggagatacg gttcaccata 215280
gcctggatgt ggtttcccag tgtgctgctg atactggggt tgttgacgcc tccgagtaac 215340
ggctgcactg tcgatgtcgg acgaaacatg tccattcgag aacagtgccg tcttcgagac 215400
ggtgcgacgt tctccaaggg agacatcgaa ggtaacttca gtgggcccgt cgtcgtggag 215460
ttggactacg aagacgtcga tattactggc gaacggcagc gacttcggtt tcatctcagc 215520
ggactcgggt gtcctacaaa ggaaaatata agaaaagaca atgaaagcga cgtcagcggt 215580
ggaattcgct gggctctata tatacaaacc ggcgacacca agtacggtat tcgtaatcag 215640
catttgagta tacggttgat gtatcctggg gaaaaaaata cacaacagct gttgggttct 215700
gatttcagtt gcgaacgtca ccggagaccg tccacgccgt tgggaaataa cgccaaagtg 215760
cctttcacga cccgcacgtc ttctacatac ggcgtcctca gcgcctttgt ggtgtggatc 215820
ggatccggcc tcaatatcat ctggtggacc ggcatcgtgc ttctggcggc ggacgctctc 215880
gggcttggcg agcgttggct gaggttggcg ctgtcccacc gggacaaaca tcacgcatcg 215940
cgaaccgcgg cgctccagtg tcaacgcgac atgttacttc ggcaacgtcg acgggctcgg 216000
cggctgcacg ccgtttctga aggcaaactg caggaagaga agaaacgaca gtctgctctg 216060
gtctggaacg ttgaggcgcg acccttttccg tccacacatc agctgattgt gctgcccct 216120 cctgtagcgt cagctcctcc tgcagttccc tcgcagcccc ccgagtattc gtctgtgttt 216180
ccgcctgtat aaaaataaag agacgggagg ctgatcgcgg ccttcagcgt ctcatttgtc 216240
tttactctcg agtgcggtcg gtgtctcgtc ggtgagacga ggccgccgcc cgacaagttc 216300
gatctcatgt cgctcttgga gcgcgaagag agttggcgtc gcgtagtcga ctactcgcac 216360
aacttgtggt gtacgtgcgg taactggcag agccacgttg agattcagga cgaggagccc 216420
aactgcgagc agccggagcc cgcacactgg ctggaatacg tggcggtcca gtggcaggcc 216480
cgggttcgcg attctcacga tcgctggtgt ctctgcaacg cctggcgtga tcacgccttg 216540
cgcggccgtt ggggtacggc gtattcctcg ggttcctcgg cctcttcctc cggtttcgtc 216600
gcggagagca agttcacctg gtggaaacga ctgcgccaca gtactcggcg ctggttgttt 216660
cgccgccggc gagctcgata cactccgtct aactgtgggg aaagtagcac tagcagcggc 216720
cagagtagcg gtgacgagag taactgcagt ctacgcaccc acggcgtgta cacacggggt 216780
gaacaacact aatcgataag tcgcgtgtag gcgactggct acatcaaccg gatatctgcg 216840
gggatttaaa aagacgaccc gttgtcatcc ggcttagagc aaaccgtcct tttatcatct 216900
tccgtcgcca tggctatgta cacatccgaa tccgaacgcg actggcgtcg tgtaatccac 216960
gactcgcacg gcctgtggtg cgactgcggc gactggcgag agcacctcta ttgtgtgtac 217020
gacagccatt ttcagcgacg acccacgacc cgagccgaac ggagggccgc caattggcgg 217080
cgacagatgc ggcggttaca ccgtctgtgg tgttttttgtc aggactggaa gtgtcacgcg 217140
ttatacgccg agtgggacgg caaagaatcc gacgacgagt cgtcggcgtc ttcctcgggc 217200
gaagcgccag agcaacaggt ccccgcttgg aagaccgtgc gagccttctc gcgggcctac 217260
catcaccgca ttaaccgggg tctgcggggc acgcccccac cgcgcaactt gccgggatac 217320
gagcacgcct ccgagggctg gcggttttgc agtcgacggg aacggcgaga ggacgatctt 217380
cgcacgcggg ctgagccgga ccgcgtggtg ttccagttag ggggagtgcc gcctcgccgt 217440
caccgggaaa cttacgtgta agaacacggc atgacaataa acaacatagc gtaaatcccc 217500
gtgtgatgtg tgtgattgac gttcaggaaa catgtcccca tcatcagcgt cacaactgac 217560
```

-continued

```
gtgggttggg tactgacgtg caggatatta cgcgagtcag agaatcgcat aagaacgggg   217620
tggtgagcgg gttcccacag gagtttctgg cacagaggca ccatgagcct taagttcccc   217680
gagagggtgg gttacgagaa attgggacac cgcccgtata ccaaacgcgt gcgggtgcat   217740
gacccgttgg gattgacgcg gtttatcatg aggcaactca tgatgtaccc gctggtgttg   217800
ccgttcactt ttccgtttta cgtgccgcgg tcctagcacg tcagtggtga cgctgataat   217860
tgcaacatgg cccatgacga acccgcttgg gacgaacgtc aataccacgt caaaccaccg   217920
tgacttggct gaacgttgaa acataaagcc aaagcgccgt cggcacttgg cttcagagca   217980
gcgcctcggg gcgatgcgac ggcgatgaac ttagagcaac tcatcaacgt ccttggtctg   218040
ctcgtctgga ttgccgctcg tgctgtcagc cgcgttggtc cgcatggctc cggactcgtt   218100
tatcgtgagc ttcatgattt ctacgggtat ttgcagctgg accttctggg accagtggtg   218160
gcggggaatc gctcagtccg gacctggaga gagcaggcgg accgagccag agggaccttc   218220
gctcggcgtt caggccttaa tactagccac atcttacctg tcggcagcat gtatcggggc   218280
tccgacacct tatccgccgg cctgtatcgt tccaaagaag aggtgttcct cctcttgaac   218340
cgctgtcacg ggccactgtc aacgccgaaa aacgcttgtc tggctgaggt tggtgtcgtt   218400
aatgaacttt ttttgtctcg cttcaatgtc ggtgattttc acggagcgtc atgggaaaac   218460
ggtaccgctc ccgatggaga gcccggggta tgctgaaatt cttcttaaaa ttacgtaaac   218520
gacgtcgtcc agtcgttgtg ccgcgattcg tacggttcat cgtctacgtc gttttgttca   218580
ccgtcgctgt gcaacgtgtg aaacaagagc gcgatgcgca ccttcggcgg tatgaagaac   218640
ggttacggaa aaatcacgca cggcgtcggc agtcttttcc gtgacttggg gcgatgggtc   218700
cgagctgcgg tatgggtcac ggcggcgtgt gtcttagtga cgaagatgcc gatgtgtgac   218760
taaaaacgtc ccagcccag agcgatgtgt ttcaataaaa aaatatgtag tatcatatta   218820
tgcgtgtcct ggttttttcat ttctggatgt atttgttaca taaaaggcgg tgggatatgg   218880
ggatgaaaca tatgtagata cgcagtttga ttatccgaac aaagctcgtg tgatgcgaaa   218940
aacggtactg caggatgaaa gtcccgttgg ggggggggga agcagagaat agtcgctttt   219000
gccgctgggc atacgctatg cttgtatttg tgactatact atgtgcagtc gtgtgtcgat   219060
gttcctattg ggaagggtgt gaatgtacga ggtataaaga atggtgggac gtagagaggc   219120
atcgctagac acaggttgat cgttgtgcta gccccacgtg agcagcgtca tgggtaaagc   219180
ggtgattaag cgtgaaaaca ccgtaagggg ggggggcag gaagcttggt ggcagtggcc   219240
gttagatacc ttacgtgtct gtattggtac atttgcgact tgtcgggtac gacggtatag   219300
tttaactatg attatattat gtatgcgcag gatacaatgc cctaaaacat tgtaacacga   219360
aactcgcgag tattaaagca attggtgtct ctgtgctagt ctaacaacac ctgtgtaatg   219420
cgtacaacga gaaaaagac gcgaaagcaa cgtgtatggg ggggggggg aataatattg   219480
ctaatcatgc gtcttgcagt acagatagcc gctgtatctt acgcgtattg tcgcaacagt   219540
tccacatcgg tgtaattgga tgtctggtac ttatcactgg cgtcgttata acattgtaaa   219600
acaagttttc gaaacataac gacagctgca aaagaaaacc agtttattga gcattgtaat   219660
ggtagtgtgt ggctatatta gaaaacgtga cgcgtcgcat gtcgcggcac aatctggcag   219720
cggggtcggg gtagggtacg gtgggaggca tgtacacaga tggaacaaaa gcagaagtaa   219780
cgtgagaagg agcatacagt ccagtatcca gcggttcctg agtagcacca cccatcaact   219840
gaatgccctc atgagtaaaa gtctgcgggc gacagccctt ggggaccgtt ggcatgggac   219900
gatcaatctc caaaccacag cgtaacaccg ttttcttcca acgtcgttga tagacgtcgt   219960
```

-continued

```
ttttacggtt actcccaaga acccagaaag tctcgtccaa gtcgtaccag gaatcttctc    220020
cggggagacg cgacggtttc caatcctcgt cgtctcgtct caaagcacgt cccaaactgg    220080
cttgaggagt caacggtggt tctgtgggtc gggtgtagcg cgagtgtttt cccttcatga    220140
gcgattcatc ctccttgcct ttaggctttt tggtcttttt gtgtatcatc tggccgccgg    220200
cctccataac caccgtggcc aagtccagtc ccagagcttg agcgtcggcg cggcgtcggg    220260
cgtcttgcag gtagtcttcc acatttgcac agatggccgg gtgtttggtg ctagggtga    220320
ggacctcagc ctcgccgcga cccggacgta gcaaaaaagc caactgcccg tgcggctcgc    220380
gcgcccacag cgcggcgcgc gggtgcaggt gcagcgcgtc ccagcgcggc cgctcccact    220440
gctcgcggtc cagctcgggc agcagccgcc gcgcggcctc ggcggcgggc gccgactcgc    220500
gccccagcgc cagcgcgccc agcacgcccg cgcgcagaaa gtgcgacagc tccgccgcca    220560
gcgggtacac gtgcccgtcc agcgggcagt acccgaacac ggcgcccagc tcgtccagca    220620
ccaccaccag catggcgcgc ggcacggtcc ccgacgccgc cggacccgcc atcgccgtcg    220680
gacccaccat caccgtcggc gccgccgctg ccgccgccgc cgcatccgtt ccgaccaccg    220740
cgtgcgtgtc cgcgtttggt acgcaaaccg cgctcccgcc ggcggcgccg tacgctgcg    220800
gaggtaaagt cacagcagac cccacggctc ccgctatcgc gcacggcgcg tccccgccgg    220860
cggcctccgt ctccgtgccg ctcgccccg ccggcaacgt cgtccccgtc gccatcgccg    220920
tcgtccccgc cgtcatcgtc gccggccccg ccgcgcagcc cagccaccgc gcgggcagca    220980
ccgcgcccag cgccagccag ccgcagcaca gacgctggtt caggtgccga cgcacggccg    221040
tcagcagcga cgcggggtgc ggcgccgacg cgaacggctc gtactgcgcc agctcctgcc    221100
acgcgcccag cagtaccatc ggctgcagtc gcctgcccgg cgtctgcagc gccaccgtcg    221160
tgccggccca ccgccggcgc agctcccgtc cgagcgcgt cgcctcctcg gcgcgcagca    221220
aggtctgtcg aagcgccggc tgaggcagca gcgtcgcgcg cggggtgccc acgcccagcc    221280
ggttgcagcg gtacacccgc accacctcgc ccgcgccgtg ccgaaaccac tcgtccgcgt    221340
cgcgcgccgc caggatcagc gtgttgttcg ccaggtcgta cacgaacacg cggaatccgg    221400
cgcccagcgc caggtacagt ccgtcctgcg cgcacagacc ctcgggatgg ccggccttgt    221460
cgcccaccgt cgggtcggcc gcggggtcta cctcgtgcac cacggtcgcc accagcacga    221520
tccacgcgtc ccgcggcgac agctgacgca ggtccgtcgc gcccacgccg ttcatctggc    221580
tgcgcggcgt caccccgcgcg tagaatccgt acggccgtcc gagcggcagc agcgtgcccg    221640
cgtcgcgctg cgaccacttg cgcatggcgc ggcccgtgct gttggccaga aacgccgcgc    221700
gccacacggc gcccatggcc tggtattcca gttccgtcag cgcctgccgc tccaccggaa    221760
tctgagacag caacaggcgc tccggcccgt gccaaaagtt gctattgttg ccgctacccg    221820
gaggggcgcc cggcggcccg cggggttcta cccgttggac gccgtggccc ggcgtcgccg    221880
aacccgcagt acttgcacca gttcccgccg ttgacgtcgc tcccatcggc acacaagaag    221940
aaggagagga agcaaccccc gaaggccctc cggcaccgcg gccgcgaccg aggggcgggg    222000
ggcgcggcga catgccgttg cgctgggcca t                                   222031
```